(12) United States Patent
Blake et al.

(10) Patent No.: US 12,215,341 B2
(45) Date of Patent: Feb. 4, 2025

(54) HYBRID IMMOLATIVE CELL-PENETRATING COMPLEXES FOR NUCLEIC ACID DELIVERY

(71) Applicant: THE BOARD OF TRUSTEES OF THE LELAND STANFORD JUNIOR UNIVERSITY, Palo Alto, CA (US)

(72) Inventors: Tim R. Blake, Palo Alto, CA (US); Robert M. Waymouth, Palo Alto, CA (US); Paul Wender, Palo Alto, CA (US); Ronald Levy, Palo Alto, CA (US); Ole Audun Werner Haabeth, Palo Alto, CA (US); Matthew Frank, Palo Alto, CA (US); Adrienne Sallets, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 912 days.

(21) Appl. No.: 17/292,370

(22) PCT Filed: Nov. 11, 2019

(86) PCT No.: PCT/US2019/060807
§ 371 (c)(1),
(2) Date: May 7, 2021

(87) PCT Pub. No.: WO2020/097614
PCT Pub. Date: May 14, 2020

(65) Prior Publication Data
US 2022/0088163 A1 Mar. 24, 2022

Related U.S. Application Data

(60) Provisional application No. 62/758,487, filed on Nov. 9, 2018.

(51) Int. Cl.
| | | |
|---|---|---|
| A61K 39/00 | (2006.01) |
| A61K 47/69 | (2017.01) |
| A61P 35/00 | (2006.01) |
| A61P 37/04 | (2006.01) |
| C08G 63/64 | (2006.01) |
| C08G 64/02 | (2006.01) |
| C12N 15/88 | (2006.01) |
| C12N 15/90 | (2006.01) |

(52) U.S. Cl.
CPC ...... *C12N 15/88* (2013.01); *A61K 39/001112* (2018.08); *A61K 39/4611* (2023.05); *A61K 39/4631* (2023.05); *A61K 39/464412* (2023.05); *A61K 39/464499* (2023.05); *A61K 47/6935* (2017.08); *A61P 35/00* (2018.01); *A61P 37/04* (2018.01); *C08G 63/64* (2013.01); *C08G 64/0291* (2013.01); *C12N 15/90* (2013.01); *A61K 2039/5158* (2013.01); *A61K 2039/545* (2013.01); *A61K 2039/6025* (2013.01); *A61K 2239/31* (2023.05); *A61K 2239/38* (2023.05)

(58) Field of Classification Search
CPC ..... A61K 39/00; A61K 47/6883; C12N 15/88
See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 2016/0348073 A1 | 12/2016 | Meissner et al. |
| 2018/0028688 A1 | 2/2018 | Waymouth et al. |

FOREIGN PATENT DOCUMENTS

| | | |
|---|---|---|
| WO | 02088318 A2 | 11/2002 |
| WO | 03106636 A2 | 12/2003 |
| WO | 2013036532 A1 | 3/2013 |
| WO | 2014099671 A1 | 6/2014 |
| WO | 2017083637 A1 | 5/2017 |
| WO | 2018022930 A1 | 2/2018 |

OTHER PUBLICATIONS

Adams et al. (1993) "Highly Specific in Vivo Tumor Targeting by Monovalent and Divalent Forms of 741F8 Anti-c-erbB-2 Single-Chain Fv", Cancer Research, 53(17):4026-4034.

Blake et al. (Jun. 19, 2014) "Organocatalytic Ring-Opening Polymerization of Morpholinones: New Strategies to Functionalized Polyesters", Journal of the American Chemical Society, 136(26):9252-9255.

Chung et al. (May 9, 2013) "Chemoselective Pd-catalyzed Oxidation of Polyols: Synthetic Scope and Mechanistic Studies", J Am Chem Soc, 135(20):7593-7602.

Cooley et al. (Nov. 18, 2009) "Oligocarbonate Molecular Transporters: Oligomerization-based Syntheses and Cell-penetrating Studies", Journal of the American Chemical Society, 131(45):16401-16403.

Dove et al. (Oct. 1, 2005) "Thiourea-Based Bifunctional Organocatalysis: Supramolecular Recognition for Living Polymerization", Journal of the American Chemical Society, 127(40):13798-13799.

Ford et al. (Jan. 2001) "Protein Transduction: An Alternative to Genetic Intervention", Gene Therapy, 8(1):1-4.

Geihe et al. (Aug. 14, 2012) "Designed Guanidinium-Rich Amphipathic Oligocarbonate Molecular Transporters Complex, Deliver and Release Sirna in Cells", Proceedings of the National Academy of Sciences of the United States of America, 109(33):13171-13176.

Gruber et al. (Jun. 1, 1994) "Efficient Tumor Cell Lysis Mediated by a Bispecific Single Chain Antibody Expressed In *Escherichia coli*", The Journal of Immunology, 152(11):5368-5374.

(Continued)

*Primary Examiner* — Gregory Listvoyb
(74) *Attorney, Agent, or Firm* — KDW Firm PLLC

(57) ABSTRACT

There are provided herein, inter alia, complexes, compositions and methods for the delivery of nucleic acid into a cell in vivo. The complexes, compositions and methods may facilitate complexation, protection, delivery and release of oligonucleotides and polyanionic cargos into target cells, tissues, and organs both in vitro and in vivo.

15 Claims, 41 Drawing Sheets

Specification includes a Sequence Listing.

(56) References Cited

OTHER PUBLICATIONS

Holliger et al. (Jul. 1993) "Diabodies": Small Bivalent and Bispecific Antibody Fragments, Proceedings of the National Academy of Sciences, 90(14):6444-6448.
Hu et al. (Jul. 1, 1996) "Minibody: A Novel Engineered Anti-Carcinoembryonic Antigen Antibody Fragment (Single-Chain Fv-CH3) Which Exhibits Rapid, High-Level Targeting of Xenografts", Cancer Research, 56:3055-3061.
Huang et al. (Aug. 27, 2014) "An improved protocol for isolation and culture of mesenchymal stem cells from mouse bone marrow", J. Otihopaedic Trans, 3(1):26-33.
Inoo et al. (Nov. 16, 2016) "Immunological Quality and Performance of Tumor Vessel-Targeting CAR-T Cells Prepared by Mrna-EP for Clinical Research", Molecular Therapy—Oncolytics, 3:1-13.
Kostelny et al. (Mar. 1, 1992) "Formation of A Bispecific Antibody by the Use of Leucine Zippers", Journal of Immunology, 148(5):1547-1553.
Mccafferty et al. (Dec. 6, 1990) "Phage Antibodies: Filamentous Phage Displaying Antibody Variable Domains", Nature, 348(6301):552-554.
Mccartney et al. (Mar. 1995) "Engineering Disulfide-linked Single-chain Fv Dimers [(Sfv')2] with Improved Solution and Targeting Properties: Anti-digoxin 26-10 (Sfv')2 and Anti-c-erbb-2 741f8 (Sfv')2 Made by Protein Folding and Bonded Through C-terminal Cysteinyl Peptides", Protein Engineering, 8(3):301-314.
Mckinlay et al. (Mar. 16, 2016) "Cell-Penetrating Guanidinium-Rich Oligophosphoesters: Effective and Versatile Molecular Transporters for Drug and Probe Delivery", Journal of the American Chemical Society, 138(10):21 pages.
Mckinlay et al. (Jan. 9, 2017) "Charge-Altering Releasable Transporters (CARTs) for the Delivery and Release of Mrna in Living Animals", Proceedings of the National Academy of Sciences of the United States of America, 114(4):E448-E456.
Pack et al. (Feb. 18, 1992) "Miniantibodies: Use of Amphipathic Helices to Produce Functional, Flexibly Linked Dimeric Fv Fragments With High Avidity in *Escherichia coli*", Biochemistry, 31(6):1579-1584.
Pratt et al. (Oct. 18, 2006) "Exploration, Optimization, and Application of Supramolecular Thiourea-Amine Catalysts for the Synthesis of Lactide (Co)polymers", Macromolecules, 39(23):7863-7871.
Pratt et al. (2008) "Tagging Alcohols With Cyclic Carbonate: A Versatile Equivalent of (Meth)acrylate For Ring-opening Polymerization", Chemical Communication, 1:114-116.
Prochiantz et al. (Feb. 2007) "For Protein Transduction, Chemistry Can Win Over Biology", Nat Methods, 4(2):119-120.
Venkataraman et al. (Nov. 4, 2015) "A Simple and Facile Approach to Aliphatic N-substituted Functional Eight-membered Cyclic Carbonates and their Organocatalytic Polymerization", Journal of the American Chemical Society, 137(43):13851-13860.
Xie, et al. (Mar. 25, 2015) "Efficient and Selective Cu/nitroxyl-catalyzed Methods for Aerobic Oxidative Lactonization of Diols", Journal of the American Chemical Society, 137(11):3767-3770.
Zhu et al. (1997) "Remodeling Domain Interfaces to Enhance Heterodimer Formation", Protein Science, 6:781-788.
Colin J. McKinlay et al., "Enhanced mRNA delivery into lymphocytes enabled by lipid-varied libraries of charge-altering releasable transporters," Proceedings of the National Academy of Sciences, vol. 115, No. 26, DOI: 10.1073/pnas. 1805358115, Jun. 11, 2018, pp. E5859-5866.

$D_{13}:A_{11}$ 7: n = 13, m = 11, R = Dansyl
$D_{18}:A_{17}$ 8: n = 18, m = 17, R = Dansyl
$A_{11}$ 9: n = 0, m = 11, R = Dansyl
Pyr-$D_{15}:A_{12}$ 10: n = 15, m = 12, R = Pyrene
Pyr-$D_{15}$ 11: n = 15, m = 0, R = Pyrene

HYBRID IMMOLATIVE CELL-PENETRATING COMPLEXES FOR NUCLEIC ACID DELIVERY

CROSS-REFERENCES TO RELATED APPLICATIONS

This application is a U.S. National Stage Entry of the International Patent Application No. PCT/US19/60807, filed on Nov. 11, 2019, which claims the benefit of U.S. Provisional Application No. 62/758,487, filed Nov. 9, 2018, which are incorporated herein in their entireties and for all purposes.

STATEMENT AS TO RIGHTS TO INVENTIONS MADE UNDER FEDERALLY SPONSORED RESEARCH AND DEVELOPMENT

This invention was made with Government support under contract DE-SC0018168 awarded by the Department of Energy, under contracts CA197353, CA031841, and CA031845 awarded by the National Institutes of Health, and under contract 1607092 awarded by the National Science Foundation. The Government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 041243-533001WO_SEQUENCE_LISTING_ST25.TXT, created on Nov. 11, 2019, having 6,992 bytes, machine format IBM-PC, MS Windows operating system, is hereby incorporated by reference.

BACKGROUND

There is a need for new materials and strategies that enable or enhance the delivery of therapeutic agents, diagnostic probes and/or research tools across the plasma membrane of cells and other biological barriers, as required for a wide range of clinical, diagnostic and/or research applications. The delivery of such cargo, e.g., nuclei acids, has considerable clinical potential in connection with vaccination strategies for infectious diseases, cancer immunotherapy, protein therapy and gene editing. Provided herein are solutions to these and other problems in the art.

BRIEF SUMMARY

In a first aspect, there is provided a cell-penetrating complex including a nucleic acid non-covalently bound to a cationic amphipathic polymer, the cationic amphipathic polymer including a pH-sensitive immolation domain.

In another aspect, there is provided a nanoparticle composition including a plurality of cell-penetrating complexes as disclosed herein.

In another aspect, there is provided a cationic amphipathic polymer of the formula: $H-L^1-[(LP^1)_{z1}-(IM)_{z2}-(LP^2)_{z3}]_{z4}-L^2-H$ (I), wherein: $L^1$ and $L^2$ are independently a bond, —C(O)O—, —O—, —S—, —NH—, —C(O)NH—, —NHC(O)—, —S(O)$_2$—, —S(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a bond or a lipophilic polymer domain, wherein at least one of $LP^1$ or $LP^2$ is a lipophilic polymer domain; IM is the pH-sensitive immolation domain; z1 and z3 are independently integers from 0 to 100, wherein at least one of z1 or z3 is not 0; z4 is an integer from 1 to 100, and z2 is an integer from 2 to 100. In embodiments, $L^1$ is substituted or unsubstituted alkylene. In embodiments, $L^1$ is peptide (e.g., an amino acid sequence).

In another aspect, there is provided a cationic amphipathic polymer of the formula: $H-L^1-[(LP^1)_{z1}-(LP^3)_{z1a}-(IM)_{z2}-(LP^2)_{z3}-(LP^4)_{z3b}]_{z4}-L^2-H$ (I), wherein: $L^1$ and $L^2$ are independently a bond, —C(O)O—, —O—, —S—, —NH—, —C(O)NH—, —NHC(O)—, —S(O)$_2$—, —S(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$, $LP^2$, $LP^3$ and $LP^4$ are independently a bond or a lipophilic polymer domain, wherein at least one of $LP^1$, $LP^2$, $LP^3$ and $LP^4$ is a lipophilic polymer domain; IM is the pH-sensitive immolation domain; z1, z1a, z3, and z3b are independently integers from 0 to 100, wherein at least one of z1, z1a, z3, or z3a is not 0; z4 is an integer from 1 to 100, and z2 is an integer from 2 to 100. In embodiments, $L^1$ is substituted or unsubstituted alkylene. In embodiments, $L^1$ is peptide (e.g., an amino acid sequence).

In another aspect, there is provided a method of transfecting a nucleic acid into a cell, the method including contacting a cell with the complex as disclosed herein.

In another aspect, there is provided a cationic amphipathic polymer of the formula: $R^{1A}-[L^1-[(LP^1)_{z1}-(IM)_{z2}-(LP^2)_{z3}]_{z4}-L^2-R^{2A}]z_5$, wherein $R^{1A}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^{2A}$ is independently hydrogen, halogen, —CCl$_3$, —CBr$_3$, —CF$_3$, —Cl$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl2, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, $LP^1$ and $LP^2$ are independently a bond or a lipophilic polymer domain, wherein at least one of $LP^1$ or $LP^2$ is a lipophilic polymer domain; IM is independently a pH-sensitive immolation domain, z5 is an integer from 1 to 10, z1 and z3 are independently integers from 0 to 100, wherein at least one of z1 or z3 is not 0; z4 is an integer from 1 to 100, and z2 is independently an integer from 2 to 100. In embodiments, $R^{1,4}$ is hydrogen. Where $R^{1,4}$ is hydrogen, z5 is 1.

In another aspect, there is provided a method of inducing an immune response in a subject in need thereof, the method having administering an effective amount of the cell-penetrating complex disclosed herewith.

BRIEF DESCRIPTION OF THE DRAWINGS

FIG. 3A: tumor size chart, FIG. 3B: Survival chart, FIG. 3C: Tumor size chart of mice re-challenged with TSA-expressing A20 lymphoma (note, overlapping lines are shown separately; the black line values are all at zero).

FIG. 4A: tumor size data. FIG. 4B: survival curve data.

FIG. 7A) Rearrangement mechanism for oligo(α-amino ester)s through tandem 5-membered then 6-membered transition states for amide formation. FIG. 7B) Synthesis of oligo (carbonate-b-α-amino ester) CARTs for mRNA delivery via OROP of cyclic carbonate and ester monomers. FIG. 7C) Amphipathic oligo(carbonate)s synthesized via previously reported OROP methodology.

FIG. 8A) Self-immolative rearrangement of the α-amino ester portion of a block co-oligomer yields the intact lipophilic oligocarbonate block with attached initiator and small molecule HEGD 2. FIG. 8B) GPC traces of protected block co-oligomer Pyr-$D_{15}$:$A_{12}$ 10, and following deprotection and base-catalyzed rearrangement compared to an independently synthesized $D_{15}$ homooligomer 11.

FIG. 9A) Flow cytometry-determined mean eGFP fluorescence values from HeLa cells treated with various transporters. FIG. 9B) Representative flow cytometry histograms of eGFP fluorescence showing % transfection in HeLa cells treated with eGFP mRNA transporters. FIG. 9C) The effect of charge ratio on eGFP expression resulting from mRNA delivery by $D_{13}$:$A_{11}$ 7. FIG. 9D) Epifluorescence microscopy images of HeLa cells treated with naked mRNA, mRNA complexed with Lipofectamine, or mRNA complexed with $D_{13}$:$A_{11}$ 7. All data shown is in HeLa cells treated with mRNA concentrations of 0.125 μg/well in 24-well plates for 8 hours.

FIG. 10A) Uptake of Cy5-mRNA/$D_{13}$:$A_{11}$ 7 complexes at 4° C., a condition that inhibits endocytosis. FIG. 10B) Relative uptake and expression of eGFP mRNA following treatment with complexes formed with degrading and non-degrading transporter systems. Filled bars represent GFP expression and open bars represent Cy5-mRNA fluorescence FIG. 10C) eGFP expression when mRNA/$D_{13}$:$A_{11}$ 7 complexes are co-treated compounds known to inhibit endosomal acidification (Concanamycin A, Con A) and with endosomal rupture agents (Chloroquine, Chl) FIG. 10D) Confocal microscopy of cells following treatment with CART $D_{13}$:$A_{11}$ 7 or non-releasing oligomer 7 after treating for 4 hours. Cells were co-treated with transporter/Cy5-mRNA complexes and TRITC-Dextran$_{4400}$.

FIG. 11A) Transfection efficiencies of eGFP mRNA delivery by $D_{13}$:$A_{11}$ ## compared to Lipofectamine in HeLa (A), J774 (B), HEK 293 (C), CHO (D) and HepG2 (E) cell lines. FIG. 11B) Delivery of Fluc mRNA by CART 7 follows the same trend in charge ratio as eGFP. Charges reported as theoretical (+/−) ratios. FIG. 11C) In vivo BLI following intramuscular injection of naked Fluc mRNA (open circles) and mRNA/$D_{13}$:$A_{11}$ ## complexes (filled circles). Bars represent average of all animals (n=3 for 1 h, 4 h, and 7 h; n=5 for 24 h and 48 h). FIG. 11D) Representative bioluminescence images following intramuscular injection of naked mRNA (left flank) or mRNA/CART complexes (right flank). FIG. 11E) In vivo BLI following IV tail vein injection of naked mRNA (open circles) and mRNA/CART complexes (filled circles). Bars represent average of all animals (n=2 for 1 h and 7 h; n=4 for 4 h, 24 h and 48 h). Dotted lines are background bioluminescent signal from an animal not injected with D-luciferin. FIG. 1F) Representative bioluminescent images of mice treated with mRNA/$D_{13}$:$A_{11}$ complexes via IV tail vein injection.

CAR-19 construct is delivered to and expressed by multiple lymphocyte lineages. 1.) Mice were injected IV with 5 ug CAR19 mRNA-CART or Irrelevant mRNA-CART (10: 1+/−ratio), 2.) 24 hours after injection spleens were isolated and homogenized, 3.) Single cell suspension was stained with fluorophores that identify cell subset and the CAR 19 construct presented on the cell surface (anti-CAR-19 antibody), 4.) Flow cytometry was used to identify cell populations and the fraction of cells within the identified populations that expressed the CAR19 protein (Percent of population expressing CAR19 construct shown in box). IMPORTANTLY, CAR-19 B cells and CAR-19 NK cells are also produced. CD-19 expressing T cells (CAR-T cells) are produced in vivo with CD-19 mRNA-CART delivery.

Figure 14:
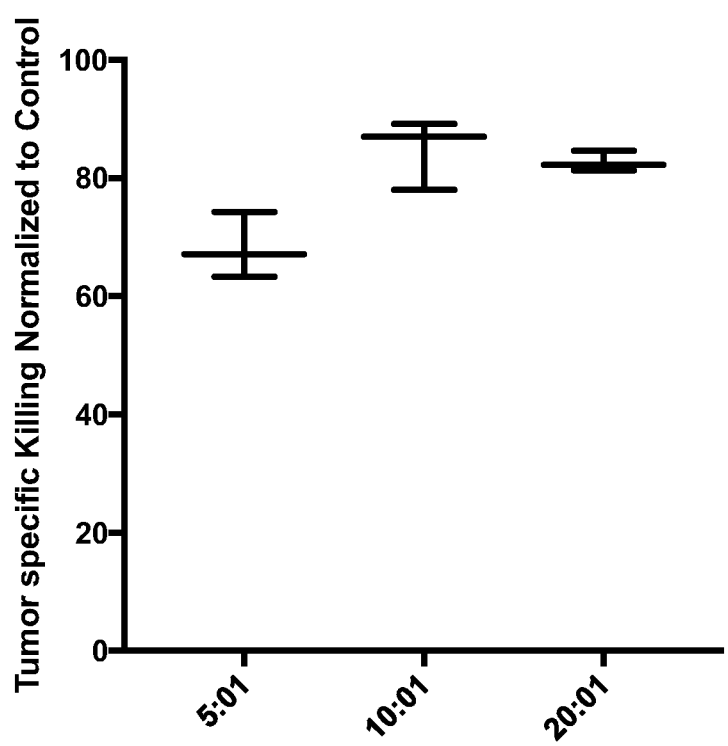

FIG. 14. Cells that express CAR19 CARs specifically kill CD19 expressing cells. Mice that were treated on two consecutive days with 5 ug CART-CAR-19 mRNA were sacrificed and spleens harvested. T cells were isolated from the spleens and these T-cells were co-cultured with CD19-expressing A20 tumor cells. 5:1, 10:1, 20:1 ratios of Effector:Target. Specific killing of the target cells were evaluated 48 hrs. later.

CAR cells isolated from treated mice kill CD19 expressing cells ex vivo. Cells that express CD19 CARs specifically kill CD19 expressing cells. Day 0: Mice injected with 5 ug CAR19 mRNA-CARTs; Day+1: Mice were injected with a second dose with 5 ug CAR19 mRNA-CARTs; Day+3: T cells were isolated from spleen and co-cultured with tumor CD19 expressing Tumor cells in 5:1, 10:1, AND 20:1 Effector:Target Ratio; Day+5: Tumor-specific Killing was quantified.

Figure 15:
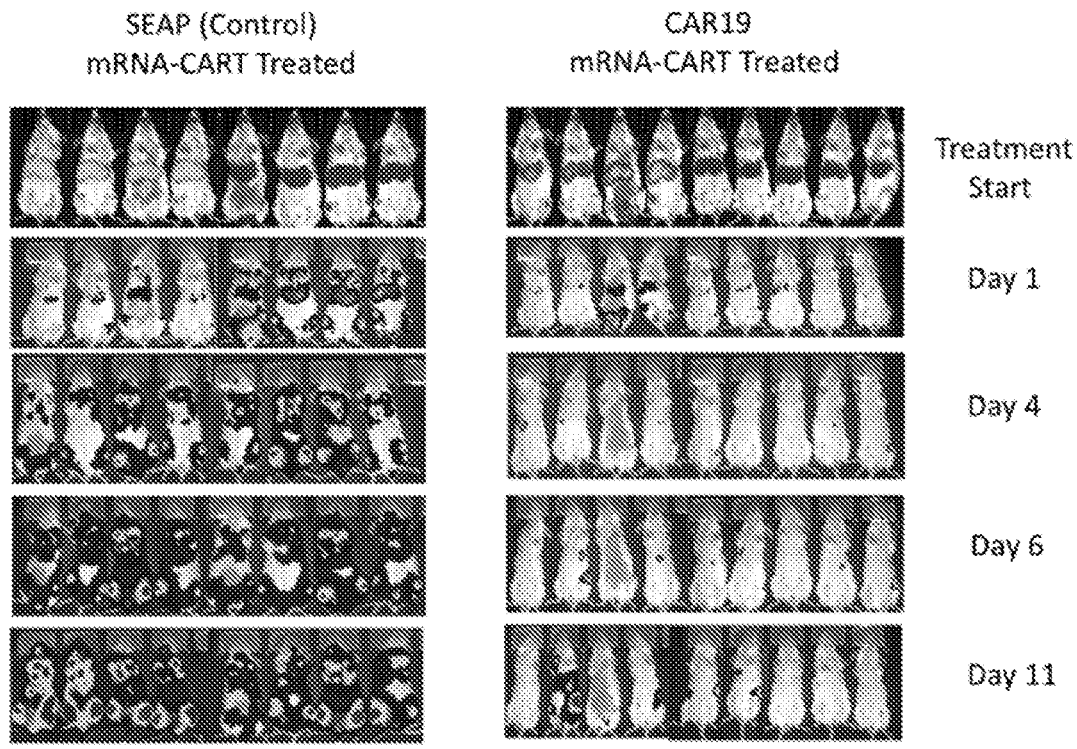

FIG. 15. Mice treated with CART-CAR-19 mRNA show dramatic regression of tumors. Mice bearing luciferase expressing A20 tumors were imaged for bioluminescence (i.e. tumor size) over 11 days. Left panel: Mice treated with irrelevant mRNA (SEAP). Right panel. Mice treated with CART-CAR-19 mRNA.

In vivo CAR-19 mRNA delivery shrinks tumors. Mice inoculated with Luciferase expressing A20 lymphoma cells via IV injection; The tumors were allowed to establish for 3 days; Tumor size/progression is directly correlated to the intensity of the luciferase signal; Mice were treated I.V. with 5 ug CART-CAR-19 mRNA; Mice were monitored over time and analyzed for changes in luciferase signal. Mice treated with CART-CAR19-mRNA Show tumor regression. Days denoted as days after the start of treatment. Treatment was administered 3 days after tumor inoculation.

Figure 16:
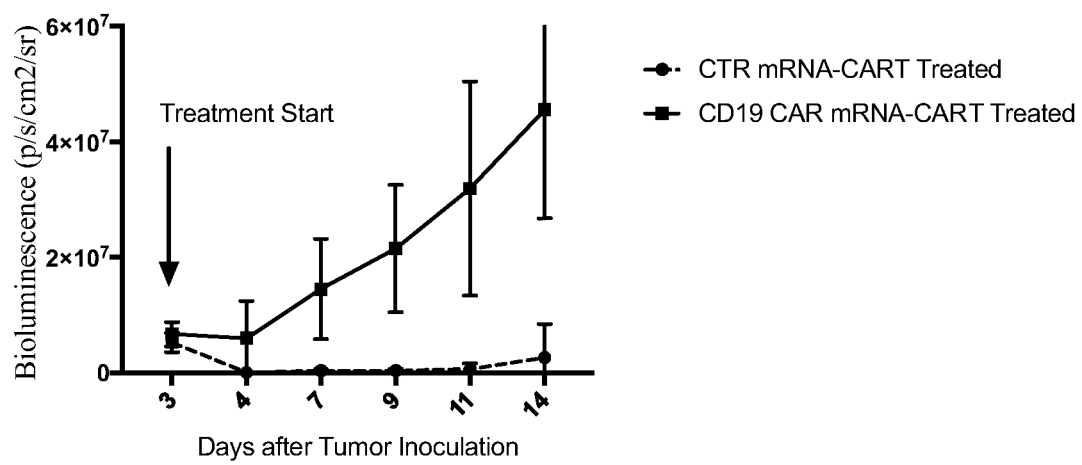

FIG. 16. Mice treated with CART-CAR-19 mRNA show dramatic regression of tumors. Mice bearing luciferase expressing A20 tumors were imaged for bioluminescence (i.e. tumor size) over 14 days. Total body bioluminescence was quantified over the course of 14 days. While CAR19 mRNA-CART treated mice showed a dramatic reduction in signal quantity, the ctr. Treated mice increased. Total body bioluminescence is a semi-quantitative measurement of tumor-burden.

Figure 17:
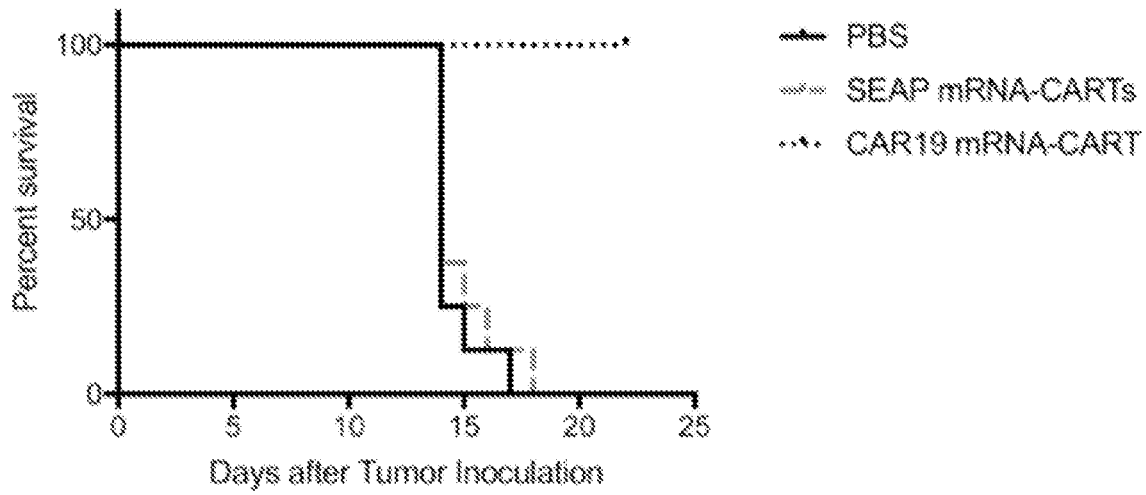

FIG. 17. Mice treated with 5 ug CART-CAR-19 mRNA. Mice treated with 5 ug irrelevant SEAP), or CART-CAR-19 mRNA. Mice were monitored for tumor burden over time and sacrificed upon onset of paraplegia, secondary subcutaneous tumors, significantly enlarged peritoneum and exterior signs of distress. In vivo CAR-19 mRNA delivery greatly prolongs survival. Mice (from previous FIG.) were monitored for tumor burden over time and sacrificed upon onset of paraplegia, secondary subcutaneous tumors, significantly enlarged peritoneum and exterior signs of distress. Data shown: Mice treated with Saline, CART-Irrelevant mRNA (SEAP), or CART-CAR-19 mRNA.

Figure 18:
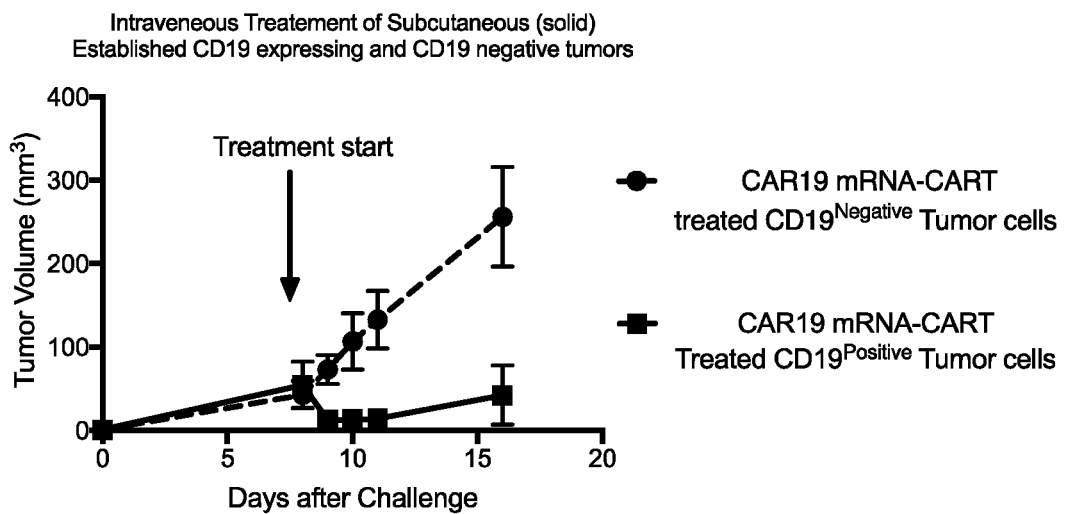

FIG. 18. Intravenous delivery of CAR19 construct enables the immune system to selectively kill tumor cells that express the CD19 molecule. Mice with established sub cutaneous CD19 expressing or CD19 negative tumors were treated with one dose of CAR19 mRNA-CART and monitored for tumor growth/regression over the course of 7 days.

Figure 19:
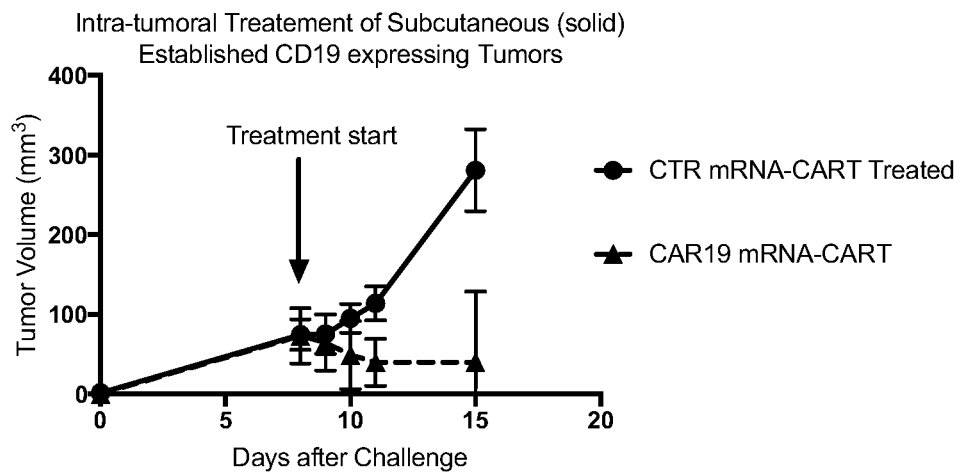

FIG. 19. Intra-tumoral delivery of CAR19 construct enables the tumor infiltrating cells to kill CD19 expressing tumor cells. Mice with established sub cutaneous CD19 expressing or CD19 negative tumors were treated with one dose of CAR19 mRNA-CART directly in to the tumor and monitored for tumor growth/regression over the course of 7 days.

Figure 20:
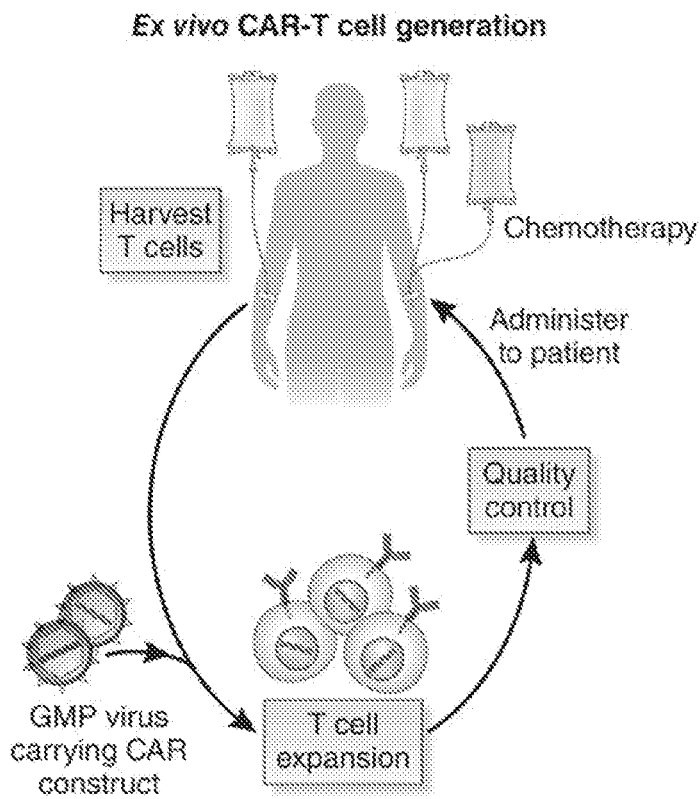

FIG. 20. Cartoon diagram of ex vivo CAR-T cell generation.

Figure 21:
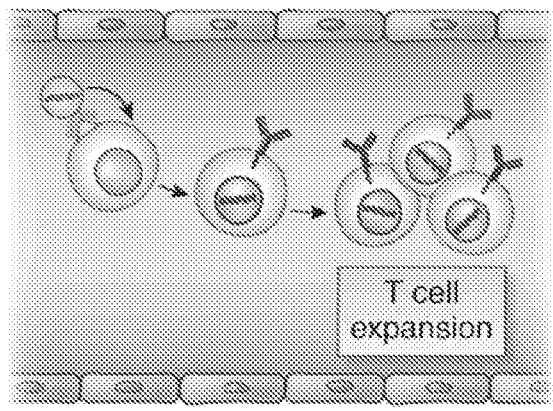

FIG. 21. Cartoon diagram of in situ genetic engineering. Concept: Express a gene (mRNA) within cells in vivo; this gene Codes for the CAR protein; The body produces its own CAR-T cells; Nothing needs to be done outside the body; No need to harvest cells from patient; No costly transport of patient cells.

Figure 22:
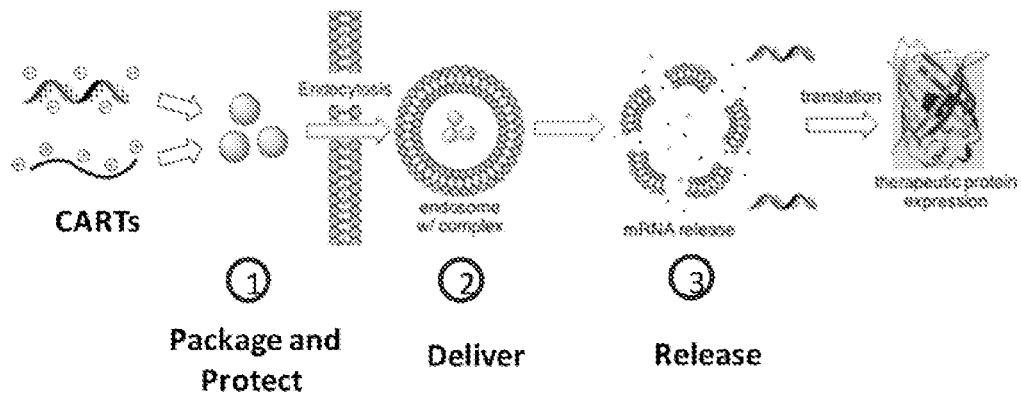

FIG. 22. Cartoon diagram of delivery of mRNA using CARTs. Requirements: T-cells (or others) must be transfected; Functional protein must be expressed; A sufficient population must express CAR; for a therapeutic response to occur.

Figure 23:
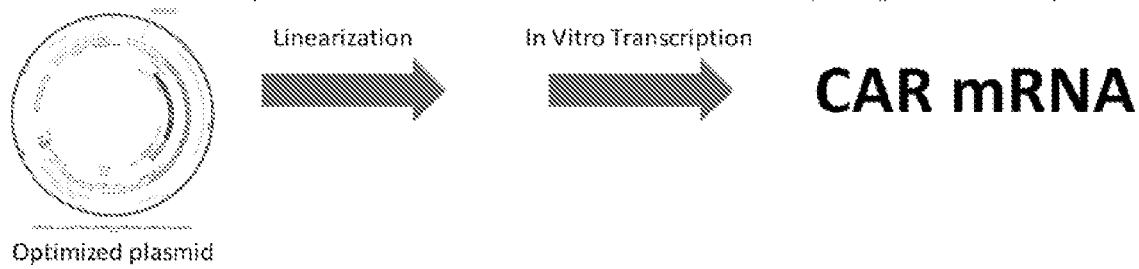

FIG. 23. Producing mRNA for in vivo CAR-T cell programming. We have the delivery vehicle to transfect T-cells and the mRNA that expresses functional CAR protein.

Figure 24:
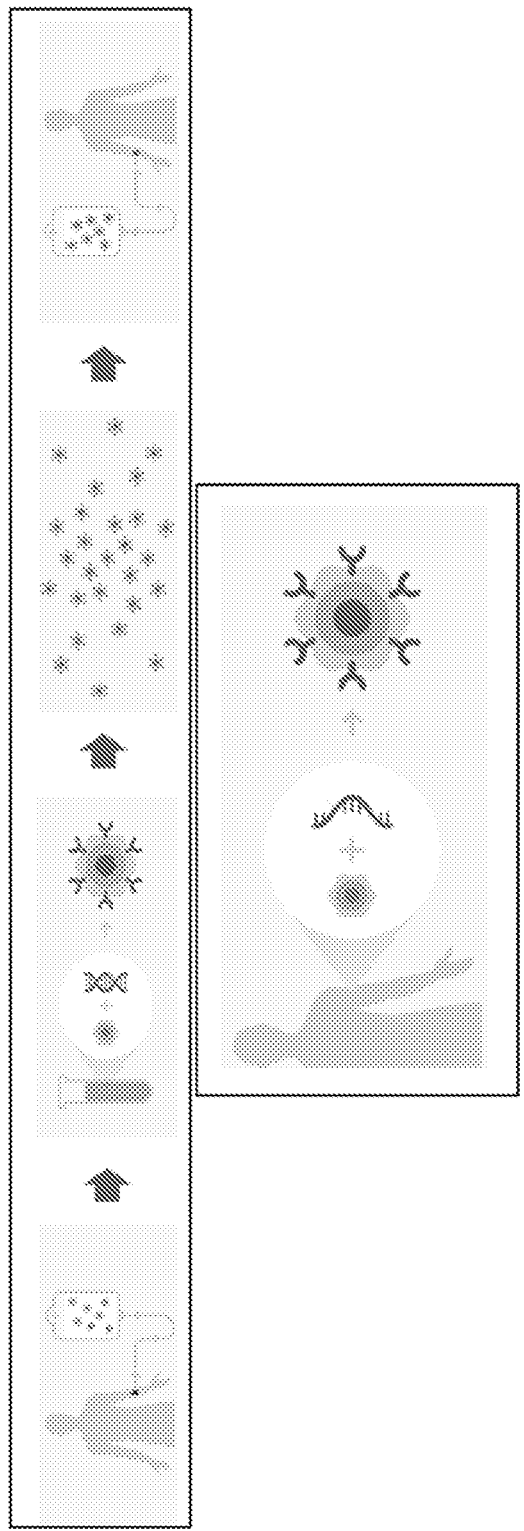

FIG. 24. Schematic for standard CAR-T cell therapy (top panel) and in vivo CAR-T cell programming (bottom panel). St FIG. 25. Cartoon diagram of CAR construct integration into T-cells and expression of CAR-encoding gene within cells in vivo.

Figure 26:
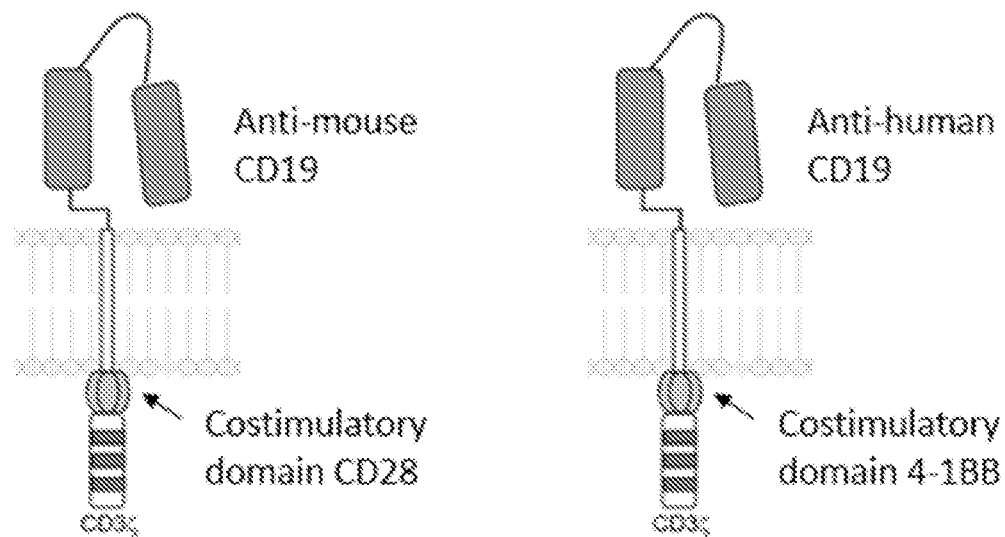

FIG. 26. Schematic representation of chimeric antigen receptor molecules (e.g., anti-mouse CD19 and anti-human CD19 CARs) delivered by the CART compounds provided herein including embodiments thereof.

Figure 27:
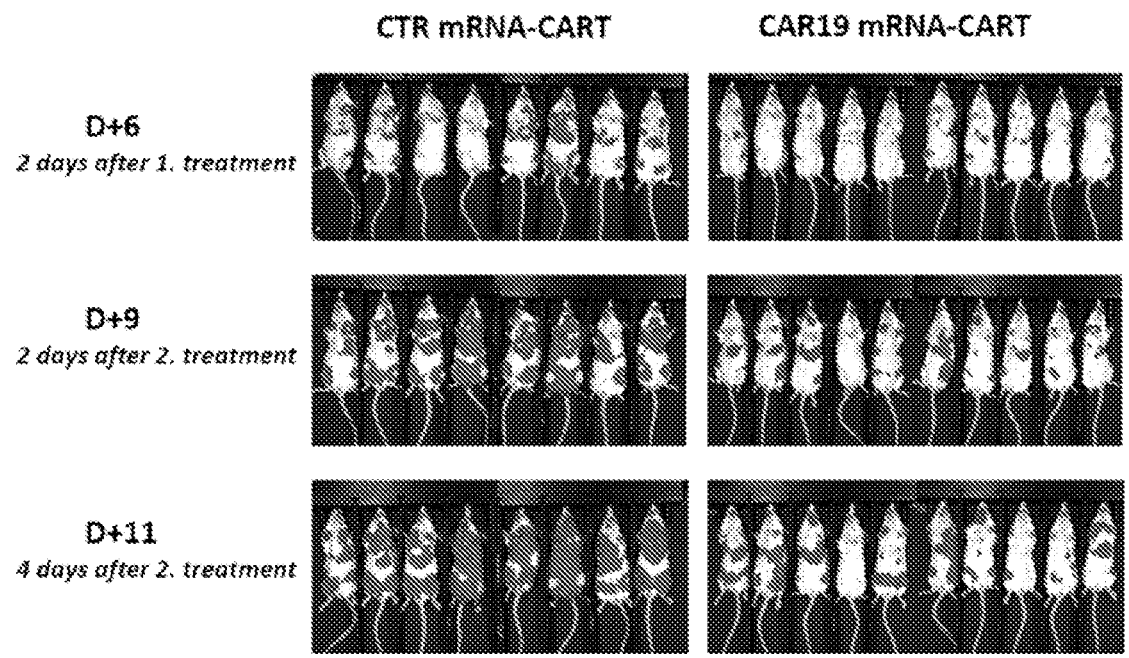

FIG. 27. Mice treated with CART-CAR-19 mRNA show regression of tumors. Mice were inoculated intravenously with $1\times10^6$ Luc-expressing A20 cells. Mice bearing the luciferase expressing CD19+ A20 tumor model were imaged for bioluminescence (i.e. tumor size). Mice were treated by IV two times with CART-CAR19 mRNA, or control CART-mRNA at day D+4 and D+7 after tumor challenge. Luminescence images were taken at the indicated timepoints. While CAR19 mRNA-CART treated mice showed a dramatic reduction in signal quantity, the CRT treated mice displayed increased signal. Total body bioluminescence is a semi-quantitative measurement of tumor-burden.

Figure 28A:
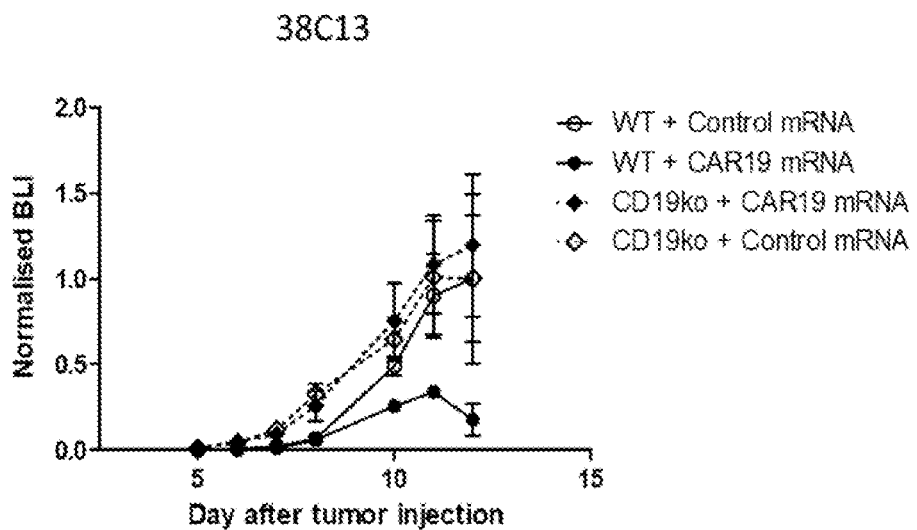
Figure 28B:
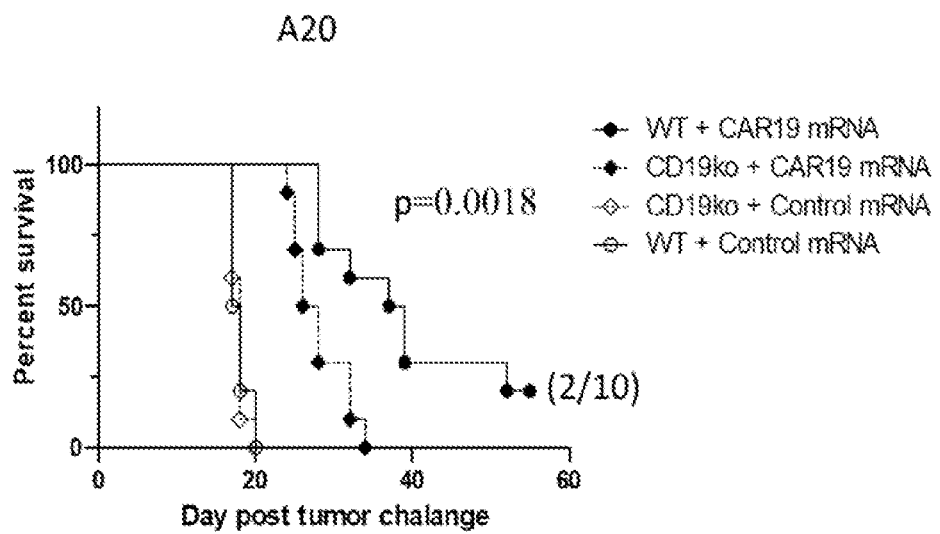

FIGS. 28A-28B. FIGS. 28A-28B. Graphs comparing in vivo CAR19 mRNA therapy in CD19+ and CD19 knock-out in both C3813 (FIG. 28A) and A20 (FIG. 28B) tumor models show specificity of the therapeutic response. Bioluminescence from firefly luciferase expressing tumor cells was used as a marker for tumor burden. Only CD19-expressing tumors are effected by CAR-19 mRNA delivery in vivo. Mice injected with Firefly Luciferase expressing WT CD19 expressing 38C13 or A20, CD19KO 38C13 or A20 B lymphomas cells ($1\times10^6$ per mouse). FIG. 28A: Tumor burden/Bioluminescence in mice with established systemic WT CD19 expressing or CD19KO 38C13 B lymphoma cells that were treated with CART-CAR19 mRNA or Control CART-mRNA. WT CD19+(black circle), and CD19KO (black diamond), and CD19+ cells with irrelevant mRNA (open circle) and CD19KO cells treated with irrelevant mRNA (open diamond). Data represented as relative increase in bioluminescence intensity over Intensity measured at treatment start. FIG. 28B: Long-term survival of mice with established systemic WT CD19 expressing or CD19KO A20 B lymphoma cells that were treated with CART-CAR19 mRNA or Control CART-mRNA. WT CD19+(black circle), and CD19KO (black diamond), and CD19+ cells with irrelevant mRNA (open circle) and CD19KO cells treated with irrelevant mRNA (open diamond).

Figure 29:
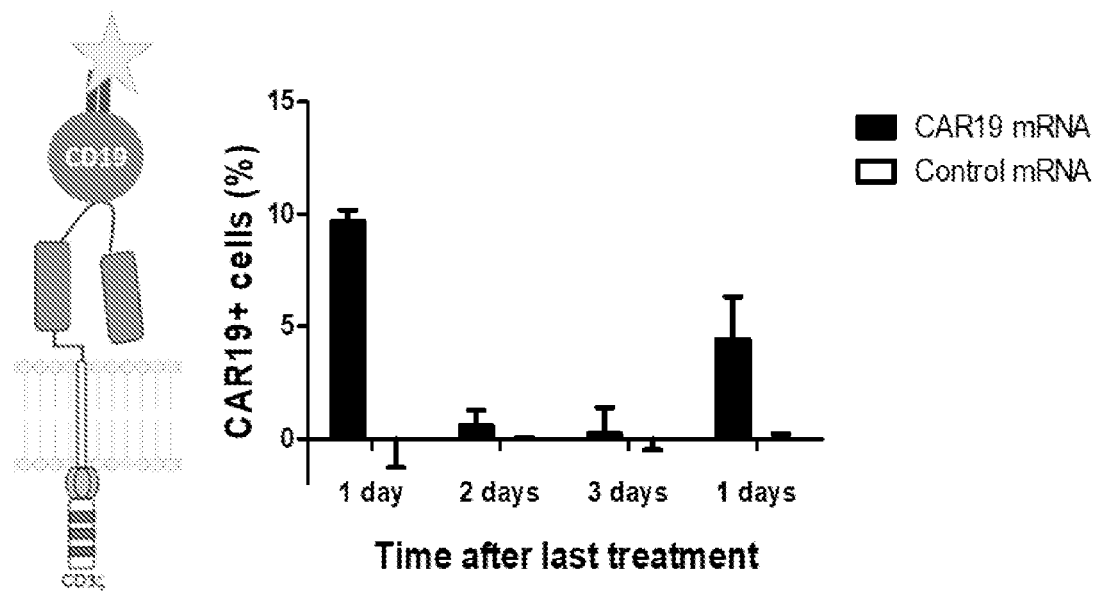

FIG. 29. CART-CAR mRNA induce transient expression of CAR19 allowing for multiple doses of therapy. Blood was drawn and CAR 19+ cells were quantified by flow cytometry. Cartoon schematic shows CART targeting CAR 19+ cell (left panel). Measurements were taken 1, 2 and 3 days after administration of either CART-irrelevant mRNA or CART-CAR19 mRNA, and after a second dose of 10 ug CART-CAR19 mRNA (right panel). The final measurement shows a reemergence of CAR-19+ cells.

Figure 30A:
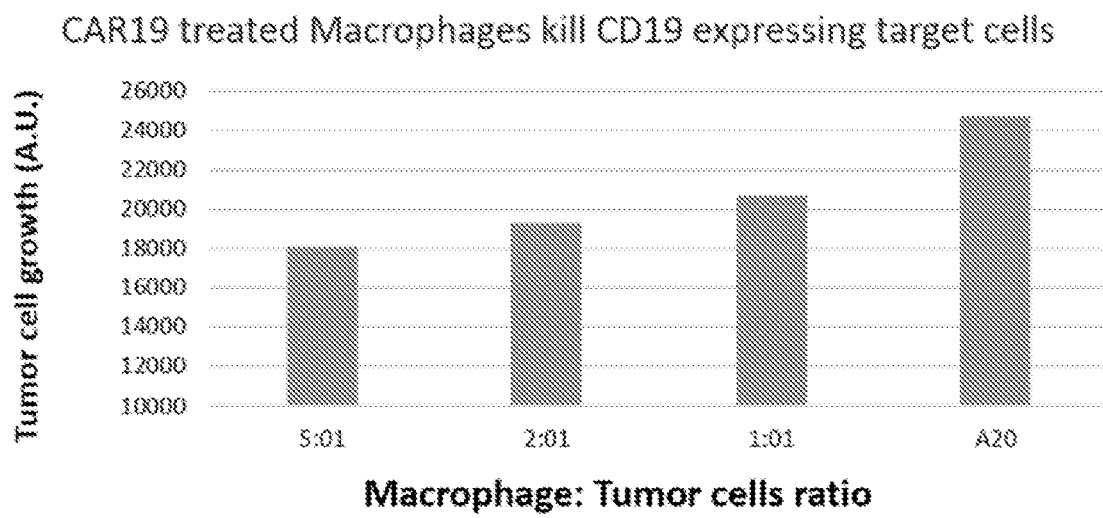
Figure 30B:
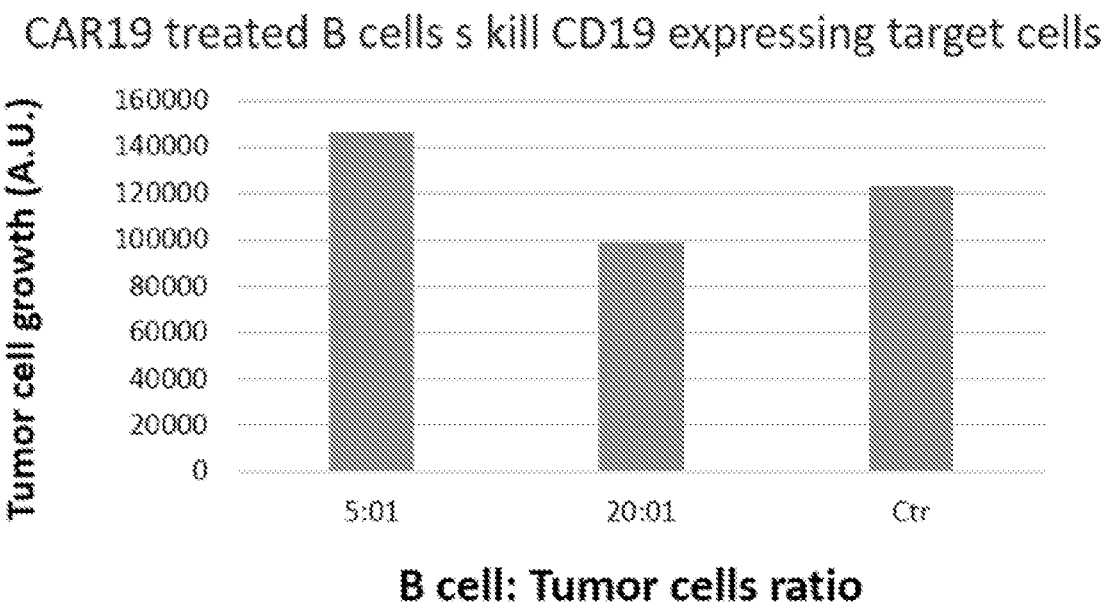
Figure 30C:
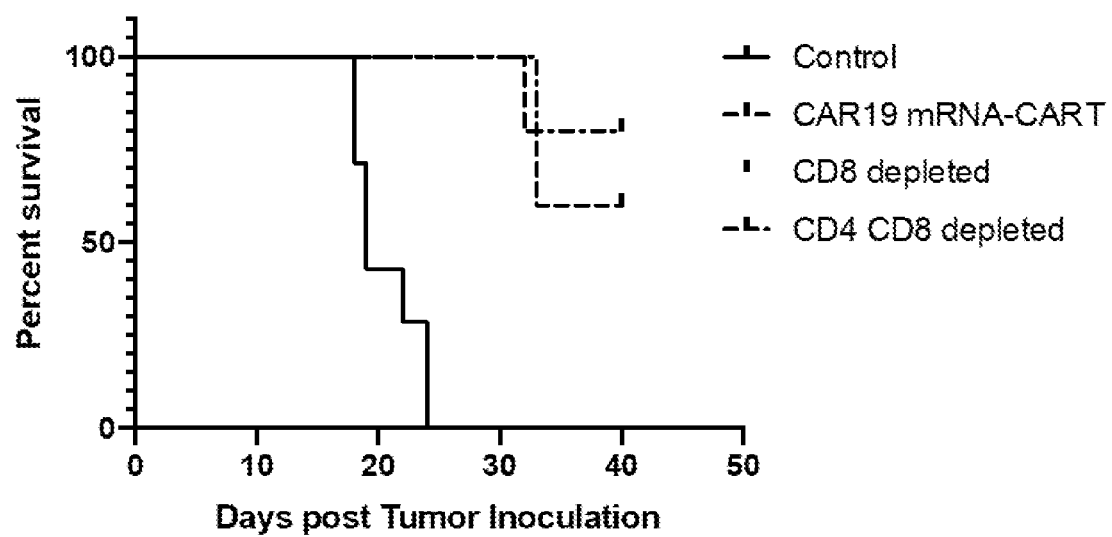

FIGS. 30A-30C. CAR CART-mRNA therapy engages more than T cells in tumor-cell killing. Macrophages (FIG. 30A) and B cells (FIG. 30B) treated with CAR19 CART-mRNA can kill CD19 expressing Tumor cells in an effector to target cell ratio dependent manner. Long term survival in CD19 expressing WT A20 tumor bearing mice upon treatment with CAR19 CART-mRNA does not depend on the presence of T cells (FIG. 30C). Mice were depleted of T cells before treatment start and depletion was maintained using aCD4 and aCD8 monoclonal Antibodies throughout the experiment.

Figure 31A:
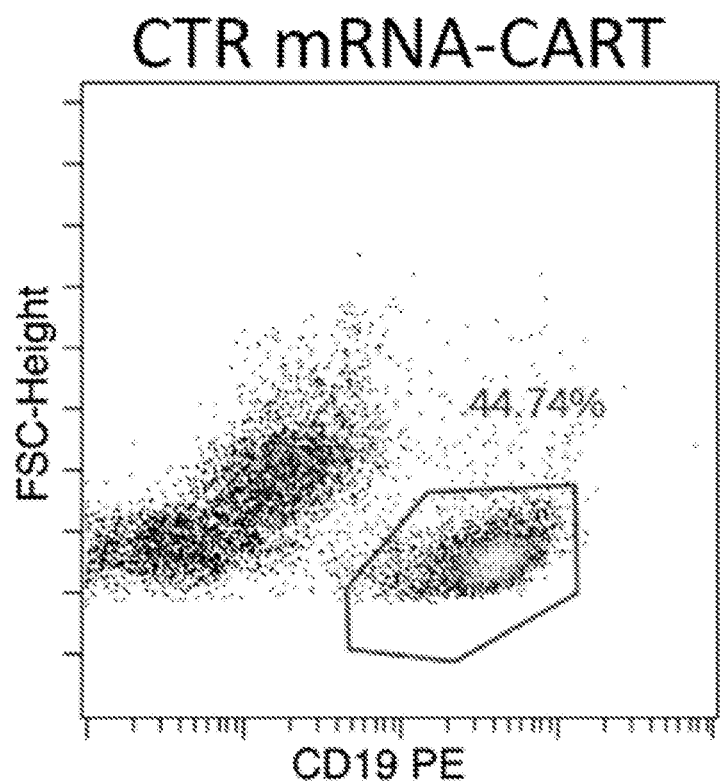
Figure 31B:
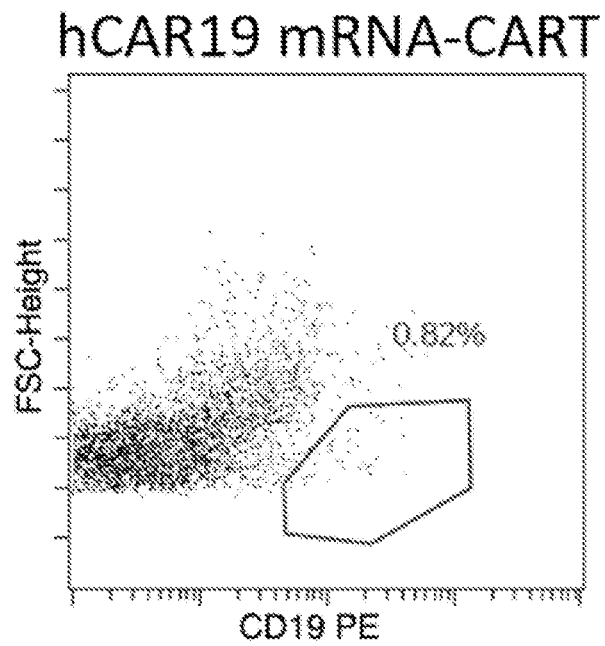
Figure 31C:
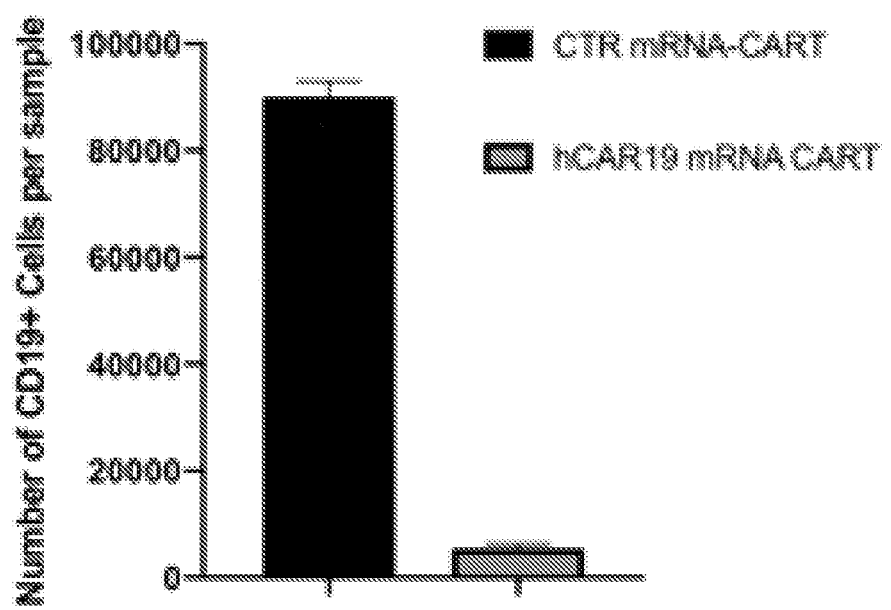

FIGS. 31A-31C. CART-mRNA humanized CAR-19 therapy in human PBMCs shows anticipated killing of native B cells observed in human clinical trials. Bulk human healthy donor PBMCs were treated with human CAR19 CART mRNA ex vivo. Twelve hrs after treatment killing of normal CD19 expressing B cells was assessed by flow cytometry.

FIG. 31A: Representative dot plot of Ctr CART-mRNA treated PBMCs. FIG. 31B: Representative dot plot of human CAR19 CART-mRNA treated PBMCs. FIG. 31C: Total number of live CD19 expressing B cells left in Ctr CART-mRNA treated PBMCs and human CAR19 CART-mRNA treated PBMCs. n=5 individual replicates.

Figure 32:
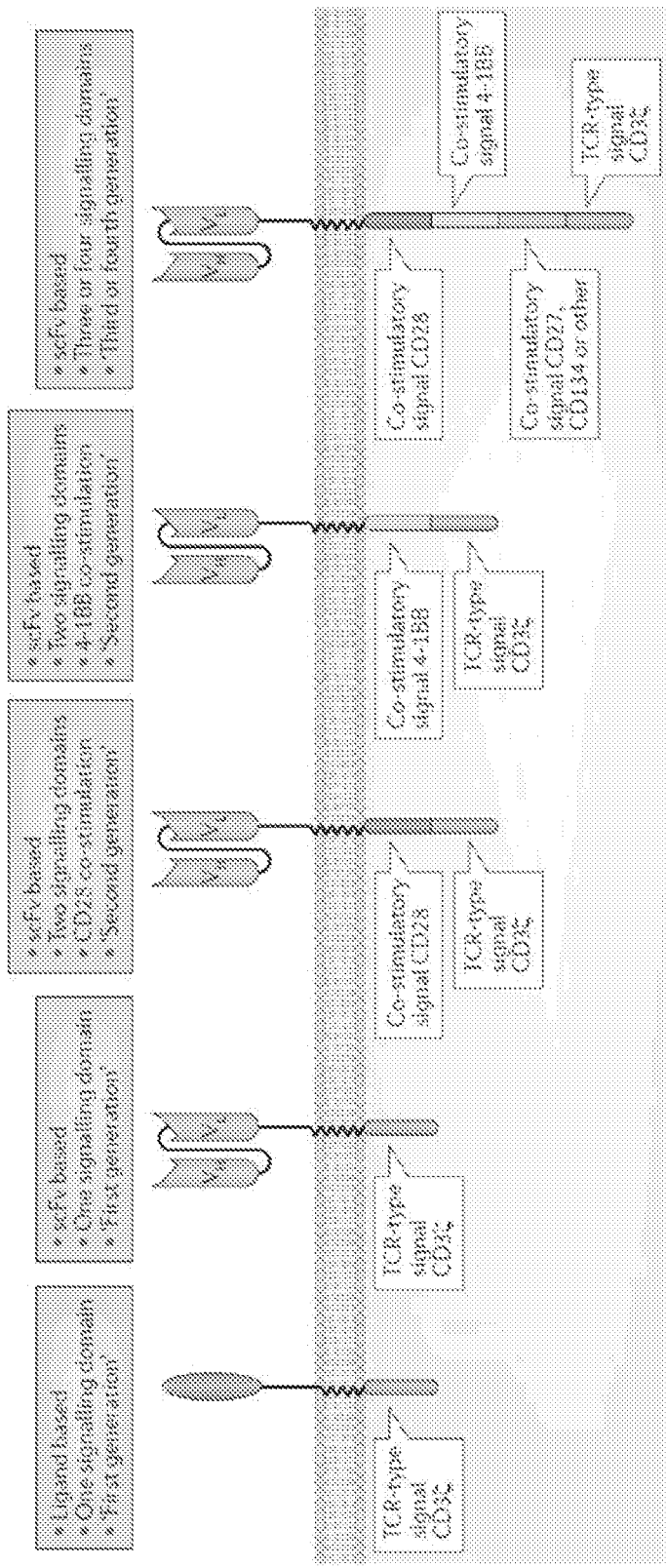

FIG. 32. Schematic representation of exemplary chimeric antigen receptors included in the cell-penetrating complexes provided herein including embodiments thereof.

Figure 33:
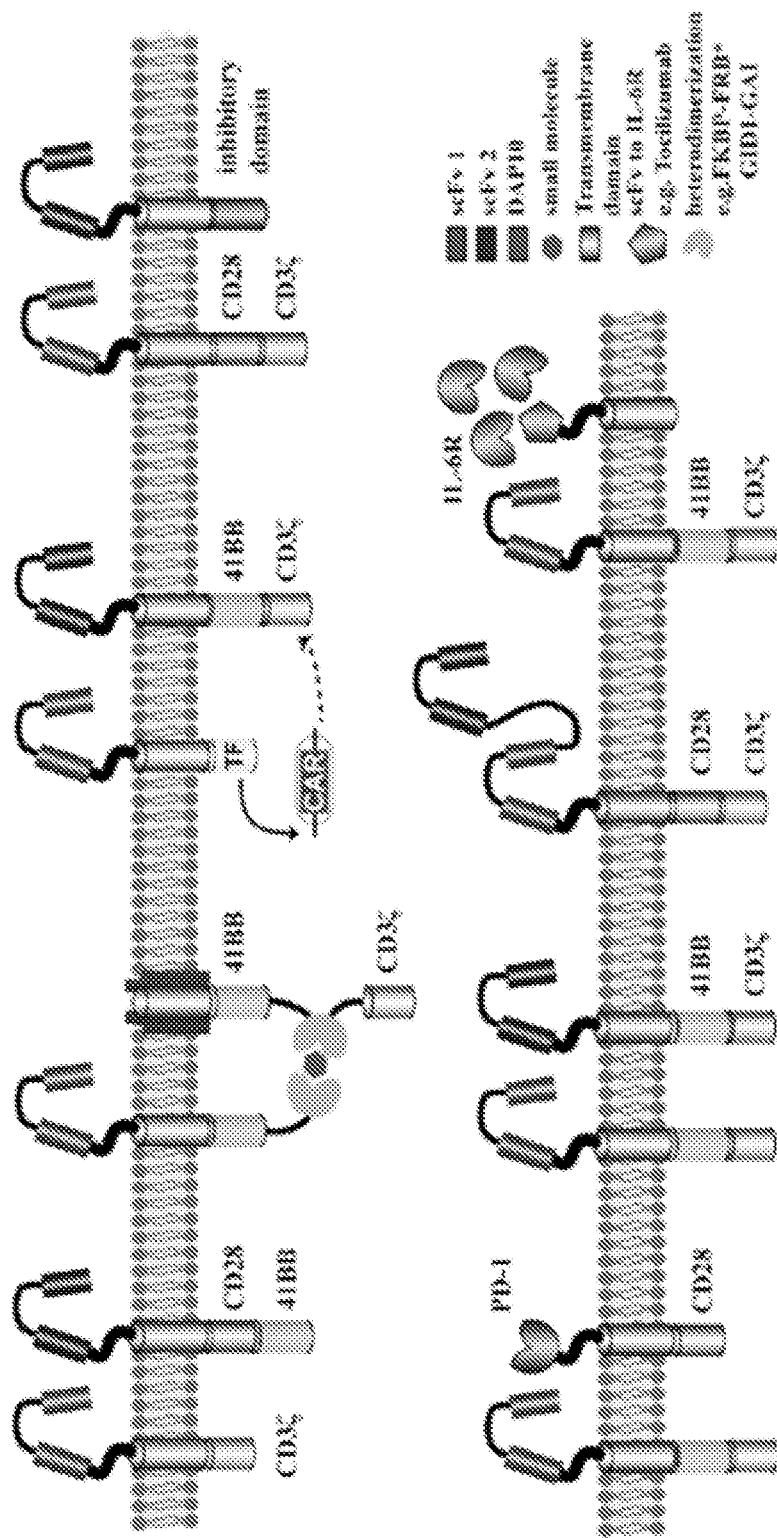

FIG. 33. Schematic representation of exemplary receptor molecules included in the cell-penetrating complexes provided herein including embodiments thereof.

Figure 34A:
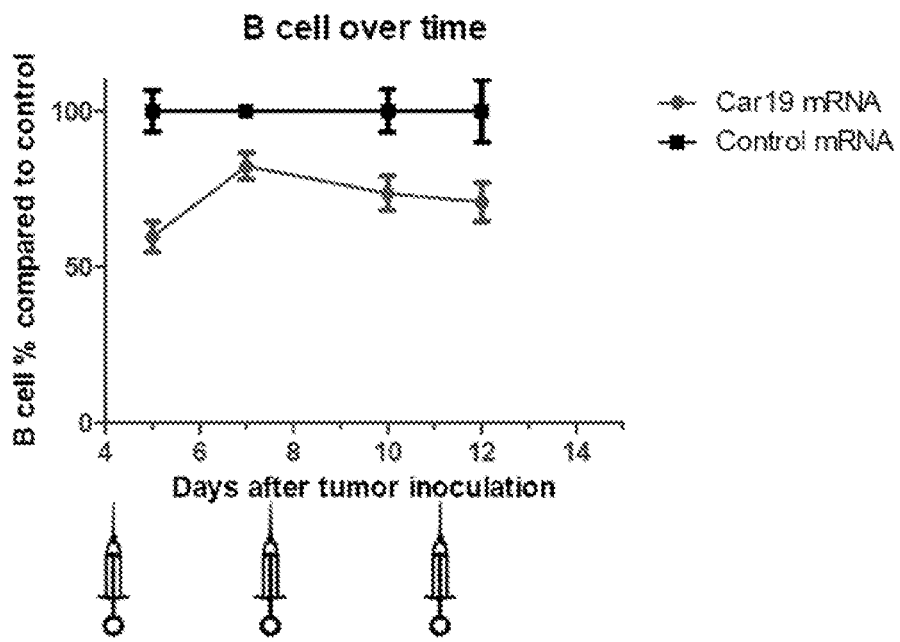
Figure 34B:
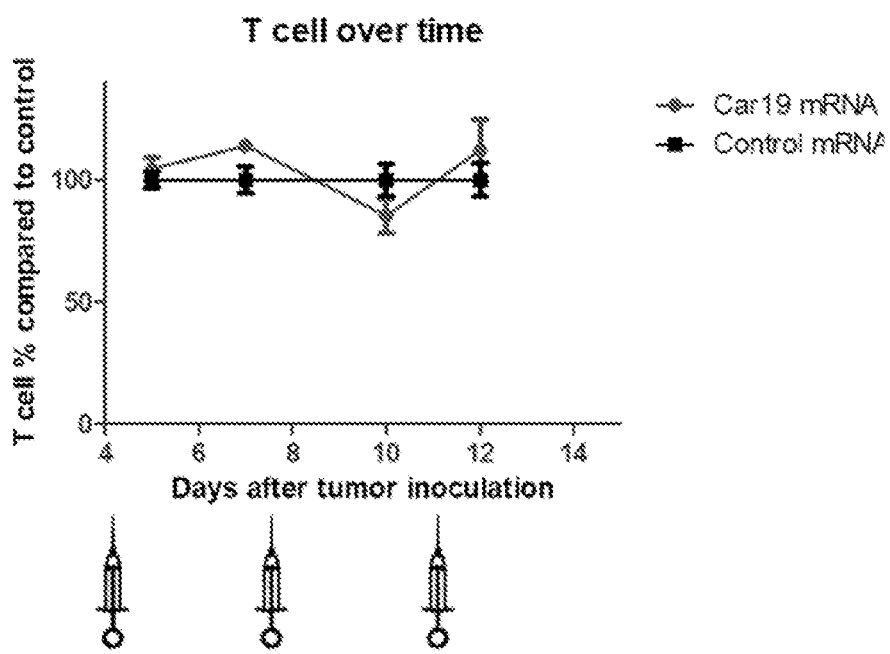

FIGS. 34A-34B. B cell depletion assay. Four days after tumors were established, the initial dose of CAR CART-mRNA was administered. At the indicated timepoints, CAR CART-mRNA was administered IV. Circulating CD19 expressing B cells were quantified on the indicated days. CAR CART-mRNA treatment resulted in a reduction in circulating CD19 expressing B cells but remained at baseline with the administration of control mRNA (SEAP) (FIG. 34A). T cells numbers were unaffected (FIG. 34B).

Figure 35A:
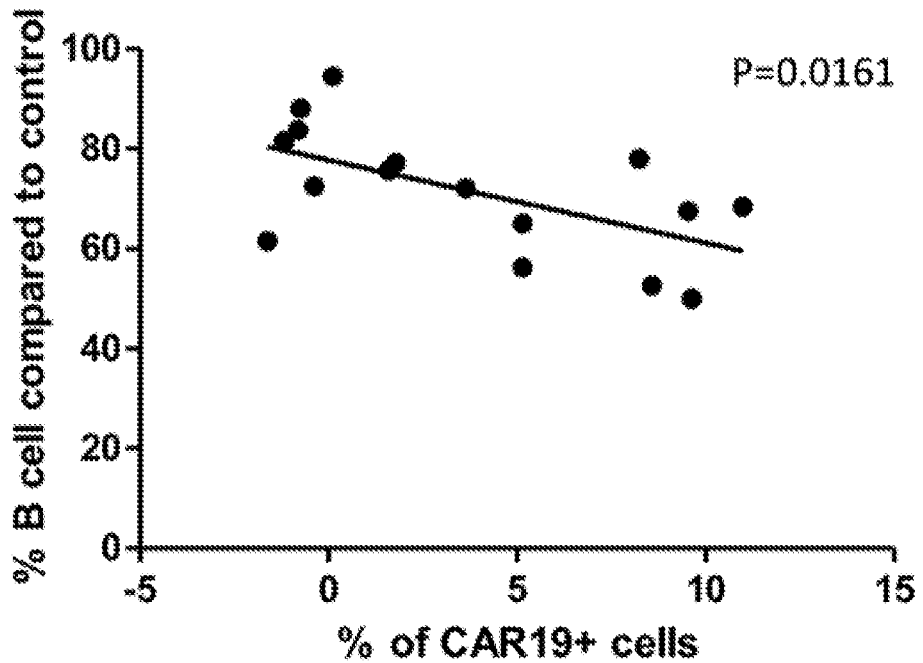
Figure 35B:
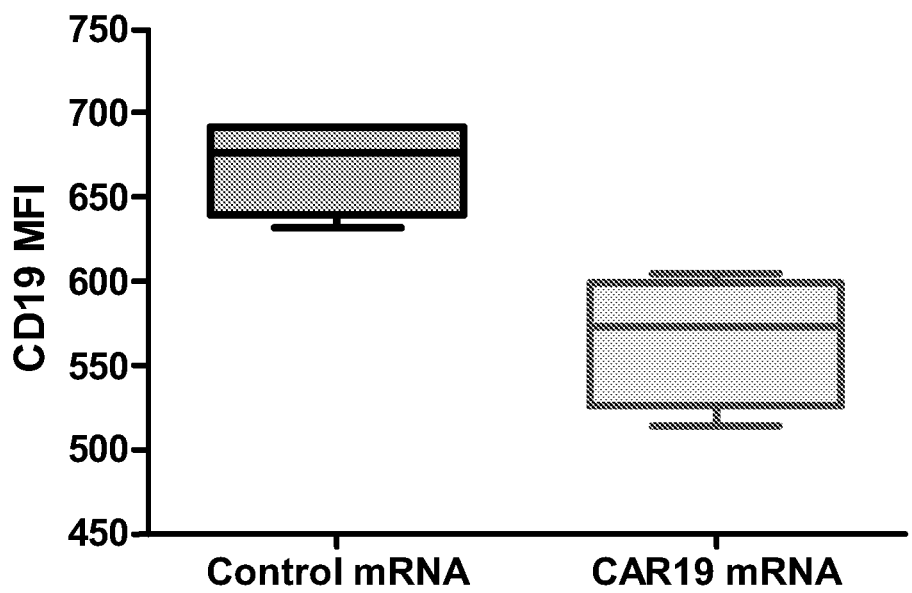

FIGS. 35A-35B. The percentage of CAR19+ cells correlates with B cell depletion. Endogenous CD19 expressing B cell quantification after treatment with CART-CAR-19 mRNA. FIG. 35A: Increased CAR-19+ cells correlate to a decrease of systemic B cells. FIG. 35B: Non-depleted B cells show low CD19 expression indicating a selective depletion of higher CD19 expressing cells.

Figure 36A:
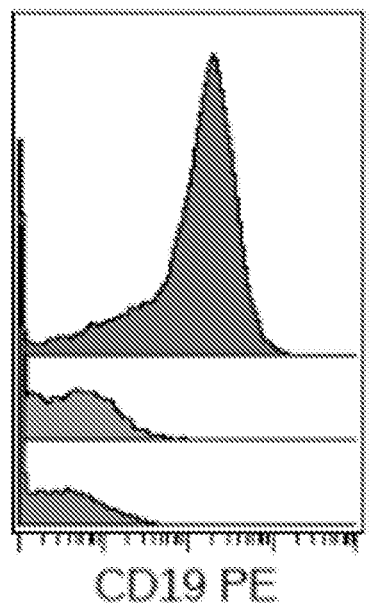
Figure 36B:
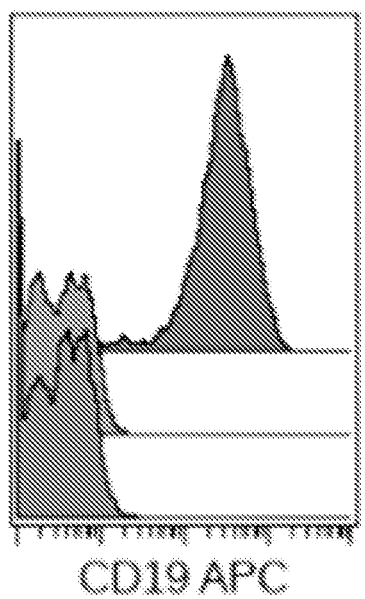

FIGS. 36A-36B. Target antigen CD19 was removed from A20 (FIG. 36A) and 38C13 (FIG. 36B) using CRISPR/Cas9 technology. Graphs show CD-19 expressing cells (top curve), Isotype control, (middle curve), CD-19 knockout (bottom curve). WT A20 and 38C13 express intermediate to high levels of CD19 on the surface (top curve).

Figure 37:
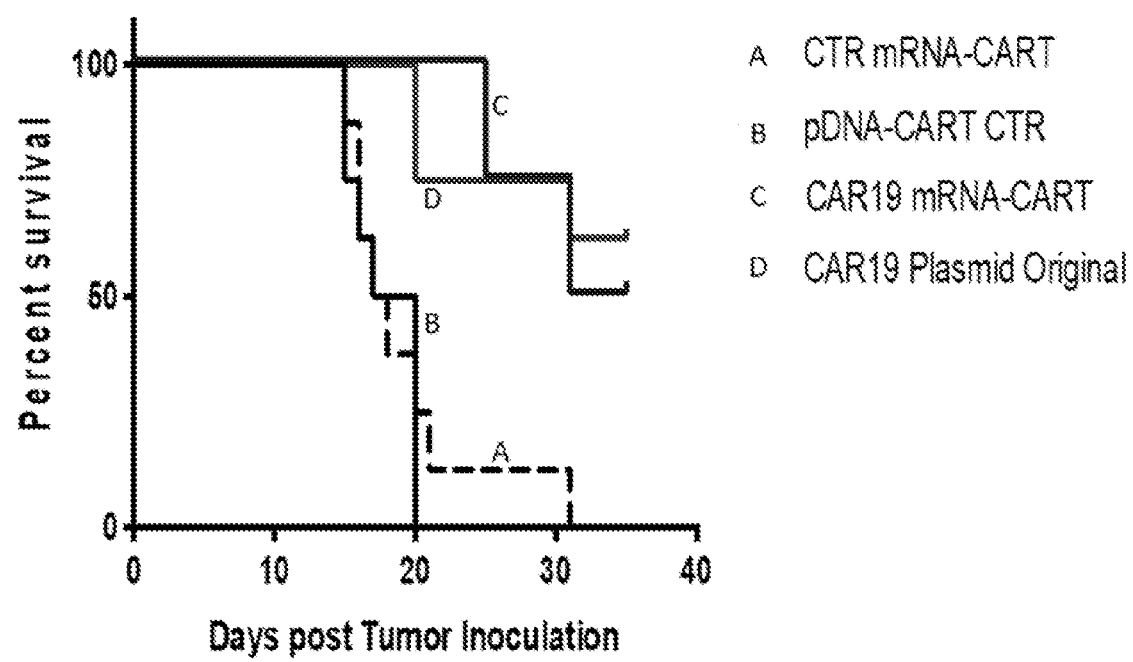

FIG. 37. DNA and mRNA provide effective therapeutic treatment vehicle-pDNA (B) vehicle-mRNA (A) CAR19-RNA (C) and CAR19-DNA (D). Mice with established CD19 expressing A20 lymphomas were treated three times with either CAR CART-mRNA (C), CAR CART-plasmid DNA (D), CTR CART-mRNA (A), or CTR CART-PLAS-MID DNA (B). Survival was measured over 35 days after tumor injection. Death due to disease defined as the onset of paraplegia.

DETAILED DESCRIPTION

While various embodiments and aspects of the present disclosure are shown and described herein, it will be obvious to those skilled in the art that such embodiments and aspects are provided by way of example only. Numerous variations, changes, and substitutions will now occur to those skilled in the art without departing from the disclosure.

It should be understood that various alternatives to the embodiments of the disclosure described herein may be employed in practicing the disclosure.

Unless the context indicates otherwise, it is specifically intended that the various features of the disclosure described herein can be used in any combination. Moreover, the disclosure also contemplates that in some embodiments any feature or combination of features set forth herein can be excluded or omitted. To illustrate, if the specification states that a complex has components A, B and C, it is specifically intended that any of A, B or C, or a combination thereof, can be omitted and disclaimed singularly or in any combination.

It must be noted that as used herein and in the appended claims, the singular forms "a", "an", and "the" include plural referents unless the context clearly dictates otherwise. Thus, for example, reference to "a cancer cell" includes a plurality of cancer cells. In other examples, reference to "a nucleic acid" or "nucleic acid" includes a plurality of nucleic acid molecules, i.e. nucleic acids.

The term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

Also as used herein, "and/or" refers to and encompasses any and all possible combinations of one or more of the associated listed items, as well as the lack of combinations when interpreted in the alternative ("or").

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

Definitions

The abbreviations used herein have their conventional meaning within the chemical and biological arts. The chemical structures and formulae set forth herein are constructed according to the standard rules of chemical valency known in the chemical sciences.

As use herein the terms "oligomer" and "polymer" refer to a compound that has a plurality of repeating subunits, (e.g., polymerized monomers). The terms "co-oligomer" or "co-polymer" refers to an oligomer or polymer that includes 2 or more different residues (monomer units or monomers, which are interchangeably used herein). The number of monomers in oligomers is generally less than the number of monomers in polymers.

Therefore, in embodiments, oligomers can have 1 to about 10 monomers, 1 to about 20 monomers, 1 to about 30 monomers, 1 to about 40 monomers, 1 to about 50 monomers, 1 to about 100 monomers, 1 to about 150 monomers, 1 to about 200 monomers, 1 to about 250 monomers, 1 to about 300 monomers, 1 to about 350 monomers, 1 to about 400 monomers, 1 to about 450 monomers or 1 to about 500 monomers is in length. In embodiments, oligomers can have less than about 500 monomers, less than about 450 monomers, less than about 400 monomers, less than about 350 monomers, less than about 300 monomers, less than about 250 monomers, less than about 200 monomers, less than about 150 monomers, less than about 100 monomers, less than about 50 monomers, less than about 40 monomers, less than about 30 monomers, less than about 20 monomers or less than about 10 monomers in length.

In the context of polymers, the number of monomers in polymers is generally more than the number of monomers in oligomers. Therefore, in embodiments, polymers can have about 500 to about 1000 monomers, about 500 to about 2000 monomers, about 500 to about 3000 monomers, about 500 to about 4000 monomers, about 500 to about 5000 monomers, about 500 to about 6000 monomers, about 500 to about 7000 monomers, about 500 to about 8000 monomers, about 500 to about 9000 monomers, about 500 to about 10000 monomers, or more than 10000 monomers in length.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-B-A-A-A-A-A-) or all three are different (e.g., -A-A-A-A-A-B-B-B-B-B-B-C-C-C-C-C-) where 'A' is a first subunit, 'B' is a second subunit, and 'C' is a third subunit, covalently bound together.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals. An alkyl may have the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred. A "lower alkyl" or "lower alkylene" is a $C_1$-$C_8$ alkyl or alkylene group.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—OCH$_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—OCH$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S-$CH_2$—$CH_2$— and —$CH_2$—S-$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the likes described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-C4) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR-C(NR'R"R'")=NR"", —NR-C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O) NR"R'", —NR"C(O)$_2$R', —NR-C(NR'R"R'")=NR"", —NR-C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI2, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, and heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, and heteroaryl, substituted with at least one substituent selected from:
(a) oxo,
halogen, —CCl$_3$, —CBr$_3$, —CF$_3$, —C$_{13}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, or heteroaryl, substituted with at least one substituent selected from: oxo,
halogen, —CCl$_3$, —CBr$_3$, —CF$_3$, —C$_{13}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OC HI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth herein.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "nucleophilic moiety" refers to a chemical species or functional group that is capable of donating one or more electrons (e.g., 2) to an electrophile. In embodiments, a nucleophilic moiety refers to a chemical species or functional group that can donate an electron to an electrophile in a chemical reaction to form a bond.

The term "electrophilic moiety" refers to a chemical species or functional group that is capable of receiving one or more electrons (e.g., 2). In embodiments, an electrophilic moiety refers to a chemical species or functional group that has a vacant orbital and can thus accept an electron to form a bond in a chemical reaction.

The term "oligoglycol moiety" refers to is a chemical entity with the general formula: $R^{400}$—O—(CH$_2$—CH$_2$—O)n$_{300}$-§ where $R^{400}$ is H, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl and n300 is an integer of 1 or more. In embodiments, $R^{400}$ is H or alkyl.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY, 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA), and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids has one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine.; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235, 033 and 5,034,506, and Chapters 6 and 7, ASC Symposium Series 580, CARBOHYDRATE MODIFICATIONS IN ANTISENSERESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo). In embodiments, the nucleic acid is RNA (e.g. mRNA). In embodiments the nucleic acid is 10 to 100,000 bases in length. In embodiments the nucleic acid is 50 and 10,000 bases in length. In embodiments the nucleic acid is 50 and 5,000 bases in length. In embodiments the nucleic acid is 50 and 1,000 bases in length.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The terms "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "IL-12 protein" or "IL-12" as used herein includes any of the recombinant or naturally-occurring forms of Interleukin 12, also known as Interleukin-12 subunit beta, or variants or homologs thereof that maintain IL-12 activity (e.g. within at least 50%, 80%, 90%, 95%, 96%, 97%, 98%, 99% or 100% activity compared to IL-12). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-12 protein. In embodiments, the IL-12 protein is substantially identical to the protein identified by the UniProt reference number P29460 or a variant or homolog having substantial identity thereto.

The term "IL-15 protein" or "IL-15" as used herein includes any of the recombinant or naturally-occurring forms of Interleukin 15, or variants or homologs thereof that maintain IL-15 activity (e.g. within at least 50%, 80%, 90%, 95%, 96%, 97%, 98%, 99% or 100% activity compared to IL-15). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-15 protein. In embodiments, the IL-15 protein is substantially identical to the protein identified by the UniProt reference number P40933 or a variant or homolog having substantial identity thereto.

The term "IL-18 protein" or "IL-18" as used herein includes any of the recombinant or naturally-occurring forms of Interleukin 18, also known as interferon-gamma inducing factor or variants or homologs thereof that maintain IL-18 activity (e.g. within at least 50%, 80%, 90%, 95%, 96%, 97%, 98%, 99% or 100% activity compared to IL-18). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-18 protein. In embodiments, the IL-18 protein is substantially identical to the protein identified by the UniProt reference number Q14116 or a variant or homolog having substantial identity thereto.

The term "IL-3 protein" or "IL-3" as used herein includes any of the recombinant or naturally-occurring forms of Interleukin-3, also known as Hematopoietic growth factor, Mast cell growth factor, P-cell-stimulating factor or variants or homologs thereof that maintain IL-3 activity (e.g. within at least 50%, 80%, 90%, 95%, 96%, 97%, 98%, 99% or 100% activity compared to IL-3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-3 protein. In embodiments, the IL-3 protein is substantially identical to the protein identified by the UniProt reference number P08700 or a variant or homolog having substantial identity thereto.

The term "IL-21 protein" or "IL-21" as used herein includes any of the recombinant or naturally-occurring forms of Interleukin-21, also known as Za11 or variants or homologs thereof that maintain IL-21 activity (e.g. within at least 50%, 80%, 90%, 95%, 96%, 97%, 98%, 99% or 100% activity compared to IL-21). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-21 protein. In embodiments, the IL-21 protein is substantially identical to the protein identified by the UniProt reference number Q9HBE4 or a variant or homolog having substantial identity thereto.

The term "IL-7 protein" or "IL-7" as used herein includes any of the recombinant or naturally-occurring forms of Interleukin-7, or variants or homologs thereof that maintain IL-7 activity (e.g. within at least 50%, 80%, 90%, 95%, 96%, 97%, 98%, 99% or 100% activity compared to IL-7). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-7 protein. In embodiments, the IL-7 protein is substantially identical to the protein identified by the UniProt reference number P13232 or a variant or homolog having substantial identity thereto.

The term "IL-9 protein" or "IL-9" as used herein includes any of the recombinant or naturally-occurring forms of Interleukin-9, also known as Cytokine P40, T-cell growth factor P40, or variants or homologs thereof that maintain IL-9 activity (e.g. within at least 50%, 80%, 90%, 95%, 96%, 97%, 98%, 99% or 100% activity compared to IL-9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-9 protein. In embodiments, the IL-9 protein is substantially identical to the protein identified by the UniProt reference number P15248 or a variant or homolog having substantial identity thereto.

The term "IFNg protein" or "IFNg" as used herein includes any of the recombinant or naturally-occurring forms of Interferon gamma, also known as IFNγ, type II interferon, or variants or homologs thereof that maintain IFNg activity (e.g. within at least 50%, 80%, 90%, 95%, 96%, 97%, 98%, 99% or 100% activity compared to IFNg). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IFNg protein. In embodiments, the IFNg protein is substantially identical to the protein identified by the UniProt reference number P01579 or a variant or homolog having substantial identity thereto.

"Contacting" is used in accordance with its plain ordinary meaning and refers to the process of allowing at least two distinct species (e.g. chemical compounds including biomolecules or cells) to become sufficiently proximal to react, interact or physically touch.

It should be appreciated, however, that the resulting reaction product can be produced directly from a reaction between the added reagents or from an intermediate from one or more of the added reagents which can be produced in the reaction mixture. In embodiments, contacting includes, for example, allowing a nucleic acid to interact with an endonuclease.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells.

The term "stem cell" or "stem cells" refers to a clonal, self-renewing cell population that is multipotent and thus can generate several differentiated cell types.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, Molecular Cloning: A Laboratory Manual, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism. Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/. By utilizing the knowledge on codon usage or codon preference in each organism, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various methods known to those skilled in the art.

A "cell culture" is an in vitro population of cells residing outside of an organism. The cell culture can be established from primary cells isolated from a cell bank or animal, or secondary cells that are derived from one of these sources and immortalized for long-term in vitro cultures.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, having the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

As used herein, the terms "specific binding" or "specifically binds" refer to two molecules forming a complex (e.g., a ribonucleoprotein and a transfection peptide) that is relatively stable under physiologic conditions.

Methods for determining whether a ligand binds another species (e.g., a protein or nucleic acid) and/or the affinity of such ligand-species interaction are known in the art. For example, the binding of a ligand to a protein can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), isothermal titration calorimetry (ITC), or enzyme-linked immunosorbent assays (ELISA).

Immunoassays which can be used to analyze immunospecific binding and cross-reactivity of the ligand include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, and fluorescent immunoassays. Such assays are routine and well known in the art.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The terms "antigen" and "epitope" interchangeably refer to the portion of a molecule (e.g., a polypeptide) which is specifically recognized by a component of the immune system, e.g., an antibody, a T cell receptor, or other immune receptor such as a receptor on natural killer (NK) cells. As used herein, the term "antigen" encompasses antigenic epitopes and antigenic fragments thereof.

An exemplary immunoglobulin (antibody) structural unit can have a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) Nature 348:552). The term "antibody" also includes bivalent or bispecific molecules, diabodies, triabodies, and tetrabodies. Bivalent and bispecific molecules are described in, e.g., Kostelny et al. (1992) J. Immunol. 148:1547, Pack and Pluckthun (1992) Biochemistry 31:1579, Hollinger et al. (1993), PNAS. USA 90:6444, Gruber et al. (1994) J Immunol. 152:5368, Zhu et al. (1997) Protein Sci. 6:781, Hu et al. (1996) Cancer Res. 56:3055, Adams et al. (1993) Cancer Res. 53:4026, and McCartney, et al. (1995) Protein Eng. 8:301.

As used herein, the terms "immolation," "self-immolation," "self-immolation mechanism," "immolation moiety," "immolation domain" and the like refer herein to the ability of a chemical group to undergo an intramolecular reaction thereby resulting in a chemical rearrangement of the chemical group and release of the rearranged chemical group from the remainder of the compound to which it was attached. A "pH-sensitive" immolation domain refers to a chemical group that undergoes an immolation reaction within a discreet pH range and does not substantially undergo the immolation reaction outside of the discreet pH range (e.g., pH about 1-5, pH about 5-7 or pH about 7-10). In embodiments, the discreet pH range is: pH 1-3, pH 2-4, pH 3-5, pH 4-6, pH 5-7, pH 6-8, pH 7-9, or pH 8-10. In embodiments, the pH-sensitive immolation region includes a cationic alpha amino ester (oligo(α-aminoester)). In embodiments, the cationic component of the cationic alpha amino ester is a positively charged nitrogen atom (e.g. a cationic amine). In embodiments, the cationic component of the cationic alpha amino ester is not a guanidinium group. In embodiments, the cationic component of the cationic alpha amino ester is not a piperidinium group.

The term "cell-penetrating complex" or the like refer, in the usual and customary sense, to a chemical complex (e.g., a complex or composition disclosed herein and embodiments thereof), capable of penetrating into a cell (a biological cell, such as a eukaryotic cell or prokaryotic cell). In embodiments, the cell-penetrating complex includes a nucleic acid ionically bound to a cationic amphipathic polymer. In embodiments, the nucleic acid is unable to substantially penetrate the cell in the absence of the cationic amphipathic polymer. Thus, in embodiments, the cationic amphipathic polymer facilitates the transport of the nucleic acid into the cell. As used herein, the terms "cationic charge altering releasable transporter," "CART" and the like refer to the cell-penetrating complexes disclosed herein. The CART compounds are able to release the nucleic acid component within the cell through the action of a pH-sensitive immolation domain within the cationic amphipathic polymer component, which reacts in response to an intracellular pH thereby releasing the nucleic acid with in the cell. In embodiments, the cationic amphipathic polymer degrades rapidly within the cell (e.g. a T1/2 of less than 6 hours at pH 7.4). At least in some embodiments, a polyplex, a complex, an electrostatic complex, a CART/mRNA complex, a CART/oligonucleotide complex and nanoparticle can interchangeably be used to refer to a cell-penetrating complex.

The term "amphipathic polymer" as used herein refers to a polymer containing both hydrophilic and hydrophobic portions. In embodiments, the hydrophilic to hydrophobic portions are present in a 1 to 1 mass ratio. In embodiments, the hydrophilic to hydrophobic portions are present in a 1 to 2 mass ratio. In embodiments, the hydrophilic to hydrophobic portions are present in a 1 to 5 mass ratio. In embodiments, the hydrophilic to hydrophobic portions are present in a 2 to 1 mass ratio. In embodiments, the hydrophilic to hydrophobic portions are present in a 5 to 1 mass ratio. An amphipathic polymer may be a diblock or triblock copolymer. In embodiments, the amphiphilic polymer may include two hydrophilic portions (e.g., blocks) and one hydrophobic portion (e.g., block).

The term "lipophilic polymer domain" or the like, often referred to as "lipid block" refers to a region of the cationic amphipathic polymer that is not hydrophilic (e.g. is insoluble in water alone). In embodiments, the lipophilic polymer domain has low solubility in water. For example, low solubility in water refers to the solubility of a lipophilic polymer domain which is about 0.0005 mg/mL to about 10 mg/mL soluble in water.

The term "initiator" refers to a compound that is involved in a reaction synthesizing a cationic amphipathic polymer having the purpose of initiating the polymerization reaction. Thus, the initiator is typically incorporated at the end of a synthesized polymer. For example, a plurality of molecules of one type (or formula) of monomer or more than one type of monomers (e.g. two different types of monomers) can be reacted with an initiator to provide a cationic amphipathic polymer. The initiator can be present on at least one end of the resulting polymer and not constitute a repeating (or polymerized) unit(s) present in the polymer.

The terms "disease" or "condition" refer to a state of being or health status of a subject capable of being treated with a compound, pharmaceutical composition, or method provided herein. The disease can be an autoimmune, inflammatory, cancer, infectious, metabolic, developmental, cardiovascular, liver, intestinal, endocrine, neurological, or other disease. In embodiments, the disease is cancer (e.g. breast cancer, ovarian cancer, sarcoma, osteosarcoma, lung cancer, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, neuroblastoma).

The term "infection" or "infectious disease" refers to a disease or condition that can be caused by organisms such as a bacterium, virus, fungi or any other pathogenic microbial agents.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As defined herein, the term "inhibition", "inhibit", "inhibiting" and the like in reference to an activity and/or functionality of a molecule (e.g. polynucleotide or protein) means negatively affecting (e.g., decreasing or reducing) the activity or function of the molecule relative to the activity or function of the protein in the absence of the inhibition. Thus, inhibition includes, at least in part, partially or totally blocking stimulation, decreasing, preventing, or delaying activation, or inactivating, desensitizing, or down-regulating signal transduction or enzymatic activity or the amount of a protein or polynucleotide. Similarly an "inhibitor" is a compound that inhibits a target bio-molecule (i.e. nucleic acid, peptide, carbohydrate, lipid or any other molecules that can be found from nature), e.g., by binding, partially or totally blocking, decreasing, preventing, delaying, inactivating, desensitizing, or down-regulating activity of the target bio-molecule. In the context of disease prevention treatment, inhibition refers to reduction of a disease or symptoms of disease.

"Treatment," "treating," and "treat" are defined as acting upon a disease, disorder, or condition with an agent to reduce or ameliorate harmful or any other undesired effects of the disease, disorder, or condition and/or its symptoms. "Treating" or "treatment of" a condition or subject in need thereof refers to (1) taking steps to obtain beneficial or desired results, including clinical results such as the reduction of symptoms; (2) inhibiting the disease, for example, arresting or reducing the development of the disease or its clinical symptoms; (3) relieving the disease, for example, causing regression of the disease or its clinical symptoms; or (4) delaying the disease. For example, beneficial or desired clinical results include, but are not limited to, reduction and/or elimination of cancer cells and prevention and/or reduction of metastasis of cancer cells.

The term "prevent," "preventing" or "prevention", in the context of a disease, refers to causing the clinical symptoms of the disease not to develop in a subject that does not yet experience or display symptoms of the disease. In embodiments, such prevention can be applied to a subject who can be considered predisposed of the disease, whereas in some other examples, the subject may not be necessarily considered predisposed to the disease.

As used herein, "administering" refers to the physical introduction of a composition to a subject, using any of the various methods and delivery systems known to those skilled in the art. Preferred routes of administration for the composition described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, the composition described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

An "anti-cancer agent" is a therapeutic having an anti-cancer activity that can be used in the treatment or prevention of cancer. An anti-cancer agent can be a large or small molecule. Example anti-cancer agents include antibodies, small molecules, and large molecules or combinations thereof. Examples of "anti-cancer activity" include, but are not limited to, reduction of cancer cell number, reduction of cancer size, killing of cancer cells, reductions and/or inhibition of metastasis and reduction of cancer cell growth and/or proliferation.

The term "associated" or "associated with" in the context of a substance or substance activity or function associated with a disease means that the disease can be caused by (in whole or in part), or a symptom of the disease can be caused by (in whole or in part) the substance or substance activity or function. When the term is used in the context of a symptom, e.g. a symptom being associated with a disease or condition, it means that a symptom can be indicative of the disease or condition present in the subject who shows the symptom.

The term "subject," "individual," "host" or "subject in need thereof" refers to a living organism suffering from a disease or condition or having a possibility to have a disease or condition in the future. A term "patient" refers to a living organism that already has a disease or condition, e.g. a patient who has been diagnosed with a disease or condition or has one or more symptoms associated with a disease or condition. Non-limiting examples include humans, other mammals, bovines, rats, mice, dogs, monkeys, goat, sheep, cows, deer, and other non-mammalian animals. In some embodiments, a patient is human.

The term "vaccine" refers to a composition that can provide active acquired immunity to and/or therapeutic effect (e.g. treatment) of a particular disease or a pathogen. A vaccine typically contains one or more agents that can induce an immune response in a subject against a pathogen or disease, i.e. a target pathogen or disease. The immunogenic agent stimulates the body's immune system to recognize the agent as a threat or indication of the presence of the target pathogen or disease, thereby inducing immunological memory so that the immune system can more easily recognize and destroy any of the pathogen on subsequent exposure. Vaccines can be prophylactic (e.g. preventing or ameliorating the effects of a future infection by any natural or pathogen, or of an anticipated occurrence of cancer in a predisposed subject) or therapeutic (e.g., treating cancer in a subject who has been diagnosed with the cancer). The administration of vaccines is referred to vaccination. In embodiments, a vaccine composition can provide nucleic acid, e.g. mRNA that encodes antigenic molecules (e.g. peptides) to a subject. The nucleic acid that is delivered via the vaccine composition in the subject can be expressed into antigenic molecules and allow the subject to acquire immunity against the antigenic molecules. In the context of the vaccination against infection disease, the vaccine composition can provide mRNA encoding antigenic molecules that are associated with a certain pathogen, e.g. one or more peptides that are known to be expressed in the pathogen (e.g. pathogenic bacterium or virus). In the context of cancer vaccine, the vaccine composition can provide mRNA encoding certain peptides that are associated with cancer, e.g. peptides that are substantially exclusively or highly expressed in cancer cells as compared to normal cells. The subject, after vaccination with the cancer vaccine composition, can have immunity against the peptides that are associated with cancer and kill the cancer cells with specificity.

The term "immune response" used herein encompasses, but is not limited to, an "adaptive immune response", also known as an "acquired immune response" in which adaptive immunity elicits immunological memory after an initial response to a specific pathogen or a specific type of cells that is targeted by the immune response, and leads to an enhanced response to that target on subsequent encounters. The induction of immunological memory can provide the basis of vaccination.

The term "immunogenic" or "antigenic" refers to a compound or composition that induces an immune response, e.g., cytotoxic T lymphocyte (CTL) response, a B cell response (for example, production of antibodies that specifically bind the epitope), an NK cell response or any combinations thereof, when administered to an immunocompetent subject. Thus, an immunogenic or antigenic composition is a composition capable of eliciting an immune response in an immunocompetent subject. For example, an immunogenic or antigenic composition can include one or more immunogenic epitopes associated with a pathogen or a specific type of cells that is targeted by the immune response. In addition, an immunogenic composition can include isolated nucleic acid constructs (such as DNA or RNA) that encode one or more immunogenic epitopes of the antigenic polypeptide that can be used to express the epitope(s) (and thus be used to elicit an immune response against this polypeptide or a related polypeptide associated with the targeted pathogen or type of cells).

According to the methods provided herein, the subject can be administered an effective amount of one or more of agents, compositions or complexes, all of which are interchangeably used herein, (e.g. cell-penetrating complex or vaccine composition) provided herein. The terms "effective amount" and "effective dosage" are used interchangeably. The term "effective amount" is defined as any amount necessary to produce a desired effect (e.g., transfection of nucleic acid into cells and exhibiting intended outcome of the transfected nucleic acid). Effective amounts and schedules for administering the agent can be determined empirically by one skilled in the art. The dosage ranges for administration are those large enough to produce the desired effects, e.g. transfection of nucleic acid, modulation in gene expression, gene-edition, induction of stem cells, induction of immune response and more. The dosage should not be so large as to cause substantial adverse side effects, such as unwanted cross-reactions, anaphylactic reactions, and the like. Generally, the dosage can vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount can show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation can depend on the purpose of the treatment, and can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

The term "kill" with respect to a cancer treatment is directed to include any type of manipulation that will lead to the death of that cancer cell or at least of portion of a population of cancer cells.

Cell-Penetrating Complexes

In a first aspect, there is provided a cell-penetrating complex including a nucleic acid non-covalently bound to a cationic amphipathic polymer, the cationic amphipathic polymer including a pH-sensitive immolation domain. In embodiments, one or more counter ions (e.g., anions) may also be present as countercharges to the positive charges in the cationic amphipathic polymer. In embodiments, the nucleic acid is non-covalently bound to the cationic amphipathic polymer. In embodiments, the nucleic acid is ionically bound to the cationic amphipathic polymer. In embodiments, the cell penetrating complex includes a plurality of optionally different nucleic acids (e.g. 1 to 10 additional nucleic acids, 1 to 5 additional nucleic acids, 1 to 5 additional nucleic acids, 2 additional nucleic acids or 1 additional nucleic acid). In embodiments, the nucleic acid is RNA. In embodiments, the nucleic acid is mRNA.

In embodiments, a ratio between the number of cations in the cationic amphipathic polymer molecules and the number of anions on the nucleic acid molecules present in a cell-penetrating complex can be about 1:1, about 5:1, about 10:1, about 20:1, about 30:1, about 40:1, about 50:1, about 60:1, about 70:1, about 80:1, about 90:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In other embodiments, a ratio between the number of anions on the nucleic acid molecules and the number of cations on the cationic amphipathic polymer molecules present in a cell-penetrating complex can be about 1:1, about 5:1, about 10:1, about 20:1, about 30:1, about 40:1, about 50:1, about 60:1, about 70:1, about 80:1, about 90:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In some preferred embodiments, this ratio is approximately 10 cationic charges on the amphipathic polymer molecule to 1 negative charge on the nucleic acid. Other embodiments can have 5 cationic charges on the amphipathic polymer molecule to 1 negative charge on the nucleic acid or 20 cationic charges on the amphipathic polymer molecule to 1 negative charge on the nucleic acid.

In embodiments, a ratio between the number of nucleic acid molecules and the number of cationic amphipathic polymer molecules present in a cell-penetrating complex can be about 1:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing. In other embodiments, a ratio between the number of cationic amphipathic polymer molecules and the number of nucleic acid molecules present in a cell-penetrating complex can be about 1:1, about 10:1, about $10^2$:1, about $10^3$:1, about $10^4$:1, about $10^5$:1, about $10^6$:1, about $10^7$:1, about $10^8$:1, about $10^9$:1, about $10^{10}$:1, or more or any intervening ranges of the foregoing.

In embodiments, the cationic amphipathic polymer may be a cationic charge altering releasable transporter (CART). In embodiments, the CART may include an oligomeric chain containing a series of cationic sequences that undergo a pH-sensitive change in charge from cationic to neutral or cationic to anionic.

In embodiments, the cationic amphipathic polymer has a pH-sensitive immolation domain and a lipophilic polymer domain. In embodiments, the lipophilic polymer domain may facilitate cell permeation, cell delivery and/or transport across cell membrane. In embodiments, the lipophilic polymer domain may be substantially insoluble in water (e.g., less than about 0.0005 mg/mL to about 10 mg/mL soluble in water). In embodiments, the lipophilic polymer domain may facilitate aggregation of the cationic amphipathic polymers into nanoparticles. In embodiments, such nanoparticles may have an average longest dimension of about 50 nm to about 500 nm. In embodiments, the lipophilic polymer domain may facilitate endosome fusion of the remnants of the cationic amphipathic polymer subsequent to entry and immolation within the endosome. In embodiments, the cell-penetrating complexes of the present disclosure protect the nucleic acid cargo from degradation. The term "nucleic acid cargo" or the like refers, in the usual and customary sense, to a species desired for transport into a cell by the cell-penetrating complex disclosed herein, and embodiments thereof.

In embodiments, the cationic amphipathic polymer has the formula (I): H-L'-[(LP$^1$)$_{z1}$-(IM)$_{z2}$-(LP$^2$)$_{z3}$]$_{z4}$-L$^2$-H (I), wherein L$_1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; LP$^1$ and LP$^2$ are independently a bond or a lipophilic polymer domain, wherein at least one of LP$^1$ or LP$^2$ is a lipophilic polymer domain; IM is the pH-sensitive immolation domain; z1 and z3 are independently integers from 0 to 100, wherein at least one of z1 or z3 is not 0; z4 is an integer from 1 to 100, and z2 is an integer from 2 to 100.

In embodiments, L$^1$ is substituted or unsubstituted C$_1$-C$_3$ alkylene. In embodiments, L$^1$ is substituted or unsubstituted methylene. In embodiments, L$^1$ is substituted or unsubstituted C$_1$-C$_6$ alkylene, or substituted or unsubstituted 2 to 6 membered heteroalkylene.

In embodiments, L$^1$ is substituted or unsubstituted C$_1$-C$_3$ alkylene, or substituted or unsubstituted 2 to 3 membered heteroalkylene.

In embodiments, L$^1$ is substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered). In embodiments, L$^1$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, L$^1$ is unsubstituted alkylene, unsubstituted heteroalkylene, unsubstituted cycloalkylene, unsubstituted heterocycloalkylene, unsubstituted arylene, or unsubstituted heteroarylene. In embodiments, L$^1$ is unsubstituted alkylene (e.g., C$_1$-C$_6$ alkylene). In embodiments, L$^1$ is a bond.

In embodiments, L$^2$ is substituted or unsubstituted C$_1$-C$_3$ alkylene. In embodiments, L$^2$ is substituted or unsubstituted methylene. In embodiments, L$^2$ is substituted or unsubstituted C$_1$-C$_6$ alkylene, or substituted or unsubstituted 2 to 6 membered heteroalkylene. In embodiments, L$^2$ is substituted or unsubstituted C$_1$-C$_3$ alkylene, or substituted or unsubstituted 2 to 3 membered heteroalkylene.

In embodiments, L$^2$ is substituted or unsubstituted alkylene (e.g., C$_1$-C$_8$, C$_1$-C$_6$, C$_1$-C$_4$, or C$_1$-C$_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$-C$_8$, C$_3$-C$_6$, C$_4$-C$_6$, or C$_5$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_{10}$ or phenylene), or substituted or unsubstituted heteroarylene (e.g., 5 to 10 membered, 5 to 9 membered, or 5 to 6 membered). In embodiments, L$^2$ is substituted (e.g., substituted with a substituent group, a size-limited substituent group, or lower substituent group) or unsubstituted alkylene, substituted (e.g., substituted with a substituent group, a size-limited substituent group, or lower substituent group) or unsubstituted heteroalkylene, substituted (e.g., substituted with a substituent group, a size-limited substituent group, or lower substituent group) or unsubstituted cycloalkylene, substituted (e.g., substituted with a substituent group, a size-limited substituent group, or lower substituent group) or unsubstituted heterocycloalkylene, substituted (e.g., substituted with a substituent group, a size-limited substituent group, or lower substituent group) or unsubstituted arylene, or substituted (e.g., substituted with a substituent group, a size-limited substituent group, or lower substituent group) or unsubstituted heteroarylene. In embodiments, L$^2$ is unsubstituted alkylene, unsubstituted heteroalkylene, unsubstituted cycloalkylene, unsubstituted heterocycloalkylene, unsubstituted arylene, or unsubstituted heteroarylene. In embodiments, L$^2$ is unsubstituted alkylene (e.g., C$_1$-C$_6$ alkylene). In embodiments, L$^2$ is a bond.

In embodiments z2 is an integer from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25. In embodiments, z1 and z3 are independently integers from 0 to 90 (e.g. 5 to 90, 10 to 90 or 20 to 90), 0 to 80 (e.g. 5 to 80, 10 to 80 or 20 to 80), 0 to 70 (e.g. 5 to 70, 10 to 70 or 20 to 70), 0 to 50 (e.g. 5 to 50, 10 to 50 or 20 to 50) or 2 to 25. In embodiments, z1 and z3 are independently integers from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25. In embodiments, z4 is an integer from 1 to 90 (e.g. 5 to 90, 10 to 90 or 20 to 90), 1 to 80 (e.g. 5 to 80, 10 to 80 or 20 to 80), 1 to 70 (e.g. 5 to 70, 10 to 70 or 20 to 70), 1 to 50 (e.g. 5 to 50, 10 to 50 or 20 to 50) or 2 to 25. In embodiments, z4 is an integer from 2 to 90 (e.g. 5 to 90, 10 to 90 or 20 to 90), 2 to 80 (e.g. 5 to 80, 10 to 80 or 20 to 80), 2 to 70 (e.g. 5 to 70, 10 to 70 or 20 to 70), 2 to 50 (e.g. 5 to 50, 10 to 50 or 20 to 50) or 2 to 25.

In embodiments of the cell-penetrating complex, the pH-sensitive immolation domain includes a first nucleophilic moiety and a first electrophilic moiety, wherein the first nucleophilic moiety is reactive with the first electrophilic moiety within a pH range and is not substantially reactive with the electrophilic moiety outside that pH range (e.g., pH about 1-5, pH about 5-7 or pH about 7-10). In embodiments, the pH range within which the first nucleophilic moiety is most reactive with the first electrophilic moiety is: pH 1-3, pH 2-4, pH 3-5, pH 4-6, pH 5-7, pH 6-8, pH 7-9, or pH 8-10. A nucleophilic moiety is used in accordance with its plain ordinary meaning in chemistry and refers to a moiety (e.g. functional group) capable of donating electrons.

In embodiments, the pH range within which the first nucleophilic moiety is most reactive with the first electrophilic moiety is pH 1-3. In embodiments, the pH range within which the first nucleophilic moiety is most reactive with the first electrophilic moiety is pH 2-4. In embodiments, the pH range within which the first nucleophilic moiety is most reactive with the first electrophilic moiety is pH 3-5. In embodiments, the pH range within which the first nucleophilic moiety is most reactive with the first electrophilic moiety is pH 4-6. In embodiments, the pH range within which the first nucleophilic moiety is most reactive with the first electrophilic moiety is pH 5-7. In embodiments, the pH range within which the first nucleophilic moiety is most reactive with the first electrophilic moiety is pH 6-8. In embodiments, the pH range within which the first nucleophilic moiety is most reactive with the first electrophilic moiety is pH 7-9. In embodiments, the pH range within which the first nucleophilic moiety is most reactive with the first electrophilic moiety is pH 8-10. In embodiments, the pH is 1. In embodiments, the pH is 2. In embodiments, the pH is 3. In embodiments, the pH is 4. In embodiments, the pH is 5. In embodiments, the pH is 6. In embodiments, the pH is 7. In embodiments, the pH is 8. In embodiments, the pH is 9. In embodiments, the pH is 10. In embodiments, the pH is about 1. In embodiments, the pH is about 2. In embodiments, the pH is about 3. In embodiments, the pH is about 4. In embodiments, the pH is about 5. In embodiments, the pH is about 6. In embodiments, the pH is about 7. In embodiments, the pH is about 8. In embodiments, the pH is about 9. In embodiments, the pH is about 10.

In embodiments, the first nucleophilic moiety is substantially protonated at low pH (e.g., pH about 1 to about 5). In embodiments, the first nucleophilic moiety is substantially protonated in the range pH 5-7. In embodiments, the first nucleophilic moiety is cationic. In embodiments, the first nucleophilic moiety includes a cationic nitrogen (e.g. a cationic amine).

In embodiments, the first nucleophilic moiety can be attached to a pH-labile protecting group. The term "pH-labile protecting group" or the like refers, in the usual and customary sense, to a chemical moiety capable of protecting another functionality to which it is attached, and which protecting group can be cleaved or otherwise inactivated as a protecting group under certain pH conditions (e.g., such as decreasing the pH). In one embodiment, the pH-labile protecting group is —CO$_2$-t-Bu, a group removed under acidic conditions (e.g., pH below 7). Additional nucleophile protecting groups could also include those that are cleaved by light, heat, nucleophile, and bases.

In embodiments of the cell-penetrating complex disclosed above and embodiments thereof, the pH-sensitive immolation domain has the structure of Formula (II) following:

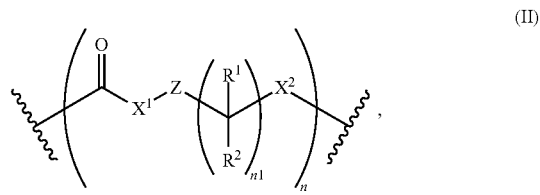

(II)

wherein n is an integer of 2 or more; n1 is an integer from 0 to 50; Z is a nucleophilic moiety; $X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—; $X^2$ is —O— or —S—, and $R^1$, $R^2$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n is an integer in the range 2-100, 2-90, 2-80, 2-70, 2-60, 2-50, 2-40, 2-30, 2-2, or 2-10. In embodiments, n1 is an integer in the range 0-25, 0-10, 0-5. In embodiments, n1 is 0, 1, 2, 3, 4 or 5. In embodiments, n1 is 1 or 2.

In embodiments, $R^1$, $R^2$, $R^5$, $R^6$, $R^7$, and $R^8$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^2$, $R^5$, $R^6$, $R^7$, and $R^8$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^2$, $R^5$, $R^6$, $R^7$, and $R^8$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^2$, $R^5$, $R^6$, $R^7$, and $R^8$ are independently hydrogen or unsubstituted alkyl (e.g., $C_1$-$C_6$ alkyl). In embodiments, $R^1$, $R^2$, $R^5$, $R^6$, $R^7$, and $R^8$ are hydrogen.

In embodiments of the cell-penetrating complex disclosed above and embodiments thereof, the pH-sensitive immolation domain has the structure following

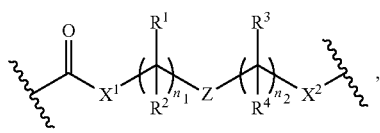

wherein $R^1$, $R^2$, $R^3$, $R^4$, $X^1$, Z and $X^2$ are as defined herein, and n1 and n2 are integers greater than 1.

In embodiments of the cell-penetrating complex disclosed herein and embodiments thereof, the pH-sensitive immolation domain has the structure of Formula (III) following:

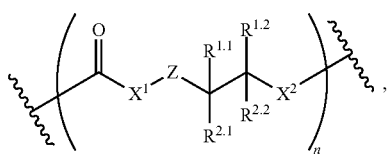

wherein n is an integer of 2 or more; Z is a nucleophilic moiety; $X^1$ is a bond, —C($R^5$)($R^6$)—, —C($R^5$)($R^6$)—C($R^7$)($R^8$)—, —O—C($R^5$)($R^6$)—, or —O—C($R_5$)($R^6$)—C($R^7$)($R_8$)—; $X^2$ is —O— or —S—, and $R_{1.1}$, $R^{1.2}$, $R^{2.1}$, $R^{2.2}$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n is an integer in the range 2-100, 2-90, 2-80, 2-70, 2-60, 2-50, 2-40, 2-30, 2-2, or 2-10. In embodiments, n is an integer in the range 2-100 or 2-50.

In embodiments, $R_{1.1}$, $R^{1.2}$, $R^{2.1}$, $R^{2.2}$, $R^5$, $R^6$, $R^7$, and $R^8$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R_{1.1}$, $R^{1.2}$, $R^{2.1}$, $R^{2.2}$, $R^5$, $R^6$, $R^7$, and $R^8$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R_{1.1}$, $R^{1.2}$, $R^{2.1}$, $R^{2.2}$, $R^5$, $R^6$, $R^7$, and $R^8$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R_{1.1}$, $R^{1.2}$, $R^{2.1}$, $R^{2.2}$, $R^5$, $R^6$, $R^7$, and $R^8$ are independently hydrogen or unsubstituted alkyl (e.g., $C_1$-$C_6$ alkyl). In embodiments, $R_{1.1}$, $R^{1.2}$, $R^{2.1}$, $R^{2.2}$, $R^5$, $R^6$, $R^7$, and $R^8$ are hydrogen.

In embodiments of the cell-penetrating complex disclosed herein and embodiments thereof, the pH-sensitive immolation domain has the structure of Formula (IV) following:

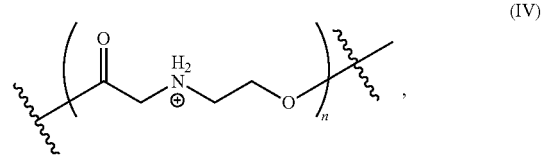

wherein n is an integer of 2 or more. In embodiments, n is an integer in the range 2-100, 2-90, 2-80, 2-70, 2-60, 2-50, 2-40, 2-30, 2-20, or 2-10. In embodiments, n is an integer in the range 2-100 or 2-50. In some embodiments, n is an integer from 2 to 50. In embodiments, n is an integer from 2 to 15.

In embodiments of the cell-penetrating complex disclosed herein and embodiments thereof, the pH-sensitive immolation domain has the structure of Formula (IVa) following:

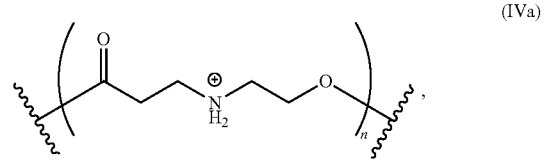

wherein n is an integer of 2 or more. In embodiments, n is an integer in the range 2-100, 2-90, 2-80, 2-70, 2-60, 2-50, 2-40, 2-30, 2-20, or 2-10. In embodiments, n is an integer in the range 2-100 or 2-50.

In embodiments of the cell-penetrating complex disclosed herein and embodiments thereof, the pH-sensitive immolation domain has the structure of Formula (V) following:

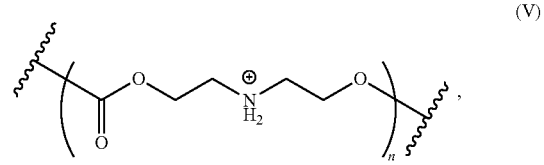

wherein n is an integer of 2 or more. In embodiments, n is an integer in the range 2-100, 2-90, 2-80, 2-70, 2-60, 2-50, 2-40, 2-30, 2-20, or 2-10. In embodiments, n is an integer in the range 2-100 or 2-50.

In embodiments of the cell-penetrating complex disclosed herein and embodiments thereof, the pH-sensitive immolation domain has the structure of Formula (Va) following:

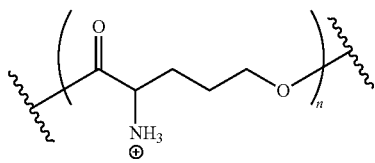

wherein n is an integer of 2 or more. In embodiments, n is an integer in the range 2-100, 2-90, 2-80, 2-70, 2-60, 2-50, 2-40, 2-30, 2-2, or 2-10. In embodiments, n is an integer in the range 2-100 or 2-50.

In embodiments, the pH-sensitive immolation domain has the structure following:

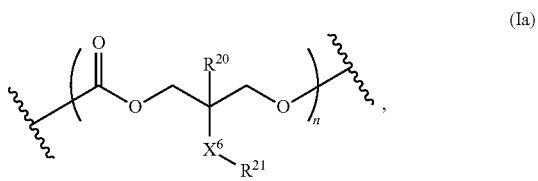

(Ia)

wherein $X^6$ is —O—, —NH—, —CONH—, —COO—, —OCO—, or —NHCO—; $R^{20}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, and $R^{21}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^{21}$ is an oligoglycol moiety. In embodiments, $R^{20}$ is an oligoglycol moiety.

In embodiments, $R^{20}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{20}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{20}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{20}$ is hydrogen or unsubstituted alkyl (e.g., $C_1$-$C_6$ alkyl). In embodiments, $R^{20}$ is hydrogen.

In embodiments, $R^{21}$ is substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{21}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{21}$ is unsubstituted alkyl, unsubstituted heteroalkyl, unsubstituted cycloalkyl, unsubstituted heterocycloalkyl, unsubstituted aryl, or unsubstituted heteroaryl. In embodiments, $R^{21}$ is hydrogen or unsubstituted alkyl (e.g., $C_1$-$C_6$ alkyl). In embodiments, $R^{21}$ is hydrogen.

In embodiments of the cell-penetrating complex disclosed herein and embodiments thereof, the pH-sensitive immolation domain has the structure following:

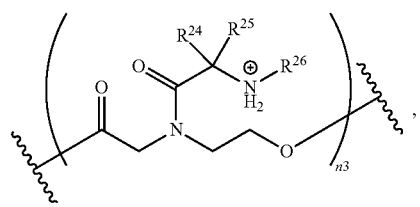

wherein $R^{24}$, $R^{25}$ and $R^{26}$ are independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, and n3 is an integer from 0 to 50.

In embodiments, $R^{24}$, $R^{25}$ and $R^{26}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{24}$, $R^{25}$ and $R^{26}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{24}$, $R^{25}$ and $R^{26}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{24}$, $R^{25}$ and $R^{26}$ are independently hydrogen or unsubstituted alkyl (e.g., $C_1$-$C_6$ alkyl). In embodiments, $R^{24}$, $R^{25}$ and $R^{26}$ are independently hydrogen.

In embodiments of the cell-penetrating complex disclosed herein and embodiments thereof, the pH-sensitive immolation domain has the structure of Formula (VI) following:

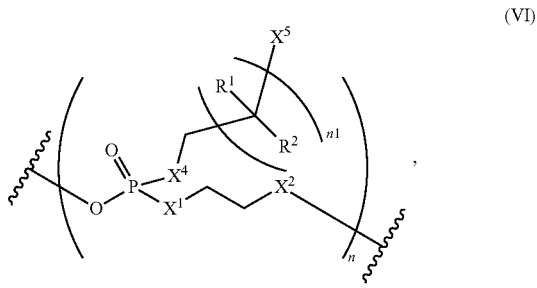

(VI)

wherein n is an integer of 2 or more; n1 is an integer from 0 to 50; $X^1$ is a bond, —O—, —$NR^5$—, —$C(R^5)(R^6)$— or —$C(R^5)(R^6)$—$C(R^7)(R^8)$—; $X^2$ is a bond, —O—, —$C(R^9)(R^{10})$— or —$C(R^9)(R^{10})$—$C(R^{11})(R^{12})$—; $X^4$ is a bond, —$NR^{16}$—, —O—, —$C(R^{16})(R^{17})$— or —$C(R^{16})(R^{17})$—$C(R^{18})(R^{19})$—; $X^5$ is a nucleophilic moiety; and $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^2$, $R^5$, $R^6$, $R^7$, $R^1$, $R^9$, $R^{10}$, $R^{11}$, $R^{12}$, $R^{16}$, $R^{17}$, $R^{18}$ and $R^{19}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are independently hydrogen or unsubstituted alkyl (e.g., $C_1$-$C_6$ alkyl). In embodiments, $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are hydrogen.

In embodiments, Z is a nucleophilic moiety. In embodiments, Z is —S—, —$OR^{13}$—, —$S^+R^{13}$—, —$NR^{13}$—, or —$N^+(R^{13})(H)$—, wherein $R^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, Z is —S—. In embodiments, Z is —$S^+R^{13}$—. In embodiments, Z is —$NR^{13}$. In embodiments, Z is —$N^+(R^{13})(H)$—. In embodiments, Z is —$S^+H$—. In embodiments, Z is —NH—. In embodiments, Z is —$N^+H_2$—. In embodiments, Z is —$O^+H$—.

In embodiments, $R^{13}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{13}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{13}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{13}$ is independently hydrogen or unsubstituted alkyl (e.g., $C_1$-$C_6$ alkyl). In embodiments, $R^{13}$ is hydrogen.

In embodiments, Z is

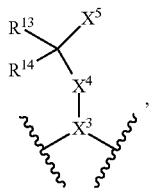

wherein $X^3$ is —C($R^{15}$)— or —N—; $X^4$ is a bond, —C(O)—, —P(O)(O$R^{16}$)$_2$—, —S(O)(O$R^{17}$)$_2$—, —C($R^{16}$)($R^{17}$)— or —C($R^{16}$)($R^{17}$)—C($R_{18}$)($R^{19}$)—; $X^5$ is a nucleophilic moiety; and $R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $X^3$ is —CH.

In embodiments, $R^{13}$, $R^{14}$, $R^{15}$, $R^{16}$, $R^{17}$, $R^{18}$ and $R^{19}$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{13}$, $R^{14}$, $R^{15}$, $R^{16}$, $R^{17}$, $R^{18}$ and $R^{19}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments $R^{13}$, $R^{14}$, $R^{15}$, $R^{16}$, $R^7$, $R^{18}$ and $R^{19}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{13}$, $R^{14}$, $R^{15}$, $R^{16}$, $R^{17}$, $R^{18}$ and $R^{19}$ are independently hydrogen or unsubstituted alkyl (e.g., $C_1$-$C_6$ alkyl).

In embodiments, $X^5$ is —N($R^{13}$)(H), wherein $R^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Further to the cell-penetrating complex disclosed herein and embodiments thereof, in embodiments the lipophilic polymer domain has the formula:

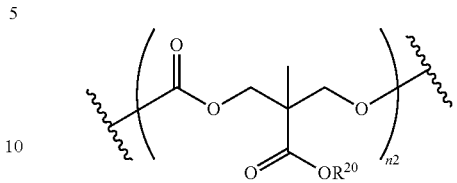

wherein, n2 is an integer from 1 to 100; $R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{20}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{20}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{20}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{20}$ is independently hydrogen or unsubstituted alkyl (e.g., $C_1$-$C_6$ alkyl).

In embodiments, $R^{20}$ is independently an unsubstituted $C_1$-$C_{30}$ alkyl. In embodiments, $R^{20}$ is independently an unsubstituted $C_1$-$C_{20}$ alkyl. In embodiments, $R^{20}$ is independently an unsubstituted $C_8$-$C_{30}$ alkyl. In embodiments, $R^{20}$ is independently an unsubstituted $C_8$-$C_{20}$ alkyl. In embodiments, $R^{20}$ is independently an unsubstituted $C_9$-$C_{20}$ alkyl. In embodiments, $R^{20}$ is independently an unsubstituted $C_9$-$C_{18}$ alkyl. In embodiments, $R^{20}$ is independently an unsubstituted $C_{18}$ alkyl. In embodiments, $R^{20}$ is independently an unsubstituted $C_{17}$ alkyl. In embodiments, $R^{20}$ is independently an unsubstituted $C_{16}$ alkyl. In embodiments, $R^{20}$ is independently an unsubstituted $C_{15}$ alkyl. In embodiments, $R^{20}$ is independently an unsubstituted $C_{14}$ alkyl. In embodiments, $R^{20}$ is independently an unsubstituted $C_{13}$ alkyl. In embodiments, $R^{20}$ is independently an unsubstituted $C_{12}$ alkyl. In embodiments, $R^{20}$ is independently an unsubstituted $C_{10}$ alkyl. In embodiments, $R^{20}$ is independently an unsubstituted $C_{10}$ alkyl. In embodiments, $R^{20}$ is independently an unsubstituted $C_9$ alkyl. In embodiments, $R^{20}$ is independently an unsubstituted $C_8$ alkyl. In embodiments, $R^{20}$ is independently an unsubstituted $C_7$ alkyl. In embodiments, $R^{20}$ is independently an unsubstituted $C_6$ alkyl. In embodiments, $R^{20}$ is independently an unsubstituted $C_5$ alkyl. In embodiments, $R^{20}$ is independently an unsubstituted $C_4$ alkyl. In embodiments, $R^{20}$ is independently an unsubstituted $C_3$ alkyl. In embodiments, $R^{20}$ is independently an unsubstituted $C_2$ alkyl.

In embodiments, $R^{20}$ is independently an unsubstituted $C_1$-$C_{30}$ alkenyl. In embodiments, $R^{20}$ is independently an unsubstituted $C_1$-$C_{20}$ alkenyl. In embodiments, $R^{20}$ is independently an unsubstituted $C_8$-$C_{30}$ alkenyl. In embodiments, $R^{20}$ is independently an unsubstituted $C_8$-$C_{20}$ alkenyl. In embodiments, $R^{20}$ is independently an unsubstituted $C_9$-$C_{20}$ alkenyl. In embodiments, $R^{20}$ is independently an unsubstituted $C_9$-$C_{18}$ alkenyl. In embodiments, $R^{20}$ is independently an unsubstituted $C_{18}$ alkenyl. In embodiments, $R^{20}$ is independently an unsubstituted $C_{17}$ alkenyl. In embodiments, $R^{20}$ is independently an unsubstituted $C_{16}$ alkenyl. In embodiments, $R^{20}$ is independently an unsubstituted $C_{15}$ alkenyl.

In embodiments, $R^{20}$ is independently an unsubstituted $C_{14}$ alkenyl. In embodiments, $R^{20}$ is independently an unsubstituted $C_{13}$ alkenyl. In embodiments, $R^{20}$ is independently an unsubstituted $C_{12}$ alkenyl. In embodiments, $R^{20}$ is independently an unsubstituted $C_{11}$ alkenyl.

In embodiments, $R^{20}$ is independently an unsubstituted $C_{10}$ alkenyl. In embodiments, $R^{20}$ is independently an unsubstituted $C_9$ alkenyl. In embodiments, $R^{20}$ is independently an unsubstituted $C_8$ alkenyl. In embodiments, $R^{20}$ is independently an unsubstituted $C_7$ alkenyl.

In embodiments, $R^{20}$ is independently an unsubstituted $C_6$ alkenyl. In embodiments, $R^{20}$ is independently an unsubstituted $C_5$ alkenyl. In embodiments, $R^{20}$ is independently an unsubstituted $C_4$ alkenyl. In embodiments, $R^{20}$ is independently an unsubstituted $C_3$ alkenyl. In embodiments, $R^{20}$ is independently an unsubstituted $C_2$ alkenyl.

In embodiments, $R^{20}$ is independently a stearyl moiety (e.g., an unsubstituted $C_{18}$ alkyl). In embodiments, $R^{20}$ is independently an oleyl moiety (e.g., an unsubstituted $C_{18}$ alkenyl). In embodiments, $R^{20}$ is independently a linoleyl moiety (e.g., an unsubstituted C18 alkenyl). In embodiments, $R^{20}$ is independently an dodecyl moiety (e.g., an unsubstituted $C_{12}$ alkyl). In embodiments, $R^{20}$ is independently an nonenyl moiety (e.g., an unsubstituted $C_9$ alkenyl). In embodiments, $R^{20}$ is independently

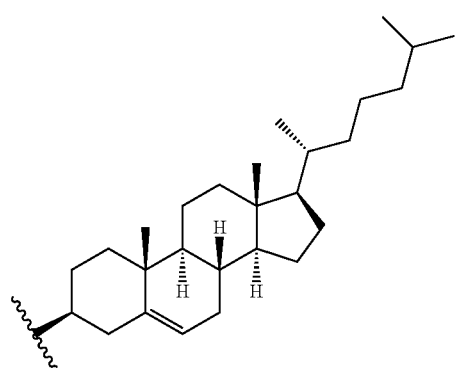

Further to the cell-penetrating complex disclosed herein and embodiments thereof, in embodiments $LP^1$ has the formula:

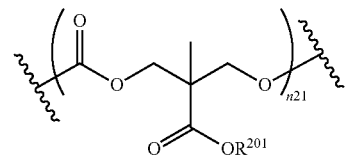

wherein, n21 is an integer from 0 to 100; $R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{201}$ is independently hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{201}$ is substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{201}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{201}$ is independently hydrogen or unsubstituted alkyl (e.g., $C_1$-$C_6$ alkyl).

In embodiments, $R^{201}$ is independently an unsubstituted $C_1$-$C_{30}$ alkyl. In embodiments, $R^{201}$ is independently an unsubstituted $C_1$-$C_{20}$ alkyl. In embodiments, $R^{201}$ is independently an unsubstituted $C_8$-$C_{30}$ alkyl. In embodiments, $R^{201}$ is independently an unsubstituted $C_8$-$C_{20}$ alkyl. In embodiments, $R^{201}$ is independently an unsubstituted $C_9$-$C_{20}$ alkyl. In embodiments, $R^{201}$ is independently an unsubstituted $C_9$-$C_{18}$ alkyl. In embodiments, $R^{201}$ is independently an unsubstituted $C_{18}$ salkyl. In embodiments, $R^{201}$ is independently an unsubstituted $C_{17}$ alkyl. In embodiments, $R^{201}$ is independently an unsubstituted $C_{16}$ alkyl. In embodiments, $R^{201}$ is independently an unsubstituted $C_{15}$ alkyl. In embodiments, $R^{201}$ is independently an unsubstituted $C_{14}$ alkyl. In embodiments, $R^{201}$ is an unsubstituted $C_{13}$ alkyl. In embodiments, $R^{201}$ is independently an unsubstituted $C_{12}$ alkyl. In embodiments, $R^{201}$ is independently an unsubstituted $C_{11}$ alkyl. In embodiments, $R^{201}$ is independently an unsubstituted $C_{10}$ alkyl. In embodiments, $R^{201}$ is independently an unsubstituted $C_9$ alkyl. In embodiments, $R^{201}$ is independently an unsubstituted $C_8$ alkyl. In embodiments, $R^{201}$ is independently an unsubstituted $C_7$ alkyl. In embodiments, $R^{201}$ is independently an unsubstituted $C_6$ alkyl. In embodiments, $R^{201}$ is independently an unsubstituted $C_5$ alkyl. In embodiments, $R^{201}$ is independently an unsubstituted $C_4$ alkyl. In embodiments, $R^{201}$ is independently an unsubstituted $C_3$ alkyl. In embodiments, $R^{201}$ is independently an unsubstituted $C_2$ alkyl.

In embodiments, $R^{201}$ is independently an unsubstituted $C_1$-$C_{30}$ alkenyl. In embodiments, $R^{201}$ is independently an unsubstituted $C_1$-$C_{20}$ alkenyl. In embodiments, $R^{201}$ is independently an unsubstituted $C_5$-$C_{30}$ alkenyl. In embodiments, $R^{201}$ is independently an unsubstituted $C_8$-$C_{20}$ alkenyl. In embodiments, $R^{201}$ is independently an unsubstituted $C_9$-$C_{20}$ alkenyl. In embodiments, $R^{201}$ is independently an unsubstituted $C_9$-$C_{18}$ alkenyl. In embodiments, $R^{201}$ is independently an unsubstituted $C_{18}$ alkenyl. In embodiments, $R^{201}$ is independently an unsubstituted $C_{17}$ alkenyl. In embodiments, $R^{201}$ is independently an unsubstituted $C_{16}$ alkenyl. In embodiments, $R^{201}$ is independently an unsubstituted $C_{15}$ alkenyl. In embodiments, $R^{201}$ is independently an unsubstituted $C_{14}$ alkenyl. In embodiments, $R^{201}$ is independently an unsubstituted $C_{13}$ alkenyl. In embodiments, $R^{201}$ is independently an unsubstituted $C_{12}$ alkenyl. In embodiments, $R^{201}$ is independently an unsubstituted $C_{11}$ alkenyl. In embodiments, $R^{201}$ is independently an unsubstituted $C_{10}$ alkenyl. In embodiments, $R^{201}$ is independently an unsubstituted $C_9$ alkenyl. In embodiments, $R^{201}$ is independently an unsubstituted $C_5$ alkenyl. In embodiments, $R^{201}$ is independently an unsubstituted $C_7$ alkenyl. In embodiments, $R^{201}$ is independently an unsubstituted $C_6$ alkenyl.

In embodiments, $R^{201}$ is independently an unsubstituted $C_5$ alkenyl. In embodiments, $R^{201}$ is independently an unsubstituted $C_4$ alkenyl. In embodiments, $R^{201}$ is independently an unsubstituted $C_3$ alkenyl. In embodiments, $R^{20'}$ is independently an unsubstituted $C_2$ alkenyl.

In embodiments, $R^{201}$ is independently a stearyl moiety (e.g., an unsubstituted $C_{18}$ alkyl). In embodiments, $R^{201}$ is independently an oleyl moiety (e.g., an unsubstituted $C_{18}$ alkenyl). In embodiments, $R^{201}$ is independently a linoleyl moiety (e.g., an unsubstituted $C_{18}$ alkenyl). In embodiments, $R^{201}$ is independently a dodecyl moiety (e.g., an unsubstituted $C_{12}$ alkyl). In embodiments, $R^{201}$ is independently a nonenyl moiety (e.g., an unsubstituted $C_9$ alkenyl). In embodiments, $R^{201}$ is independently

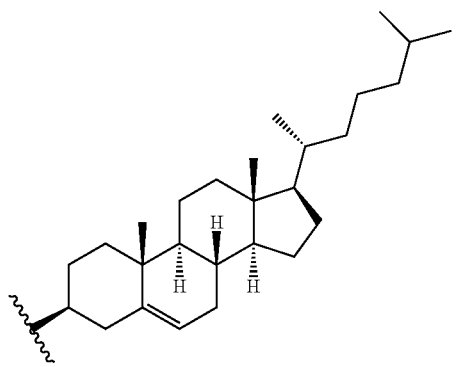

Further to the cell-penetrating complex disclosed herein and embodiments thereof, in embodiments $LP^2$ has the formula:

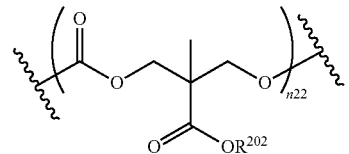

wherein, n22 is an integer from 0 to 100; $R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{202}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{202}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{202}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{202}$ is independently hydrogen or unsubstituted alkyl (e.g., $C_1$-$C_6$ alkyl).

In embodiments, $R^{202}$ is independently an unsubstituted $C_1$-$C_{30}$ alkyl. In embodiments, $R^{202}$ is independently an unsubstituted $C_1$-$C_{20}$ alkyl. In embodiments, $R^{202}$ is independently an unsubstituted $C_8$-$C_{30}$ alkyl. In embodiments, $R^{202}$ is independently an unsubstituted $C_5$-$C_{20}$ alkyl. In embodiments, $R^{202}$ is independently an unsubstituted $C_9$-$C_{20}$ alkyl. In embodiments, $R^{202}$ is independently an unsubstituted $C_9$-$C_{18}$ alkyl. In embodiments, $R^{202}$ is independently an unsubstituted $C_{15}$ alkyl. In embodiments, $R^{202}$ is independently an unsubstituted $C_{17}$ alkyl. In embodiments, $R^{202}$ is independently an unsubstituted $C_{16}$ alkyl. In embodiments, $R^{202}$ is independently an unsubstituted $C_{15}$ alkyl. In embodiments, $R^{202}$ is independently an unsubstituted $C_{14}$ alkyl. In embodiments, $R^{202}$ is independently an unsubstituted $C_{13}$ alkyl. In embodiments, $R^{202}$ is independently an unsubstituted $C_{12}$ alkyl. In embodiments, $R^{202}$ is independently an unsubstituted $C_{11}$ alkyl. In embodiments, $R^{202}$ is independently an unsubstituted $C_{10}$ alkyl. In embodiments, $R^{202}$ is independently an unsubstituted $C_9$ alkyl. In embodiments, $R^{202}$ is independently an unsubstituted $C_8$ alkyl. In embodiments, $R^{202}$ is independently an unsubstituted $C_7$ alkyl. In embodiments, $R^{202}$ is independently an unsubstituted $C_6$ alkyl. In embodiments, $R^{202}$ is independently an unsubstituted $C_5$ alkyl. In embodiments, $R^{202}$ is independently an unsubstituted $C_4$ alkyl. In embodiments, $R^{202}$ is independently an unsubstituted $C_3$ alkyl. In embodiments, $R^{202}$ is independently an unsubstituted $C_2$ alkyl.

In embodiments, $R^{202}$ is independently an unsubstituted $C_1$-$C_{30}$ alkenyl. In embodiments, $R^{202}$ is independently an unsubstituted $C_1$-$C_{20}$ alkenyl. In embodiments, $R^{202}$ is independently an unsubstituted $C_8$-$C_{30}$ alkenyl. In embodiments, $R^{202}$ is independently an unsubstituted $C_8$-$C_{20}$ alkenyl. In embodiments, $R^{202}$ is independently an unsubstituted $C_9$-$C_{20}$ alkenyl. In embodiments, $R^{202}$ is independently an unsubstituted $C_9$-$C_{18}$ alkenyl. In embodiments, $R^{202}$ is independently an unsubstituted $C_{18}$ alkenyl. In embodiments, $R^{202}$ is independently an unsubstituted $C_{17}$ alkenyl. In embodiments, $R^{202}$ is independently an unsubstituted $C_{16}$ alkenyl. In embodiments, $R^{202}$ is independently an unsubstituted Cis alkenyl. In embodiments, $R^{202}$ is independently an unsubstituted $C_{14}$ alkenyl. In embodiments, $R^{202}$ is independently an unsubstituted $C_{13}$ alkenyl. In embodiments, $R^{202}$ is independently an unsubstituted $C_{12}$ alkenyl. In embodiments, $R^{202}$ is independently an unsubstituted Cu alkenyl. In embodiments, $R^{202}$ is independently an unsubstituted $C_{10}$ alkenyl. In embodiments, $R^{202}$ is independently an unsubstituted $C_9$ alkenyl. In embodiments, $R^{202}$ is independently an unsubstituted $C_8$ alkenyl. In embodiments, $R^{202}$ is independently an unsubstituted $C_7$ alkenyl. In embodiments, $R^{202}$ is independently an unsubstituted $C_6$ alkenyl. In embodiments, $R^{202}$ is independently an unsubstituted $C_5$ alkenyl. In embodiments, $R^{202}$ is independently an unsubstituted $C_4$ alkenyl. In embodiments, $R^{202}$ is independently an unsubstituted $C_3$ alkenyl. In embodiments, $R^{202}$ is independently an unsubstituted $C_2$ alkenyl.

In embodiments, $R^{202}$ is independently a stearyl moiety (e.g., an unsubstituted $C_{18}$ alkyl). In embodiments, $R^{202}$ is independently an oleyl moiety (e.g., an unsubstituted $C_{18}$ alkenyl). In embodiments, $R^{202}$ is independently an linoleyl moiety (e.g., an unsubstituted Cis alkenyl). In embodiments, $R^{202}$ is independently an dodecyl moiety (e.g., an unsubstituted $C_{12}$ alkyl). In embodiments, $R^{202}$ is independently an nonenyl moiety (e.g., an unsubstituted $C_9$ alkenyl). In embodiments, $R^{202}$ is independently

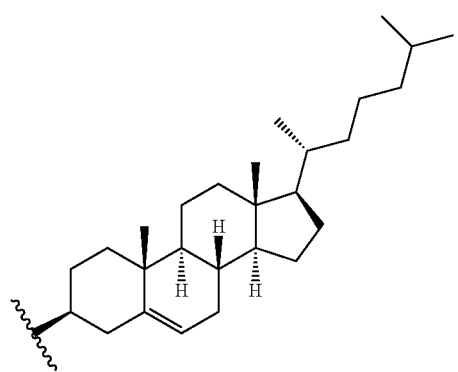

In embodiments, the lipophilic polymer domain is a compound of Formula (Ia) following:

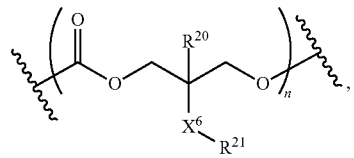

wherein $X^6$ is independently —O—, —NH—, —$CO_2$—, —CONH—, —OC(O)—, or —NHCO—, $R^{20}$ is independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, $R^{21}$ is independently hydrogen or substituted or unsubstituted alkyl, and n is as defined herein. In embodiments, $R^{20}$ is an oligoglycol moiety.

In embodiments of the cell-penetrating complex disclosed herein and embodiments thereof, the pH-sensitive immolation domain has the structure:

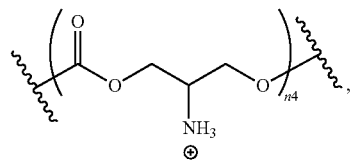

wherein n4 is an integer from 0 to 50. In embodiments, n4 is 0 to 10. In embodiments, n4 is an integer from 1 to 15.

In embodiments of the cell-penetrating complex disclosed herein and embodiments thereof, the lipophilic polymer has the structure:

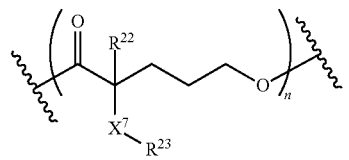

wherein $X^7$ is independently —O—, —NH—, —$CO_2$—, —CONH—, —OC(O)— or —NHCO—; $R^{22}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, and $R^{23}$ is independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^{22}$ is an oligoglycol moiety. In embodiments, $R^{23}$ is an oligoglycol moiety.

In embodiments, $R^{22}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{22}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{22}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{22}$ is independently hydrogen or unsubstituted alkyl (e.g., $C_1$-$C_6$ alkyl).

In embodiments, the lipophilic polymer domain may be a compound of Formula (Ib) following:

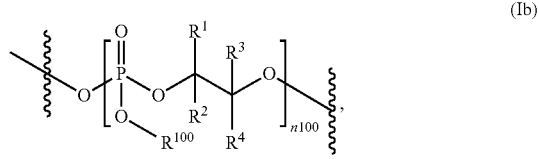

(Ib)

wherein $R^{100}$ is independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; $R^1$, $R^2$, $R^3$, and $R^4$ are independently hydrogen, substituted or unsubstituted heteroalkyl, substituted or unsubstituted heterocycloalkyl, substituted or unsubstituted aryl, or substituted or unsubstituted heteroaryl, and n100 is an integer of 2 or more.

In embodiments, $R^1$, $R^2$, $R^3$, and $R^4$ are independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^1$, $R^2$, $R^3$, and $R^4$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^1$, $R^2$, $R^3$, and $R^4$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$, $R^2$, $R^3$, and $R^4$ are independently hydrogen or unsubstituted alkyl (e.g., $C_1$-$C_6$ alkyl). In embodiments, $R^1$, $R^2$, $R^3$, and $R^4$ are independently hydrogen.

In embodiments, the lipophilic polymer domain may be a compound of Formula (Ic) following:

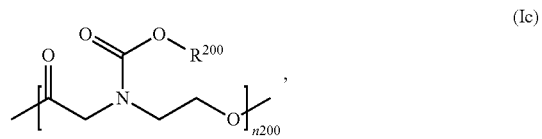

(Ic)

wherein $R^{200}$ is independently substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, and n200 is an integer of 2 or more. In embodiments $R^{200}$ is independently an oligoglycol moiety. In embodiments, $R^{200}$ is independently an amine-terminated oligoglycol moiety. The term "oligoglycol moiety" refers to

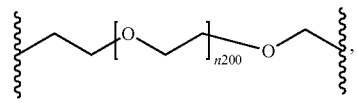

and "amine-terminated oligoglycol moiety" refers to

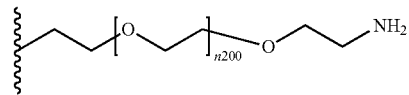

wherein n200 is an integer of 2 or more.

In embodiments, $R^{200}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{200}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{200}$ is independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{200}$ is independently hydrogen or unsubstituted alkyl (e.g., $C_1$-$C_6$ alkyl). In embodiments, $R^{200}$ is independently hydrogen.

In embodiments, the lipophilic polymer domain may be a compound of Formula (Id) following:

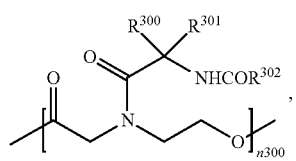

(Id)

wherein $R^{300}$, $R^{301}$, and $R^{302}$ are independently hydrogen, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl, and n300 is as defined herein. In embodiments $R^{300}$ and $R^{301}$ are independently hydrogen or substituted or unsubstituted alkyl. In embodiments $R^{302}$ is independently an oligoglycol moiety. In embodiments, $R^{302}$ is independently an amine-terminated an oligoglycol moiety. In embodiments $R^{300}$, $R^{301}$, and $R^{302}$ are independently hydrogen.

In embodiments, $R^{300}$, $R^{301}$, and $R^{302}$ are independently hydrogen, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{300}$, $R^{301}$, and $R^{302}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{300}$, $R^{300}$, and $R^{302}$ are independently unsubstituted alkyl, unsubstituted heteroalkyl, unsubstituted cycloalkyl, unsubstituted heterocycloalkyl, unsubstituted aryl, or unsubstituted heteroaryl. In embodiments, $R^{300}$, $R^{301}$, and $R^{302}$ are independently hydrogen or unsubstituted alkyl (e.g., $C_1$-$C_6$ alkyl).

In one aspect, the disclosures herewith provide a cell-penetrating complex having a nucleic acid non-covalently bound to a cationic amphipathic polymer. The cationic amphipathic polymer can have a pH-sensitive immolation domain. In some embodiments, the cationic amphipathic polymer has a pH-sensitive immolation domain and a lipophilic polymer domain. In some embodiments, the cell-penetrating complex has a cationic amphipathic polymer of the following formula (VII):

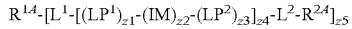

wherein $R^{1A}$ is hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —O $CHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —O $CHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —$S(O)_2$ —, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is a pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

In embodiments, RA is independently a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^{1A}$ is independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{1A}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{1A}$ is independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{1A}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{1A}$ is independently substituted or unsubstituted alkyl (e.g., $C_1$-$C_8$ alkyl, $C_1$-$C_6$ alkyl, or $C_1$-$C_4$ alkyl). In embodiments, $R^{1A}$ is independently substituted alkyl (e.g., $C_1$-$C_8$ alkyl, $C_1$-$C_6$ alkyl, or $C_1$-$C_4$ alkyl). In embodiments, $R^{1A}$ is independently an unsubstituted alkyl (e.g., $C_1$-$C_8$ alkyl, $C_1$-$C_6$ alkyl, or $C_1$-$C_4$ alkyl). In embodiments, $R^{1A}$ is independently substituted or unsubstituted heteroalkyl (e.g., 2 to 8 membered heteroalkyl, 2 to 6 membered heteroalkyl, or 2 to 4 membered heteroalkyl). In embodiments, $R^{1A}$ is independently substituted heteroalkyl (e.g., 2 to 8 membered heteroalkyl, 2 to 6 membered heteroalkyl, or 2 to 4 membered heteroalkyl). In embodiments, $R^{1A}$ is independently an unsubstituted heteroalkyl (e.g., 2 to 8 membered heteroalkyl, 2 to 6 membered heteroalkyl, or 2 to 4 membered heteroalkyl). In embodiments, $R^{1A}$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^{1A}$ is independently an unsubstituted cycloalkyl (e.g., $C_3$-$C_8$ cycloalkyl, $C_3$-$C_6$ cycloalkyl, or $C_5$-$C_6$ cycloalkyl). In embodiments, $R_{1A}$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is independently substituted heterocycloalkyl (e.g., 3 to 8 membered heterocycloalkyl, 3 to 6 membered heterocycloalkyl, or 5 to 6 membered heterocycloalkyl). In embodiments, RA is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{1A}$ is independently substituted or unsubstituted aryl (e.g., $C_6$-$C_{10}$ aryl, $C_{10}$ aryl, or phenyl). In embodiments, $R^{1A}$ is substituted aryl (e.g., $C_6$-$C_{10}$ aryl, $C_{10}$ aryl, or phenyl). In embodiments, $R^{1A}$ is independently an unsubstituted aryl (e.g., $C_6$-$C_{10}$ aryl, $C_{10}$ aryl, or phenyl). In embodiments, $R^{1A}$ is independently substituted or unsubstituted heteroaryl (e.g., 5 to 10 membered heteroaryl, 5 to 9 membered heteroaryl, or 5 to 6 membered heteroaryl). In embodiments, $R^{1A}$ is independently substituted heteroaryl (e.g., 5 to 10 membered heteroaryl, 5 to 9 membered heteroaryl, or 5 to 6 membered heteroaryl). In embodiments, $R^{1A}$ is independently an unsubstituted heteroaryl (e.g., 5 to 10 membered heteroaryl, 5 to 9 membered heteroaryl, or 5 to 6 membered heteroaryl).

In embodiments, $R^{1A}$ is independently a substituted or unsubstituted aryl. In some other embodiments, $R^{1A}$ is independently a substituted or unsubstituted phenyl. In still some other embodiments, $R^{1A}$ is independently a substituted or unsubstituted aryl. In still some other embodiments, $R^{1A}$ is independently a substituted or unsubstituted phenyl or naphthalenyl.

In embodiments, $R^{2A}$ is independently independently substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, $R^{2A}$ is independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl. In embodiments, $R^{2A}$ is independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{2A}$ is independently hydrogen, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^{2A}$ is independently substituted or unsubstituted alkyl (e.g., $C_1$-$C_8$ alkyl, $C_1$-$C_6$ alkyl, or $C_1$-$C_4$ alkyl). In embodiments, $R^{2A}$ is independently substituted alkyl (e.g., $C_1$-$C_8$ alkyl, $C_1$-$C_6$ alkyl, or $C_1$-$C_4$ alkyl). In embodiments, $R^{2A}$ is independently an unsubstituted alkyl (e.g., $C_1$-$C_8$ alkyl, $C_1$-$C_6$ alkyl, or $C_1$-$C_4$ alkyl). In embodiments, $R^{2A}$ is independently substituted or unsubstituted heteroalkyl (e.g., 2 to 8 membered heteroalkyl, 2 to 6 membered heteroalkyl, or 2 to 4 membered heteroalkyl). In embodiments, $R^{2A}$ is independently substituted heteroalkyl (e.g., 2 to 8 membered heteroalkyl, 2 to 6 membered heteroalkyl, or 2 to 4 membered heteroalkyl). In embodiments, $R^{2A}$ is independently an unsubstituted heteroalkyl (e.g., 2 to 8 membered heteroalkyl, 2 to 6 membered heteroalkyl, or 2 to 4 membered heteroalkyl). In embodiments, $R^{2A}$ is independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is independently substituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{2A}$ is independently substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently substituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently an unsubstituted heterocycloalkyl (e.g., 3 to 8 membered heterocycloalkyl, 3 to 6 membered heterocycloalkyl, or 5 to 6 membered heterocycloalkyl). In embodiments, $R^{2A}$ is independently substituted or unsubstituted aryl (e.g., $C_6$-$C_{10}$ aryl, $C_{10}$ aryl, or phenyl). In embodiments, $R^{2A}$ is substituted aryl (e.g., $C_6$-$C_{10}$ aryl, $C_{10}$ aryl, or phenyl). In embodiments, $R^{2A}$ is independently an unsubstituted aryl (e.g., $C_6$-$C_{10}$ aryl, $C_{10}$ aryl, or phenyl). In embodiments, $R^{2A}$ is independently substituted or unsubstituted heteroaryl (e.g., 5 to 10 membered heteroaryl, 5 to 9 membered heteroaryl, or 5 to 6 membered heteroaryl). In embodiments, $R^{2A}$ is independently substituted heteroaryl (e.g., 5 to 10 membered heteroaryl, 5 to 9 membered heteroaryl, or 5 to 6 membered heteroaryl). In embodiments, $R^{2A}$ is independently an unsubstituted heteroaryl (e.g., 5 to 10 membered heteroaryl, 5 to 9 membered heteroaryl, or 5 to 6 membered heteroaryl).

In some embodiments, the cell-penetrating complex can have a cationic amphipathic polymer having the following formula (VIII):

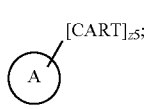

(VIII)

wherein
Ring A is a substituted or unsubstituted cycloalkyl, substituted or unsubstituted heterocycloalkyl, substituted or unsubstituted aryl, or substituted or unsubstituted heteroaryl;
CART has the formula: $-L^1-[(LP^1)_{z1}-(IM)_{z2}-(LP^2)_{z3}]_{z4}-L^2-R^{2A}$
wherein,
$R^{2A}$ is hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a bond or a lipophilic polymer domain, wherein at least one of $LP^1$ or $LP^2$ is a lipophilic polymer domain; IM is a pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In some embodiments, in the above-formula (VIII), Ring A is a substituted or unsubstituted aryl. In some other embodiments, Ring A is a substituted or unsubstituted phenyl. In still some other embodiments, Ring A is a substituted or unsubstituted aryl. In still some other embodiments, Ring A is a substituted or unsubstituted phenyl or naphthalenyl.

In embodiments, Ring A is an unsubstituted aryl (i.e. unsubstituted beyond the CART moiety). In embodiments, Ring A is an unsubstituted phenyl (i.e. unsubstituted beyond the CART moiety). In embodiments, Ring A is an unsubstituted phenyl or naphthalenyl (i.e. unsubstituted beyond the CART moiety). In embodiments, Ring A is a substituted aryl (i.e. substituted in addition to the CART moiety). In embodiments, Ring A is a substituted phenyl (i.e. substituted in addition to the CART moiety). In embodiments, Ring A is a substituted phenyl or naphthalenyl (i.e. substituted in addition to the CART moiety).

In embodiments, the cell-penetrating complex has a detectable agent (e.g., fluorophore).

In embodiments, $R^{1A}$ is an aryl substituted with a methoxy linker. In embodiments, $R^{1A}$ is an aryl substituted with a linker (e.g., —CH$_2$—O—). A non-limiting example wherein RIA is an aryl substituted with a methoxy linker has the formula:

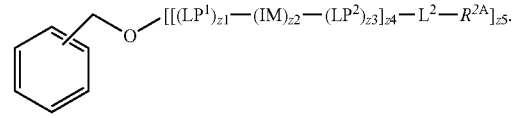

In some embodiments, a cationic amphipathic polymer has the formula (IX):

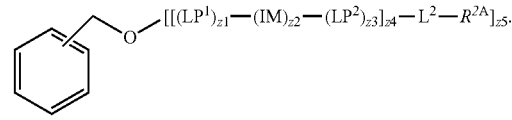

In some embodiments, a cationic amphipathic polymer has the formula (X):

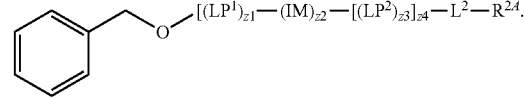

In some embodiments, a cationic amphipathic polymer can have the formula (XI):

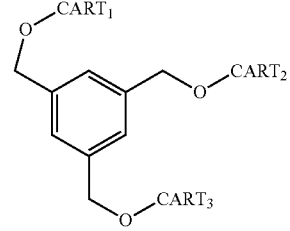

wherein CART$_1$, CART$_2$ AND CART$_3$ are independently a CART moiety as defined in formula (VIII) (e.g., $-L^1-[(LP^1)_{z1}-(IM)_{z2}-(LP^2)_{z3}]_{z4}-L^2-R^{2A}$). In embodiments each CART moiety is optionally different.

In embodiments, the cationic amphipathic polymer has the formula:
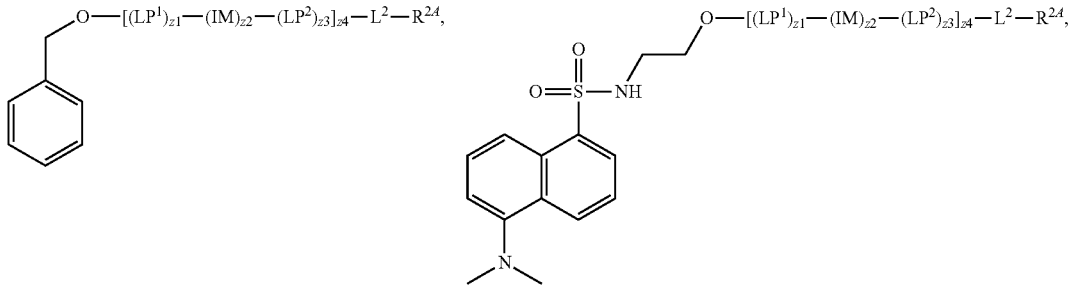
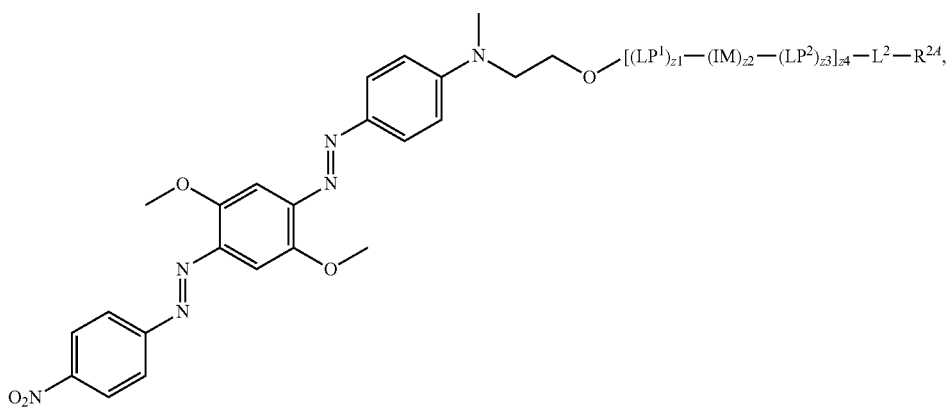
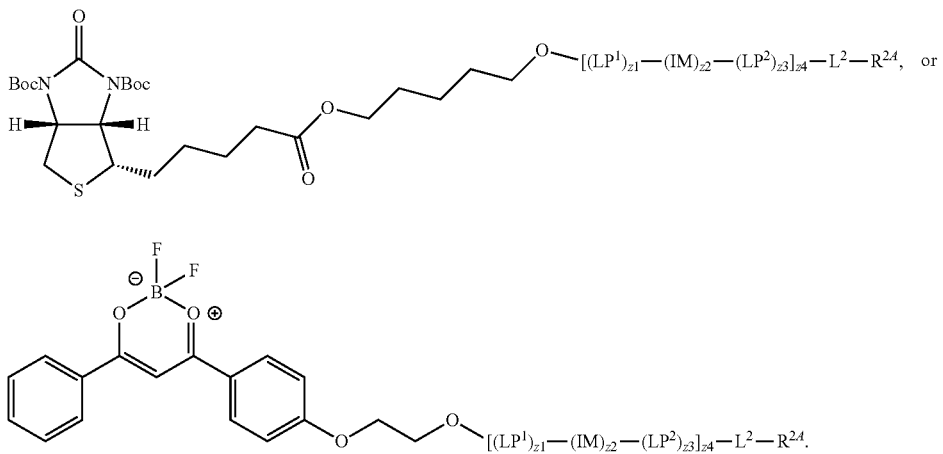

In embodiments, the cationic amphipathic polymer has the formula:
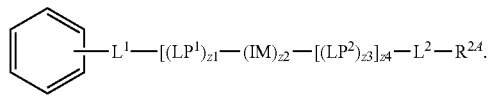
In embodiments, the cationic amphipathic polymer has the formula:
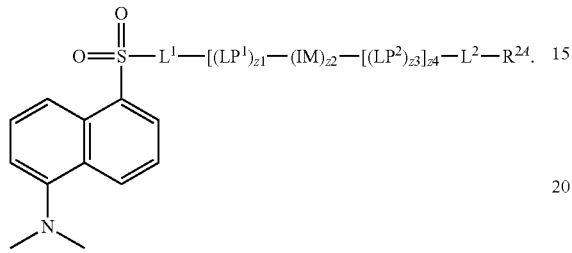
In embodiments, the cationic amphipathic polymer has the formula:
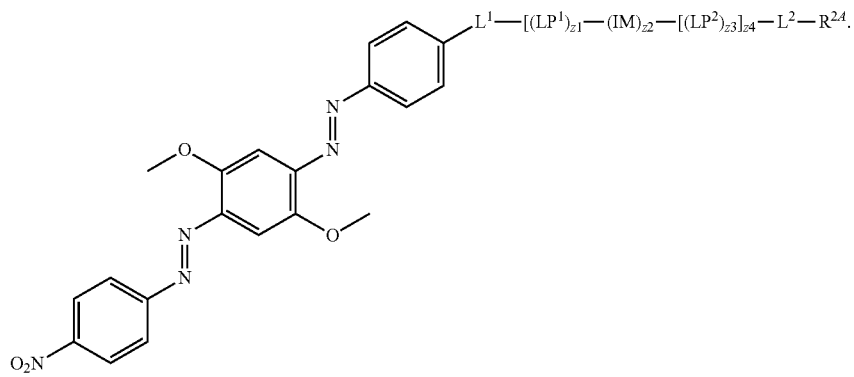
In embodiments, the cationic amphipathic polymer has the formula:
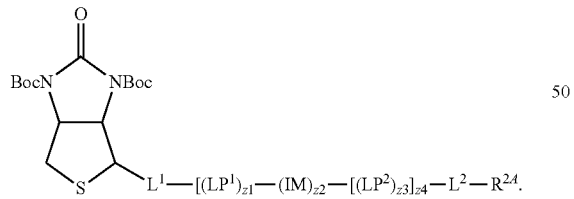
In embodiments, the cationic amphipathic polymer has the formula:
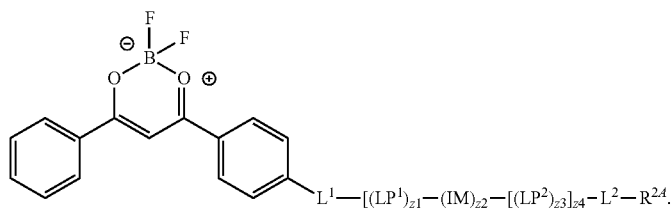

In embodiments, Ring A is substituted with a detectable agent through a linker (e.g., a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene).

In some embodiments, the cell-penetrating complex has a cationic amphipathic polymer having any of the foregoing formula in which $L^1$ is —CH$_2$—O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is —CH$_2$—O—.

In some embodiments, the cationic amphipathic polymer can have an of the foregoing formula in which $L^1$ is —CH$_2$—O—,

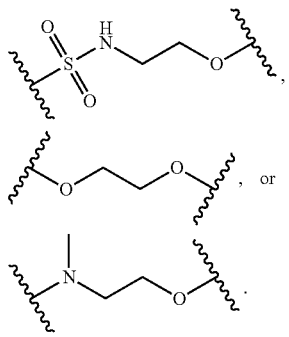

In embodiments, $L^1$ is —CH$_2$—O—. In embodiments, $L^1$ is

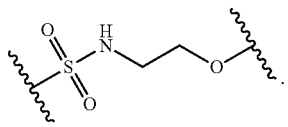 [SMILES: *OCCNS(*)(=O)=O]

In embodiments, $L^1$ is

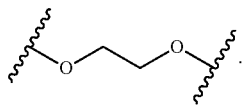 [SMILES: *OCCO*]

In embodiments, $L^1$ is

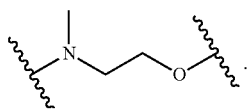 [SMILES: *OCCN(*)C]

In some embodiments, a cationic amphipathic polymer can have any of the foregoing formula in which z1 and z3 are independently integers from 0 to 100, wherein at least one of z1 or z3 is not 0 and z4 is an integer from 1 to 100. In some embodiments, z1, z3 and z4 can be independently integers in the range 2-100, 2-90, 2-80, 2-70, 2-60, 2-50, 2-40, 2-30, 2-2, or 2-10, wherein at least one of z1 or z3 is not 0. In embodiments, z1, z3 and z4 can be independently integers in the range 2-100 or 2-50, wherein at least one of z1 or z3 is not 0.

In embodiments, z1 is an integer from 0 to 100. In embodiments, z1 is an integer from 0 to 90. In embodiments, z1 is an integer from 0 to 80. In embodiments, z1 is an integer from 0 to 70. In embodiments, z1 is an integer from 0 to 60. In embodiments, z1 is an integer from 0 to 50. In embodiments, z1 is an integer from 0 to 40. In embodiments, z1 is an integer from 0 to 30. In embodiments, z1 is an integer from 0 to 20. In embodiments, z1 is an integer or 0 to 10. In embodiments, z1 is an integer from 5 to 100. In embodiments, z1 is an integer from 15 to 100. In embodiments, z1 is an integer from 25 to 100. In embodiments, z1 is an integer from 35 to 100. In embodiments, z1 is an integer from 45 to 100. In embodiments, z1 is an integer from 55 to 100. In embodiments, z1 is an integer from 65 to 100. In embodiments, z1 is an integer from 75 to 100. In embodiments, z1 is an integer from 85 to 100. In embodiments, z1 is an integer from 95 to 100. In embodiments, z1 is 0. In embodiments, z1 is 1. In embodiments, z1 is 2. In embodiments, z1 is 3. In embodiments, z1 is 4. In embodiments, z1 is 5. In embodiments, z1 is 6. In embodiments, z1 is 7. In embodiments, z1 is 8. In embodiments, z1 is 9. In embodiments, z1 is 10. In embodiments, z1 is 11. In embodiments, z1 is 12. In embodiments, z1 is 13. In embodiments, z1 is 14. In embodiments, z1 is 15. In embodiments, z1 is 16. In embodiments, z1 is 17. In embodiments, z1 is 18. In embodiments, z1 is 19. In embodiments, z1 is 20. In embodiments, z1 is 21. In embodiments, z1 is 22. In embodiments, z1 is 23. In embodiments, z1 is 24. In embodiments, z1 is 25. In embodiments, z1 is 26. In embodiments, z1 is 27. In embodiments, z1 is 28. In embodiments, z1 is 29. In embodiments, z1 is 30. In embodiments, z1 is 31. In embodiments, z1 is 32. In embodiments, z1 is 33. In embodiments, z1 is 34. In embodiments, z1 is 35. In embodiments, z1 is 36. In embodiments, z1 is 37. In embodiments, z1 is 38. In embodiments, z1 is 39. In embodiments, z1 is 40. In embodiments, z1 is 41. In embodiments, z1 is 42. In embodiments, z1 is 43. In embodiments, z1 is 44. In embodiments, z1 is 45. In embodiments, z1 is 46. In embodiments, z1 is 47. In embodiments, z1 is 48. In embodiments, z1 is 49. In embodiments, z1 is 50. In embodiments, z1 is 51. In embodiments, z1 is 52. In embodiments, z1 is 53. In embodiments, z1 is 54. In embodiments, z1 is 55. In embodiments, z1 is 56. In embodiments, z1 is 57. In embodiments, z1 is 58. In embodiments, z1 is 59. In embodiments, z1 is 60. In embodiments, z1 is 61. In embodiments, z1 is 62. In embodiments, z1 is 63. In embodiments, z1 is 64. In embodiments, z1 is 65. In embodiments, z1 is 66. In embodiments, z1 is 67. In embodiments, z1 is 68. In embodiments, z1 is 69. In embodiments, z1 is 70. In embodiments, z1 is 71. In embodiments, z1 is 72. In embodiments, z1 is 73. In embodiments, z1 is 74. In embodiments, z1 is 75. In embodiments, z1 is 76. In embodiments, z1 is 77. In embodiments, z1 is 78. In embodiments, z1 is 79. In embodiments, z1 is 80. In embodiments, zA is 81. In embodiments, z1 is 82. In embodiments, z1 is 83. In embodiments, z1 is 84. In embodiments, z1 is 85. In embodiments, z1 is 86. In embodiments, z1 is 87. In embodiments, z1 is 88. In embodiments, z1 is 89. In embodiments, z1 is 90. In embodiments, z1 is 91. In embodiments, z1 is 92. In embodiments, z1 is 93. In embodiments, z1 is 94. In embodiments, z1 is 95. In embodiments, z1 is 96. In embodiments, z1 is 97. In embodiments, z1 is 98. In embodiments, z1 is 99. In embodiments, z1 is 100.

In embodiments, z3 is an integer from 0 to 100. In embodiments, z3 is an integer from 0 to 90. In embodiments, z3 is an integer from 0 to 80. In embodiments, z3 is an integer from 0 to 70. In embodiments, z3 is an integer from 0 to 60. In embodiments, z3 is an integer from 0 to 50. In embodiments, z3 is an integer from 0 to 40. In embodiments, z3 is an integer from 0 to 30. In embodiments, z3 is an integer from 0 to 20. In embodiments, z3 is an integer from or 0 to 10. In embodiments, z3 is an integer from 5 to 100. In embodiments, z3 is an integer from 15 to 100. In embodiments, z3 is an integer from 25 to 100. In embodiments, z3 is an integer from 35 to 100. In embodiments, z3 is an integer from 45 to 100. In embodiments, z3 is an integer from 55 to 100. In embodiments, z3 is an integer from 65 to 100. In embodiments, z3 is an integer from 75 to 100. In embodiments, z3 is an integer from 85 to 100. In embodiments, z3 is an integer from 95 to 100. In embodiments, z3 is 0. In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7. In embodiments, z3 is 8. In embodiments, z3 is 9. In embodiments, z3 is 10. In embodiments, z3 is 11. In embodiments, z3 is 12. In embodiments, z3 is 13. In embodiments, z3 is 14. In embodiments, z3 is 15. In embodiments, z3 is 16. In embodiments, z3 is 17. In embodiments, z3 is 18. In embodiments, z3 is 19. In embodiments, z3 is 20. In embodiments, z3 is 21. In embodiments, z3 is 22. In embodiments, z3 is 23. In embodiments, z3 is 24. In embodiments, z3 is 25. In embodiments, z3 is 26. In embodiments, z3 is 27. In embodiments, z3 is 28. In embodiments, z3 is 29. In embodiments, z3 is 30. In embodiments, z3 is 31. In embodiments, z3 is 32. In embodiments, z3 is 33. In embodiments, z3 is 34. In embodiments, z3 is 35. In embodiments, z3 is 36. In embodiments, z3 is 37. In embodiments, z3 is 38. In embodiments, z3 is 39. In embodiments, z3 is 40. In embodiments, z3 is 41. In embodiments, z3 is 42. In embodiments, z3 is 43. In embodiments, z3 is 44. In embodiments, z3 is 45. In embodiments, z3 is 46. In embodiments, z3 is 47. In embodiments, z3 is 48. In embodiments, z3 is 49. In embodiments, z3 is 50. In embodiments, z3 is 51. In embodiments, z3 is 52. In embodiments, z3 is 53. In embodiments, z3 is 54. In embodiments, z3 is 55. In embodiments, z3 is 56. In embodiments, z3 is 57. In embodiments, z3 is 58. In embodiments, z3 is 59. In embodiments, z3 is 60. In embodiments, z3 is 61. In embodiments, z3 is 62. In embodiments, z3 is 63. In embodiments, z3 is 64. In embodiments, z3 is 65. In embodiments, z3 is 66. In embodiments, z3 is 67. In embodiments, z3 is 68. In embodiments, z3 is 69. In embodiments, z3 is 70. In embodiments, z3 is 71. In embodiments, z3 is 72. In embodiments, z3 is 73. In embodiments, z3 is 74. In embodiments, z3 is 75. In embodiments, z3 is 76. In embodiments, z3 is 77. In embodiments, z3 is 78. In embodiments, z3 is 79. In embodiments, z3 is 80. In embodiments, z3 is 81. In embodiments, z3 is 82. In embodiments, z3 is 83. In embodiments, z3 is 84. In embodiments, z3 is 85. In embodiments, z3 is 86. In embodiments, z3 is 87. In embodiments, z3 is 88. In embodiments, z3 is 89. In embodiments, z3 is 90. In embodiments, z3 is 91. In embodiments, z3 is 92. In embodiments, z3 is 93. In embodiments, z3 is 94. In embodiments, z3 is 95. In embodiments, z3 is 96. In embodiments, z3 is 97. In embodiments, z3 is 98. In embodiments, z3 is 99. In embodiments, z3 is 100.

In embodiments, z4 is an integer from 1 to 100. In embodiments, z4 is an integer from 1 to 90. In embodiments, z4 is an integer from 1 to 80. In embodiments, z4 is an integer from 1 to 70. In embodiments, z4 is an integer from 1 to 60. In embodiments, z4 is an integer from 1 to 50. In embodiments, z4 is an integer from 1 to 40. In embodiments, z4 is an integer from 1 to 30. In embodiments, z4 is an integer from 1 to 20. In embodiments, z4 is an integer from or 1 to 10. In embodiments, z4 is an integer from 5 to 100. In embodiments, z4 is an integer from 15 to 100. In embodiments, z4 is an integer from 25 to 100. In embodiments, z4 is an integer from 35 to 100. In embodiments, z4 is an integer from 45 to 100. In embodiments, z4 is an integer from 55 to 100. In embodiments, z4 is an integer from 65 to 100. In embodiments, z4 is an integer from 75 to 100. In embodiments, z4 is an integer from 85 to 100. In embodiments, z4 is an integer from 95 to 100. In embodiments, z4 is 1. In embodiments, z4 is 2. In embodiments, z4 is 3. In embodiments, z4 is 4. In embodiments, z4 is 5. In embodiments, z4 is 6. In embodiments, z4 is 7. In embodiments, z4 is 8. In embodiments, z4 is 9. In embodiments, z4 is 10. In embodiments, z4 is 11. In embodiments, z4 is 12. In embodiments, z4 is 13. In embodiments, z4 is 14. In embodiments, z4 is 15. In embodiments, z4 is 16. In embodiments, z4 is 17. In embodiments, z4 is 18. In embodiments, z4 is 19. In embodiments, z4 is 20. In embodiments, z4 is 21. In embodiments, z4 is 22. In embodiments, z4 is 23. In embodiments, z4 is 24. In embodiments, z4 is 25. In embodiments, z4 is 26. In embodiments, z4 is 27. In embodiments, z4 is 28. In embodiments, z4 is 29. In embodiments, z4 is 30. In embodiments, z4 is 31. In embodiments, z4 is 32. In embodiments, z4 is 33. In embodiments, z4 is 34. In embodiments, z4 is 35. In embodiments, z4 is 36. In embodiments, z4 is 37. In embodiments, z4 is 38. In embodiments, z4 is 39. In embodiments, z4 is 40. In embodiments, z4 is 41. In embodiments, z4 is 42. In embodiments, z4 is 43. In embodiments, z4 is 44. In embodiments, z4 is 45. In embodiments, z4 is 46. In embodiments, z4 is 47. In embodiments, z4 is 48. In embodiments, z4 is 49. In embodiments, z4 is 50. In embodiments, z4 is 51. In embodiments, z4 is 52. In embodiments, z4 is 53. In embodiments, z4 is 54. In embodiments, z4 is 55. In embodiments, z4 is 56. In embodiments, z4 is 57. In embodiments, z4 is 58. In embodiments, z4 is 59. In embodiments, z4 is 60. In embodiments, z4 is 61. In embodiments, z4 is 62. In embodiments, z4 is 63. In embodiments, z4 is 64. In embodiments, z4 is 65. In embodiments, z4 is 66. In embodiments, z4 is 67. In embodiments, z4 is 68. In embodiments, z4 is 69. In embodiments, z4 is 70. In embodiments, z4 is 71. In embodiments, z4 is 72. In embodiments, z4 is 73. In embodiments, z4 is 74. In embodiments, z4 is 75. In embodiments, z4 is 76. In embodiments, z4 is 77. In embodiments, z4 is 78. In embodiments, z4 is 79. In embodiments, z4 is 80. In embodiments, z4 is 81. In embodiments, z4 is 82. In embodiments, z4 is 83. In embodiments, z4 is 84. In embodiments, z4 is 85. In embodiments, z4 is 86. In embodiments, z4 is 87. In embodiments, z4 is 88. In embodiments, z4 is 89. In embodiments, z4 is 90. In embodiments, z4 is 91. In embodiments, z4 is 92. In embodiments, z4 is 93. In embodiments, z4 is 94. In embodiments, z4 is 95. In embodiments, z4 is 96. In embodiments, z4 is 97. In embodiments, z4 is 98. In embodiments, z4 is 99. In embodiments, z4 is 100.

In embodiments, n is an integer from 2 to 100. In embodiments, n is an integer from 2 to 90. In embodiments, n is an integer from 2 to 80. In embodiments, n is an integer from 2 to 70. In embodiments, n is an integer from 2 to 60. In embodiments, n is an integer from 2 to 50. In embodiments, n is an integer from 2 to 40. In embodiments, n is an integer from 2 to 30. In embodiments, n is an integer from 2 to 20. In embodiments, n is an integer from or 2 to 10. In embodiments, n is an integer from 5 to 100. In embodiments, n is an integer from 15 to 100. In embodiments, n is an integer from 25 to 100. In embodiments, n is an integer from 35 to 100. In embodiments, n is an integer from 45 to 100. In embodiments, n is an integer from 55 to 100. In embodiments, n is an integer from 65 to 100.

In embodiments, n is an integer from 75 to 100. In embodiments, n is an integer from 85 to 100. In embodiments, n is an integer from 95 to 100. In embodiments, n is 2. In embodiments, n is 3. In embodiments, n is 4. In embodiments, n is 5. In embodiments, n is 6.

In embodiments, n is 7. In embodiments, n is 8. In embodiments, n is 9. In embodiments, n is 10. In embodiments, n is 11. In embodiments, n is 12. In embodiments, n is 13. In embodiments, n is 14. In embodiments, n is 15. In embodiments, n is 16. In embodiments, n is 17. In embodiments, n is 18. In embodiments, n is 19. In embodiments, n is 20. In embodiments, n is 21. In embodiments, n is 22. In embodiments, n is 23. In embodiments, n is 24. In embodiments, n is 25. In embodiments, n is 26. In embodiments, n is 27. In embodiments, n is 28. In embodiments, n is 29. In embodiments, n is 30. In embodiments, n is 31. In embodiments, n is 32. In embodiments, n is 33. In embodiments, n is 34. In embodiments, n is 35. In embodiments, n is 36. In embodiments, n is 37. In embodiments, n is 38. In embodiments, n is 39. In embodiments, n is 40. In embodiments, n is 41. In embodiments, n is 42. In embodiments, n is 43. In embodiments, n is 44. In embodiments, n is 45. In embodiments, n is 46. In embodiments, n is 47. In embodiments, n is 48. In embodiments, n is 49. In embodiments, n is 50. In embodiments, n is 51. In embodiments, n is 52. In embodiments, n is 53. In embodiments, n is 54. In embodiments, n is 55. In embodiments, n is 56. In embodiments, n is 57. In embodiments, n is 58. In embodiments, n is 59. In embodiments, n is 60. In embodiments, n is 61. In embodiments, n is 62. In embodiments, n is 63. In embodiments, n is 64. In embodiments, n is 65. In embodiments, n is 66. In embodiments, n is 67. In embodiments, n is 68. In embodiments, n is 69. In embodiments, n is 70. In embodiments, n is 71. In embodiments, n is 72. In embodiments, n is 73. In embodiments, n is 74. In embodiments, n is 75. In embodiments, n is 76. In embodiments, n is 77. In embodiments, n is 78. In embodiments, n is 79. In embodiments, n is 80. In embodiments, n is 81. In embodiments, n is 82. In embodiments, n is 83. In embodiments, n is 84. In embodiments, n is 85. In embodiments, n is 86. In embodiments, n is 87. In embodiments, n is 88. In embodiments, n is 89. In embodiments, n is 90. In embodiments, n is 91. In embodiments, n is 92. In embodiments, n is 93. In embodiments, n is 94. In embodiments, n is 95. In embodiments, n is 96. In embodiments, n is 97. In embodiments, n is 98. In embodiments, n is 99. In embodiments, n is 100.

In embodiments, n1 is an integer from 0 to 50. In embodiments, n1 is an integer from 2 to 45. In embodiments, n1 is an integer from 0 to 40. In embodiments, n1 is an integer from 0 to 30. In embodiments, n1 is an integer from 0 to 20. In embodiments, n1 is an integer from or 0 to 10. In embodiments, n1 is an integer from 5 to 50. In embodiments, n1 is an integer from 15 to 50. In embodiments, n1 is an integer from 25 to 50. In embodiments, n1 is an integer from 35 to 50. In embodiments, n1 is an integer from 45 to 50.

In embodiments, n1 is 0. In embodiments, n1 is 1. In embodiments, n1 is 2. In embodiments, n1 is 3. In embodiments, n1 is 4. In embodiments, n1 is 5. In embodiments, n1 is 6. In embodiments, n1 is 7. In embodiments, n1 is 8. In embodiments, n1 is 9. In embodiments, n1 is 10. In embodiments, n1 is 11. In embodiments, n1 is 12. In embodiments, n1 is 13. In embodiments, n1 is 14. In embodiments, n1 is 15. In embodiments, n1 is 16. In embodiments, n1 is 17. In embodiments, n1 is 18. In embodiments, n1 is 19. In embodiments, n1 is 20. In embodiments, n1 is 21. In embodiments, n1 is 22. In embodiments, n1 is 23. In embodiments, n1 is 24. In embodiments, n1 is 25. In embodiments, n1 is 26. In embodiments, n1 is 27. In embodiments, n1 is 28. In embodiments, n1 is 29. In embodiments, n1 is 30. In embodiments, n1 is 31. In embodiments, n1 is 32. In embodiments, n1 is 33. In embodiments, n1 is 34. In embodiments, n1 is 35. In embodiments, n1 is 36. In embodiments, n1 is 37. In embodiments, n1 is 38. In embodiments, n1 is 39. In embodiments, n1 is 40. In embodiments, n1 is 41. In embodiments, n1 is 42. In embodiments, n1 is 43. In embodiments, n1 is 44. In embodiments, n1 is 45. In embodiments, n1 is 46. In embodiments, n1 is 47. In embodiments, n1 is 48. In embodiments, n1 is 49. In embodiments, n1 is 50.

In embodiments, n is an integer from 1 to 100. In embodiments, n is an integer from 1 to 90. In embodiments, n is an integer from 1 to 80. In embodiments, n is an integer from 1 to 70. In embodiments, n is an integer from 1 to 60. In embodiments, n is an integer from 1 to 50. In embodiments, n is an integer from 1 to 40. In embodiments, n is an integer from 1 to 30. In embodiments, n is an integer from 1 to 20. In embodiments, n is an integer from or 1 to 10. In embodiments, n is an integer from 5 to 100. In embodiments, n is an integer from 15 to 100. In embodiments, n is an integer from 25 to 100. In embodiments, n is an integer from 35 to 100. In embodiments, n is an integer from 45 to 100. In embodiments, n is an integer from 55 to 100. In embodiments, n is an integer from 65 to 100. In embodiments, n is an integer from 75 to 100. In embodiments, n is an integer from 85 to 100. In embodiments, n is an integer from 95 to 100. In embodiments, n2 is 1. In embodiments, n2 is 2. In embodiments, n2 is 3. In embodiments, n2 is 4. In embodiments, n2 is 5. In embodiments, n2 is 6. In embodiments, n2 is 7. In embodiments, n2 is 8. In embodiments, n2 is 9. In embodiments, n2 is 10. In embodiments, n2 is 11. In embodiments, n2 is 12. In embodiments, n2 is 13. In embodiments, n2 is 14. In embodiments, n2 is 15. In embodiments, n2 is 16. In embodiments, n2 is 17. In embodiments, n2 is 18. In embodiments, n2 is 19. In embodiments, n2 is 20. In embodiments, n2 is 21. In embodiments, n2 is 22. In embodiments, n2 is 23. In embodiments, n2 is 24. In embodiments, n2 is 25. In embodiments, n2 is 26. In embodiments, n2 is 27. In embodiments, n2 is 28. In embodiments, n2 is 29. In embodiments, n2 is 30. In embodiments, n2 is 31. In embodiments, n2 is 32. In embodiments, n2 is 33. In embodiments, n2 is 34. In embodiments, n2 is 35. In embodiments, n2 is 36. In embodiments, n2 is 37. In embodiments, n2 is 38. In embodiments, n2 is 39. In embodiments, n2 is 40. In embodiments, n2 is 41. In embodiments, n2 is 42. In embodiments, n2 is 43. In embodiments, n2 is 44. In embodiments, n2 is 45. In embodiments, n2 is 46. In embodiments, n2 is 47. In embodiments, n2 is 48. In embodiments, n2 is 49. In embodiments, n2 is 50. In embodiments, n2 is 51. In embodiments, n2 is 52. In embodiments, n2 is 53. In embodiments, n2 is 54. In embodiments, n2 is 55. In embodiments, n2 is 56. In embodiments, n2 is 57. In embodiments, n2 is 58. In embodiments, n2 is 59. In embodiments, n2 is 60. In embodiments, n2 is 61. In embodiments, n2 is 62. In embodiments, n2 is 63. In embodiments, n2 is 64. In embodiments, n2 is 65. In embodiments, n2 is 66. In embodiments, n2 is 67. In embodiments, n2 is 68. In embodiments, n2 is 69. In embodiments, n2 is 70. In embodiments, n2 is 71. In embodiments, n2 is 72. In embodiments, n2 is 73. In embodiments, n2 is 74. In embodiments, n2 is 75. In embodiments, n2 is 76. In embodiments, n2 is 77. In embodiments, n2 is 78. In embodiments, n2 is 79. In embodiments, n2 is 80. In embodiments, n2 is 81. In embodiments, n2 is 82. In embodiments, n2 is 83. In embodiments, n2 is 84. In embodiments, n2 is 85. In embodiments, n2 is 86. In embodiments, n2 is 87. In embodiments, n2 is 88. In embodiments, n2 is 89. In embodiments, n2 is 90. In embodiments, n2 is 91. In embodiments, n2 is 92. In embodiments, n2 is 93. In embodiments, n2 is 94. In embodiments, n2 is 95. In embodiments, n2 is 96. In embodiments, n2 is 97. In embodiments, n2 is 98. In embodiments, n2 is 99. In embodiments, n2 is 100.

In embodiments, z2 is an integer from 2 to 100. In embodiments, z2 is an integer from 2 to 90. In embodiments, z2 is an integer from 2 to 80. In embodiments, z2 is an integer from 2 to 70. In embodiments, z2 is an integer from 2 to 60. In embodiments, z2 is an integer from 2 to 50. In embodiments, z2 is an integer from 2 to 40. In embodiments, z2 is an integer from 2 to 30. In embodiments, z2 is an integer from 2 to 20. In embodiments, z2 is an integer from or 2 to 10. In embodiments, z2 is an integer from 5 to 100. In embodiments, z2 is an integer from 15 to 100. In embodiments, z2 is an integer from 25 to 100. In embodiments, z2 is an integer from 35 to 100. In embodiments, z2 is an integer from 45 to 100. In embodiments, z2 is an integer from 55 to 100. In embodiments, z2 is an integer from 65 to 100. In embodiments, z2 is an integer from 75 to 100. In embodiments, z2 is an integer from 85 to 100. In embodiments, z2 is an integer from 95 to 100. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9. In embodiments, z2 is 10. In embodiments, z2 is 11. In embodiments, z2 is 12. In embodiments, z2 is 13. In embodiments, z2 is 14. In embodiments, z2 is 15. In embodiments, z2 is 16. In embodiments, z2 is 17. In embodiments, z2 is 18. In embodiments, z2 is 19. In embodiments, z2 is 20. In embodiments, z2 is 21. In embodiments, z2 is 22. In embodiments, z2 is 23. In embodiments, z2 is 24. In embodiments, z2 is 25. In embodiments, z2 is 26. In embodiments, z2 is 27. In embodiments, z2 is 28. In embodiments, z2 is 29. In embodiments, z2 is 30. In embodiments, z2 is 31. In embodiments, z2 is 32. In embodiments, z2 is 33. In embodiments, z2 is 34. In embodiments, z2 is 35. In embodiments, z2 is 36. In embodiments, z2 is 37. In embodiments, z2 is 38. In embodiments, z2 is 39. In embodiments, z2 is 40. In embodiments, z2 is 41. In embodiments, z2 is 42. In embodiments, z2 is 43. In embodiments, z2 is 44. In embodiments, z2 is 45. In embodiments, z2 is 46. In embodiments, z2 is 47. In embodiments, z2 is 48. In embodiments, z2 is 49. In embodiments, z2 is 50. In embodiments, z2 is 51. In embodiments, z2 is 52. In embodiments, z2 is 53. In embodiments, z2 is 54. In embodiments, z2 is 55. In embodiments, z2 is 56. In embodiments, z2 is 57. In embodiments, z2 is 58. In embodiments, z2 is 59. In embodiments, z2 is 60. In embodiments, z2 is 61. In embodiments, z2 is 62. In embodiments, z2 is 63. In embodiments, z2 is 64. In embodiments, z2 is 65. In embodiments, z2 is 66. In embodiments, z2 is 67. In embodiments, z2 is 68. In embodiments, z2 is 69. In embodiments, z2 is 70. In embodiments, z2 is 71. In embodiments, z2 is 72. In embodiments, z2 is 73. In embodiments, z2 is 74. In embodiments, z2 is 75. In embodiments, z2 is 76. In embodiments, z2 is 77. In embodiments, z2 is 78. In embodiments, z2 is 79. In embodiments, z2 is 80. In embodiments, z2 is 81. In embodiments, z2 is 82. In embodiments, z2 is 83. In embodiments, z2 is 84. In embodiments, z2 is 85. In embodiments, z2 is 86. In embodiments, z2 is 87. In embodiments, z2 is 88. In embodiments, z2 is 89. In embodiments, z2 is 90. In embodiments, z2 is 91. In embodiments, z2 is 92. In embodiments, z2 is 93. In embodiments, z2 is 94. In embodiments, z2 is 95. In embodiments, z2 is 96. In embodiments, z2 is 97. In embodiments, z2 is 98. In embodiments, z2 is 99. In embodiments, z2 is 100.

In embodiments, z5 is 1. In embodiments, z5 is 2. In embodiments, z5 is 3. In embodiments, z5 is 4. In embodiments, z5 is 5. In embodiments, z5 is 6. In embodiments, z5 is 7. In embodiments, z5 is 8. In embodiments, z5 is 9. In embodiments, z5 is 10.

In some embodiments, a cationic amphipathic polymer can have any of the foregoing formula in which z2 is an integer from 2 to 100. In some embodiments, z2 can be an integer in the range 2 to 100, 2-90, 2 to 80, 2 to 70, 2 to 60, 2 to 50, 2 to 40, 2 to 30, 2 to 20, or 2 to 10. In embodiments, z2 can be an integer in the range 2 to 100 or 2 to 50.

In some embodiments, a cationic amphipathic polymer can have any of the foregoing formula in which z5 is an integer from 1 to 3. In some other embodiments, z5 is 1 or 3. In still some other embodiments, z5 is 1. In some still other embodiments, z5 is 3.

In some embodiments, a cationic amphipathic polymer can have any of the foregoing formula in which $R^2$ is hydrogen.

In some embodiments, a cationic amphipathic polymer can have any of the foregoing formula in which $L^2$ is a bond.

In embodiments, CART has the formula:

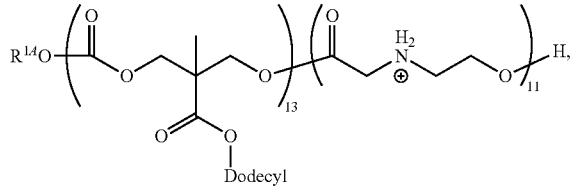

-continued
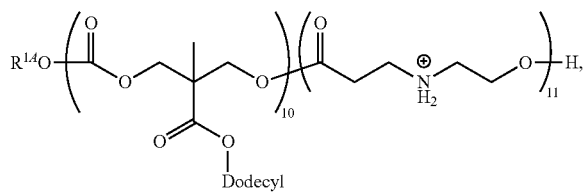
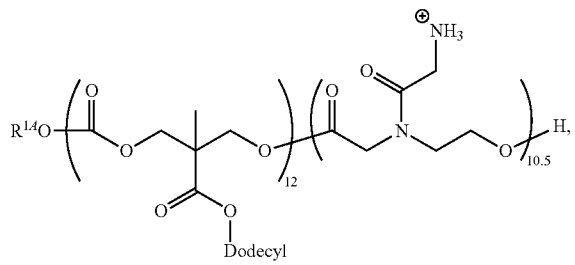
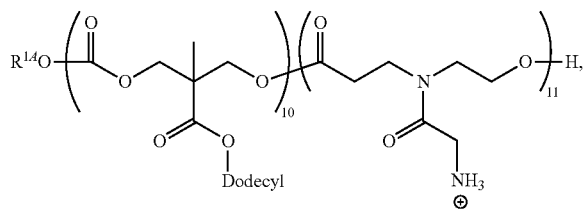
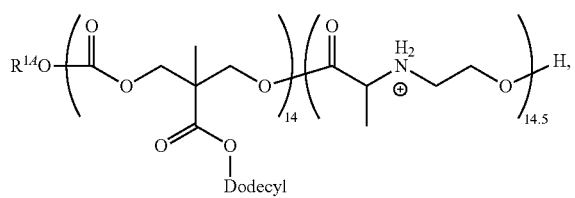
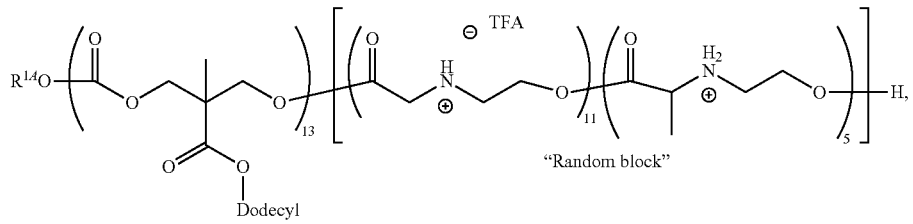
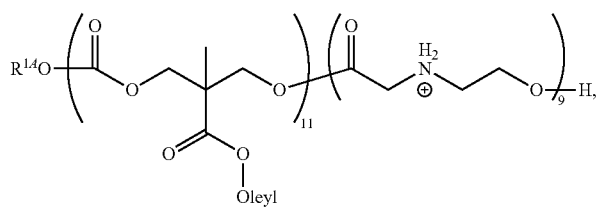
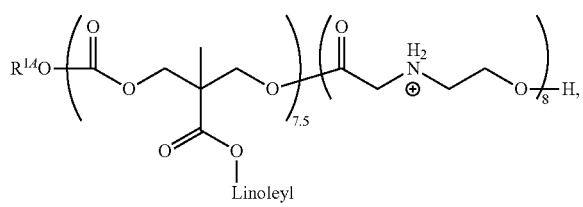
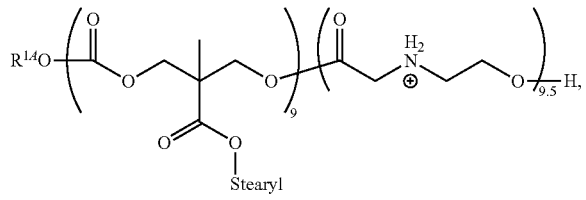

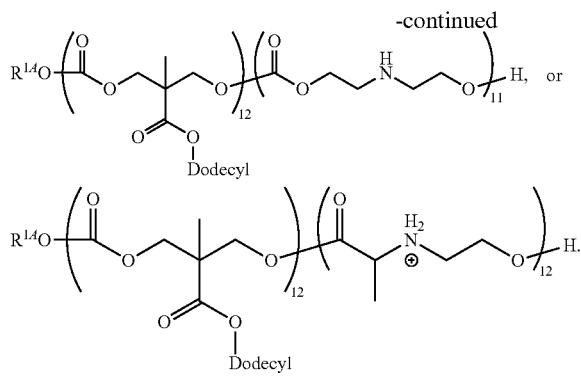

In some embodiments, a pH-sensitive immolation domain can have the formula:

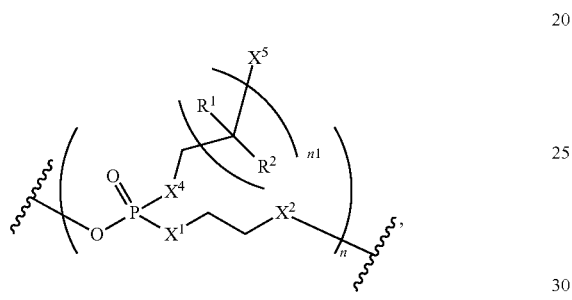

wherein n is an integer of 2 or more; n1 is an integer from 0 to 50; $X^1$ is a bond, —O—, —NR$^5$—, —C(R$^5$)(R$^6$)— or —C(R$^5$)(R$^6$)—C(R$^7$)(R$^8$)—; $X^2$ is a bond, —O—, —C(R$^9$)(R$^{10}$)— or —C(R$^9$)(R$^{10}$)—C(R$^{11}$)(R$^{12}$)—; $X^4$ is a bond, —C(O)—, —P(O)(OR$^{16}$)$_2$—, —S(O)(OR$^{17}$)$_2$—, —C(R$^{16}$)(R$^{17}$)— or —C(R$^{16}$)(R$^{17}$)—C(R$^{18}$)(R$^{19}$)—; $X^5$ is a nucleophilic moiety; and $R^1$, $R^2$, $R^5$, $R^6$, $R^7$, $R^8$, $R^9$, $R^{10}$, $R^{11}$, $R^{12}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In some embodiments, in a pH-sensitive immolation domain having any of the designated foregoing formula, Z is —S—, —S$^+$R$^{13}$—, —NR$^3$—, or —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In some embodiments, in a pH-sensitive immolation domain having any of the designated foregoing formula, Z is —S—, —S$^+$R$^{13}$—, —NR$^{13}$—, or —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In some embodiments, a pH-sensitive immolation domain can have one of the following formula: In embodiments of the cell-penetrating complex disclosed herein and embodiments thereof, the pH-sensitive immolation domain has the structure of Formula (IV) following:

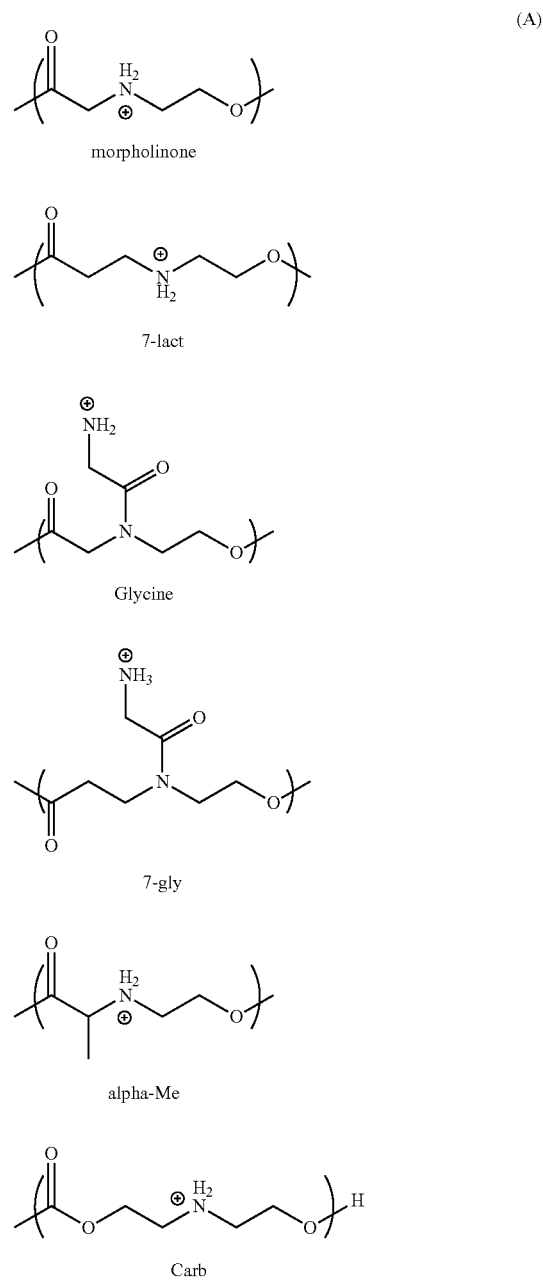

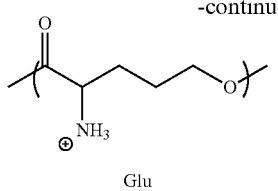

Glu

In some embodiments, a lipophilic polymer domain, or interchangeably referred to a lipophilic polymer domain, can have one of the following variations of R group:

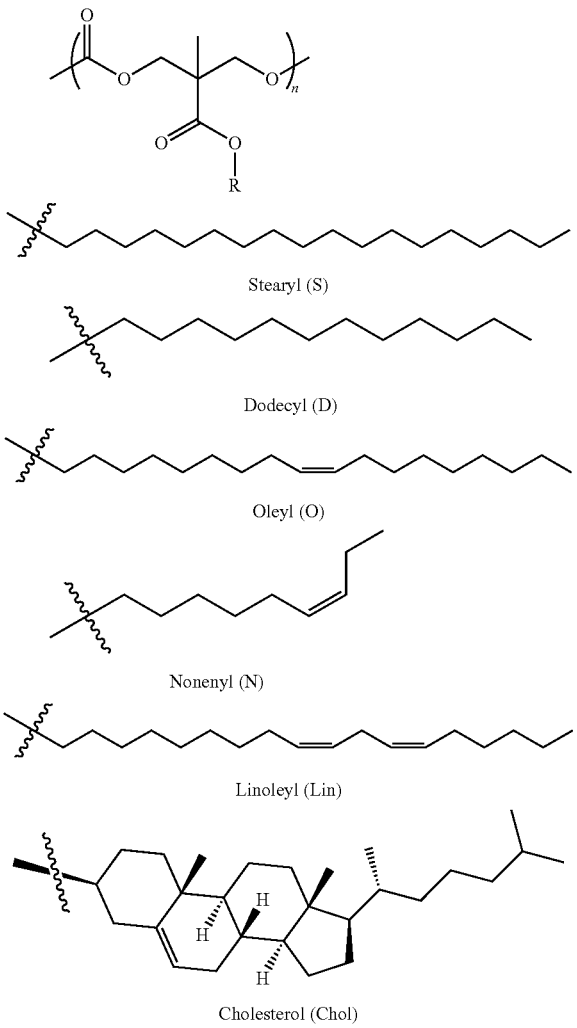

Further to the cell-penetration complex disclosed herein and embodiments thereof, in embodiments, the nucleic acid may be DNA or RNA, such as messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). The cell-penetration complex may further include a protein or peptide.

Further to the cell-penetration complex disclosed herein and embodiments thereof, in embodiments the cell-penetrating complex further includes a plurality of lipophilic moieties.

Further to the cell-penetration complex disclosed herein and embodiments thereof, in embodiments the cell-penetrating complex further includes a plurality of immolation domains.

Further to the cell-penetration complex disclosed herein and embodiments thereof, in embodiments, the counter-anion to the above cationic sequences can include common counterions known in the art, such as for example acetate, trifluoroacetate, triflate, chloride, bromide, sulfate, phosphate, succinate, or citrate. In embodiments, the counteranion is acetate, trifluoroacetate, triflate, chloride, bromide, sulfate, phosphate, succinate, or citrate.

Transfection

In another aspect, there is provided a method of transfecting a nucleic acid into a cell, the method including contacting a cell with a cell-penetrating complex as disclosed herein, or embodiment thereof.

In embodiments, the method further includes allowing the cationic amphipathic polymer to degrade within the cell thereby forming a degradation product. In embodiments, the degradation product is a substituted or unsubstituted diketopiperazine.

Further to any embodiment of the method of transfecting a nucleic acid into a cell, in embodiments the nucleic acid is an mRNA. In embodiments, the method further includes allowing the mRNA to be expressed in the cell. In embodiments, the cell forms part of an organism. In embodiments, the organism is a human.

Provided herein, inter alia, are novel materials and strategies that enable or enhance the complexation, protection, delivery and release of oligonucleotides and polyanionic cargos, e.g., messenger RNA (mRNA), into target cells, tissues, and organs both in vitro and in vivo.

For example, one strategy disclosed herein for mRNA delivery is accomplished using biodegradable poly(carbonate-co-aminoester)s oligomers and variations thereof which were discovered to electrostatically complex polyanions such as mRNA, producing noncovalent macromolecular particles that protect the mRNA cargo, readily enter cells and uniquely release oligonucleotide cargos. The mRNA released in the cell is then converted by cellular processes into peptides and proteins whose sequence and thus activity is determined by the mRNA sequence.

Thus, there is provided, for example, greatly increased improved cellular transfection efficiency over the use of nucleic acids themselves and known gene delivery vectors. The materials and strategy used for the delivery of mRNA can also be used to deliver other oligonucleotides such as siRNA, pDNA, shRNA, and gDNA. They can additionally be utilized to deliver other anionic biomolecules such as heparin, inorganic polyphosphate, and inositol polyphosphates (e.g., IP3, IP7, IP8). This delivery can be achieved with a variety of human and non-human cell lines, as well as through multiple modes of administration in vivo including but not limited to intramuscular, intravenous, intraperitoneal, intraocular, intranasal, subcutaneous, buccal and topical. The poly(carbonate-co-aminoester)s disclosed herein can be utilized, for example, as customizable, biodegradable, biocompatible materials for applications in biomedical therapies, imaging and devices. The copolymerization with biodegradable, non-toxic compounds materials such as valerolactone, caprolactone, lactide, and cyclic carbonates allows for tuning physical and biological properties including cargo release rates, hydrophobicity, incorporation of targeting ligands, biodistribution, and toxicity.

Accordingly, in some embodiments, the agents provided herein include oligomers, polymers, co-oligomers, and copolymers which may be derived from cyclic amino-ester and cyclic methyl trimethylene carbonate (MTC) monomers. Cyclic amino-esters have the base structure of morpholin-2-one and homologs thereof, with multiple substitution patterns possible including the following.

(1) N-acylation with a variety of hydrophobic groups (e.g., R=alkyl, alkenyl, aryl, polycycles including steroids, heterocycles), cationic groups (e.g., ammonium, phosphonium, sulfonium, guanidinium, including acylation with amino acids such as glycine, lysine, ornithine, arginine), anionic groups (e.g., carboxylate, sulfate, phosphate), or hydrophilic (e.g., PEG) carbamates. Protection of the morpholine nitrogen with N-Boc or N-Cbz groups followed by organocatalytic ring opening oligomerization or polymerization can afford upon deprotection cationic polymer or oligomer backbones.

(2) Alpha-alkylation or functionalization next to the ester carbonyl with the aforementioned possible functionalities selected to allow for cargo complexation and subsequent cargo release by biodegradation.

(3) Alkylation proximal to the morpholine nitrogen with the aforementioned functionalities.

(4) A combination of the above modifications.

Additionally, copolymers or co-oligomers (block or statistical) can be made by mixing two or more morpholin-2-one monomers, or by the copolymerization (or co-oligomerization) of one or multiple morpholin-2-one monomers with one or multiple cyclic carbonate monomers described herein. These carbonate monomers can incorporate a similar variety of side chain functionality, notably lipophilic groups or cationic groups to modulate oligonucleotide stability, delivery, and release properties. Furthermore, a variety of other commercially available cyclic ester monomers can be used including but not limited to lactide, glycolide, valerolactone, and/or caprolactone to incorporate lipophilic functionality.

The synthesis of polyaminoesters and poly(carbonate-co-aminoester)s is achieved through the ring-opening polymerization and/or copolymerization of morpholine-2-one and cyclic carbonate monomers. The N-Boc protected morpholinone (MBoc) polymerizes to high conversion (>85%), tunable Mn (1 kDa-20 kDa), and low molecular weight distributions (Mw/Mn-1.1-1.3) using an organocatalytic system. Post-polymerization deprotection of the Boc groups affords a cationic (diprotic, secondary amine) water-soluble polymer (−0.5M in D20, stable for >3 days). Furthermore, copolymerization of MBoc with MTC-dodecyl carbonate monomers followed by deprotection give rise to moderately charged cationic materials in high yield (>60%) with narrow polydispersity <1.4 PDI) and tunable block length. Block length is controlled by the ratio of initiator to monomer.

The polyaminoesters and poly(carbonate-co-aminoester)s are biocompatible and biodegradable. The cationic polyaminoesters rapidly degrade through a novel pH- and buffer-dependent immolation mechanism to generate in one embodiment bis-N-hydroxyethy-2,5-piperizinedionebis-hydroxyethyl glycine. This unforeseen degradation produces a product that is nontoxic at treatment concentrations, and the monomeric form (the expected product of further hydrolysis) is a natural biomarker for phospholipid modification in the Maillard reaction. The carbonate segment of the aminoester/carbonate copolymers degrades through hydrolysis and decarboxylation, and its byproducts have previously been shown to be non-toxic. The new poly- and oligo (carbonate-co-aminoester)s exhibit unanticipated performance as gene delivery agents due to their unique degradation mechanism. These new materials non-covalently complex, protect, deliver, and release mRNA at moderate theoretical charge ratios (e.g., about 10:1) resulting in exceptional transfection efficiencies (in some cases >99%) and robust induction of gene expression in vitro and in vivo. This strategy is effective for the delivery of mRNA molecules of different lengths (1000 and 2000 nucleotide transcripts tested). In one embodiment, gene delivery is achieved through formulation of cationic poly(carbonate-co-aminoester)s with anionic cargos to form self-assembled particles 200-400 nm in size. These particles are stable on the timescales necessary for intracellular gene delivery, and then they release the oligonucleotide cargo once inside the cell. While not bound to any particular theory, these materials degrade to the bis-N-hydroxyethyl-2,5-piperizinedione product bis-hydroxyethyl glycine. Treatment of a variety of human and non-human cell lines (e.g., HeLa, HaCaT, J774, HEK293) with the mRNA/amphiphile complex results in the induction of protein expression (e.g., GFP, luciferase) in vitro and in vivo through multiple modes of administration (intramuscular and intravenous tested).

Protein expression has been measured using mRNA encoding fluorescent reporter genes by flow cytometry and fluorescence microscopy (GFP), as well as bioluminescence (firefly luciferase). The poly(carbonate-co-aminoester)s have been shown to be more efficient transfection agents than the commercial standard Lipofectamine 2000, as well as many other lead compounds previously described for siRNA delivery.

In embodiments, gene delivery is achieved by formulation of the mixed amphipathic oligomer with an mRNA cargo in the presence of third components selected to tune stability and size of the resulting complex, increase cellular uptake, tune rate of mRNA release from the complex, and enhance expression of the cargo mRNA. Tertiary components include but are not limited to coordinating metal such as $Zn^{+2}$, $Mg^{+2}$, $Ca^{+2}$, etc; dynamic non-covalent cross linkers such as carbohydrates, counterions such as $Cl^-$, $AcO^-$, succinate, and citrate; and solubility modulators such as lipids and PEGs.

Applications of this technology may include: Clinical Applications: (1a) Nucleic acid transfection vectors: While utilizing DNA and RNA has been proposed to treat genetic disease for many years, the greatest obstacle to clinical use of gene therapy remains the effective delivery of the oligonucleotide cargos (1b) RNA Vaccination to prevent infectious diseases: mRNA-based vaccines display strong safety advantages over DNA vaccines, however they are clinically currently limited by mRNA delivery into cells. This application is currently being investigated clinically, but the most advanced technologies require removal of primary cells from patients for in vitro transfection with electroporation, followed by subsequent reintroduction of the transformed cells into the patient. This method can be significantly improved using our delivery technology to directly induce mRNA expression in vivo. (1c) Stem cell induction: pluripotency can be induced in undifferentiated stem cells by using our technology to induce the expression of 4 known transcription factors. The modular nature of the poly(carbonate-co-aminoester) delivery vehicles enables facile delivery of all four necessary mRNA transcripts simultaneously. (1) Basic research applications including, but not limited to: in vitro transfection of cultured cells, gene editing using CRISPR/Cas9, pathway validation using combination gene expression (mRNA translation) and gene knockdown (RNAi). Cancer immunotherapy, allergy tolerance, protein replacement therapy, gene editing, diagnostics, Advantages of the presently disclosed complexes, compositions and methods may include, for example:

(1) Higher mRNA transfection efficiency in vitro than commercially available transfection agents such as Lipofectamine 2000, even in difficult-to-transfect cell lines such as J774 macrophages, thereby improving efficacy while increasingly tolerability.

(2) Robust gene expression in vivo (BALB/c mice), demonstrating the clinical applicability of this technology, thereby avoiding toxicities of cationic carriers such as lipofectamine and providing a clinical alternative to ex-vivo methods of gene delivery and expression.

(3) Differential in vivo gene expression can be achieved using distinct routes of administration, with liver and spleen expression dominating upon intravenous injection, while local expression is sustained at the site of administration with an intramuscular (for example) delivery. Nasal delivery provides a route to mucosal membrane and/or lung uptake.

(4) Rapid degradation to known metabolites (bis-hydroxyethylglycine) which enables efficient gene expression (5) Release of mRNA in a pH-dependent manner, such as with oligonucleotide-bearing particles displaying stability in low pH environments (such as the skin or intestinal tract), but degrading in higher pH environments.

(6) Materials are easily accessed through metal-free synthesis to make oligomers, polymers, or block/statistical copolymers or co-oligomers with targeted molecular weight and a high degree of control over dispersity.

(7) Materials are amenable to targeting through addition of targeting ligands such as folate or biotin to the surface of the formed particle or through attachment to monoclonal antibodies.

(8) The specific immolation mechanism of the cationic polyaminoester domain to an isolable neutral small molecule results in the formation of the biocompatible/biodegradable product, bis-N-hydroxyethyl-2,5-piperizinedione, a cyclic dimer of hydroxyethylglycine.

Features of the complexes, compositions and methods include the following. In embodiments, the poly(carbonate-co-aminoester)s poly(aminoesters)s and the cationic materials derived thereof that can exhibit at least one of the following properties and functions:

(1) A specific, pH-responsive immolation mechanism of the cationic polyaminoesters that results in bio-compatible/biodegradable hydroxyethylglycine dimers; domain of these materials that leads to the release of the oligonucleotide cargo is unique even among other responsive biomaterials in that it occurs via an unanticipated intramolecular bond-forming event that results in irreversible neutralization of the cationic ammonium to rapidly trigger the release of the anionic cargo.

(2) An isolable product of intramolecular degradation, such as bis-N-hydroxyethyl-2,5-pipericla-7-inedione, which further degrades to hydroxyethyl glycine.

(3) Providing a temporal window of activity, such that the anionic cargo is electrostatically packaged into particles for delivery, then rapidly released following cellular internalization.

(4) Enablement of copolymerization of multiple lactone monomers with control over macromolecular architecture. Functionalized monomers may be polymerized in block or statistical architectures, and this further allows the combination of multiple monomer types such as cyclic carbonates or phosphates.

(5) The use of these materials in vivo may occur without acute toxicity, even when administered locally or systemically, indicative of high tolerability at concentrations necessary for a therapeutic response.

(6) Use as gene delivery vehicles, poly(carbonate-co-aminoester)s enable the efficient delivery and release of oligonucleotides including messenger RNA. Amphipathic block co-oligomers of MTC-dodecyl carbonate and N-Boc morpholine-2-one monomers can be formulated with large anionic cargos such as mRNA, to form stable, sub-400 nm particles. These resulting particles may effectively be taken up by cells and release their mRNA cargo, resulting in robust gene expression. This concept has been demonstrated in vitro in multiple cell lines as well as in vivo in mouse studies. The efficacy of these materials has been shown to be due to the pH-responsive rearrangement of the cationic aminoester block to form the neutral small molecule bis-N-hydroxyethl-2,5-piperidinedione bis-hydroxyethylglycine. While other cationic gene delivery vehicles have been previously reported, these oligo (carbonate-co-aminoester)s are unique and among the top performers, due to their unique ability to release the mRNA (or other oligonucleotide) cargo on a time scale appropriate for cellular uptake and their tolerability.

(7) The empirically determined optimal length for mRNA delivery teaches away from our prior art in that diblocks of average DP 12 for both MTC-dodecyl carbonate and N-Boc morpholine-2-one domains perform optimally. This length is much shorter than commercially available cationic polyamine vectors such as PEI; it is also longer than our previously discovered siRNA delivery vectors (Reference WO2013036532 A1 and PNAS 2012, 109 (33), 13171-13176).

In one aspect, provided herewith is a method of transfecting a nucleic acid into a cell, The method can have contacting a cell with a cell-penetrating complex described elsewhere in this application. In some embodiments, the method can cause gene-edition in the cell. In embodiments, the gene-edition can encompass genome-edition or genome editing which is a type of genetic engineering in which DNA is inserted, deleted or replaced in the genome of a living organism using an isolated or engineered nuclease system. In certain embodiments, the method disclosed herein can be used to deliver a genetic tool or system that can cause gene-edition in the transfected cells. Some non-limiting examples of a genetic tool or system for gene-edition include a CRISPR-Cas system and transposon system.

In one aspect, a nucleic acid (i.e. the cargo nucleic acid) transfected by the transfection method according to some embodiments can have one or more vectors having a first nucleotide sequence encoding a CRISPR-Cas system guide RNA that hybridizes with a target sequence in the genome of the cell and a second nucleotide sequence encoding a Cas9 protein. In certain embodiments, the first and second nucleotide sequence can be located on the same or different vectors.

In general, a system adopting CRISPR/Cas9 offers a high degree of fidelity and relatively simple construction for gene edition. The system can depend on two factors for its specificity: a target sequence and a protospacer adjacent motifs (PAM). The target sequence can be, e.g. 20 bases long as part of each CRISPR locus in a crRNA array. A crRNA array can have multiple unique target sequences. Cas9 proteins can select a correct location on the host's genome by utilizing the sequence to bind with base pairs on the host DNA. The PAM sequence on the host genome can be recognized by Cas9. Once the elements are assembled, e.g. into one or more plasmids and transfected into cells, the Cas9 protein with the help of the crRNA can find the correct sequence in the host cell's DNA and—depending on the Cas9 variant—creates a single or double strand break in the DNA. Properly spaced breaks in the host DNA can trigger homology directed repair. Providing a DNA repair template can allow for the insertion of a specific DNA sequence at an intended location within the genome.

Once incorporated, the new sequence is now part of the cell's genetic material and can pass into its daughter cells. Many online tools are available in the art to aid in designing effective sgRNA sequences. According to some embodiments, the method and composition according to certain embodiments herewith can deliver or transfect a nucleotide sequence encoding CRISPR-Cas system guide RNA and a nucleotide sequence encoding a Cas9 protein to induce gene-edition in the transfected cells.

In some embodiments, a cargo nucleic acid transfected by the transfection method according to certain embodiments can have a CRISPR RNA (crRNA). In some embodiments, this crRNA can be in the same vector of the first nucleotide sequence encoding a CRISPR-Cas system guide RNA.

In some embodiments, a cargo nucleic acid transfected by the transfection method according to certain embodiments can have a transactivating RNA (tracrRNA). In some embodiments, this tracrRNA can be in the same vector of the second nucleotide sequence encoding a Cas9 protein.

In some embodiments, the Cas9 protein utilized in the transfection method according to some embodiments can be codon optimized for expression in the transfected cell.

In another aspect, a nucleic acid (i.e. the cargo nucleic acid) transfected by the transfection method according to some embodiments can have one or more vectors having a first nucleotide sequence encoding a transposase and a second nucleotide sequence having a nucleic acid sequence of a gene of interest flanked by a transposase recognition site. In some embodiments, the first and second nucleotide sequences can be located on the same or different vectors.

A transposable element (or transposon) generally refers to a DNA sequence that can change its position within a genome, sometimes creating or reversing mutations and altering the cell's genetic composition and genome size. Transposase generally refers to an enzyme that can bind to a transposon and catalyze the movement of the transposon to another part of the genome by, e.g. a cut and paste mechanism or a replicative transposition mechanism. Introduction of transposase and a gene of interest flanked by a transposase recognition site in cells can induce insertion of the gene of interest into a cellular genome. According to some embodiments, the method and composition according to certain embodiments herewith can deliver or transfect a nucleic acid encoding a transposase and a gene of interest to induce gene-edition in the transfected cells.

In some embodiments, the transposase used in the transfection method according to some embodiments can recognize and excise a genomic sequence. In some other embodiments, the nucleic acid sequence of the gene of interest that is transfected via the transfection method can be integrated into a genome of the transfected cell.

In some embodiments, the gene-editing done via the transfection method according to some embodiments can cause one or more of the following: a DNA deletion, a gene disruption, a DNA insertion, a DNA inversion, a point mutation, a DNA replacement, a knock-in, and a knock-down.

Methods of Inducing an Immune Response

In another aspect, provided herein are methods of inducing an immune response in a subject. In some embodiments, the methods can treat and/or prevent a disease or condition using a cell-penetrating complex. The methods generally involve administering a subject in need thereof a therapeutically effective amount of a cell-penetrating complex or a pharmaceutical composition having the cell-penetrating complex described herein, alone (e.g., in monotherapy) or in combination (e.g., in combination therapy) with one or more additional ingredients, e.g., a pharmaceutically acceptable excipient and/or additional therapeutic agent.

In some embodiments, a cell-penetrating complex or a pharmaceutical composition having the cell-penetrating complex can be used as a vaccine that can induce an immune response in a subject who was administered with the cell-penetrating complex or a pharmaceutical composition thereof.

In some embodiments, the vaccine can have a prophylactic activity such that the vaccine can prevent or reduce a likelihood of the occurrence of a disease or condition in a subject. In embodiments, where the vaccine is used for a prophylactic purpose, a subject can be an animal who does not have the disease or condition, e.g. a human who was not diagnosed with the disease or condition or who does not have a noticeable symptom associated with the disease or condition. In some other embodiments, the vaccine has a therapeutic effect such that the vaccine can be used to treat a disease or condition. Some examples of therapeutic vaccines can include, but are not limited to, cancer vaccines that can be administered to a patient who already suffers from cancer. The cancer vaccines can exhibit one or more anticancer activity, e.g. reduction of cancer cell number, reduction of cancer size, killing of cancer cells, reductions and/or inhibition of metastasis and reduction of cancer cell growth and/or proliferation. In some other embodiments, cancer vaccines can also be used for a prophylactic purpose, especially in a subject who is considered predisposed of cancer but presently does not have the cancer. The prophylactic vaccine can be administered to the predisposed subject with a certain cancer and prevents or reduce a likelihood of the occurrence of the cancer in the subject.

In one aspect, the disclosures herewith provide a method of inducing an immune response against a disease in a subject in need thereof. The method can contain administering an effective amount of a cell-penetrating complex to a subject.

In some embodiments, a cell-penetrating complex can be used as a vaccine that can induce an immune response in a subject who is administrated with the complex. The complex can contain a nucleic acid non-covalently bound to a cationic amphipathic polymer and the cationic amphipathic polymer can have a pH-sensitive immolation domain.

In some embodiments, a disease or condition that is targeted by the vaccine or vaccine composition can include, but not limited to, an autoimmune, inflammatory, cancer, infectious, metabolic, developmental, cardiovascular, liver, intestinal, endocrine, neurological, or other disease.

In some embodiments, the nucleic acid that is contained in the vaccine or composition thereof can be a nucleic acid sequence encoding an antigenic or immunogenic epitope. For example, when an infectious disease is concerned, the nucleic acid contained in the vaccine can encode one or more peptides that are known to be expressed in the pathogen (e.g. pathogenic bacterium or virus) of the infectious disease and can induce an immune response when administered in a subject. In another example where the disease is a specific type of cancer, the nucleic acid administered to a subject using the vaccine composition can encode one or more peptides associated with the cancer, e.g. a peptide that is substantially exclusively expressed in the type of cancer or its expression level is notably higher in the cancer cells as compared to non-cancer cells. When the nucleic acid encoding antigenic or immunogenic peptide(s) is administered to a subject and delivered (i.e. transfected) into certain cells of the subject, the transfected nucleic acid can be eventually translated and expressed into the antigenic peptide(s). Since the expressed peptide(s) is antigenic or immunogenic, an immune response against the expressed peptide can be induced in the subject. The induced immune response can function to treat the target disuse, e.g. by reducing the population of affected cells with specificity if the subject already suffers from the disease, exhibiting a therapeutic effect. Alternatively, the subject can have an acquired immune response via this vaccination in which adaptive immunity can elicit immunological memory after an initial response to the immunogenic peptides that is targeted by the immune response, and leads to an enhanced response to that target on subsequent encounters, exhibiting a prophylactic effect.

In some embodiments, vaccination can provide dual activities of therapeutic and prophylactic effects by delivering two separate types (or sequences) of nucleic acids in a single vaccine composition. The two separate nucleic acids can encode two different immunogenic peptides. Therefore, in some embodiments, the vaccine composition can transfect (1) a first nucleic acid encoding a first immunogenic peptide that can induce more immediate treatment effect to an existing disease or condition and (2) a second nucleic acid encoding a different, second immunogenic peptide that is aimed to induce adaptive immunity in the subject for future occurrence of a different disease or condition. In some embodiments, the vaccine can deliver two or more different nucleic acids to a subject and each nucleic acid independently exhibits a therapeutic or prophylactic effect, respectively.

In embodiments a vaccine composition can have two or more different types (or different formulas) of cationic amphipathic polymer. Alternatively, a vaccine composition can have only a single type (or single formula) of cationic amphipathic polymer. In some embodiments, a single type of cationic amphipathic polymer can be non-covalently bound to one type (sequence) of nucleic acid. Alternatively, a single type of cationic amphipathic polymer can be non-covalently bound to two or more types (sequences) of nucleic acid. Therefore in embodiments, a mixture of different types of cationic amphipathic polymers, each of which is bound to a different sequence of nucleic acid, can be administered together to a subject in order to deliver two or more sequences (or types) of nucleic acids. Alternatively, a single type (or formula) of cationic amphipathic polymer that is bound to multiple types (or sequences) of nucleic acid can be administered to a subject in order to deliver two or more sequences (or types) of nucleic acid. Still alternatively, a single type (or formula) of cationic amphipathic polymer that is bound to a single sequence (or type) of nucleic acid can be administered to a subject.

In some embodiments, the nucleic acid that is contained the vaccine or composition thereof can be messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). In alternative embodiments, the nucleic acid that is contained the vaccine or composition thereof can be mRNA. In some embodiments, nucleic acid is transfected into one or more cells in the subject via vaccination. In some embodiments, one or more than one nucleic acid sequences can be transfected via a vaccine composition. Therefore, in some embodiments, a vaccine composition contains two different nucleic acids, each of which encodes different antigenic peptides, respectively. Accordingly, when the vaccine is administered into a subject in need of the vaccination, two or more types of antigenic epitopes can be expressed and induce immune responses in the subject. In alternative embodiments, one type of nucleic acid can be transfected via vaccination such that one type of epitope can be expressed and induce an immune response in the subject.

In some embodiments, a method of inducing an immune response in a subject in need thereof can have administering one or more additional pharmaceutical composition in an effective amount to the subject, in addition to administering an effective amount of a cell-penetrating complex to the subject. In some embodiments, the additional pharmaceutical composition can contain an anti-cancer agent and optionally a pharmaceutically acceptable carrier. The additional anti-cancer agents can be, for example, antibodies, small molecules, and large molecules or combinations thereof. Examples of anti-cancer activity include, but are not limited to, reduction of cancer cell number, reduction of cancer size, killing of cancer cells, reductions and/or inhibition of metastasis and reduction of cancer cell growth and/or proliferation. In embodiments, the administration of the cell-penetrating complex and additional pharmaceutical composition can exhibit a synergistic effect that is more than a sum of individual administration.

Compositions

In one aspect, the disclosures herewith provides a cationic amphipathic polymer as described herein. In some embodiments, the cationic amphipathic polymer can be non-covalently bound to a nucleic acid. In some embodiments, the cationic amphipathic polymer can have one or more lipophilic polymer domain and one or more pH-sensitive immolation domain. In some embodiments, a cationic amphipathic polymer can be formulated into a composition with one or more optional ingredient. The cationic amphipathic polymer or composition thereof can be formulated into a cell-penetrating complex via non-covalent binding with one or more nucleic acids.

In another aspect, the disclosures herewith provides a cell penetrating complex that contains a nucleic acid and a cationic amphipathic polymer. In some embodiments, the cationic amphipathic polymer can be non-covalently bound to a nucleic acid. In some embodiments, the cationic amphipathic polymer can have one or more lipophilic polymer domain and one or more pH-sensitive immolation domain. In some embodiments, the cell-penetrating complex can be formulated into a composition with one or more optional ingredient.

In some embodiments, a cationic amphipathic polymer or a cell-penetrating complex can be formulated into a composition that can be used to transfect nucleic acid into cells. These compositions that are capable of transfecting nucleic acid into cells are referred to as transfection compositions at least in some embodiments. In some embodiments, a cargo nucleic acid that can be bound to a cationic amphipathic polymer and form a cell-penetrating complex can be a messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). The transfection composition that has a cationic amphipathic polymer but not a cargo nucleic acid can be formulated with the cargo nucleic acid, e.g. contacting (or mixing) the cationic amphipathic polymer and the nucleic acid before transfection.

In embodiments, the transfection of using the composition and method disclosed herein can change one or more cellular properties. In embodiments, the transfection can result in changing a gene expression profile in the transfected cells, e.g. reducing or increasing the expression of one or more gene products (e.g. RNA or peptide). In some other examples, the transfection can result in changing a genome structure, e.g. gene-editing via transfecting components of CRISPR/Cas9 system or a transposon system. In some other examples, the transfection can result in modulating the activity of a cellular pathway. Therefore, in some of such examples, the transfection can result in induction of stem cells. In some other examples, the composition can deliver or (transfect) a cargo nucleic acid that has a therapeutic effect such that the transfection can treat and/or prevent a disease or condition. In some embodiments, the composition delivering (or transfecting) therapeutic cargo nucleic acids can induce an immune response in a subject that was administered with the composition. As apparent from the foregoing, depending on the cargo nucleic acid and the functionality thereof, the compositions according to the present disclosures, including a composition having a cationic amphipathic polymer or a cell-penetrating complex can be used to provide a variety of results in the transfected cells or the administered subject.

Pharmaceutical Compositions

In some embodiments, compositions having a cationic amphipathic polymer or a cell-penetrating complex can be used for a therapeutic purpose. In some embodiments, a therapeutic purpose encompasses a prophylactic purpose (a purpose of preventing a disease or condition from occurring) and a treatment purpose (a purpose of treating an existing disease or condition). When the composition has a cationic amphipathic polymer but not a cargo nucleic acid, the cargo nucleic acid, which can exhibit a therapeutic effect, can be non-covalently bound to the cationic amphipathic polymer, before administration to a subject.

In some embodiments, a composition can be a vaccine or a composition thereof, i.e. a composition that contains the vaccine and optionally a pharmaceutically acceptable carrier. The vaccine or vaccine composition can be used to prevent and/or treat a disease or condition or a pathogen associated with the disease or condition. In some embodiments, the vaccine or vaccine composition contains a cell-penetrating complex which has a cationic amphipathic polymer and a cargo nucleic acid. In some embodiments, the cell-penetrating complex, when administered to a subject, can induce an immune response, i.e. immunogenic. This immunogenicity can be induced, at least in part, when one or more antigenic peptides encoded by the cargo nucleic acid are expressed in the transfected cells.

In one aspect, a cationic amphipathic polymer or a cell-penetrating complex disclosed herein can be formulated in a pharmaceutical composition. The cationic amphipathic polymer can have a pH-sensitive immolation domain. In one embodiment, the pharmaceutical composition can further contain a pharmaceutically acceptable excipient and/or a pharmaceutically acceptable carrier.

In some embodiments, pharmaceutical compositions can have a cell-penetrating complex, which has a nucleic acid non-covalently bound to a cationic amphipathic polymer, as an active ingredient and further contain pharmaceutically acceptable excipients or additives depending on the route of administration. Examples of such excipients or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used can be chosen from, but not limited to, the above or combinations thereof, as appropriate, depending on the dosage form of the present disclosure.

In some embodiments, the pharmaceutically acceptable carrier is an immunological adjuvant. In embodiments, the immunological adjuvant can include, but is not limited to, agonists of Toll-like Receptors (TLRs), agonists of the STING pathway, agonistic antibodies against CD40, OX40, CTLA4, PD1, or PD1-L, Freund's adjuvant, bryostatins and ligands for CD40, OX40, CD137, PD1, CTLA4 and any combinations thereof. In some embodiments, the adjuvant can increase immunogenicity that is induced when a cell-penetrating complex by co-administered with the complex to a subject.

Formulation of the pharmaceutical compositions of the present disclosure can vary according to the route of administration selected (e.g., solution, emulsion). Routes of administration can be, for example, intramuscular, subcutaneous, intravenous, intralymphatic, subcutaneous, intramuscular, intraocular, topical skin, topical conjunctival, oral, intravessical (bladder), intraanal and intravaginal.

In some embodiments, the composition can include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, the formulation is a controlled release formulation. The term "controlled release formulation" includes sustained release and time-release formulations. Controlled release formulations are well-known in the art. These include excipients that allow for sustained, periodic, pulse, or delayed release of the composition. Controlled release formulations include, without limitation, embedding of the composition into a matrix; enteric coatings; micro-encapsulation; gels and hydrogels; implants; and any other formulation that allows for controlled release of a composition.

In one aspect is provided a kit of parts having a cell-penetrating complex or composition thereof. In another aspect is provided a kit of parts having a cationic amphipathic polymer that is not bound to a nucleic acid or composition thereof. The kit can further contain a document or an instruction that describes a protocol for making a cell-penetrating complex using a cationic amphipathic polymer and a cargo nucleic acid. The document or instruction of the kit can also describe a protocol for administering the composition to a subject in need thereof.

Therapeutic formulations described herein can be prepared for storage by mixing the active ingredients, i.e., immunogenic agent(s) having the desired degree of purity with optional physiologically acceptable carriers, excipients or stabilizers. Acceptable carriers, excipients, or stabilizers can be nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound (e.g., a second active agent in addition to the immunogenic agent(s) that has a cell-penetrating complex), which may be selected for complementary activities that do not adversely affect each other. Such molecules can be suitably present in combination in amounts that can be effective, for the purpose intended.

Administration

In some aspects provided are methods for delivering a composition to cells or a subject so as to provide a desired activity into the cells or subject. In some embodiments, the composition can contain a cell-penetrating complex having a cargo nucleic acid that is non-covalently bound to a cationic amphipathic polymer. The cargo nucleic acid, when transfected into the cells or administered to the subject, can provide a variety of intended effects, depending on the nature of the nucleic acid sequence. Some non-limiting examples of intended effects include modulation on gene expression, modulation of cellular pathways, genome-edition and induction of an immune response. In some embodiments, the composition can be administered to a subject in an effective amount that is sufficient to achieve at least part of the intended effects in the subject.

"Administration," "administering" and the like, when used in connection with a composition refer both to direct administration, which may be administration to cells in vitro, administration to cells in vivo, administration to a subject by a medical professional or by self-administration by the subject and/or to indirect administration, which may be the act of prescribing a composition of the disclosure. When used herein in reference to a cell, refers to introducing a composition to the cell. Typically, an effective amount is administered, which amount can be determined by one of skill in the art. Any method of administration may be used. Compounds (e.g., drugs and antibodies) may be administered to the cells by, for example, addition of the compounds to the cell culture media or injection in vivo. Administration to a subject can be achieved by, for example, intravascular injection, direct intratumoral delivery, and the like.

Administering may mean oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the disclosure can be administered alone or can be co-administered to the patient. Co-administration is meant to include simultaneous or sequential administration of the compounds individually or in combination (more than one compound).

The dosage and frequency (single or multiple doses) administered to a subject can vary depending upon a variety of factors, for example, whether the subject suffers from another disease, its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

In some embodiments, the subject is a mammal, for example a human, a non-human primate, a murine (i.e., mouse and rat), a canine, a feline, or an equine. In one embodiment, the subject is a human.

In some embodiments, a composition can be administered in a dose (or an amount) of about 1 ng/kg of subject body weight, about 10 ng/kg of subject body weight, about 50 ng/kg of subject body weight, about 100 ng/kg of subject body weight, about 500 ng/kg of subject body weight, about 1 µg/kg of subject body weight, about 10 µg/kg of subject body weight, about 50 µg/kg of subject body weight, about 100 µg/kg of subject body weight, about 150 µg/kg of subject body weight, about 200 µg/kg of subject body weight, about 250 µg/kg of subject body weight, about 300 µg/kg of subject body weight, about 350 µg/kg of subject body weight, about 375 sg/kg of subject body weight, about 400 µg/kg of subject body weight, about 450 µg/kg of subject body weight, about 500 µg/kg of subject body weight, about 550 µg/kg of subject body weight, about 600 µg/kg of subject body weight, about 650 µg/kg of subject body weight, about 700 µg/kg of subject body weight, about 750 µg/kg of subject body weight, about 800 µg/kg of subject body weight, about 850 µg/kg of subject body weight, about 900 µg/kg of subject body weight, about 1 mg/kg of subject body weight, about 10 mg/kg of subject body weight, about 50 mg/kg of subject body weight, about 100 mg/kg of subject body weight, about 500 mg/kg of subject body weight, about 1 g/kg of subject body weight or more or any intervening ranges of the of the foregoing. In some embodiments, a composition can be administered in a dose (or an amount) of about 0.5 μg, about 1.0 μg, about 1.5 μg, about 2.0 μg, about 2.5 μg, about 3.0 μg, about 3.5 μg, about 4.0 μg, about 4.5 μg about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 1.0 mg, about 1.5 mg, about 2.0 mg, about 2.5 mg, about 3.0 mg, about 3.5 mg, about 4.0 mg, about 4.5 mg about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 1 g or more or any intervening ranges of the foregoing. In some embodiments, a composition can be administered in a dose (or an amount) of about 7.5 μg or about 0.375 mg/kg of subject body weight. Administration can be repeated over a desired period, e.g., repeated over a period of about 1 day to about 5 days or once every several days, for example, about five days, over about 1 month, about 2 months, etc. The weight herein can be a weight of a cell-penetrating complex or a weight of a composition or pharmaceutical formulation thereof. In some embodiments, In one embodiment, a composition can be administered systemically or locally (e.g. intratumoral injection, intravenous injection) at intervals of 6 hours, 12 hours, daily or every other day or on a weekly or monthly basis to elicit the desired benefit or otherwise provide a therapeutic effect.

In one embodiment, a response rate to a composition, in particular a cancer vaccine, can be reduced as compared to baseline reference or control reference. The term "response rate" is used herein in its customary sense to indicate the percentage of patients who respond with cancer recession following treatment. Response rates include, for example, partial or complete recession. A partial response includes an about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, or about 99% recession of cancer cells. In some embodiments, the control reference is obtained from a healthy subject, a cancer subject (e.g., the cancer subject being treated or another cancer subject), or any population thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Compositions and Methods

The compositions and methods provided herein are, inter alia, useful for the delivery of nucleic acids encoding receptor proteins (e.g., chimeric antigen receptors, T cell receptors) to cells in vivo. The compostions provided herein are surprisingly non-immunogenic and provide for superior means for the targeted delivery of nucleic acids to cells such as myeloid or lymphoid cells to a subject in need thereof in vivo. Using the methods and compositions provided herein nucleic acids encoding multiple genes can be easily formulated and delivered in vivo. The compositions and methods provide for a robust expression in vivo and can deliver DNA or mRNA. In embodiments, nucleic acids that encode surface or secreted proteins can be co-delivered (form part of the complexes provided herein). The surface or secreted proteins may enhance the effector function, reduce adverse effects and inhibit suppression of the receptor protein (e.g., CAR) delivered). In one aspect, a cell-penetrating complex including a nucleic acid non-covalently bound to a cationic amphipathic polymer is provided, the cationic amphipathic polymer including a pH-sensitive immolation domain and a lipophilic polymer domain, wherein the cationic amphipathic polymer has the formula:

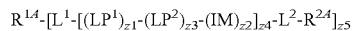

wherein $R^{1A}$ is hydrogen, halogen, —CCl$_3$, —CBr$_3$, —CF$_3$, —C$_{I3}$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$C$_1$, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain; IM is the pH-sensitive immolation domain; $z5$ is an integer from 1 to 10; $z1$ and $z3$ are independently integers from 0 to 100, wherein at least one of $z1$ or $z3$ is not 0; $z4$ is an integer from 1 to 100, and $z2$ is an integer from 2 to 100.

The substituents of the above formula are defined as described throughout the entire application. Thus, in other embodiments of the compounds herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene. In some embodiments, the compound is a chemical species set forth in the Examples section, figures, or tables below.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

$R^{1A}$ is hydrogen, halogen, —$CCl_3$, —$CBr_3$, —$CF_3$, —$Cl_3$, $CHCl_2$, —$CHBr_2$, —$CHF_2$, —$CHI_2$, —$CH_2C_1$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCHBr_2$, —O$CHI_2$, —$OCHF_2$, —$OCH_2C_1$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$ may be independently hydrogen, halogen, —$CCl_3$, —$CBr_3$, —$CF_3$, —$Cl_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, or —$OCH_2I$, or —$OCH^2F$. In embodiments, $R^{1A}$ is independently $R^{1A1}$-substituted or unsubstituted (e.g., $C_1$-$C_{20}$ or $C_1$-$C_6$) alkyl, $R^{1A1}$— substituted or unsubstituted (e.g., 2 to 20 membered or 2 to 6 membered) heteroalkyl, $R^{1A1}$-substituted or unsubstituted (e.g., $C_3$-$C_8$ or $C_5$-$C_7$) cycloalkyl, $R^{1A1}$-substituted or unsubstituted (e.g., 3 to 8 membered or 3 to 6 membered) heterocycloalkyl, $R^{1A1}$-substituted or unsubstituted (e.g., $C_5$-$C_{10}$ or $C_5$-$C_6$) aryl, or $R^{1A1}$-substituted or unsubstituted (e.g., 5 to 10 membered or 5 to 6 membered) heteroaryl.

$R^{1A1}$ may be independently hydrogen, halogen, —$CC_3$, —$CBr_3$, —$CF_3$, —$Cl_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHC_2$, —$OCHBr_2$, —$OCHI_2$, —$OCHF_2$, —$OCH_2Cl$, —$OCH_2Br$, —$OCH_2I$, or —$OCH_2F$. In embodiments, $R^{1A1}$ is independently $R^{1A2}$-substituted or unsubstituted (e.g., $C_1$-$C_{20}$ or $C_1$-$C_6$) alkyl, $R^{1A2}$-substituted or unsubstituted (e.g., 2 to 20 membered or 2 to 6 membered) heteroalkyl, $R^{1A2}$-substituted or unsubstituted (e.g., $C_3$-$C_8$ or $C_5$-$C_7$) cycloalkyl, $R^{1A2}$-substituted or unsubstituted (e.g., 3 to 8 membered or 3 to 6 membered) heterocycloalkyl, $R^{1A2}$-substituted or unsubstituted (e.g., $C_5$-$C_{10}$ or $C_5$-$C_6$) aryl, or $R^{1A2}$-substituted or unsubstituted (e.g., 5 to 10 membered or 5 to 6 membered) heteroaryl.

$R^{1A2}$ may be independently hydrogen, halogen, —$CCl_3$, —$CBr_3$, —$CF_3$, —$C_{13}$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2C_1$, —$OCH_2Br$, —$OCH_2I$, or —$OCH_2F$. In embodiments, $R^{1A2}$ is independently $R^{1A3}$-substituted or unsubstituted (e.g., $C_1$-$C_{20}$ or $C_1$-$C_6$) alkyl, $R^{1A3}$_substituted or unsubstituted (e.g., 2 to 20 membered or 2 to 6 membered) heteroalkyl, $R^{1A3}$-substituted or unsubstituted (e.g., $C_3$-$C_8$ or $C_5$-$C_7$) cycloalkyl, $R^{1A3}$-substituted or unsubstituted (e.g., 3 to 8 membered or 3 to 6 membered) heterocycloalkyl, $R^{1A3}$-substituted or unsubstituted (e.g., $C_5$-$C_{10}$ or $C_5$-$C_6$) aryl, or $R^{1A3}$-substituted or unsubstituted (e.g., 5 to 10 membered or 5 to 6 membered) heteroaryl.

$R^{1A3}$ may be independently hydrogen, halogen, —$CCl_3$, —$CBr_3$, —$CF_3$, —$Cl_3$, $CHC_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, or —$OCH_2F$. In embodiments, $R^{1A3}$ is independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$R^{2A}$ may be independently hydrogen, halogen, —$CCl_3$, —$CBr_3$, —$CF_3$, —$Cl_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, or —$OCH_2F$. In embodiments, $R^{2A}$ is independently $R^{2A}1$-substituted or unsubstituted (e.g., $C_1$-$C_{20}$ or $C_1$-$C_6$) alkyl, $R^{2A}1$-substituted or unsubstituted (e.g., 2 to 20 membered or 2 to 6 membered) heteroalkyl, $R^{2A}1$-substituted or unsubstituted (e.g., $C_3$-$C_8$ or $C_5$-$C_7$) cycloalkyl, $R^{2A1}$-substituted or unsubstituted (e.g., 3 to 8 membered or 3 to 6 membered) heterocycloalkyl, $R^{2A1}$-substituted or unsubstituted (e.g., $C_5$-$C_{10}$ or $C_5$-$C_6$) aryl, or $R^{2A1}$-substituted or unsubstituted (e.g., 5 to 10 membered or 5 to 6 membered) heteroaryl.

$R^{2A1}$ may be independently hydrogen, halogen, —CCl$_3$, —CBr$_3$, —CF$_3$, —C$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, $R^{2A1}$ is independently $R^{2A2}$-substituted or unsubstituted (e.g., $C_1$-$C_{20}$ or $C_1$-$C_6$) alkyl, $R^{2A2}$-substituted or unsubstituted (e.g., 2 to 20 membered or 2 to 6 membered) heteroalkyl, $R^{2A2}$-substituted or unsubstituted (e.g., $C_3$-$C_8$ or $C_5$-$C_7$) cycloalkyl, $R^{2A2}$-substituted or unsubstituted (e.g., 3 to 8 membered or 3 to 6 membered) heterocycloalkyl, $R^{2A2}$-substituted or unsubstituted (e.g., $C_5$-$C_{10}$ or $C_5$-$C_6$) aryl, or $R^{2A2}$-substituted or unsubstituted (e.g., 5 to 10 membered or 5 to 6 membered) heteroaryl.

$R^{2A2}$ may be independently hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, $R^{2A2}$ is independently $R^{2A3}$-substituted or unsubstituted (e.g., $C_1$-$C_{20}$ or $C_1$-$C_6$) alkyl, $R^{2A3}$-substituted or unsubstituted (e.g., 2 to 20 membered or 2 to 6 membered) heteroalkyl, $R^{2A3}$-substituted or unsubstituted (e.g., $C_3$-$C_8$ or $C_5$-$C_7$) cycloalkyl, $R^{2A3}$-substituted or unsubstituted (e.g., 3 to 8 membered or 3 to 6 membered) heterocycloalkyl, $R^{2A3}$-substituted or unsubstituted (e.g., $C_5$-$C_{10}$ or $C_5$-$C_6$) aryl, or $R^{2A3}$-substituted or unsubstituted (e.g., 5 to 10 membered or 5 to 6 membered) heteroaryl.

$R^{2A3}$ may be independently hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, $R^{2A3}$ is independently unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$L^1$ is independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is unsubstituted (e.g., $C_1$-$C_{20}$ or $C_1$-$C_6$) alkylene, unsubstituted (e.g., 2 to 20 membered or 2 to 6 membered) heteroalkylene, unsubstituted (e.g., $C_3$-$C_8$ or $C_5$-$C_7$) cycloalkylene, unsubstituted (e.g., 3 to 8 membered or 3 to 6 membered) heterocycloalkylene, unsubstituted (e.g., $C_5$-$C_{10}$ or $C_5$-$C_6$) arylene, or unsubstituted (e.g., 5 to 10 membered or 5 to 6 membered) heteroarylene. In embodiments, $L^1$ is $R^{L1}$-substituted (e.g., $C_1$-$C_{20}$ or $C_1$-$C_6$) alkylene, $R^{L1}$-substituted (e.g., 2 to 20 membered or 2 to 6 membered) heteroalkylene, $R^{L1}$-substituted (e.g., $C_3$-$C_8$ or $C_5$-$C_7$) cycloalkylene, $R^{L1}$-substituted (e.g., 3 to 8 membered or 3 to 6 membered) heterocycloalkylene, $R^{L1}$-substituted (e.g., $C_5$-$C_{10}$ or $C_5$-$C_6$) arylene, or $R^{L1}$-substituted (e.g., 5 to 10 membered or 5 to 6 membered) heteroarylene. $R^{L1}$ may be independently hydrogen, halogen, =O, =S, —CF$_3$, —CN, —CCl$_3$, —COOH, —CH$_2$COOH, —CONH$_2$, —OH, —SH, —SO$_2$Cl, —SO$_3$H, —SO$_4$H, SO$_2$NH$_2$, —NO$_2$, —NH$_2$, —NHNH$_2$, —ONH$_2$, —NHC=(O)NHNH$_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

$L^2$ is independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is unsubstituted (e.g., $C_1$-$C_{20}$ or $C_1$-$C_6$) alkylene, unsubstituted (e.g., 2 to 20 membered or 2 to 6 membered) heteroalkylene, unsubstituted (e.g., $C_3$-$C_8$ or $C_5$-$C_7$) cycloalkylene, unsubstituted (e.g., 3 to 8 membered or 3 to 6 membered) heterocycloalkylene, unsubstituted (e.g., $C_5$-$C_{10}$ or $C_5$-$C_6$) arylene, or unsubstituted (e.g., 5 to 10 membered or 5 to 6 membered) heteroarylene. In embodiments, $L^2$ is $R^{L2}$-substituted (e.g., $C_1$-$C_{20}$ or $C_1$-$C_6$) alkylene, $R^{L2}$-substituted (e.g., 2 to 20 membered or 2 to 6 membered) heteroalkylene, $R^{L2}$-substituted (e.g., $C_3$-$C_8$ or $C_5$-$C_7$) cycloalkylene, $R^{L2}$-substituted (e.g., 3 to 8 membered or 3 to 6 membered) heterocycloalkylene, $R^{L2}$-substituted (e.g., $C_5$-$C_{10}$ or $C_5$-$C_6$) arylene, or $R^{L2}$-substituted (e.g., 5 to 10 membered or 5 to 6 membered) heteroarylene. $R^{L2}$ may be independently hydrogen, halogen, =O, =S, —CF$_3$, —CN, —CCl$_3$, —COOH, —CH$_2$COOH, —CONH$_2$, —OH, —SH, —SO$_2$C$_1$, —SO$_3$H, —SO$_4$H, SO$_2$NH$_2$, —NO$_2$, —NH$_2$, —NHNH$_2$, —ONH$_2$, —NHC=(O)NHNH$_2$, unsubstituted (e.g., $C_1$-$C_{20}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, the cationic amphipathic polymer has the formula:

wherein

Ring A is a substituted or unsubstituted cycloalkyl, substituted or unsubstituted heterocycloalkyl, substituted or unsubstituted aryl, or substituted or unsubstituted heteroaryl; CART has the formula: $-L^1-[(LP^1)_{z1}-(LP^2)_{z3}-(IM)_{z2}]_{z4}-L^2-R^{24}$ wherein, $R^{24}$ is hydrogen, halogen, —CCl$_3$, —CBr$_3$, —CF$_3$, —C$_{I3}$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkyl, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a lipophilic polymer domain; IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl.

In embodiments, the cationic amphipathic polymer has the formula:

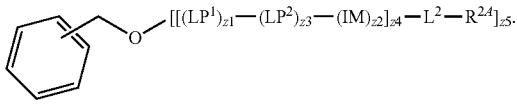

In embodiments, the cationic amphipathic polymer has the formula:

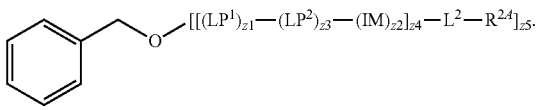

In embodiments, the cationic amphipathic polymer has the formula:

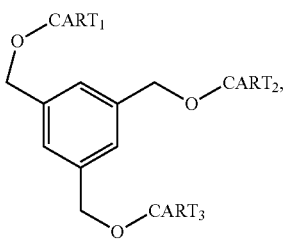

wherein CART$_1$, CART$_2$ and CART$_3$ are independently CART as defined herein.

In embodiments, z5 is an integer from 1 to 3. In embodiments, z5 is 1 or 3. In embodiments, z5 is 1. In embodiments, z5 is 3. In embodiments, $R^{24}$ is hydrogen. In embodiments, $L^2$ is a bond.

In embodiments, the pH-sensitive immolation domain has the formula:

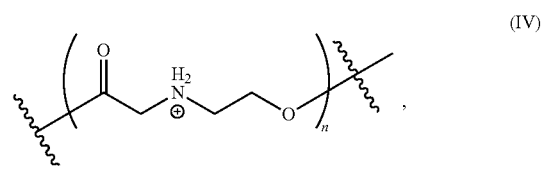

(IV)

wherein n is an integer of 2 or more. In embodiments, n is an integer in the range of 2-50. In embodiments, n is 7.

In embodiments, the lipophilic polymer domain has the formula:

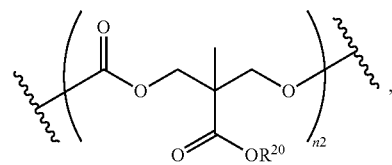

wherein n2 is an integer from 1 to 100;

$R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $LP^1$ has the formula:

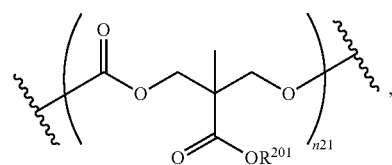

wherein n21 is an integer from 1 to 100;

$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^{201}$ is independently $R^{201A}$-substituted or unsubstituted (e.g., $C_1$-$C_{30}$ or $C_1$-$C_6$) alkyl, $R^{201A}$-substituted or unsubstituted (e.g., 2 to 20 membered or 2 to 6 membered) heteroalkyl, $R^{201A}$-substituted or unsubstituted (e.g., $C_3$-$C_8$ or $C_5$-$C_7$) cycloalkyl, $R^{201A}$-substituted or unsubstituted (e.g., 3 to 8 membered or 3 to 6 membered) heterocycloalkyl, $R^{201A}$-substituted or unsubstituted (e.g., $C_5$-$C_{10}$ or $C_5$-$C_6$) aryl, or $R^{201A}$-substituted or unsubstituted (e.g., 5 to 10 membered or 5 to 6 membered) heteroaryl.

In embodiments, $R^{201A}$ is independently $R^{201B}$-substituted or unsubstituted (e.g., $C_1$-$C_{30}$ or $C_1$-$C_6$) alkyl, $R^{201B}$-substituted or unsubstituted (e.g., 2 to 20 membered or 2 to 6 membered) heteroalkyl, $R^{201B}$-substituted or unsubstituted (e.g., $C_3$-$C_8$ or $C_5$-$C_7$) cycloalkyl, $R^{201B}$-substituted or unsubstituted (e.g., 3 to 8 membered or 3 to 6 membered) heterocycloalkyl, $R^{201B}$-substituted or unsubstituted (e.g., $C_5$-$C_{10}$ or $C_5$-$C_6$) aryl, or $R^{201B}$. substituted or unsubstituted (e.g., 5 to 10 membered or 5 to 6 membered) heteroaryl.

In embodiments, $R^{201B}$ is independently unsubstituted (e.g., $C_1$-$C_{30}$ or $C_1$-$C_6$) alkyl, unsubstituted (e.g., 2 to 20 membered or 2 to 6 membered) heteroalkyl, unsubstituted (e.g., $C_3$-$C^8$ or $C^5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, n21 is 5 and $R^{201}$ is unsubstituted $C_{18}$ alkenyl. In embodiments, the unsubstituted $C_{18}$ alkenyl is oleyl.

In embodiments, n21 is an integer from 0 to 100. In embodiments, n21 is an integer from 0 to 90. In embodiments, n21 is an integer from 0 to 80. In embodiments, n21 is an integer from 0 to 70. In embodiments, n21 is an integer from 0 to 60. In embodiments, n21 is an integer from 0 to 50. In embodiments, n21 is an integer from 0 to 40. In embodiments, n21 is an integer from 0 to 30. In embodiments, n21 is an integer from 0 to 20. In embodiments, n21 is an integer from or 0 to 10. In embodiments, n21 is an integer from 5 to 100. In embodiments, n21 is an integer from 15 to 100. In embodiments, n21 is an integer from 25 to 100. In embodiments, n21 is an integer from 35 to 100. In embodiments, n21 is an integer from 45 to 100. In embodiments, n21 is an integer from 55 to 100. In embodiments, n21 is an integer from 65 to 100. In embodiments, n21 is an integer from 75 to 100. In embodiments, n21 is an integer from 85 to 100. In embodiments, n21 is an integer from 95 to 100. In embodiments, n21 is 0. In embodiments, n21 is 1. In embodiments, n21 is 2. In embodiments, n21 is 3. In embodiments, n21 is 4. In embodiments, n21 is 5. In embodiments, n21 is 6. In embodiments, n21 is 7. In embodiments, n21 is 8. In embodiments, n21 is 9. In embodiments, n21 is 10. In embodiments, n21 is 11. In embodiments, n21 is 12.

In embodiments, n21 is 13. In embodiments, n21 is 14. In embodiments, n21 is 15. In embodiments, n21 is 16. In embodiments, n21 is 17. In embodiments, n21 is 18. In embodiments, n21 is 19. In embodiments, n21 is 20. In embodiments, n21 is 21. In embodiments, n21 is 22. In embodiments, n21 is 23. In embodiments, n21 is 24. In embodiments, n21 is 25. In embodiments, n21 is 26. In embodiments, n21 is 27. In embodiments, n21 is 28. In embodiments, n21 is 29. In embodiments, n21 is 30. In embodiments, n21 is 31. In embodiments, n21 is 32. In embodiments, n21 is 33. In embodiments, n21 is 34. In embodiments, n21 is 35. In embodiments, n21 is 36. In embodiments, n21 is 37. In embodiments, n21 is 38. In embodiments, n21 is 39. In embodiments, n21 is 40. In embodiments, n21 is 41. In embodiments, n21 is 42. In embodiments, n21 is 43. In embodiments, n21 is 44. In embodiments, n21 is 45. In embodiments, n21 is 46. In embodiments, n21 is 47. In embodiments, n21 is 48. In embodiments, n21 is 49. In embodiments, n21 is 50. In embodiments, n21 is 51. In embodiments, n21 is 52. In embodiments, n21 is 53. In embodiments, n21 is 54. In embodiments, n21 is 55. In embodiments, n21 is 56. In embodiments, n21 is 57. In embodiments, n21 is 58. In embodiments, n21 is 59. In embodiments, n21 is 60. In embodiments, n21 is 61. In embodiments, n21 is 62. In embodiments, n21 is 63. In embodiments, n21 is 64. In embodiments, n21 is 65. In embodiments, n21 is 66. In embodiments, n21 is 67. In embodiments, n21 is 68. In embodiments, n21 is 69. In embodiments, n21 is 70. In embodiments, n21 is 71. In embodiments, n21 is 72. In embodiments, n21 is 73. In embodiments, n21 is 74. In embodiments, n21 is 75. In embodiments, n21 is 76. In embodiments, n21 is 77. In embodiments, n21 is 78. In embodiments, n21 is 79. In embodiments, n21 is 80. In embodiments, n21 is 81. In embodiments, n21 is 82. In embodiments, n21 is 83. In embodiments, n21 is 84. In embodiments, n21 is 85. In embodiments, n21 is 86. In embodiments, n21 is 87. In embodiments, n21 is 88. In embodiments, n21 is 89. In embodiments, n21 is 90. In embodiments, n21 is 91. In embodiments, n21 is 92. In embodiments, n21 is 93. In embodiments, n21 is 94. In embodiments, n21 is 95. In embodiments, n21 is 96. In embodiments, n21 is 97. In embodiments, n21 is 98. In embodiments, n21 is 99. In embodiments, n21 is 100.

In embodiments, $LP^2$ has the formula:

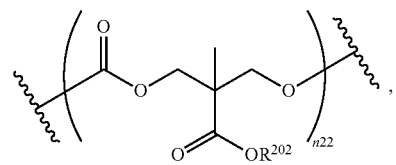

wherein n22 is an integer from 1 to 100; $R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n22 is 5 and $R^{202}$ is unsubstituted $C_9$ alkenyl. In embodiments, the unsubstituted $C_9$ alkenyl is nonenyl.

In embodiments, $R^{202}$ is independently $R^{202A}$-substituted or unsubstituted (e.g., $C_1$-$C_{30}$ or $C_1$-$C_6$) alkyl, $R^{202A}$-substituted or unsubstituted (e.g., 2 to 20 membered or 2 to 6 membered) heteroalkyl, $R^{202A}$-substituted or unsubstituted (e.g., $C_3$-$C_8$ or $C_5$-$C_7$) cycloalkyl, $R^{202A}$-substituted or unsubstituted (e.g., 3 to 8 membered or 3 to 6 membered) heterocycloalkyl, $R^{202A}$-substituted or unsubstituted (e.g., $C_5$-$C_{10}$ or $C_5$-$C_6$) aryl, or $R^{202A}$-substituted or unsubstituted (e.g., 5 to 10 membered or 5 to 6 membered) heteroaryl.

In embodiments, $R^{202A}$ is independently $R^{202B}$-substituted or unsubstituted (e.g., $C_1$-$C_{30}$ or $C_1$-$C_6$) alkyl, $R^{202B}$-substituted or unsubstituted (e.g., 2 to 20 membered or 2 to 6 membered) heteroalkyl, $R^{202B}$-substituted or unsubstituted (e.g., $C_3$-$C_8$ or $C_5$-$C_7$) cycloalkyl, $R^{202B}$-substituted or unsubstituted (e.g., 3 to 8 membered or 3 to 6 membered) heterocycloalkyl, $R^{202B}$-substituted or unsubstituted (e.g., $C_5$-$C_{10}$ or $C_5$-$C_6$) aryl, or $R^{202B}$-substituted or unsubstituted (e.g., 5 to 10 membered or 5 to 6 membered) heteroaryl.

In embodiments, $R^{202B}$ is independently unsubstituted (e.g., $C_1$-$C_{30}$ or $C_1$-$C_6$) alkyl, unsubstituted (e.g., 2 to 20 membered or 2 to 6 membered) heteroalkyl, unsubstituted (e.g., $C_3$-$C_8$ or $C_5$-$C_7$) cycloalkyl, unsubstituted (e.g., 3 to 8 membered or 3 to 6 membered) heterocycloalkyl, unsubstituted (e.g., $C_5$-$C_{10}$ or $C_5$-$C_6$) aryl, or unsubstituted (e.g., 5 to 10 membered or 5 to 6 membered) heteroaryl.

In embodiments, n22 is an integer from 0 to 100. In embodiments, n22 is an integer from 0 to 90. In embodiments, n22 is an integer from 0 to 80. In embodiments, n22 is an integer from 0 to 70. In embodiments, n22 is an integer from 0 to 60. In embodiments, n22 is an integer from 0 to 50. In embodiments, n22 is an integer from 0 to 40. In embodiments, n22 is an integer from 0 to 30. In embodiments, n22 is an integer from 0 to 20. In embodiments, n22 is an integer from or 0 to 10. In embodiments, n22 is an integer from 5 to 100. In embodiments, n22 is an integer from 15 to 100. In embodiments, n22 is an integer from 25 to 100. In embodiments, n22 is an integer from 35 to 100. In embodiments, n22 is an integer from 45 to 100. In embodiments, n22 is 93. In embodiments, n22 is 94. In embodiments, n22 is 95. In embodiments, n22 is 96. In embodiments, n22 is 97. In embodiments, n22 is 98. In embodiments, n22 is 99. In embodiments, n22 is 100.

In embodiments, the cationic amphipathic polymer has the formula:

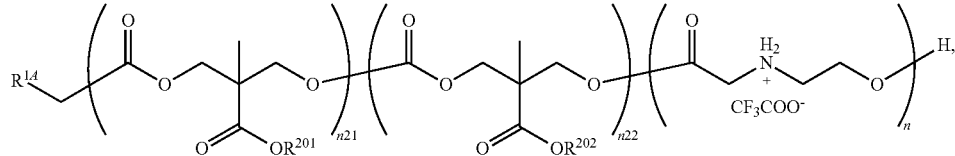

embodiments, n22 is an integer from 55 to 100. In embodiments, n22 is an integer from 65 to 100. In embodiments, n22 is an integer from 75 to 100. In embodiments, n22 is an integer from 85 to 100. In embodiments, n22 is an integer from 95 to 100. In embodiments, n22 is 0. In embodiments, n22 is 1. In embodiments, n22 is 2. In embodiments, n22 is 3. In embodiments, n22 is 4. In embodiments, n22 is 5. In embodiments, n22 is 6. In embodiments, n22 is 7. In embodiments, n22 is 8. In embodiments, n22 is 9. In embodiments, n22 is 10. In embodiments, n22 is 11. In embodiments, n22 is 12.

In embodiments, n22 is 13. In embodiments, n22 is 14. In embodiments, n22 is 15. In embodiments, n22 is 16. In embodiments, n22 is 17. In embodiments, n22 is 18. In embodiments, n22 is 19. In embodiments, n22 is 20. In embodiments, n22 is 21. In embodiments, n22 is 22. In embodiments, n22 is 23. In embodiments, n22 is 24. In embodiments, n22 is 25. In embodiments, n22 is 26. In embodiments, n22 is 27. In embodiments, n22 is 28. In embodiments, n22 is 29. In embodiments, n22 is 30. In embodiments, n22 is 31. In embodiments, n22 is 32. In embodiments, n22 is 33. In embodiments, n22 is 34. In embodiments, n22 is 35. In embodiments, n22 is 36. In embodiments, n22 is 37. In embodiments, n22 is 38. In embodiments, n22 is 39. In embodiments, n22 is 40. In embodiments, n22 is 41. In embodiments, n22 is 42. In embodiments, n22 is 43. In embodiments, n22 is 44. In embodiments, n22 is 45. In embodiments, n22 is 46. In embodiments, n22 is 47. In embodiments, n22 is 48. In embodiments, n22 is 49. In embodiments, n22 is 50. In embodiments, n22 is 51. In embodiments, n22 is 52. In embodiments, n22 is 53. In embodiments, n22 is 54. In embodiments, n22 is 55. In embodiments, n22 is 56. In embodiments, n22 is 57. In embodiments, n22 is 58. In embodiments, n22 is 59. In embodiments, n22 is 60. In embodiments, n22 is 61. In embodiments, n22 is 62. In embodiments, n22 is 63. In embodiments, n22 is 64. In embodiments, n22 is 65. In embodiments, n22 is 66. In embodiments, n22 is 67. In embodiments, n22 is 68. In embodiments, n22 is 69. In embodiments, n22 is 70. In embodiments, n22 is 71. In embodiments, n22 is 72. In embodiments, n22 is 73. In embodiments, n22 is 74. In embodiments, n22 is 75. In embodiments, n22 is 76. In embodiments, n22 is 77. In embodiments, n22 is 78. In embodiments, n22 is 79. In embodiments, n22 is 80. In embodiments, n22 is 81. In embodiments, n22 is 82. In embodiments, n22 is 83. In embodiments, n22 is 84. In embodiments, n22 is 85. In embodiments, n22 is 86. In embodiments, n22 is 87. In embodiments, n22 is 88. In embodiments, n22 is 89. In embodiments, n22 is 90. In embodiments, n22 is 91. In embodiments, n22 is 92. In wherein n21 is 5, $R^{201}$ is oleyl, n22 is 5, $R^{202}$ is nonenyl and n is 7.

In embodiments, the nucleic acid is an messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA). In embodiments, the nucleic acid includes a sequence encoding a chimeric antigen receptor (CAR).

In an aspect, a nanoparticle composition including a plurality of cell-penetrating complexes as provided herein including embodiments thereof is provided.

In an aspect, a pharmaceutical composition including the complex as provided herein including embodiments thereof and a pharmaceutically acceptable carrier is provided.

In an aspect, method of transfecting a nucleic acid into a cell is provided, the method including contacting a cell with the complex as provided herein including embodiments thereof.

In embodiments, the cationic amphipathic polymer is allowed to degrade within the cell thereby forming a degradation product. In embodiments, the degradation product is a substituted or unsubstituted diketopiperazine.

In embodiments, the nucleic acid includes a CAR encoding messenger RNA (mRNA).

In embodiments, the methods further include allowing the mRNA to be expressed in the cell. In embodiments, the cell is an eukaryotic cell. In embodiments, the cell is a mammalian or human cell. In embodiments, the cell forms part of an organism. In embodiments, the organism is a human. In embodiments, the cell is a lymphoid cell or a myeloid cell. In embodiments, the cell is a T cell. In embodiments, the cell is a myeloid cell.

In an aspect is provided, a method of inducing an immune response in a subject in need thereof, the method including administering an effective amount of the complex as provided herein including embodiments thereof. In embodiments, the immune response is an anti-cancer immune response.

In an aspect, a method of treating cancer in a subject in need thereof is provided. The method includes administering an effective amount of the complex as provided herein including embodiments thereof. In embodiments, the administering includes intravenous injection or subcutaneous injection.

In an aspect, a method of transfecting a nucleic acid encoding a chimeric antigen receptor (CAR) into a cell is provided. The method includes contacting a cell with a cell-penetrating complex including a nucleic acid non-covalently bound to a cationic amphipathic polymer, the cationic amphipathic polymer including a pH-sensitive immolation domain and a lipophilic polymer domain, and the nucleic acid including a sequence encoding a chimeric antigen receptor.

In embodiments, the cationic amphipathic polymer has the formula:

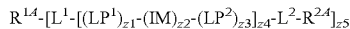

$R^{1A}\text{-}[L^1\text{-}[(LP^1)_{z1}\text{-}(IM)_{z2}\text{-}(LP^2)_{z3}]_{z4}\text{-}L^2\text{-}R^{2A}]_{z5}$ wherein
$R^{1A}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$C$_1$, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —CCl$_3$, —CBr$_3$, —CF$_3$, —C$_{13}$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain; IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, the cationic amphipathic polymer has the formula:

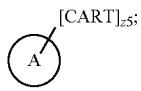

wherein Ring A is a substituted or unsubstituted cycloalkyl, substituted or unsubstituted heterocycloalkyl, substituted or unsubstituted aryl, or substituted or unsubstituted heteroaryl; CART has the formula: -$L^1$-[(LP$^1$)$_{z1}$-(IM)$_{z2}$-(LP$^2$)$_{z3}$]$_{z4}$-$L^2$-$R^{2A}$ wherein,
$R^{2A}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$ —, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl. In embodiments, the cationic amphipathic polymer has the formula:

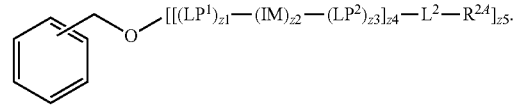

In embodiments, the cationic amphipathic polymer has the formula:

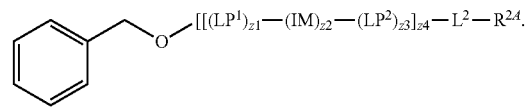

In embodiments, the cationic amphipathic polymer has the formula:

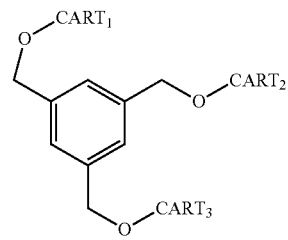

wherein $CART_1$, $CART_2$ and $CART_3$ are independently CART as defined herein.

In embodiments, the $L^1$ is $-CH_2-O-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the pH-sensitive immolation domain has the formula:

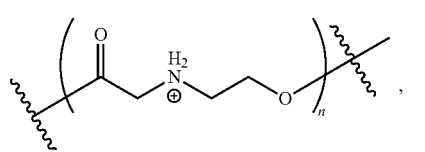

(IV)

wherein n is an integer of 2 or more.

In embodiments, the cationic amphipathic polymer has the formula:

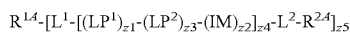

$R^{1A}$-$[L^1$-$[(LP^1)_{z1}$-$(LP^2)_{z3}$-$(IM)_{z2}]_{z4}$-$L^2$-$R^{2A}]_{z5}$ wherein $R^{1A}$ is hydrogen, halogen, $-CCl_3$, $-CBr_3$, $-CF_3$, $-C_{13}$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, $-CCl_3$, $-CBr_3$, $-CF_3$, $-C_{13}$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a lipophilic polymer domain;

IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, the cationic amphipathic polymer has the formula:

wherein Ring A is a substituted or unsubstituted cycloalkyl, substituted or unsubstituted heterocycloalkyl, substituted or unsubstituted aryl, or substituted or unsubstituted heteroaryl;

CART has the formula: $-L^1$-$[(LP^1)_{z1}$-$(LP^2)_{z3}$-$(IM)_{z2}]_{z4}$-$L^2$-$R^{2A}$ wherein, $R^{2A}$ is hydrogen, halogen, $-CCl_3$, $-CBr_3$, $-CF_3$, $-Cl_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCl_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, $-C(O)O-$, $-O-$, $-S-$, $-NH-$, $-C(O)NH-$, $-NHC(O)-$, $-S(O)_2-$, $-S(O)NH-$, $-NHC(O)NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $LP^1$ and $LP^2$ are independently a lipophilic polymer domain;

IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl.

In embodiments, the cationic amphipathic polymer has the formula:

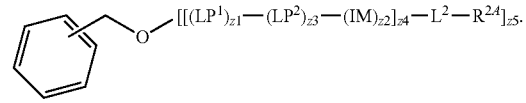

In embodiments, the cationic amphipathic polymer has the formula:

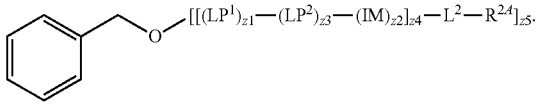

In embodiments, the cationic amphipathic polymer has the formula:

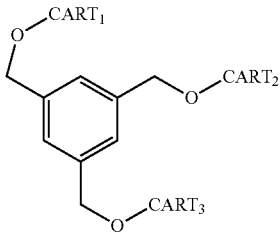

wherein $CART_1$, $CART_2$ and $CART_3$ are independently CART as defined herein.

In embodiments, z5 is an integer from 1 to 3. In embodiments, z5 is 1 or 3. In embodiments, z5 is 1. In embodiments, z5 is 3. In embodiments, $R^{24}$ is hydrogen. In embodiments, $L^2$ is a bond.

In embodiments, the pH-sensitive immolation domain has the formula:

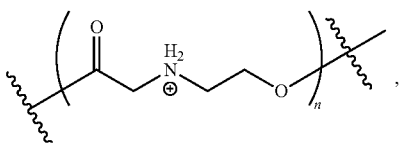

(IV)

wherein n is an integer of 2 or more. In embodiments, n is an integer in the range of 2-50. In embodiments, n is 7.

In embodiments, the lipophilic polymer domain has the formula:

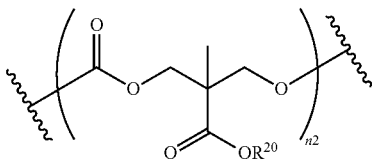

wherein n2 is an integer from 1 to 100; $R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $LP^1$ has the formula:

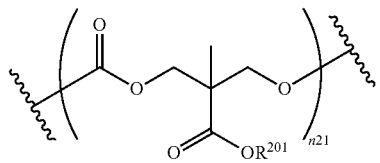

wherein n21 is an integer from 0 to 100; $R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n21 is 5 and $R^{201}$ is unsubstituted $C_{18}$ alkenyl.

In embodiments, $LP^2$ has the formula:

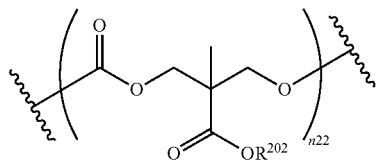

wherein n22 is an integer from 1 to 100; $R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, n22 is 5 and $R^{202}$ is unsubstituted $C_9$ alkenyl.

In embodiments, the cell is an eukaryotic cell. In embodiments, the cell is a mammalian or human cell. In embodiments, the cell forms part of an organism. In embodiments, the organism is a human. In embodiments, the cell is a lymphoid cell or a myeloid cell. In embodiments, the cell is a T cell. In embodiments, the cell is a myeloid cell.

In one aspect, a cationic amphipathic polymer is provided. The cationic amphipathic polymer has the formula:

$$R^{1A}\text{-}[L^1\text{-}[(LP^1)_{z1}\text{-}(LP^2)_{z3}\text{-}(IM)_{z2}]_{z4}\text{-}L^2\text{-}R^{24}]_{z5}$$

wherein
$R^{1A}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{24}$ is hydrogen, halogen, —CCl$_3$, —CBr$_3$, —CF$_3$, —Cl$_3$, CHCl$_2$, —CHBr$_2$, —CHF$_2$, —CH$_{12}$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)

H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

LP$^1$ and LP$^2$ are independently a lipophilic polymer domain; IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100.

In embodiments, the cationic amphipathic polymer has the formula:

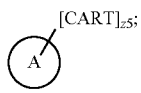

wherein

Ring A is a substituted or unsubstituted cycloalkyl, substituted or unsubstituted heterocycloalkyl, substituted or unsubstituted aryl, or substituted or unsubstituted heteroaryl; CART has the formula: -L$^1$-[(LP$^1$)$_{z1}$-(LP$^2$)$_{z3}$-(IM)$_{z2}$]$_{z4}$-L$^2$-R$^{24}$ wherein, R$^{24}$ is hydrogen, halogen, —CCl$_3$, —CBr$_3$, —CF$_3$, —C$_{I3}$, CHCl$_2$, —CHBr$_2$, —CHF$_2$, —CH$_{I2}$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCH$_{I2}$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; LP$^1$ and LP$^2$ are independently a lipophilic polymer domain; IM is the pH-sensitive immolation domain; z5 is an integer from 1 to 10; z1 and z3 are independently integers from 0 to 100, wherein at least one of z1 or z3 is not 0; z4 is an integer from 1 to 100, and z2 is an integer from 2 to 100. In embodiments, Ring A is a substituted or unsubstituted aryl. In embodiments, Ring A is a substituted or unsubstituted phenyl. In embodiments, Ring A is a substituted or unsubstituted aryl. In embodiments, Ring A is a substituted or unsubstituted phenyl or naphthalenyl.

In embodiments, the cationic amphipathic polymer has the formula:

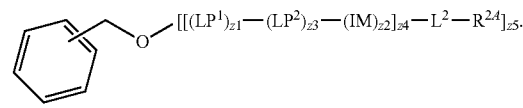

In embodiments, the cationic amphipathic polymer has the formula:

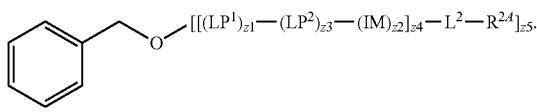

In embodiments, the cationic amphipathic polymer has the formula:

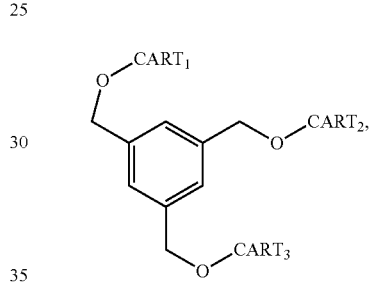

wherein CART$_1$, CART$_2$ and CART$_3$ are independently CART as defined herein.

In embodiments, z5 is an integer from 1 to 3. In embodiments, z5 is 1 or 3. In embodiments, z5 is 1. In embodiments, z5 is 3. In embodiments, R$^{24}$ is hydrogen. In embodiments, L$^2$ is a bond.

In embodiments, the pH-sensitive immolation domain has the formula:

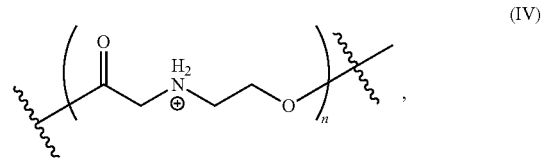

(IV)

wherein n is an integer of 2 or more. In embodiments, n is an integer in the range of 2-50. In embodiments, n is 7.

In embodiments, the lipophilic polymer domain has the formula:

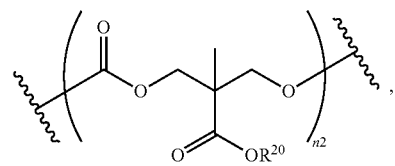

wherein n2 is an integer from 1 to 100; $R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $LP^1$ has the formula:

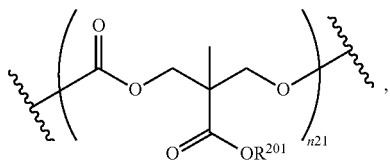

wherein n21 is an integer from 1 to 100;
$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, n21 is 5 and $R^{201}$ is unsubstituted Cis alkenyl. In embodiments, unsubstituted $C_{18}$ alkenyl is oleyl.

In embodiments, $LP^2$ has the formula:

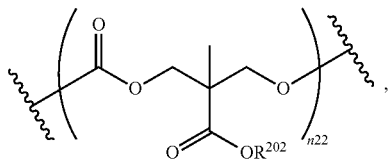

wherein n22 is an integer from 1 to 100;
$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, n22 is 5 and $R^{202}$ is unsubstituted $C_9$ alkenyl. In embodiments, the unsubstituted $C_9$ alkenyl is nonenyl.

In embodiments, the cationic amphipathic polymer has the formula:

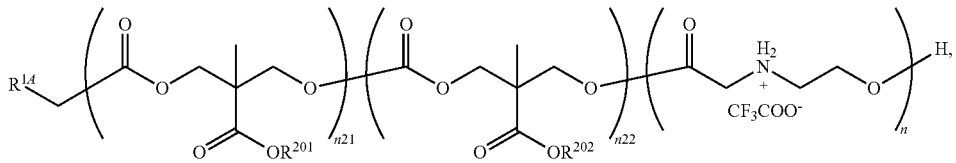

wherein n21 is 5, $R^{201}$ is oleyl, n22 is 5, $R^{202}$ is nonenyl and n is 7.

In an aspect a method of transfecting a nucleic acid encoding a receptor protein into a cell in a subject is provided. The method includes administering to a subject a cell-penetrating complex including a nucleic acid encoding a receptor protein bound to a compound, wherein the compound degrades upon delivery into the cell, thereby transfecting a nucleic acid encoding a receptor protein into a cell in a subject. A "receptor protein" a referred to herein is a protein expressed by a cell on its surface and capable of binding a ligand. Non-limiting examples of receptor proteins include chimeric antigen receptors, T cell receptors, B cell receptors, growth factor receptors, and cytokine receptors. In embodiments, the receptor protein is a chimeric antigen receptor. In embodiments, the receptor protein is a T cell receptor. In embodiments, the receptor protein is an antibody. In embodiments, the receptor protein is anti-$IL^{10}$. In embodiments, the receptor protein is anti-PD1. In embodiments, the receptor protein is anti-$PDL^1$. In embodiments, the receptor protein is anti-TGFbeta. In embodiments, the receptor protein is anti-TNF alpha. In embodiments, the receptor protein is anti-IL-6.

In an aspect a method of transfecting a nucleic encoding a secreted protein into a cell in a subject is provided. The method includes administering to a subject a cell-penetrating complex including a nucleic acid encoding a secreted protein bound to a compound, wherein the compound degrades upon delivery into the cell, thereby transfecting a nucleic acid encoding a secreted protein into a cell in a subject. A "secreted protein" a referred to herein is a protein secreted by a cell to its extracellular environment. Non-limiting examples of secreted proteins include growth factors or cytokines. In embodiments, the secreted protein is an interleukin. In embodiments, the secreted protein is IL-12. In embodiments, the secreted protein is IL-15. In embodiments, the secreted protein is IL-18. In embodiments, the secreted protein is IL-3. In embodiments, the secreted protein is IL-21. In embodiments, the secreted protein is IL-7. In embodiments, the secreted protein is IL-9. In embodiments, the secreted protein is IFNg. In embodiments, the secreted protein is an IL-1R antagonist.

In another aspect a method of transfecting a nucleic acid encoding a T cell receptor (TCR) into a cell in a subject is provided. The method includes administering to a subject a cell-penetrating complex including a nucleic acid encoding a TCR bound to a compound, wherein the compound degrades upon delivery into the cell, thereby transfecting a nucleic acid encoding a TCR into a cell in a subject.

In another aspect a method of transfecting a nucleic acid encoding a chimeric antigen receptor (CAR) into a cell in a subject is provided. The method includes administering to a subject a cell-penetrating complex including a nucleic acid encoding a CAR bound to a compound, wherein the compound degrades upon delivery into said cell, thereby transfecting a nucleic acid encoding a CAR into a cell in a subject.

In embodiments, the cellular receptor is a T cell receptor (TCR). In embodiments, the cellular receptor is a chimeric antigen receptor (CAR). In embodiments, the CAR is a Lewis Y antigen CAR (i.e., a chimeric antigen receptor binding to Lewis Y antigen). In embodiments, the CAR is an anti-CD44v6 CAR. In embodiments, the CAR is an anti-NKG2D ligand CAR. In embodiments, the CAR is an anti-folate receptor beta CAR. In embodiments, the CAR is an anti-CD38 CAR. In embodiments, the CAR is an anti-CD20 CAR. In embodiments, the CAR is an anti-CD22 CAR. In embodiments, the CAR is an anti-FLT3 CAR. In embodiments, the CAR is an anti-CD7 CAR. In embodiments, the CAR is an anti-CD33 CAR. In embodiments, the CAR is an anti-CD123 CAR. In embodiments, the CAR is an anti-CLEC12A CAR.

In embodiments, the compound is a cationic amphipathic polymer compound. In embodiments, the compound is a compound provided herein including embodiments thereof. In embodiments, the nucleic acid is an mRNA. In embodiments, the nucleic acid is a DNA. In embodiments, the CAR is an anti-CD19 CAR. In embodiments, the nucleic acid further encodes an effector enhancing protein. The effector enhancing protein may be secreting protein or a receptor protein as provided herein (e.g., IL-12, anti PD1). In embodiments, the nucleic acid is a plurality of nucleic acids. Where the nucleic acid provided herein is a plurality of nucleic acids, the complex provided herein may include more than one nucleic acids (2, 3, 4, 5, 6, 7, or more) bound to the compound provided herein including embodiments thereof. In embodiments, the nucleic acid is a polycistronic nucleic acid.

In embodiments, the cell is a myeloid cell or a lymphoid cell. In embodiments, the cell is a myeloid cell. In embodiments, the cell is a lymphoid cell. In embodiments, the cell is a T cell, a B cell, or a natural killer cell. In embodiments, the cell is a T cell. In embodiments, the cell is a B cell. In embodiments, the cell is a natural killer cell. In embodiments, the cell is a macrophage, an eosinophil or a neutrophil. In embodiments, the cell is a macrophage. In embodiments, the cell is an eosinophil. In embodiments, the cell is a neutrophil. In embodiments, the administering is intravenous, subcutaneous or intratumoral. In embodiments, the administering is intravenous. In embodiments, the administering subcutaneous. In embodiments, the administering intratumoral.

EXAMPLES

Example 1

General Methods and Experimental Materials

Reagents were purchased from Sigma-Aldrich and used as received unless otherwise indicated. 1-(3,5-Bis-trifluoromethyl-phenyl)-3-cyclohexyl-thiourea (*Macromolecules* 39(23):7863-7871), MTC-guanidine monomer (*J Am Chem Soc* 131(45):16401-16403), MTC-dodecyl monomer (*Proc Natl Acad Sci* 109(33):13171-13176), MTC-piperidine monomer (*Chem Commun* (1):114-116), N-Boc morpholinone monomer (*J Am Chem Soc* 136(26):9252-9255), and dansyl alcohol (*J Am Chem Soc* 131(45):16401-16403) were all prepared according to literature procedures. Unless otherwise noted, all commercial solvents and reagents were used without further purification. Methylene chloride ($CH_2Cl_2$) and tetrahydrofuran (THF) were passed through an alumina drying column (Solv-tek Inc.) using nitrogen pressure. Petroleum ether, pentane, hexane, ethyl acetate (EtOAc), and methanol (MeOH) were obtained from Fisher Scientific. Deuterated solvents were purchased from Cambridge Isotope Laboratories. Regenerated cellulose dialysis membranes (Spectra/Por® 6 Standard RC; MWCO 1000) were purchased from Spectrum Laboratories, Inc.

mRNAs

In all following examples, eGFP mRNA (5meC, Ψ, L-6101), Fluc mRNA (5meC, Ψ, L-6107), OVA mRNA (5meC, Ψ, L-7210) and Cy5-eGFP mRNA (5meC, Ψ, L-6402) were purchased from TriLink BioTechnologies Inc.

Instrumentation

Particle size was measured by dynamic light scattering on a Malvern Zetasizer Nano ZS90. Flow cytometry analysis was performed on a BD LSRII FACS Analyzer (Stanford University Shared FACS Facility). Laser scanning confocal microscopy was carried out using a Leica SP8 White Light Confocal microscope with a 40× HC PL APO, CS2 oil objective lens (Stanford University Cell Sciences Imaging Facility). Bioluminescence was measured using a charge-coupled device (CCD) camera (IVIS 100, Xenogen Corp., Alameda, CA) and analyzed using Living Image Software (Perkin-Elmer). Epifluorescence microscopy was performed on a Zeiss Axio Observer.Z1 with an X-Cite 120Q wide-field excitation light source and a GFP filter set. Images were acquired with a CoolSNAP $HQ^2$ camera and transferred to a computer for image analysis.

Cell Lines

HeLa, J774, HepG2, and HEK-293 cells were maintained in Dulbecco's Modified Eagle Medium (DMEM) supplemented with 10% fetal bovine serum (FBS) and 1% penicillin/streptomycin. CHO cells were maintained in F12 media supplemented with 10% FBS and 1% penicillin/streptomycin. All cells were grown at 37° C. in a 5% $CO_2$ atmosphere. Cells were passaged at approximately 80% confluence.

Mesenchymal stem cells (MSCs) were prepared according to the method of Huang et al (*J. Orthopaedic Trans.* 3(1):26-33). Briefly, femurs were excised from two 8-week-old female CD1 mice, and the tissue was removed from the outside of the bone. The ends of the bones were then cut with a sterile scissors. The marrow was flushed from the four bones with DMEM 10% fetal calf serum containing penicillin/streptomycin using a 3 mL syringe and a 25 g needle in a 10 cm tissue culture treated petri dish. The marrow was disrupted and dispersed by pipetting, but not filtered or otherwise manipulated. The dish was incubated for 6 days, whereupon a characteristic monolayer developed. The culture was then washed twice with PBS, and trypsinized with 0.25% trypsin (Gibco) for 5 min at 37° C. The cells were then collected and transferred to a 75 $cm^2$ tissue culture flask, and incubated for 3 days, until 90% confluence was achieved. The culture could be maintained for two more passages, but growth was greatly reduced upon four passages. For transfection, the cells were plated at $1.2 \times 10^4$ per well in 24-well plates.

Example 2

Synthesis of Monomers

In some examples, CARTs of varied cationic immolative domains are generated from new lactone or carbonate monomers. Examples of synthesis of precursors and monomers are described:

Example 2.1. Synthesis of tert-butyl 2-oxomorpholine-4-carboxylate (N-Boc morpholinone)

In these examples, synthesis of the N-Boc morpholinone monomer was adapted from the literature: Chung, et al. *J. Am. Chem. Soc.*, 2013, 135 (20), 7593-7602

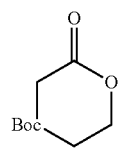

N-Boc morpholinone

Synthesis of tert-butyl 2-oxomorpholine-4-carboxylate: 2.086 g (10.2 mmol) tert-butyl bis(2-hydroxyethyl)carbamate was dissolved in 75 mL CH$_3$CN and bubbled with oxygen for 5 minutes. 398 mg (0.38 mmol) of [(neocuproine)Pd(OAc)]$_2$(OTf)$_2$ was added, resulting in the formation of a dark red solution. The reaction was placed in an oil bath at 60° C. and oxygen was bubbled through the reaction mixture, monitoring by TLC (1:1 hexanes:EtOAc). After 24 hours 263 mg (0.25 mmol) of [(neo)Pd(OTf)(Ac)]$_2$ was added to the reaction. After 48 hours an additional 426 mg (0.41 mmol) of [(neocuproine)Pd(OAc)]2(OTf)$_2$ was added to the reaction. After a total of 72 hours oxygen flow was stopped and the reaction was allowed to cool to room temperature. The reaction mixture was concentrated to 5-10 mL, resulting in a black non-viscous mixture and loaded onto a plug of SiO$_2$, eluting with 1:1 hexane:EtOAc. Concentration afforded 1.766 g yellow oil (8.78 mmol, 86.4%), which solidified on standing. This crude product was dissolved in 10 mL Et$_2$O followed by addition of 20 mL hexanes and stored at −30° C. overnight. Precipitate was collected by filtration, washing with pentane, to afford 1.54 g white powder (7.67 mmol, 76% yield). $^1$H NMR (500 MHz, CDC$_3$): δ 4.41 (br, 2H), 4.26 (s, 2H), 3.66 (t, 2H), 1.47 (s, 9H). $^{13}$C NMR (125 MHz, CD$_3$Cl): δ 28.24, 40.63, 45.49, 67.19, 81.33, 153.49, 166.63. HRMS (m/z): M+ calc'd for C$_9$H$_{15}$NO$_4$Na, 224.0893; Found, 224.0896.

Example 2.2. Synthesis of tert-butyl 7-oxo-1,4-oxazepane-4-carboxylate (7-lact)

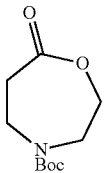

7-lact monomer

A flame dried flask was charged with tert-butyl 4-oxopiperidine-1-carboxylate (205.8 mg, 1.03 mmol) and DCM (10 mL) then stirred at 0 C for 15 minutes. mCPBA (600.1 mg, 2.9 mmol) in DCM (5 mL) was added in two portions then allowed to warm to room temperature. After 18 hours the reaction mixture was transferred to a separatory funnel and washed with saturated NaCHO3 (20 mL×3) then dried with Na2SO4 and filtered. Removal of solvent under reduced pressure afforded 317.0 mg white solid. Silica gel chromatography was performed, eluting with 9:1 DCM:EtOAc. Concentration of the relevant fractions afforded 151.0 mg (0.71 mmol, 68.9% yield) of a white solid. $^1$H NMR (500 MHz, CD$_3$Cl): δ 4.21 (s, 2H), 3.82 (s, 2H), 3.65 (s, 2H), 2.81 (s, 2H), 1.46 (s, 9H). $^{13}$C NMR (101 MHz, CD$_3$Cl): δ 173.9, 154.4, 81.1, 69.5, 47.3, 41.3, 37.6, 28.4

Example 2.3. Synthesis of tert-butyl (2-(bis(2-hydroxyethyl)amino)-2-oxoethyl)carbamate

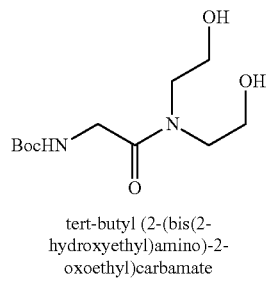 [SMILES: CC(C)(C)OC(=O)NCC(=O)N(CCO)CCO]

tert-butyl (2-(bis(2-hydroxyethyl)amino)-2-oxoethyl)carbamate

A flame dried flask was charged with diethanolamine (225 mg, 2.15 mmol) and methyl (tert-butoxycarbonyl)glycinate (370 mg, 1.95 mmol) then stirred in a heat bath at 75 C. After 18 hours the reaction was run through a plug of silica, eluting with acetone. Solvent was removed under reduced pressure yielding 505.1 mg pale yellow oil (1.93 mmol, 99% yield). $^1$H NMR (500 MHz, CD$_3$Cl): δ 5.7-5.6 (br, 1H), 3.99 (d, 2H), 3.78-3.65 (m, 4H), 3.53-3.35 (m, 4H), 3.05 (br, 1H). $^{13}$C NMR (101 MHz, CD$_3$Cl): δ 170.4, 156.3, 79.9, 60.0, 51.1, 42.4, 28.3

Example 2.4. Synthesis of tert-butyl (2-oxo-2-(2-oxomorpholino)ethyl)carbamate(Glycine Monomer)

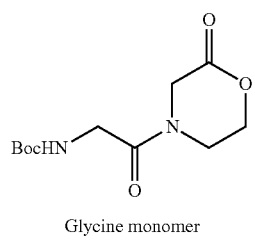 [SMILES: CC(C)(C)OC(=O)NCC(=O)N1CCOC(=O)C1]

Glycine monomer

A flame dried flask was charged with diol (450 mg, 1.72 mmol) and acetonitrile (12 mL) then bubbled with air for 5 minutes. Pd(Neo)OAc (84.1 mg, 0.16 mmol, 9.4 mol %) was added to the reaction and allowed to stir at 50 C under constant air flow. After 18 hours the reaction was concentrated, triturated with EtOAc (30 mL) then filtered to yield 220 mg foamy orange residue. Silica gel chromatography was performed, eluting with 100% EtOAc. Concentration of the relevant fractions afforded 53.1 mg (0.205 mmol, 12% yield) of a clear oil, which solidified upon standing. $^1$H NMR (500 MHz, CD$_3$Cl): δ 5.45-5.3 (br, 1H), 4.5-4.45 (q, 2H), 4.28-4.4 (d, 2H), 4.0-3.93 (dd, 2H), 3.85-3.7 (dt, 2H), 1.45 (s, 9H)$^{13}$C NMR (125 MHz, CD$_3$Cl): δ 167.7, 166.1, 164.8, 155.8, 80.2, 66.9, 65.9, 45.8, 44.1, 42.4, 41.2, 39.3, 28.3, 15.316

Example 2.5. Synthesis of 7-Gly (Ketone)

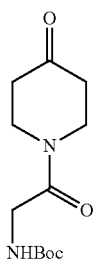

7-gly ketone

To a flask charged with hydroxybenzotriazole (600 mg, 4.4 mmol), EDC-HCl (453 mg, 2.9 mmol), (tert-butoxycarbonyl)glycine (520 mg), in 10 mL THF was added TEA (500 uL) and allowed to stir for 20 min. A solution of 4-piperidinone-HCl-monohydrate (462 mg, 3.0 mmol), in 10:1 mixture of THF:H$_2$O (11 ml total) was added in one portion. The reaction was allowed to stir overnight. The reaction was concentrated under reduced pressure then taken up in 15 mL EtOAc and washed with AcOH (500 uL) in H2O (10 mL), the aqueous phase was extracted with 15 mL EtOAc. The combined organic layers were then washed with NaHCO$_3$ (2×20 mL) and brine (1× 20 mL) then dried with MgSO$_4$. Concentration under reduced pressure yielded 375 mg white crystalline powder (50% yield) which was used without further purification.

Example 2.6. Synthesis of 7-Gly Monomer

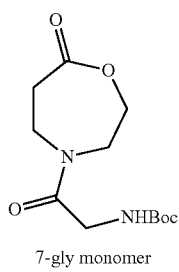 [SMILES: CC(C)(C)OC(=O)NCC(=O)N1CCOC(=O)CC1]

7-gly monomer

7-Gly Monomer: To a flask charged with N-glycinyl(Boc) 4-piperidinone (28 mg, 0.11 mmol) was added mCPBA (60 mg, 0.35 mmol) in 5 mL DCM. The reaction was allowed to stir at OC for 2 hours, then another portion of mCPBA (20 mg, 0.12 mmol) in 2 mL DCM was added to the reaction mixture and allowed to stir overnight. The reaction was concentrated under reduced pressure then taken up in 10 mL EtOAc and washed with NaHCO (4× 10 mL) then dried with MgSO$_4$. The crude product was purified by SiO$_2$ chromoatography using 9:1 EtOAc:DCM solvent system. Concentration of the relevant fractions under reduced pressure yielded 21 mg pdt (71% yield).

Example 2.7. Synthesis of 8-Membered Carbonate Based Monomer

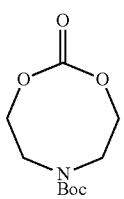

8-membered carbonate monomer 8-membered carbonate based monomer: These examples were prepared via the literature procedure reported in J. Am. Chem. Soc. 2015, 137, 13851-13860

Example 2.8. Synthesis of Tert-Butyl (2-Oxotetrahydro-2H-pyran-3-yl)carbamate (Mglut)

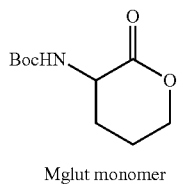 [SMILES: CC(C)(C)OC(=O)NC1CCCOC1=O]

Mglut monomer

Synthesis of Tert-Butyl (2-Oxotetrahydro-2H-pyran-3-yl) carbamate (Mglut): 1.078 g (4.9 mmol) (S)-(−)-2-(Boc-amino)-1,5-pentanediol was dissolved in 10 ml CH$_3$CN (0.49 M) and bubbled with air for 5 minutes. 0.233 g (0.45 mmol) of [(neo)Pd(OTf)(OAc)]$_2$ was added, turning the clear solution orange, which darkened to black. The reaction was placed in an oil bath at 45° C. and air was bubbled through the reaction mixture. The reaction was monitored by 1H NMR, looking for disappearance of the lactol peak at 5.1 ppm. Over the course of 44 hours a total of 0.310 g (0.6 mmol, 12 mol %) of [(neo)Pd(OTf)(OAc)]2 was added in portions to the reaction, based on reaction progress. At 44 hours $^1$H NMR showed the reaction was complete. Airflow was stopped and the reaction was allowed to cool to room temperature. The reaction mixture was concentrated and the residue taken up in 50 mL EtOAc and sonicated, then filtered through a plug of celite then concentrated, yielding 0.940 g pink-orange oil, which solidified on standing. Silica gel chromatography was performed, eluting with 4:1 DCM: EtOAc. Concentration of the relevant fractions afforded 0.480 g (2.23 mmol) of white solid (46% yield). Spectral data is consistent with previous report. Xie, X. and Stahl, S. S. J. Am. Chem. Soc., 2015, 137 (11): 3767-3770

Example 2.9. Synthesis of Phosphoester-Based Monomers

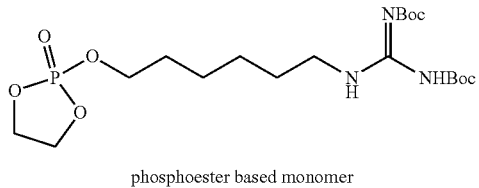

phosphoester based monomer

Phosphoester-based monomers: Some examples include the synthesis of a phosphate or phosphoester-based cationic immolation domain. In one example of this, the requisite monomers were synthesized according to previous literature procedure (McKinlay, C. J. et. al. *J. Am. Chem. Soc.* 2016, 138 (10), 3510-3517, WO2017083637 A1). Briefly (for the example 2-(6-bis-boc guanidino hexyloxy)-1,3,2-dioxaphospholane-2-oxide): 2-chloro-1,3,2-dioxaphospholane-2-oxide (797 mg, 5.59 mmol, 1.25 eq.) was weighed out into a schlenk flask under an inert $N_2$ atmosphere(glove box). This was placed on ice under nitrogen, and THF (75 mL) was added. In a separate vial, guan hexanol (7.16 g, 20.0 mmol, 1 eq.) was dissolved in THF (10 mL) and triethylamine (2.8 mL, 20 mmol, 1 eq) was added. Vial contents were added via syringe to Schlenk flask dropwise over the course of 10 minutes and allowed to react for 20 hours. Following reaction, product was filtered over a pad of Celite®. Crude product was dissolved in a small amount (5 mL) THF and triturated with 20 mL dry pentane. Product oiled out in a −55° C. freezer overnight. Removed pentane layer and dried under vacuum for 10 hours to afford pure product as a slightly-yellow oil (79% yield). This monomer was synthesized and deprotected according to standard procedure below.

Example 3

Polymerization of CARTs
General Procedure

To a solution of monomer and initiator in toluene is added a solution of DBU:TU co-catalytic system. The reaction is stirred for 2 hours, then the monomer having the immolative domain is added as a solid and then stirred for 2 hours. The reaction is quenched with acetic acid (or benzoic acid) then dialyzed in DCM against MeOH. After dialysis, removal of solvent under reduced pressure yields pure oligomer. The oligomer is then deprotected using TFA/DCM or HCl/$Et_2O$ to afford the amphiphilic CART. The CART is diluted to 2.0 mM in DMSO and then used for transfection studies with no further purification.

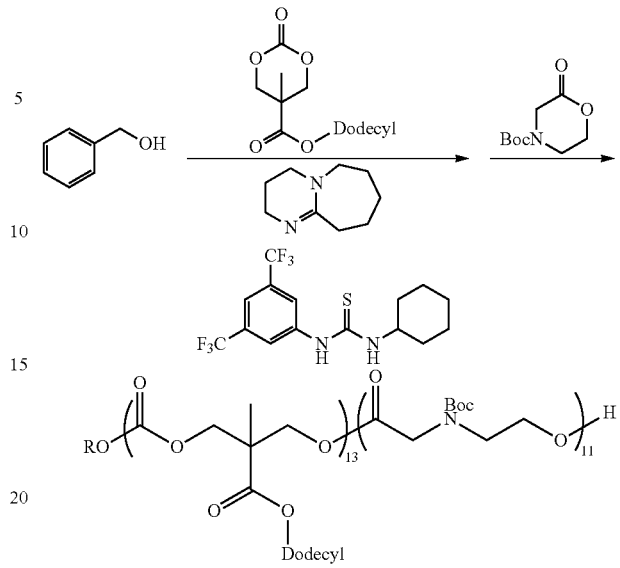

Deprotection including the use of TFA/DCM or HCl $Et_2O$

Example of TFA deprotection: To 10.5 mg oligomer dissolved in 1.0 mL dry DCM is added 100 uL TFA. The reaction is stirred for 8 hours. Removing solvent under reduced pressure yielded 10.3 mg CART (TFA salt) as a residue.

Examples of HCl deprotection: To 15 mg protected CART is added 2.0 M HCl in $Et_2O$ in two portions (2 mL total). The reaction was stirred for 18 hours then concentrated under reduced pressure to yield 12.1 mg CART (HCl salt) as a residue.

Examples of initiators: Monofunctional alcohols (i.e. Benzyl alcohol, 1-pyrenebutanol) PEG, fluorescent dyes (Dansyl, BHQ, BDK), multifunctional alcohols (tris benzyl alcohol, PEG diol), targeting ligands (Biotin, Folate) and conjugation ligands (Biotin).

Parent morpholinone based carts are adapted from that described in the literature report: McKinlay, et al. PNAS, 2017, E448-E456

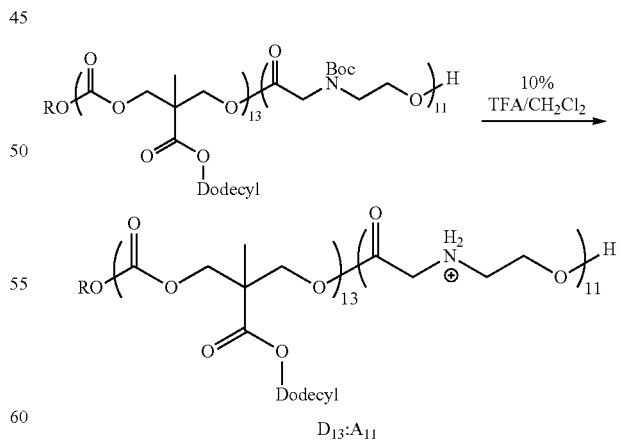

Preparation of Co-oligomers $D_n:A_m$. For the representative synthesis of $D_{13}:A11$:

A flame-dried vial was charged with MTC-dodecyl monomer 5 (33.2 mg, 0.1 mmol), dansyl initiator 3 (3.9 mg, 0.013 mmol), and 50 μL $CH_2Cl_2$. Diazabicycloundecene (DBU)

(0.8 mg, 0.005 mmol) and thiourea catalyst (TU) (2.0 mg, 0.005 mmol) in 50 μL CH$_2$Cl$_2$ were added to the reaction vial and allowed to stir. After 2 h, N-Boc monomer (22.3 mg, 0.11 mmol) was added to the vial as a solid and the reaction was allowed to stir for 3 h. After a total of 5 h, the reaction was quenched with five drops of AcOH then concentrated under reduced pressure. The crude material was dialyzed in CH$_2$Cl$_2$ against MeOH (1.0-kDa dialysis bag). Concentration afforded 37.9 mg pale green residue. End group analysis (2.8 ppm) by 1 H NMR shows DP 13:11.

To 23.5 mg oligomer dissolved in 0.8 mL dry DCM is added 20 uL TFA. The reaction is stirred for 18 hours. Removing solvent under reduced pressure yielded 23.1 mg CART as a residue.

aCl-based CARTs

Examples of CARTs of varied cationic immolative domains are as follows:

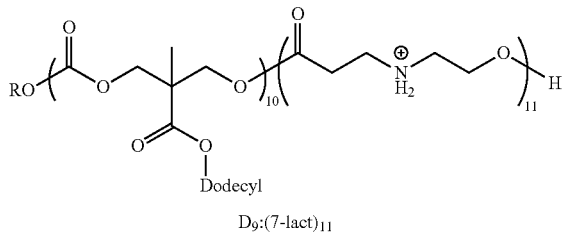

D$_9$:(7-lact)$_{11}$

A flame-dried vial was charged with dodecyl-MTC (33.0 mg, 0.1 mmol) and 1-pyrene butanol (2.3 mg, 0.0083 mmol), and 50 μL toluene. DBU (0.76 mg, 0.005 mmol) and TU (1.85 mg, 0.005 mmol) in 50 μL toluene were added to the reaction vial and allowed to stir. After 2 hours 7-lact (Example 1.2) (21.5 mg, 0.1 mmol) was added as a solid and the reaction was stirred. After stirring an additional 2 hours the reaction was quenched with one drop of acetic acid. The crude material was dialyzed in DCM against MeOH (1.0 kDa dialysis bag). Concentration under reduced pressure yielded 41 mg (76% yield).

To 10.5 mg oligomer dissolved in 1.0 mL dry DCM is added 100 uL TFA. The reaction is stirred for 8 hours. Removing solvent under reduced pressure yielded 10.3 mg CART as a residue.

6-Gly-based CARTs

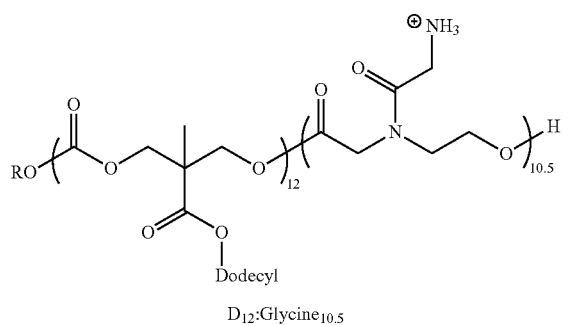

D$_{12}$:Glycine$_{10.5}$

A flame-dried vial was charged with dodecyl-MTC (32.8 mg, 0.1 mmol) and 1-pyrene butanol (2.3 mg, 0.0083 mmol), and 50 μL DCM. DBU (0.76 mg, 0.005 mmol) and TU (1.85 mg, 0.005 mmol) in 50 μL DCM were added to the reaction vial and allowed to stir. After 2 hours tert-butyl (2-oxo-2-(2-oxomorpholino)ethyl)carbamate (36 mg, 0.14 mmol) was added as a solid and the reaction was stirred. After stirring an additional 2 hours the reaction was quenched with one drop of acetic acid. The crude material was dialyzed in DCM against MeOH (1.0 kDa dialysis bag). Concentration under reduced pressure yielded 47 mg (68% yield).

To 11.1 mg oligomer dissolved in 1.0 mL dry DCM is added 100 uL TFA. The reaction is stirred for 8 hours. Removing solvent under reduced pressure yielded 11 mg CART as a residue 7-Gly-based CARTs

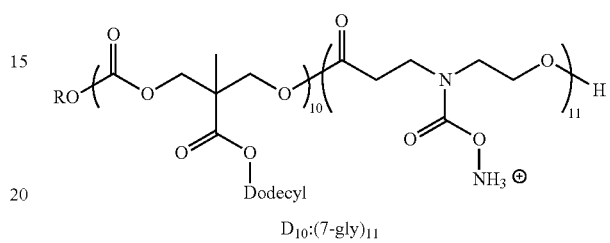

D$_{10}$:(7-gly)$_{11}$

A flame-dried vial was charged with dodecyl-MTC (32.2 mg, 0.1 mmol) and benzyl alcohol (0.9 mg, 0.0083 mmol), and 50 μL toluene. DBU (0.76 mg, 0.005 mmol) and TU (1.85 mg, 0.005 mmol) in 50 μL toluene were added to the reaction vial and allowed to stir. After 2 hours tert-butyl (2-oxo-2-(7-oxo-1,4-oxazepan-4-yl)ethyl)carbamate (32.1 mg, 0.1 mmol) was added as a solid and the reaction was stirred. After stirring an additional 2 hours the reaction was quenched with one drop of acetic acid. The crude material was dialyzed in DCM against MeOH (1.0 kDa dialysis bag). Concentration under reduced pressure yielded 49 mg (77% yield).

To 21 mg oligomer dissolved in 2.0 mL dry DCM is added 200 uL TFA. The reaction is stirred for 8 hours. Removing solvent under reduced pressure yielded 21.3 mg CART as a clear yellow residue.

Carb-Based CARTs

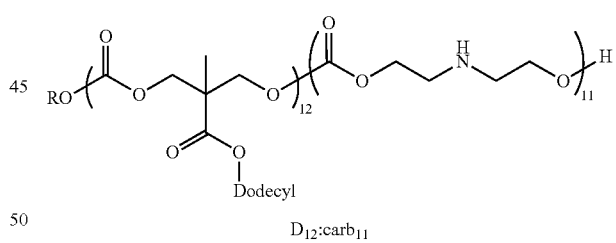

D$_{12}$:carb$_{11}$

A flame-dried vial was charged with dodecyl-MTC (33.1 mg, 0.1 mmol) and 5-(dimethylamino)-N-(2-hydroxyethyl) naphthalene-1-sulfonamide (Dansyl alcohol) (2.8 mg, 0.0083 mmol), and 50 DCM. DBU (0.76 mg, 0.005 mmol) and TU (1.85 mg, 0.005 mmol) in 50 μL DCM were added to the reaction vial and allowed to stir. After 2 hours 8-carb (23.2 mg, 0.1 mmol) was added as a solid. After stirring an additional 2 hours the reaction was quenched with one drop of acetic acid. The crude material was dialyzed in DCM against MeOH (1.0 kDa dialysis bag). Concentration under reduced pressure yielded 54.1 mg (96% yield).

To 12 mg oligomer dissolved in 1.0 mL dry DCM is added 100 uL TFA. The reaction was stirred for 9 hours. Removing solvent under reduced pressure yielded 12 mg CART as a residue.

Glu-Based CARTs

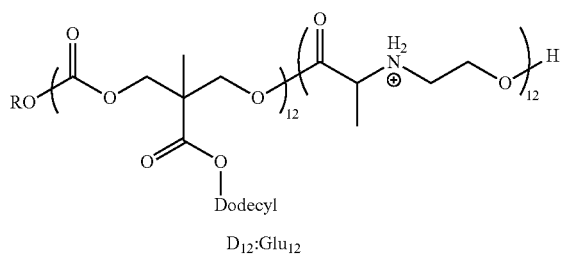

$D_{12}:Glu_{12}$

A flame-dried vial was charged with dodecyl-MTC (15.5 mg, 0.05 mmol) and benzyl alcohol (0.5 mg, 0.004 mmol), and 50 DCM. DBU (0.4 mg, 0.0025 mmol) and TU (0.9 mg, 0.0025 mmol) in 50 µL DCM were added to the reaction vial and allowed to stir. After 2 hours tert-Butyl (2-Oxotetrahydro-2H-pyran-3-yl)carbamate ($M_{Glut}$) (18.1 mg, 0.084 mmol) was added as a solid. After stirring an additional 2 hours the reaction was quenched with one drop of acetic acid. The crude material was dialyzed in DCM against MeOH (1.0 kDa dialysis bag). Concentration under reduced pressure yielded 17.9 mg (51% yield).

To 9.0 mg oligomer dissolved in 1.0 mL dry DCM is added 100 uL TFA. The reaction was stirred for 9 hours. Removing solvent under reduced pressure yielded 9.0 mg CART as a residue.

Additional examples of CARTs synthesized through these methods are detailed in the following table:

Example 4

CART/Nucleic Acid Complexes

In some examples, CART/mRNA polyplexes were prepared by mixing 5.71 µL RNAse-free PBS (adjusted to pH 5.5 with 1N HCl) and eGFP mRNA (from a 0.2 µg/µL stock in PBS pH 7.4) with 0.59 µL CART (from a 2 mM stock in DMSO) to achieve a 10:1+/−CART/mRNA ratios. These CART/mRNA complexes were incubated for 20 s at room temperature prior to treatment or analysis.

In comparative examples, the corresponding amount of other CART was used to equate to the same 10:1+/−charge ratio.

DLS Characterization of Particle Size and Zeta Potential

Certain examples demonstrate dynamic light scattering (DLS) can be used to analyze CART $D_{13}:A_{11}$ and polyelectrolyte complexes formed between it and eGFP mRNA. At pH 5.5, the hydrodynamic diameter of the resulting polyplexes was 254±10 nm. When these polyplexes were added to cell media, a change in hydrodynamic diameter from 254 nm to 512 nm occurred over two hours.

When the CART/mRNA complexes are added to unbuffered water, sizes remain at 257±24 nm over the full two-hour experiment.

Zeta potential measurements are in line with particle size data, with surface charge starting at +33±7 mV and evolving to −30±3 mV over two hours. This is consistent with the cationic ammoniums rearranging to neutral amides, leaving the surface predominantly anionic due to the associated oligonucleotide. While not being bound by theory, the differences in rates of rearrangement for the homo-oligomer (minutes) and the mRNA polyplexes (hours) appear to reflect a complexation-dependent increase in stability of the α-amino ester materials in buffered aqueous environments. This enables CART/mRNA complexes to remain stable over therapeutically relevant timescales at pH 7.4 prior to intracellular degradation.

| Entry | Trivial Name | Initiator | Lipid Block | Lipid Block Length (n) | Cationic Block | Cationic Block Length (m) |
|---|---|---|---|---|---|---|
| 1 | A13 | Dansyl | — | 0 | A | 13 |
| 2 | D13 | Dansyl | Dodecyl | 13 | — | 0 |
| 3 | D13:A11 | Dansyl | Dodecyl | 13 | A | 11 |
| 4 | D8:A11 | Dansyl | Dodecyl | 8 | A | 11 |
| 5 | D18:A17 | Dansyl | Dodecyl | 18 | A | 17 |
| 6 | BHQ-D10:A12 | BHQ | Dodecyl | 10 | A | 12 |
| 7 | BDK-D10:A10 | BDK | Dodecyl | 10 | A | 10 |
| 8 | 3arm-D9:A13 | 3-arm | Dodecyl | 9 | A | 13 |
| 9 | Chol13:A11 | Bn | Chol | 13 | A | 11 |
| 10 | N25:A32 | BDK | Nonenyl | 25 | A | 32 |
| 11 | N7:A4 | Bn | Nonenyl | 7 | A | 4 |
| 12 | N10:A10 | Bn | Nonenyl | 10 | A | 10 |
| 13 | N11:A11 | Bn | Nonenyl | 11 | A | 11 |
| 14 | S9.5:A9 | Bn | Stearyl | 9.5 | A | 9 |
| 15 | S14:A9 | Bn | Stearyl | 14 | A | 9 |
| 16 | O22:A29 | BDK | Oleyl | 22 | A | 29 |
| 17 | O12:A7 | Bn | Oleyl | 12 | A | 7 |
| 18 | O11:A9 | Bn | Oleyl | 11 | A | 9 |
| 19 | O11:A12 | Bn | Oleyl | 11 | A | 12 |
| 20 | L7.5:A8 | Bn | Linoleyl | 7.5 | A | 8 |
| 21 | L10:A10 | Bn | Linoleyl | 10 | A | 10 |
| 22 | D9:(7-lact)11 | Bn | Dodecyl | 9 | 7-lact | 11 |
| 23 | D12:Glycine10.5 | Bn | Dodecyl | 12 | Glycine | 10.5 |
| 24 | D10:(7-gly)11 | Bn | Dodecyl | 10 | 7-gly | 11 |
| 25 | D14(alpha-Me14.5 | Bn | Dodecyl | 14 | Alpha-Me | 14.5 |
| 26 | D12:carb11 | Bn | Dodecyl | 12 | Carb | 11 |
| 27 | D12:Glu12 | Bn | Dodecyl | 12 | Glu | 12 |

As a comparative example, when complexes were formed with non-immolative transporters $D_{13}$:$G_{12}$ (FIG. 7B), particles were also formed on the order of 250 nm. However, the sizes and zeta potentials of these particles did not change as a function of time, indicating that no degradation was occurring.

As a comparative example, the size of the formulated polyplexes was not cargo-dependent. When polyplexes were formed with luciferase (Fluc) mRNA, which is approximately twice the length of eGFP (Fluc=1929 nt vs. eGFP=996 nt), and added to cell media at pH 7.4, the polyplexes exhibited the same behavior as those formed with eGFP mRNA, suggesting that CART-enabled delivery could be general, working with a variety of mRNA sizes.

Specifically for these examples, mRNA/co-oligomer complexes were prepared at a 10:1 (cation:anion) charge ratio as above using 500 ng eGFP mRNA and added to 120 μL RNase-free PBS pH 5.5, 7.4, or neutral RNAse-free water. The solution was immediately transferred to a disposable clear plastic cuvette and the size measured. Size measurements were taken at the initial time (1 min) and at 15 min intervals over 2 h. The sizes reported are the z-averages. Zeta potential measurements were taken by diluting the mRNA:co-oligomer complexes formulated for DLS into 800 μL water, transferring to zeta cell (DTS1060) and measuring zeta potential. All values reported are the average of a minimum of three trial runs. Error was expressed as ±SD. In some other examples, the ratio between cation and anion can be at about 1:1, about 1:2, about 1:3, about 1:4, about 1:5, about 1:6, about 1:7, about 1:8, about 1:9, about 1:10, at about 1:11, about 1:12, about 1:13, about 1:14, about 1:15, about 1:16, about 1:17, about 1:18, about 1:19, about 1:20, about 1:30 or more. In some other examples, the ratio between anion and cation can be at about 1:1, about 1:2, about 1:3, about 1:4, about 1:5, about 1:6, about 1:7, about 1:8, about 1:9, about 1:10, at about 1:11, about 1:12, about 1:13, about 1:14, about 1:15, about 1:16, about 1:17, about 1:18, about 1:19, about 1:20, about 1:30 or more.

Example 5 mRNA Delivery by CARTs
eGFP mRNA Delivery and Expression in Multiple Cell Lines

In some examples, CART, $D_{13}$:$A_{11}$, afforded excellent eGFP expression in HeLa cells with >99% transfection efficiency and high mean fluorescent intensity. (FIGS. 9A, B, D)

For example transfections by CART, $D_{13}$:$A_{11}$, HeLa cells were seeded at 40,000 cells/well in 24-well plates and allowed to adhere overnight. Oligomer/mRNA polyplexes were prepared by mixing RNase-free PBS pH 5.5 and eGFP mRNA with various amounts of oligomer from DMSO stock solutions, to achieve specific co-oligomer/mRNA ratios (optimized to a theoretical cation:anion ratio of 10:1, 8.4 μL total volume). The complexes were incubated for 20 s at room temperature prior to treatment. The Lipofectamine™ 2000 control was prepared in OptiMEM per the manufacturer's instructions. The cells were washed with serum-free DMEM and mRNA/Lipo solution was added to a final volume of 200 μL/well and 125 ng mRNA/well. After washing with serum-free DMEM, 2.5 μL of the mRNA/co-oligomer complexes was added to a total volume of 200 μL, all conditions in triplicate, for a final mRNA concentration of 125 ng/well. The cells were incubated for 8 h at 37° C., then trypsinized with trypsin-EDTA (0.05%) for 10 min at 37° C. Serum-containing DMEM was added, and the contents of each well centrifuged, the supernatant removed, and the pelleted cells were re-dispersed in PBS (125 μL) and transferred to FACS tubes, and read on a flow cytometry analyzer (LSR-II.UV, Stanford University). The data presented (FIG. 9) are the geometric mean fluorescent signals from 10,000 cells analyzed. For transfection efficiency, untreated cells were gated for no eGFP expression, and the data presented are the percentage of 10,000 cells analyzed with higher eGFP expression than untreated cells. Error is expressed as ±SD. Note: All other cell lines were used as above in their respective media. For HepG2 cells, 5 mM EDTA was added to the PBS used to re-suspend the cell pellets for flow cytometry.

Figure 9A:
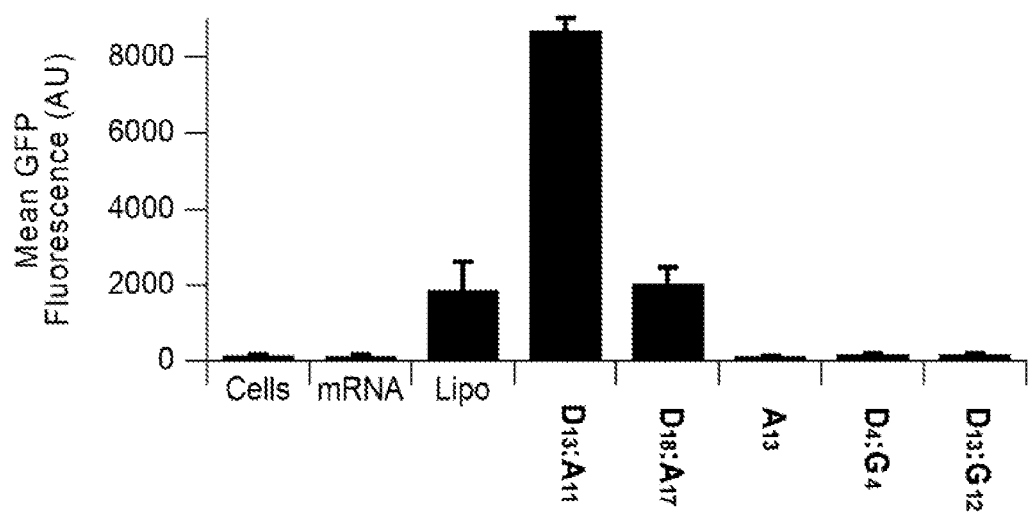
FIGS. 9A-9D. Show data related to evaluation of CARTs for eGFP mRNA delivery.

A second CART with longer block lengths ($D_{18}$:$A_{17}$) provided high transfection efficiency (>90%) but lower mean transfection values (FIG. 9A). In comparative examples, complexes formed with α-amino ester homo-oligomer $A_{13}$ induced no eGFP expression, which showed that a hydrophobic domain was necessary for oligonucleotide delivery. As a further comparative example, when HeLa cells were treated with mRNA formulated with Lipofectamine, only modest levels of eGFP expression were observed, and only approximately 50% of the cells exhibited fluorescence.

Figure 9B:
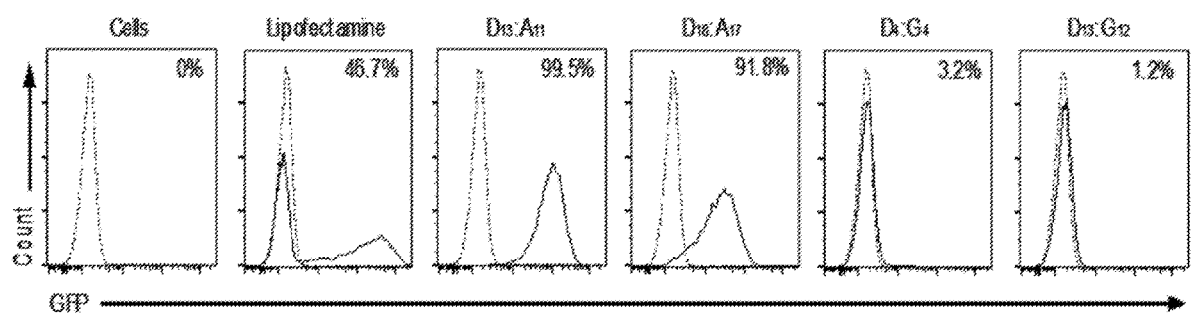
Figure 9C:
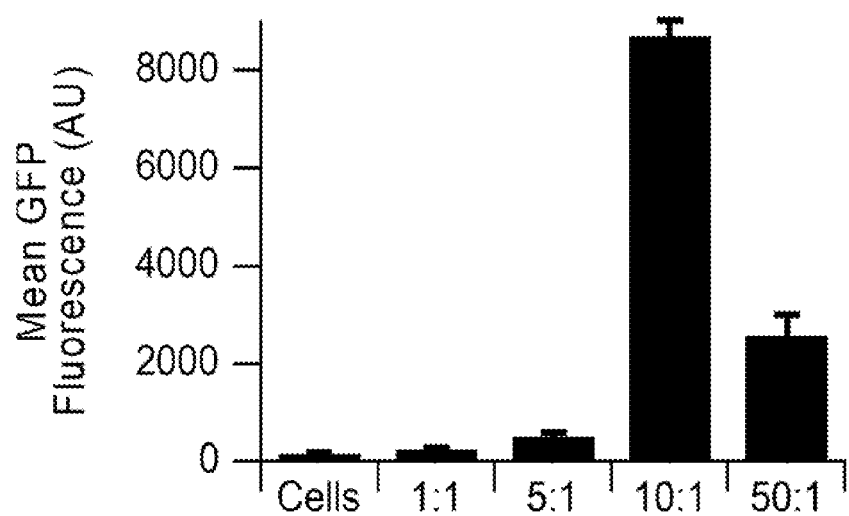
Figure 9D:
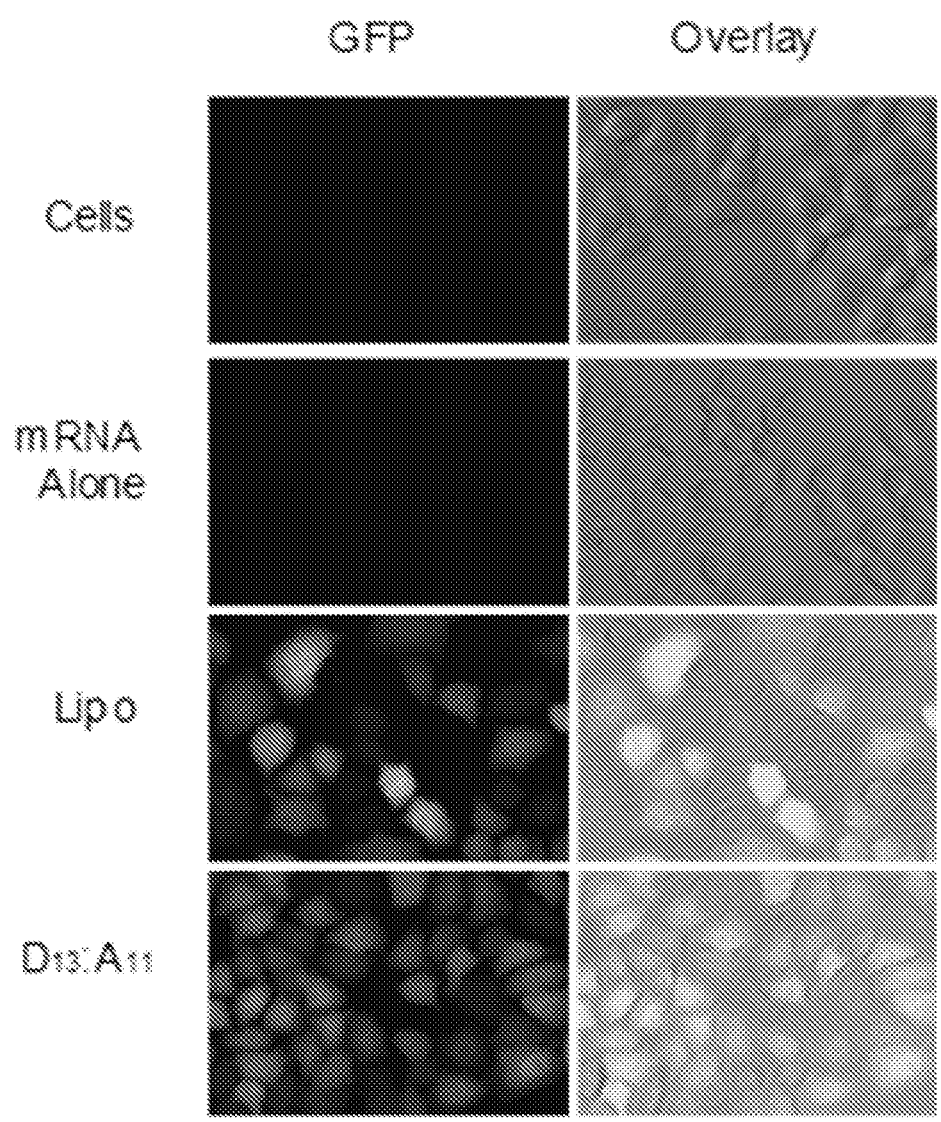

In some other examples, in order to optimize the delivery parameters by CART $D_{13}$:$A_{11}$, the charge ratio of cationic oligomer to anionic mRNA was varied from 1:1 to 50:1 (+/−) and the resulting eGFP fluorescence was determined (FIG. 9C). Values are reported as the theoretical (+/−) charge ratio of moles of ammonium cations to moles of phosphate anions, assuming full amine protonation and phosphate deprotonation. eGFP expression showed a roughly parabolic dependence on charge ratio with maximum eGFP fluorescence resulting from complexes formed at a 10:1 (+/−) charge ratio. This value is higher than what was observed with guanidinium-rich oligocarbonate complexes used for siRNA delivery, which performed optimally at a 4.8:1 charge ratio. Epifluorescence microscopy was further used to confirm flow cytometry results (FIG. 9D). HeLa cells treated with CART/mRNA complexes show significant fluorescence in nearly all viewable cells. In contrast, cells treated with Lipofectamine showed partial eGFP expression, while leaving others untransfected.

Figure 6:
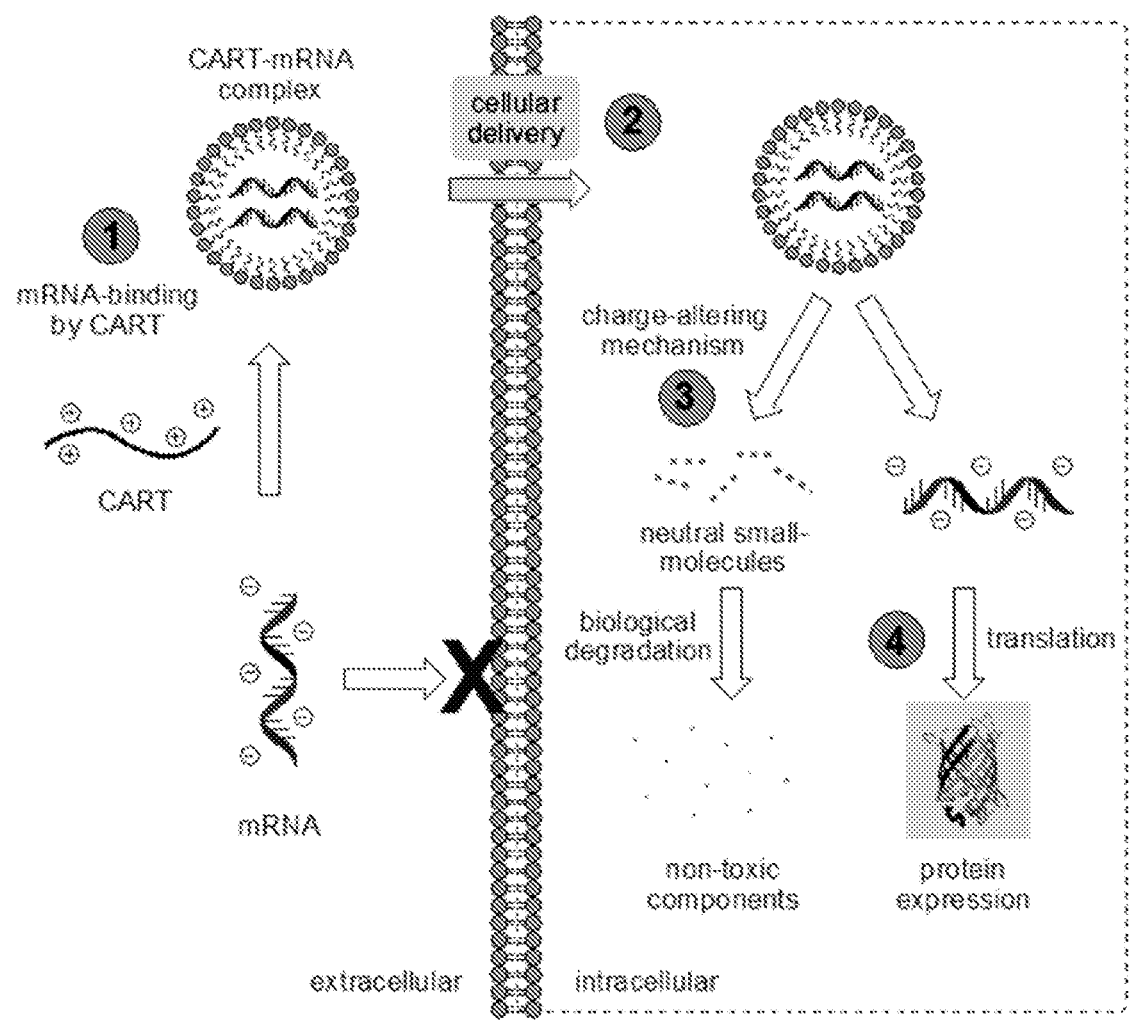
FIG. 6. Shows diagrams illustrating charge-alternating releasable transporters (CARTs) for mRNA delivery.
Figure 11A:
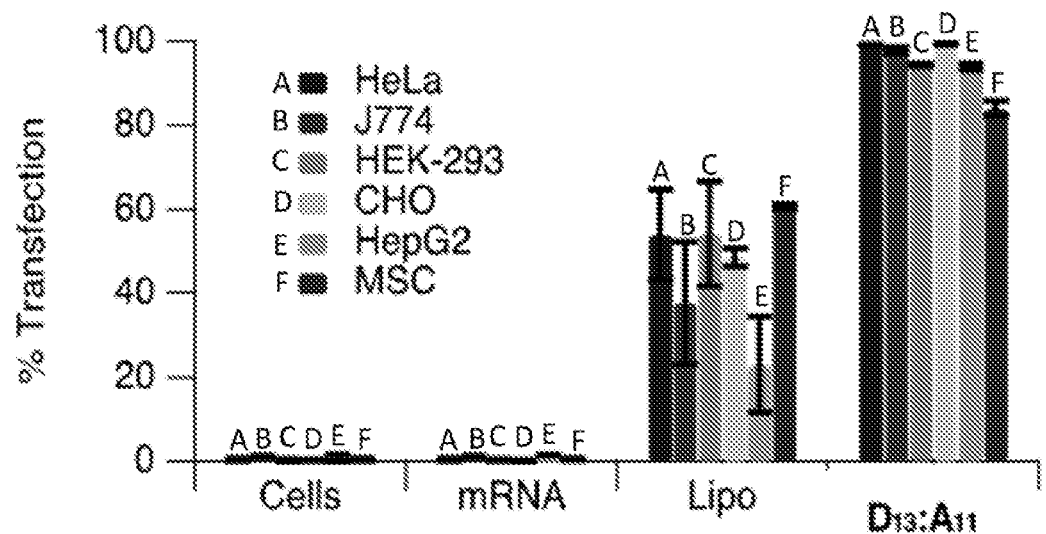
FIGS. 11A-11F. Show applications of mRNA delivery using CARTs in multiple cell lines and mice.

In further examples, eGFP mRNA expression following delivery by CART, $D_{13}$:$A_{11}$ was assayed in a panel of cell lines, including those typically considered to be difficult to transfect. In addition to HeLa cells, mRNA expression was compared to that of Lipofectamine in murine macrophage (J774), human embryonic kidney (HEK-293), Chinese hamster ovary (CHO), and human hepatocellular carcinoma (HepG2) cells by treating with CART complexes formed with eGFP mRNA (FIG. 6A). In all cell lines tested, the percentage of cells expressing eGFP using the CART $D_{13}$:$A_{11}$ was >90%, while treatment with Lipofectamine induced expression in only 22-55% of the cells (FIG. 11A). This suggests that this delivery system is general for a variety of human and non-human cell types. In addition to immortalized cell lines, mRNA expression was also observed in primary CD1 mouse-derived mesenchymal stem cells (MSCs) with high transfection efficiency (>85%).

Other examples have shown CART activity in other cell lines which are much more challenging to transfect, including Jurkat T-cells (11% transfection with CARTs vs. 7% for Lipofectamine), primary T-cells (6% transfection vs. 0% for Lipo), as well as 3T3 fibroblasts (70% for CARTs vs. 59% for Lipo) and trophoblast stem cells (19% for CARTs vs. 69% for Lipo).

Figure 11B:
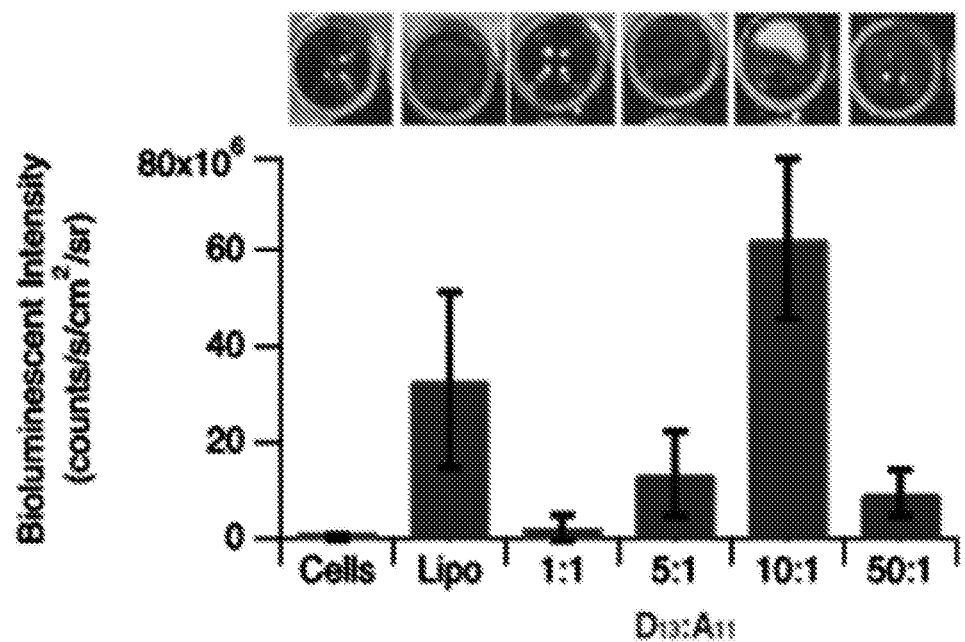

In some examples, consistent mRNA transfection by CART $D_{13}:A_{11}$ is also observed using mRNA of different lengths such as the larger firefly luciferase (Fluc) mRNA, substantially outperforming Lipofectamine by >3-fold (FIG. 11B). Analogous to trends observed with eGFP mRNA, a 10:1 (cation:anion) ratio resulted in the highest level of Flue bioluminescence, despite the difference in mRNA lengths, indicating that delivery efficiency is largely independent of cargo size.

For these examples, HeLa cells were seeded 10,000 cells/well in black 96-well plates and allowed to adhere overnight. mRNA polyplexes and Lipofectamine™ 2000 control were prepared as above using Fluc mRNA (final concentration of 50 ng mRNA/well in 50 μL total volume). All conditions were performed in replicates of six. Cells were incubated with treatment for 8 h at 37° C., then medium was removed and 100 μL of a D-luciferin solution (300 μg/mL) in DMEM was added to the cells. The resultant luminescence was measured using an IVIS 50 or IVIS 200 (Xenogen Product line of Perkin-Elmer) charge-coupled device camera and Living Image Software. Data represent the average of three experiments with error expressed as ±SD.

Charge-Altering Immolation Domains

By delivering a mixture of eGFP mRNA and Cy5-labeled eGFP mRNA, analysis of mRNA internalization and expression can be decoupled and simultaneously quantified; Cy5 fluorescence indicates internalized mRNA, irrespective of localization, and eGFP fluorescence denotes cytosolic release and subsequent expression of mRNA. This method reveals the effect of backbone structure and cation type by comparing the cellular uptake and mRNA expression of two oligomers to CART $D_{13}:A_{11}$: non-immolative, guanidinium-containing $D_{13}:G_{12}$, and non-immolative, ammonium-containing $D_{13}:Pip_{13}$.

Figure 10A:
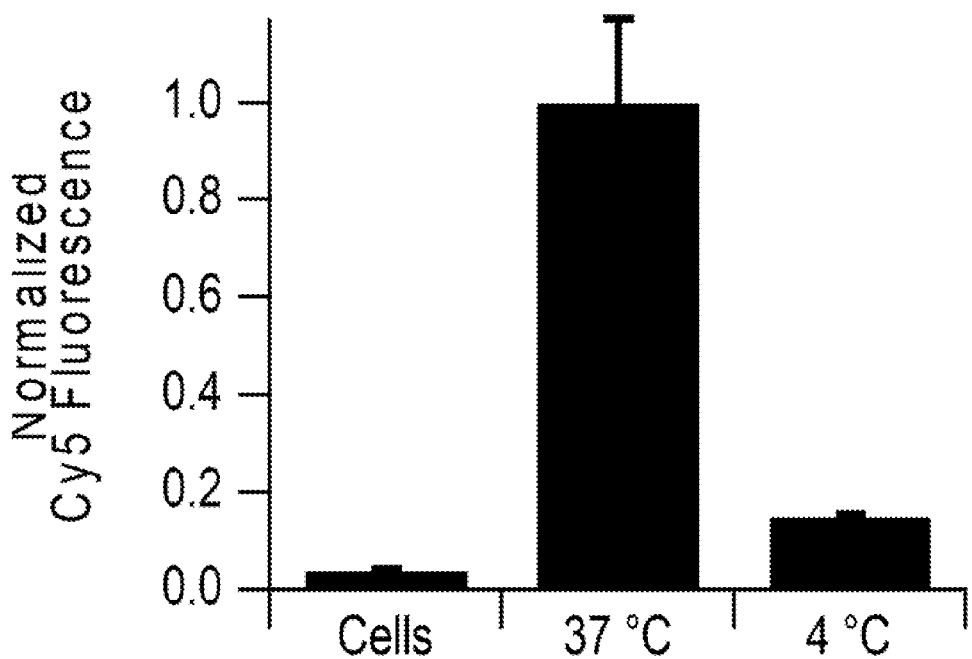
FIGS. 10A-10D. Show that expression of mRNA is due to the charge-altering, self-immolative mechanism that drives mRNA release and endosomal escape by CART oligomers.
Figure 10B:
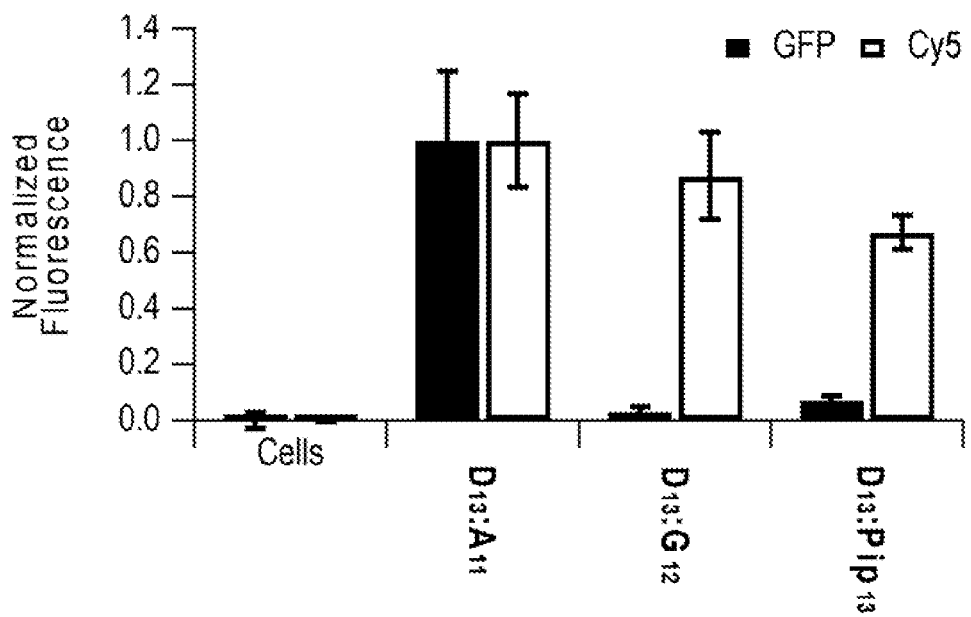

In these examples, when Cy-5 mRNA was formulated with CART, $D_{13}:A_{11}$, high levels of both intracellular Cy5 and eGFP fluorescence were observed (FIGS. 10B, D). As comparative examples, when the non-immolative, guanidinium-containing $D_{13}:G_{12}$, or non-immolative, ammonium-containing $D_{13}:Pip_{13}$ were used, only Cy5-fluorescence was observed. This example indicates that all three mRNA complexes are internalized by cells efficiently, but without a rapidly degrading backbone, the non-immolative polyplexes derived from $D_{13}:G_{12}$ and $D_{13}:Pip_{13}$ did not release mRNA on a timescale necessary to enable detectable levels of translation. The lack of eGFP expression by complexes formed with ammonium-containing $D_{13}:Pip_{13}$ further suggests that the efficacy of CART, $D_{13}:A_{11}$ is not simply due to the difference in electrostatic binding affinity of ammonium versus guanidinium cations. Rather, the specific, controlled loss of cationic charge through immolative rearrangement is crucial for efficacy.

Specifically in these examples, to measure cellular uptake and release of oligomer/mRNA polyplexes, HeLa cells were treated with polyplexes prepared as above using Cy5-labeled eGFP mRNA at a final concentration of 62.5 ng mRNA/well. Cells were prepared and analyzed by flow cytometry for both eGFP and Cy5 fluorescence as above.

Figure 10C:
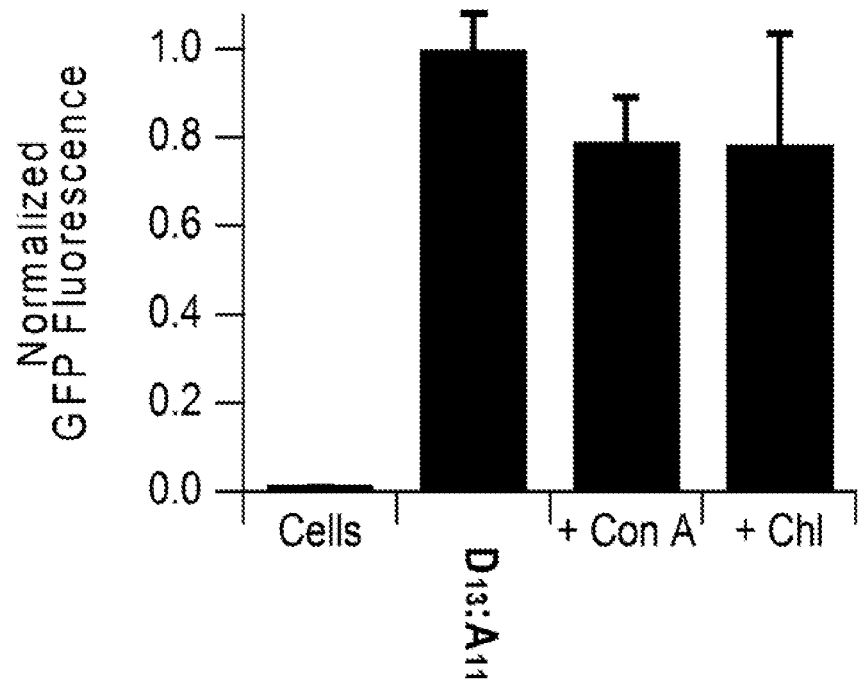
Figure 10D:
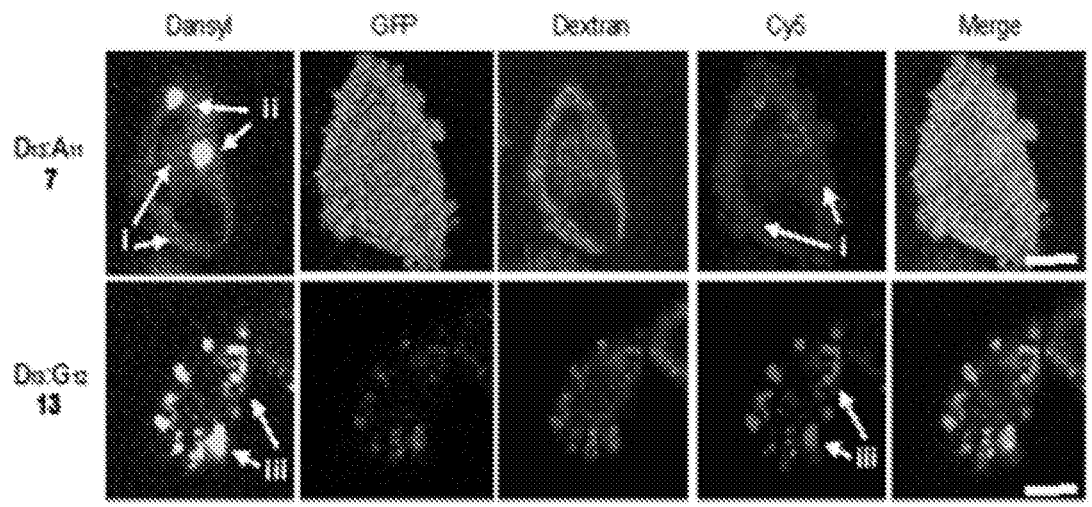

Additional examples confirm the necessity of immolation in current embodiments using confocal microscopy. The CART-mediated mRNA release and endosomal escape by CART, $D_{13}:A_{11}$ compared to an ineffective transporter ($D_{13}:G_{12}$) was further confirmed by confocal microscopy with simultaneous detection of dansylated transporter, Cy5-mRNA, and tetramethylrhodamine (TRITC)-Dextran$_{4400}$, a stain for endosomal compartments. When cells were imaged 4 h after treatment with CART $D_{13}:A_{11}$/Cy5-mRNA complexes, diffuse fluorescence was observed for both the Cy5 and Dansyl fluorophores, indicating that those materials successfully escaped the endosome and dissociated from the polyplexes (FIG. 10D). Diffuse fluorescence from (TRITC)-Dextran$_{4400}$ is also observed, which can be attributed to endosomal rupture and release of the entrapped dextran. As a comparative example, when cells are treated with non-immolative $D_{13}:G_{12}$/Cy5-mRNA complexes, both the Cy5 and Dansyl fluorescence remain punctate and co-localized. These signals also strongly overlap with punctate TRITC-Dextran$_{4400}$, indicative of endosomal entrapment (FIG. 10D). Taken together, these data strongly suggest that the charge-altering behavior of CART $D_{13}$:Ani enables endosomal rupture and mRNA release, contributing to the high performance of these materials for mRNA delivery.

Specifically for confocal microscopy examples: HeLa cells were seeded in an 8-chambered glass-bottomed dish (Nunc Lab-Tek II, Thermo Scientific) at 10,000 cells/well and allowed to adhere overnight. Prior to treatment, cells were washed with serum-free DMEM, and 200 μL of serum-free DMEM with 100 μM TRITC-Dextran (Sigma, avg. mol. wt.=4,400) was added to each well. Cy5-eGFP mRNA polyplexes were prepared as above (final concentration of 125 ng mRNA/well) and added to each corresponding well. Cells were incubated for 4 h at 37° C., then media was removed and 500 μL of PBS containing 10 mM HEPES buffer solution was added. Cells were imaged using Leica SP8 White Light Confocal microscope tuned for DAPI (Dansyl), GFP, DsRed (TRITC-Dextran), and Cy5.

In Vivo Delivery of mRNA by CARTs

Figure 11C:
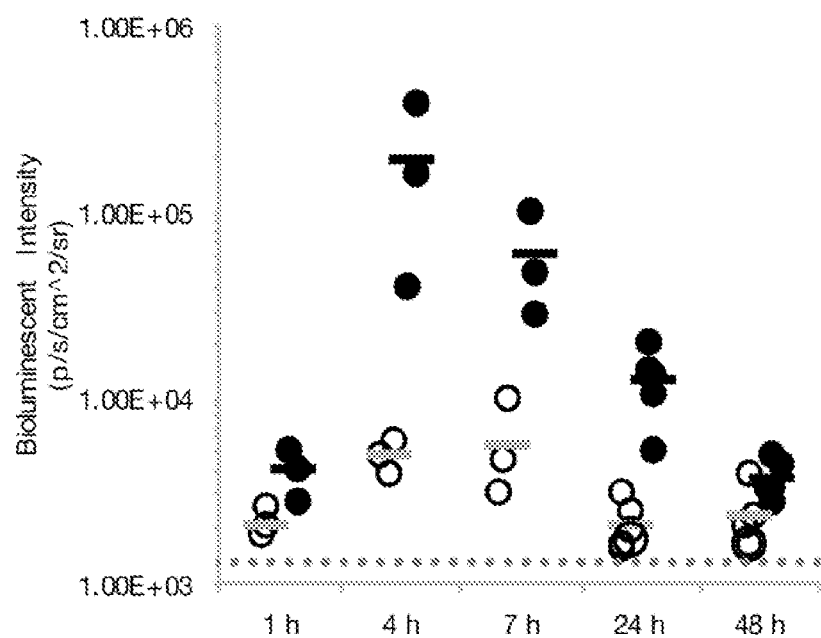
Figure 11D:
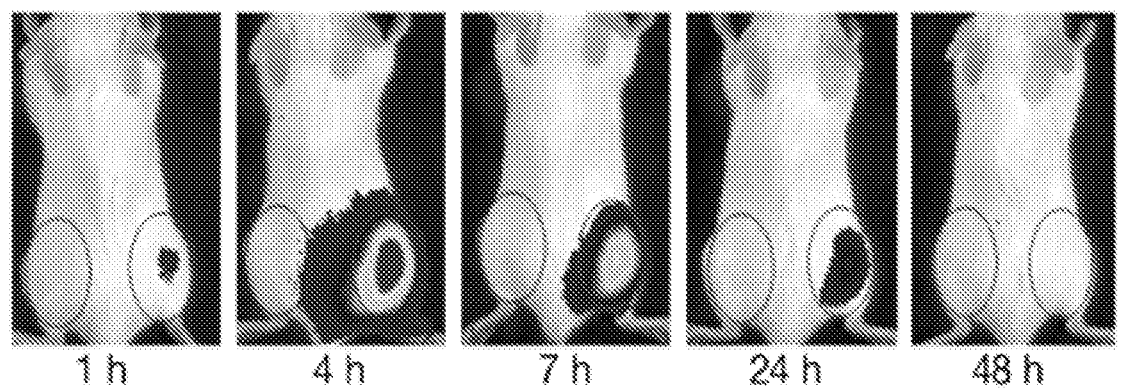

In certain examples, CARTs such as $D_{13}:A_{11}$ have exhibited excellent gene expression in vivo. In one example, CART $D_{13}$:Ani complexed with luciferase mRNA and administered intramuscularly into Balb/c mice demonstrates high levels of bioluminescence. As a comparative example, mRNA that has not been complexed with a delivery agent shows no resulting bioluminescence. This expression peaked at 4 h, and was still observable after 48 h. In these examples, 7.5 μg of luciferase mRNA was complexed with $D_{13}:A_{11}$ at a 10:1 charge ratio in a total volume of 75 μL of PBS (pH 5.5) and injected into the right thigh muscle of Balb/c mice (FIGS. 11C, D).

Figure 11E:
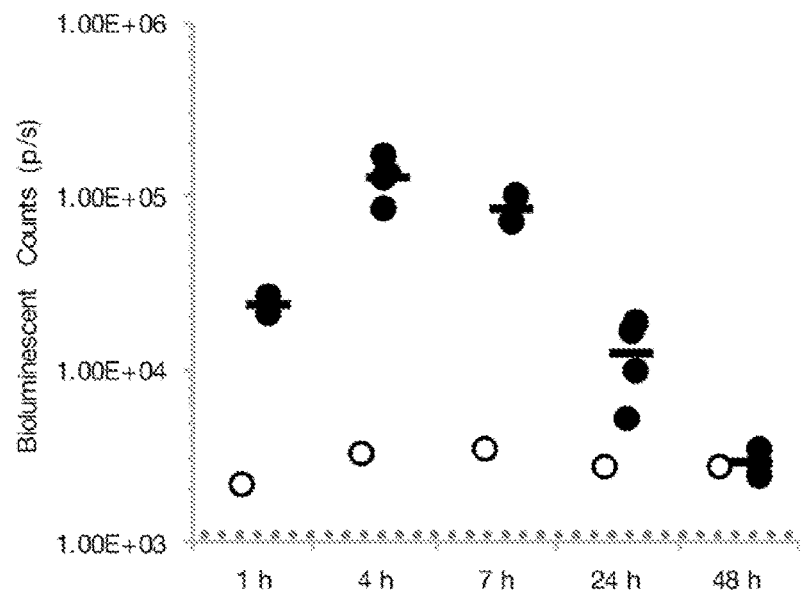
Figure 11F:
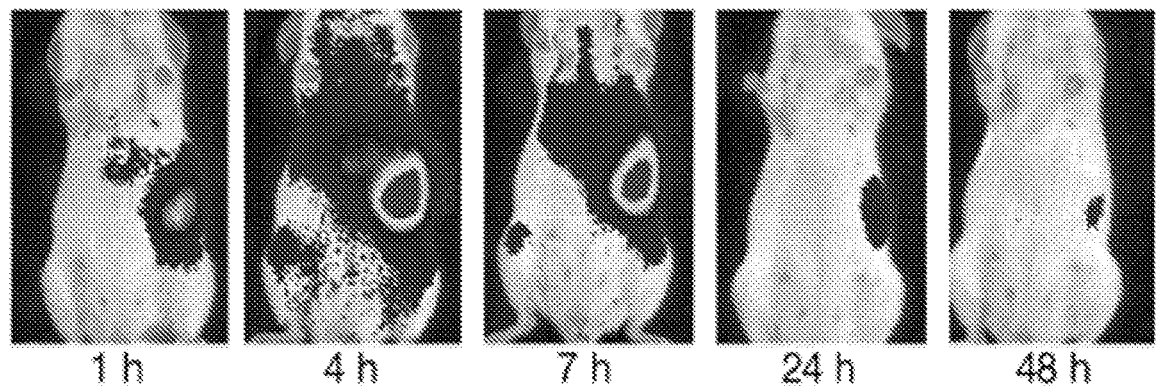
Figure 12:
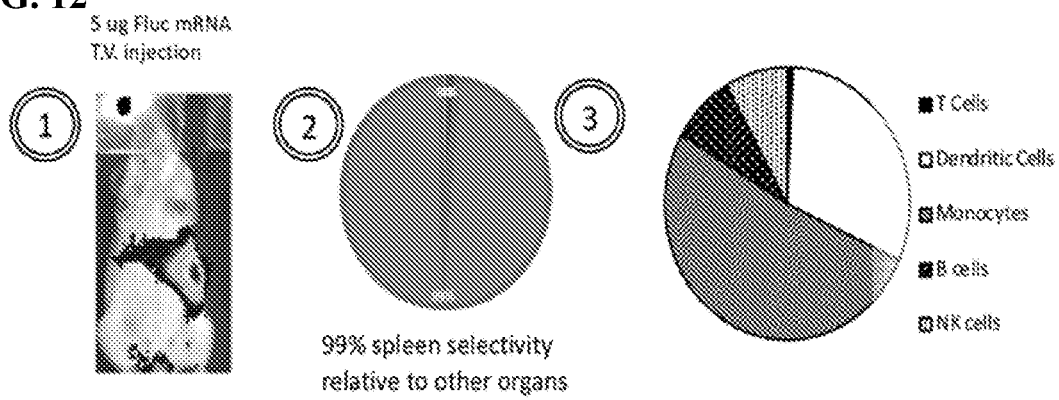
FIG. 12. In vivo bioluminescent imaging of mice transfected with BDK-CART-Fluc mRNA. Mice were injected through the tail vein with 150 uL PBS containing 5 ug Fluc mRNA packaged with BDK (fluorescent) CART. 1. Mice were imaged for bioluminescent distribution. 2. Mice were sacrificed and liver spleen and lung were harvested. Quantification of BLI from these organs revealed a relative ratio of 99:1 (99%) from the spleen to (liver+lungs). 3. The spleens from these mice were harvested and homogenized. Flow cytometry gating on the BDK fluorophore was used to phenotype cell populations from the spleen.
Figure 12:
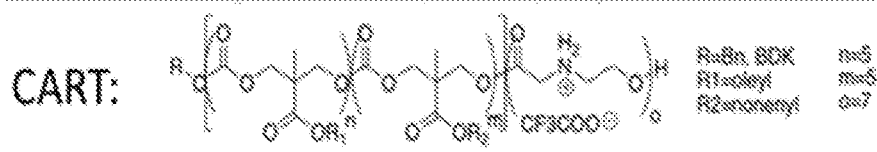
Figure 13:
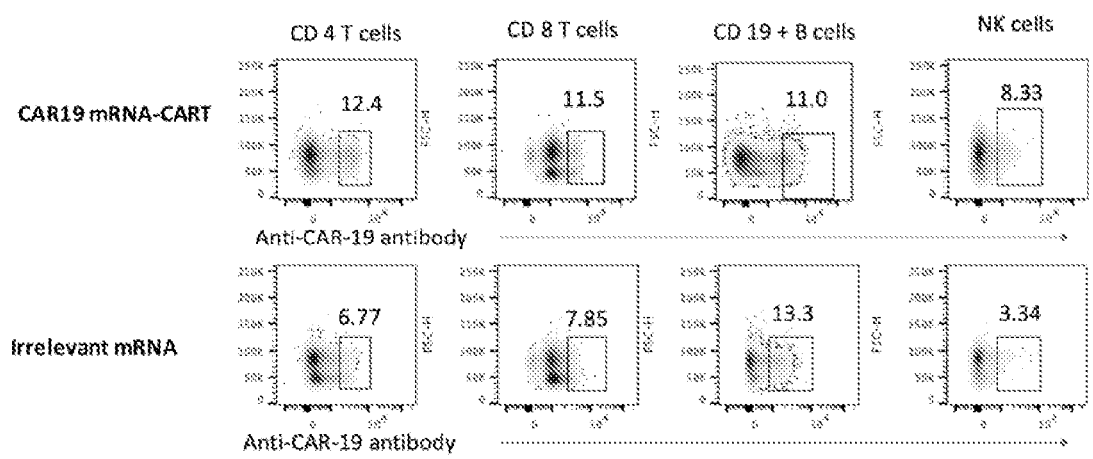
FIG. 13. Anti CD-19 expressing T cells (CAR-T cells) are produced in vivo with CAR19 mRNA-CART delivery. Percentage of population of each cell lineage that express the CAR-19 construct on the cell surface (top row) Mice treated with 5 ug CAR19 mRNA-CART (Bottom row) Mice treated with 5 ug irrelevant (SEAP) mRNA-CART. Cells were assayed 36 hrs post treatments. We propose that cell lines other than T cells may also contribute to the therapeutic effect if they get the CAR19 construct.

In an additional example, $D_{13}:A_{11}$ complexed with luciferase mRNA shows high levels of bioluminescence when administered through an intravenous tail-vein injection. High levels of expression persisted for 24 h, with detectable bioluminescence after 48 h. Bioluminescence is primarily localized in these images to the spleen and liver (FIGS. 11E, F). No bioluminescent signals were observed when naked mRNA was administered IV. For all mice studied, no toxicity was observed immediately after injection or for several weeks following treatment.

As additional examples, IV administration of Fluc mRNA complexed with CARTs $O_{11}:A_9$, $D_{12}:Gly_{10.5}$, and $D_{14}$:a-methyl$_{14.5}$ all resulted in significant luciferase expression in the liver and/or spleen. In these examples, 7.5 μg of luciferase mRNA was complexed with the CART at a 10:1 charge ratio in a total volume of 75 μL of PBS (pH 5.5) and injected into the tail vein of Balb/c mice.

In an additional example, $D_{13}:A_{11}$ complexed with luciferase mRNA shows high levels of bioluminescence when administered via an intratumoral injection. In this example 4 g of luciferase mRNA was complexed with $D_{13}:A_{11}$ at a 10:1 charge ratio in a total volume of 75 μL of PBS (pH 5.5) and injected into the center of a solid subcutaneous A20 lymphoma tumor.

In an additional example, CARTs $O_{11}:A_9$, $D_{12}:Gly_{10.5}$, and $D_{14}:a\text{-methyh}_{14.5}$, complexed with luciferase mRNA show high levels of bioluminescence when administered through subcutaneous injection. In this example 5 μg of luciferase mRNA was complexed with $D_{13}:A_{11}$ at a 10:1 charge ratio in a total volume of 75 μL of PBS (pH 5.5) and injected under the skin on the back of a Balb/C mouse.

As a comparative example, when the prior art $D_{12}:G_{12}$ was complexed with Fluc mRNA, no resulting bioluminescence was observed. In this example 5 μg of luciferase mRNA was complexed with $D_{13}:A_{11}$ at a 10:1 charge ratio in a total volume of 75 μL of PBS (pH 5.5) and injected under the skin on the back of a Balb/C mouse.

mRNA Delivery and Expression with New Charged Domains

Comparative examples: Using the charge-altering motif demonstrated by the original embodiment, new monomers and new CART oligomers of varied chemical structure were synthesized. These CARTs were shown to effectively package and transfect fluorescently labeled (Cy5) mRNA, with some variations (such as $D_9:(7\text{-lact})_{11}$ and $D_{12}:(7\text{-glycine})_{11}$ resulting in higher (1.1 to 1.2×) intracellular Cy5 fluorescence than the parent $D_{13}$:Ani system. Some varieties of these CARTs (a-Me, a-Me-co-A) show some mRNA expression.

Lipophilic Polymer Domains

Some examples include CARTs containing variation in the lipophilic polymer domain (or interchangeably lipid blocks) of the material. Applicants have demonstrated the synthesis of CARTs containing cholesterol, nonenyl, stearyl, oleyl, and linoleyl side chains incorporated as the lipophilic polymer domain. When complexed with eGFP mRNA, these variants show varying performance with oleyl and linoleyl-functionalized materials giving similar transfection efficiencies to the dodecyl-based system.

Some work suggests that lipid block or lipophilic polymer domain variations affect the particle size and zeta potential, as measured by dynamic light scattering, with linoleyl and oleyl materials retaining positive zeta potentials for longer than the stearyl and dodecyl-based CARTs.

New Initiators

Some examples have explored variations of the initiating alcohol for ring-opening polymerization in order to incorporate additional functionality into the CARTs. Initiators that have been explored include fluorophores (Dansyl and BDK), branched (3-arm) moieties, a fluorescent quencher (BHQ) and biotinylated derivatives. CARTs of similar monomer block lengths that contain a different initiator functionality generally show similar eGFP mRNA transfection efficiencies as the original embodiment.

In some embodiments, the initiator can have the following formula:

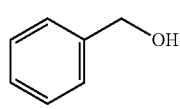

Bn-initiator
(Standard)

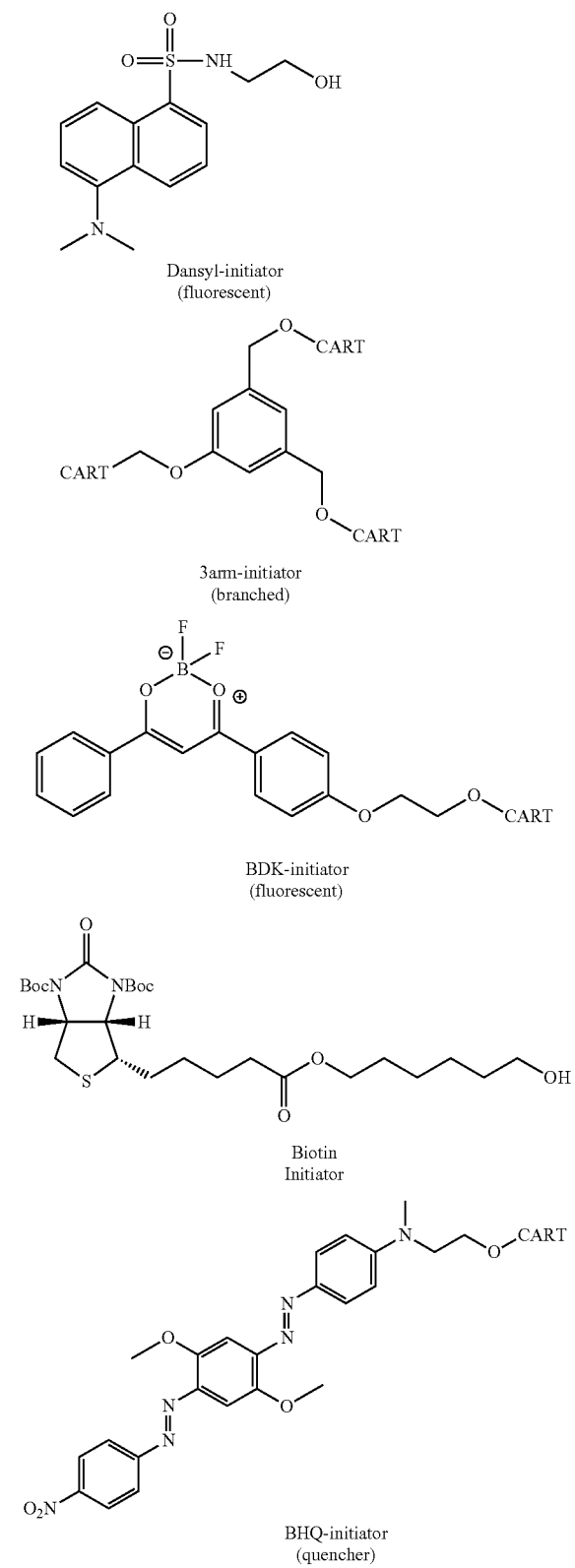

Fluorescent initiators have been used to independently track uptake of cargo (mRNA) and transporter (Dansyl or BDK) by flow cytometry and confocal microscopy. A quenching initiator has been used to monitor the release of a fluorescently-labeled mRNA or miRNA cargo by monitoring the re-appearance of fluorescence upon release from the quenched particle.

Initial results suggest that a 3-armed initiator may introduce structural changes into CART/mRNA particles (e.g., size and zeta potential) while maintaining mRNA transfection efficiency.

Initial results suggest that the biotin-derived initiator can be used either for the targeting of cancer cells or to attach additional cargos through biotin/streptavidin complementarity.

Example 6

Counterion

Prior examples have involved a Boc-deprotection using trifluoroacetic acid, which results in the trifluoroacetate counteranion to the ammonium cation. The applicants have also demonstrated similar efficacy for CARTs deprotected under different conditions including hydrochloric acid (HCl) to afford the chloride counterion. The resulting CART salts show nearly identical transfection efficiency/expression to the original embodiment.

Example 7

Combinations of mRNAs

In some embodiments, multiple mRNAs can be combined into a single CART complex. One example of this is the co-formulation of CART $D_{13}$:Ani with binary mixtures of eGFP mRNA and mCherry mRNA. Under these conditions, the resulting ratio of eGFP to mCherry is reflective of the feed ratio of mRNA transcripts into the complex. Additional flow cytometric analysis demonstrates that all cells are either doubly positive or doubly negative, suggesting that both transcripts are incorporated into the same CART/mRNA particle rather than separate particles containing each transcript. This co-formulation is achieved through simple mixing of the two transcripts before the addition of CART and treatment, and requires no additional optimization.

In an additional example, simultaneous expression of multiple mRNA transcripts was demonstrated by co-formulating CART $D_{13}$:$A_{11}$/mRNA complexes with binary mixtures of eGFP and Fluc mRNA. These polyplexes induce expression of two unique proteins at levels proportional to the mass % of that transcript in the formulation.

Example 8

Other Oligonucleotide Cargos

In addition to work on mRNA delivery, the applicants have also explored our various CART systems for the delivery of other nucleic acid cargos. Uptake and activity of siRNA, miRNA, minicircle DNA, and pDNA were shown to be amenable to CART technology. For many of these cargoes, CART optimization was empirically determined (e.g. charge ratios, length/degree of unsaturation of lipid domain).

siRNA

Several CARTs, including the unsubstituted morpholinone ($D_{13}$:$A_{11}$) and the 7-membered glycine-functionalized lactone ($D_{10}$:(7-gly)ii), have demonstrated a high level of efficacy for siRNA-induced gene knockdown. It was unexpected that systems such as ($D_{10}$:(7-gly)$_{11}$) that showed uptake of a fluorescent mRNA but no resulting mRNA translation would nevertheless result in >85% knockdown of protein expression by delivery of siRNA at a low siRNA dose (e.g. 5 pmoles/well).

Comparative example: These two CART delivery agents significantly out-performed prior art consisting of non-releasing transporters such as D:G 4:4 (Reference WO2013036532 A1 and *PNAS* 2012, 109 (33), 13171-13176) which only demonstrated 50% knockdown under these conditions.

Specifically, siRNA knockdown experiments were performed according to a procedure modified from (Geihe, et. al. *PNAS* 2012, 109 (33), 13171-13176.) TdTomato/EGFP expressing HaCaT cells were plated at 10,000 cells/well in a 96-well plate and allowed to incubate at 37° C. for 18-24 hours. siRNA/CART complexes were prepared by first pre-mixing 2 µL of a 25 µM stock of CBL3 siRNA with 17.60 µL of PBS at pH 5.5. CART was added to this from a 2 mM stock in DMSO to achieve a net cation:anion charge ratio of 10:1. The solution was mixed for 20 seconds before adding 5 µL to each of 3 wells of a 96-well plate containing 100 µL of serum-free DMEM resulting in a net concentration of 5 pmol/well of siRNA. Cells were incubated for 4 hours with the complexes after which time the media was replaced with serum-containing DMEM and cells were incubated for 48 hours. After that incubation, cells were washed with PBS, trypsinized, and analyzed by flow cytometry. Normalized percent tdTOM expression was calculated with the following formula: (mean fluorescence tdTOM$_{treated\ cells}$/mean fluorescence EGFP$_{treated\ cells}$)/(mean fluorescence tdTOM$_{untreated\ cells}$/mean fluorescence EGFP$_{untreated\ cells}$)×100.

miRNA

In some examples, the nucleic acid cargo is a fluorescently-labeled miRNA. Flow cytometry analysis shows robust uptake of the labeled miRNA using CART $D_{13}$:$A_{11}$ compared to other transfection methods such as Lipofectamine and poly(lactic-co-glycolic acid) nanoparticles. In these examples, the optimum charge ratio for uptake of miRNA is 20:1 (cation:anion), which is higher than has been observed for mRNA (10:1).

Specifically, miRNA uptake was measured using a Cy5-labeled miRNA. Briefly, HeLa cells were plated at 40,000 cells/well in a 24-well plate and allowed to adhere overnight at 37° C. CART/miRNA complexes were prepared by first pre-mixing 2.1 µL of a 0.2 µg/µL stock of Cy5-miRNA (Sequence: Cy5-UpCpApACAUCAGUCUGAUAA-pGpCpUpA) with 5.72 µL of PBS at pH 5.5. Then, immediately before transfection, CART was added to this from a 2 mM stock in DMSO to achieve a net cation:anion charge ratio of 10:1. This was mixed for 20 seconds before adding 5 µL to each of 3 wells of the 24-well plate containing 200 µL serum-free DMEM for a final miRNA concentration of 125 ng/well. This was incubated for 8 hours at 37° C. Following this time, cells were washed with PBS, trypsinized, and intracellular Cy5-fluorescence determined by flow cytometry.

pDNA

In some examples, the nucleic acid cargo is dual-stranded plasmid-DNA (pDNA) rather than the aforementioned RNA cargos. In these cases, CARTs show improved efficacy (approx. 2.5-fold) over commercial agents such as Lipofectamine, resulting in higher transfection efficiency and median fluorescence intensity. Specifically, a plasmid coding for pPKCδ-GFP was used as a fluorescent reporter. In some cases, CARTs containing different lipid block or lipophilic polymer domains were more efficacious for plasmid delivery than CART $D_{13}:A_{11}$, with the oleyl- and linoleyl-functionalized materials showing the highest transfection efficiencies.

Particle sizes for CART/pDNA complexes were generally smaller than the analogous mRNA-containing particles, with hydrodynamic diameters from 90-110 nm for most compounds, and 390 nm for the linoleyl-functionalized CART. Zeta potential follows the same trend as mRNA particles starting at approximately +40 mV and decreasing to −40 mV as the charge-altering rearrangement occurs.

Specific experimental details for transfection: for example transfections by CART $O_{11}:A_9$, CHO cells were seeded at 40,000 cells/well in 24-well plates and allowed to adhere overnight. pDNA:CART complexes were prepared by mixing PBS pH 5.5 and pPKCδ-GFP with various amounts of oligomer from DMSO stock solutions, to achieve specific pDNA/CART ratios (optimized to a theoretical cation:anion ratio of 25:1, 115 µL total volume). The complexes were incubated for 20 s at room temperature prior to treatment. The Lipofectamine 2000 control was prepared in OptiMEM per the manufacturer's instructions. The cells were washed with serum-free F-12 medium and pDNA/Lipofectamine solution was added for a final volume of 500 µL/well and 679 ng pDNA/well. After washing with serum-free F-12 medium, 37.5 µL of the pDNA/CART complexes was added to each of three wells for a total volume of 500 µL and a final pDNA concentration of 674 ng/well. The cells were incubated for 24 h at 37° C., at which time the medium was replaced with serum-containing F-12 medium. The cells were incubated for a further 24 h and then trypsinized with trypsin-EDTA (0.25%) for 5 min at 37° C. Serum-containing F-12 medium was added and the contents of each well centrifuged. The supernatant was removed and the pelleted cells were re-dispersed in PBS (200 µL), transferred to FACS tubes, and read on a flow cytometry analyzer (LSR-II.UV, Stanford University). The data presented are the geometric mean fluorescent signals from 5,000-10,000 cells analyzed. For transfection efficiency, untreated cells were gated for no eGFP expression, and the data presented are the percentage of cells analyzed with higher eGFP expression than untreated cells. Error is expressed as +SD.

Stable Transfection by Delivery of CART/pTransposase

In some examples, multiple plasmids could be simultaneously delivered such as a combination of plasmids separately encoding pLuciferase (containing transposase recognition sites) and pTransposase, resulting in stable expression of the target luciferase gene. After 6 days, CART $O_{11}:A_9$ significantly outperformed Lipofectamine, with a greater than 10-fold increase in bioluminescence levels.

For these examples, CHO cells were seeded at 10,000 cells per well in black 96-well plates and allowed to adhere overnight at 37° C. pDNA:CART complexes were prepared by first pre-mixing PBS at pH 5.5 with either 470 ng pDNA encoding for both firefly luciferase and tdTomato or 585 ng total of the same plasmid mixed with pTransposase in a 2:1 ratio. Lipofectamine controls were made up in serum-free OptiMEM medium according to the manufacturer's specifications. Immediately before transfection, CART was added to the plasmid/PBS solutions from a 2 mM stock solution in DMSO to achieve a net +/−charge ratio of 5:1. The resulting complexes were incubated at room temperature for 20 s prior to addition to cells. Cells were rinsed with serum-free F-12 medium, then 7.3 µL of complex was added to each of 3 wells of the 96-well plate containing serum free media for a final volume of 50 µL per well and a pDNA concentration of 137 or 171 ng/well. Cells were incubated with treatment for 24 hours at 37° C. at which time the medium was replaced with 100 µL of serum-containing F-12 medium with 0.3 mg/mL luciferin. The resultant bioluminescence was measured using an IVIS 50 or IVIS 200 (Xenogen Product line of Perkin-Elmer) charge-coupled device camera and Living Image Software. Error expressed as ±SD. Upon confluency, cells were passaged using 0.25% trypsin to new wells.

Further examples have confirmed the effective delivery and stable transfection with multiple plasmids using CARTs. In these cases, a combination of plasmids separately encoding pLuciferase (both conferring puromycin resistance and containing transposase recognition sites) and pTransposase, resulting in stable expression of the target luciferase gene in conjunction with puromycin resistance. Puromycin selection over several generations validated the stable transfection, with a two-fold increase in bioluminescence relative to Lipofectamine.

For these examples, CHO cells were seeded at 10,000 cells per well in black 96-well plates and allowed to adhere overnight at 37° C. pDNA:CART complexes were prepared by mixing PBS at pH 5.5 with 585 ng pLuc-tdTom/pTransposase mix encoding for firefly luciferase and tdTomato. The Lipofectamine 2000 control was prepared in serum-free OptiMEM medium according to the manufacturer's specifications. Immediately before transfection, CART was added to the pDNA/PBS solution from a 2 mM stock solution in DMSO to achieve a net +/−charge ratio of 5:1. Complexes were incubated at room temperature for 20 s prior to addition to cells. Cells were rinsed with serum-free F-12 medium, then 7.3 µL of complex was added to each of 3 wells of the 96-well plate containing serum free media for a final volume of 50 µL per well and a pDNA concentration of 171 ng/well. After 24 hours, the medium was replaced with 100 µL of serum-containing F-12 medium with 0.3 mg/mL luciferin and 6 µg/mL puromycin. Cells were imaged daily using an IVIS 50 or IVIS 200 (Xenogen Product line of Perkin-Elmer) charge-coupled device camera and Living Image Software. Error expressed as ±SD. Cells were passaged 72 hours after end of treatment using 20 µL of 0.25% trypsin per well. Cells were incubated for 5 minutes and then diluted with 80 µL serum-containing F-12 medium for a final volume of 100 µL per well. From each well, 30 µL of the cell solution was added to each of 3 new wells and diluted with 70 µL of serum-containing F-12 media with 0.3 mg/mL luciferin and 6 µg/mL puromycin. The remaining 10 µL of cell solution in the original wells were diluted with 90 µL of serum-containing F-12 medium with 0.3 mg/mL luciferin and 6 µg/mL puromycin for a final volume of 100 µL in each well.

Minicircle-DNA

Further examples have shown the effective delivery of minicircle-DNA (mcDNA) using CARTs. In these cases, a minicircle-DNA coding for luciferase was delivered to HeLa cells by both CART $D_{13}:A_{11}$, and Oleyl CART $O_{11}:A_9$. This resulted in high levels of luciferase expression (approx. 10-fold higher) compared to both Lipofectamine and polyethyleneimine (PEI) formulations.

Specifically, minicircle DNA uptake and expression was measured using luciferase reporter system. Briefly, HeLa cells were plated at 15,000 cells/well in a 96-well plate and allowed to adhere overnight at 37° C. CART/minicircle DNA complexes were prepared by first pre-mixing 2.1 µL of a 0.2 µg/µL stock of minicircle DNA containing the firefly luciferase gene and a constitutive promoter with 5.71 µL of PBS at pH 5.5. Lipofectamine and PEI controls were made up according to manufacturer's specifications. Then, immediately before transfection, CART was added to this from a 2 mM stock in DMSO to achieve a net cation:anion charge ratio of 10:1 (or any other charge ratio to be tested). This was mixed for 20 seconds before adding 2.5 μL to each of 6 wells of the 96-well plate containing 100 μL serum-free DMEM for a final minicircle DNA concentration of 62.5 ng/well. This was incubated for 8 hours at 37° C., then media was replaced with serum-containing DMEM containing 0.3 mg/mL luciferin, and cells were imaged for bioluminescence using an IVIS camera system.

Example 9

CRISPR/Cas9 Editing

In some examples of CART-mediated transfection, successful knock-in of a target gene through specific CRISPR/Cas9 gene editing is demonstrated. In this case, an mRNA coding for Cas9 was co-formulated with $D_{13}$:$A_{11}$ along with a sgRNA targeting the untranslated region of the murine beta-actin gene. Also co-formulated was a minicircle-DNA containing the luciferase or mCherry gene and the same CRISPR cleavage site from the beta-actin gene, and no promoter. Using this system, expression of the reporter gene would only occur if Cas9 cleavage resulted in both the murine genome and the minicircle resulted in insertion of the minicircle vector into the beta-actin untranslated region such that it was under control of the beta-actin promoter.

The co-formulation of Cas9 mRNA and sgRNA constructs with a fluorescent reporter gene was performed to ensure that the presence of these cargos did not disrupt nucleic acid delivery by CARTs. In this case, eGFP mRNA was formulated as a 50% w/w mixture with either Cas9 mRNA or sgRNA, or a formulation consisting of 50% eGFP mRNA, 25% Cas9 mRNA, and 25% sgRNA. In both of these examples, the cellular eGFP fluorescence was approximately 50% that of a formulation consisting entirely of eGFP mRNA. This same result was obtained with both CART $D_{13}$:$A_{11}$ and $O_{11}$:$A_9$. This supports the successful co-formulation of CRISPR components by the aforementioned CARTs.

Additional characterization by DLS (according to standard procedure) demonstrated that particles formed with either $D_{13}$:$A_{11}$ or $O_{11}$:$A_9$ and the mixture of Cas9 mRNA and sgRNA were approximately 173 nm in size, which is consistent with sizes observed for other mRNA transcripts.

When 3T3 murine fibroblasts were treated with complexes formulated as above with the luc minicircle construct, a significant bioluminescent readout was observed. This signal was not observed when a scrambled sgRNA sequence was used, confirming that it was due to a specific insertion of the luciferase gene into the 3T3 genome. The resulting bioluminescence increased when a higher ratio of minicircle-DNA in the formulation was used. Additionally, when complexes were formed with the mCherry-containing minicircle and exposed to 3T3 fibroblasts, flow cytometry analysis indicated that there was strong mCherry fluorescence in approximately 2% of the target population, indicating efficient genomic integration.

Specifically, CRISPRJCas9 gene editing was in 3T3 fibroblasts according to the following general procedure. Briefly, HeLa cells were plated at 40,000 cells/well in a 24-well plate and allowed to adhere overnight at 37° C. CART/oligonucleotide complexes were prepared by first pre-mixing 134 ng Cas9 mRNA, 134 ng sgRNA, and 134 ng minicircle DNA containing the luciferase gene with 22.8 μL of PBS at pH 5.5. Then, immediately before transfection, CART was added to this from a 2 mM stock in DMSO to achieve a net cation:anion charge ratio of 10:1. This was mixed for 20 seconds before adding 7.5 μL to each of 3 wells of the 24-well plate containing 400 μL serum-free DMEM for a final concentration of each component of 40 ng. This was incubated for 8 hours at 37° C. Following this time, media was replaced with serum-containing DMEM and left for 24-48 hours. After incubation, media was replaced with serum-containing DMEM with 0.3 mg/mL luciferin and cells were imaged for bioluminescence using an IVIS camera system.

Example 10 mRNA Vaccination

Figure 2:
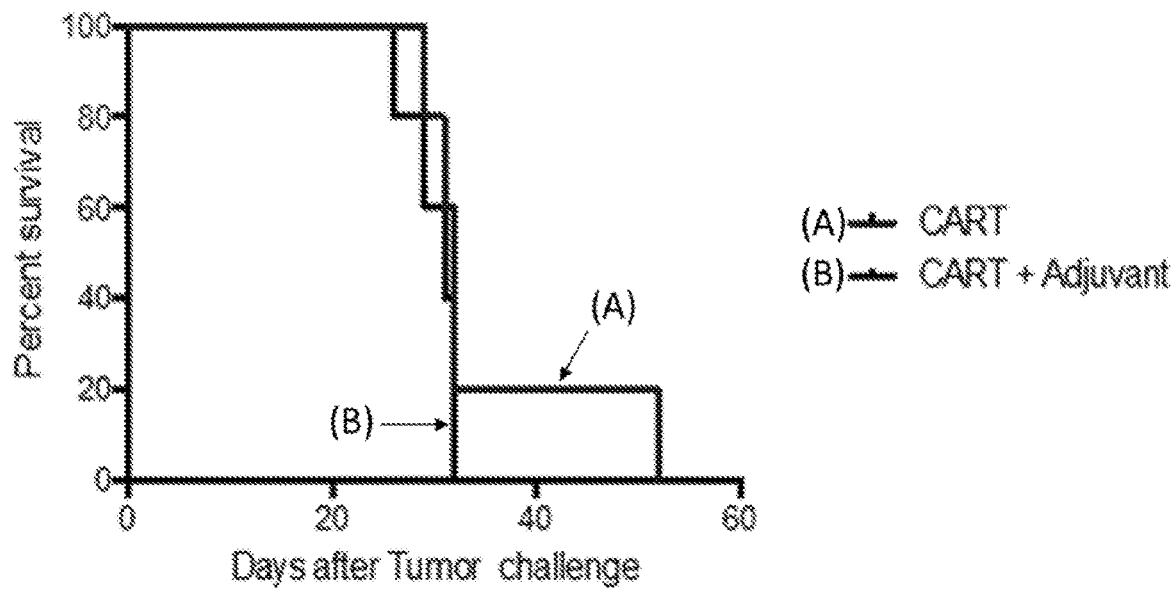
FIG. 2. Shows data illustrating anti-tumor immunogenicity of CARTs and the combination of CARTs and adjuvant.

In vaccination examples, neither CARTs alone nor CART combined with adjuvant (with no mRNA present) induce protective anti-tumor immunity in the surrogate antigen model (FIG. 2). Specifically in this example, mice aged 6-8 weeks were simultaneously inoculated with 107 Tumor-specific antigen (TSA)-expressing A20 cells and treated with either 206 μg CART alone or 206 μg CART+50 μg adjuvant by subcutaneous injections on a different anatomical site than the tumor. Tumor size was measured daily and mice with a tumor diameter >15 mm were euthanized according to the animal protocol. No prolongation of life was observed in inoculated mice for either of these control groups. CARTs do not illicit an immune response.

Prophylactic Vaccination Through Simultaneous Tumor Exposure

Figure 3A:
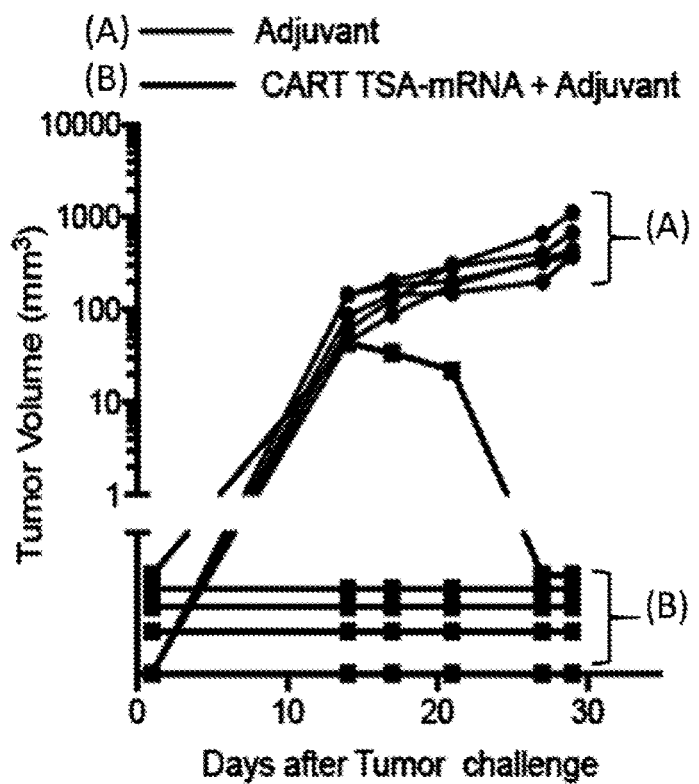
FIGS. 3A-3C. Show data illustrating the efficacy of the prophylactic vaccination strategy.
Figure 3B:
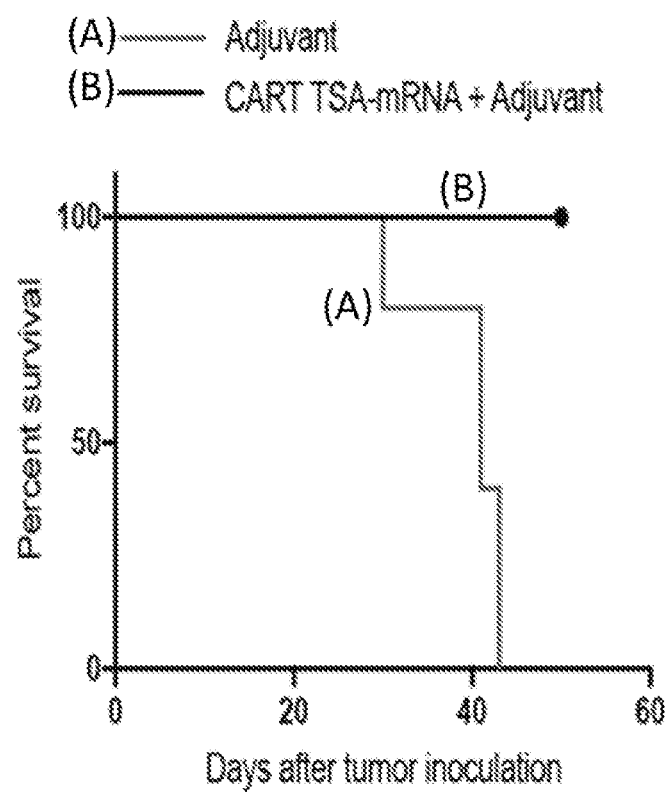
Figure 3C:
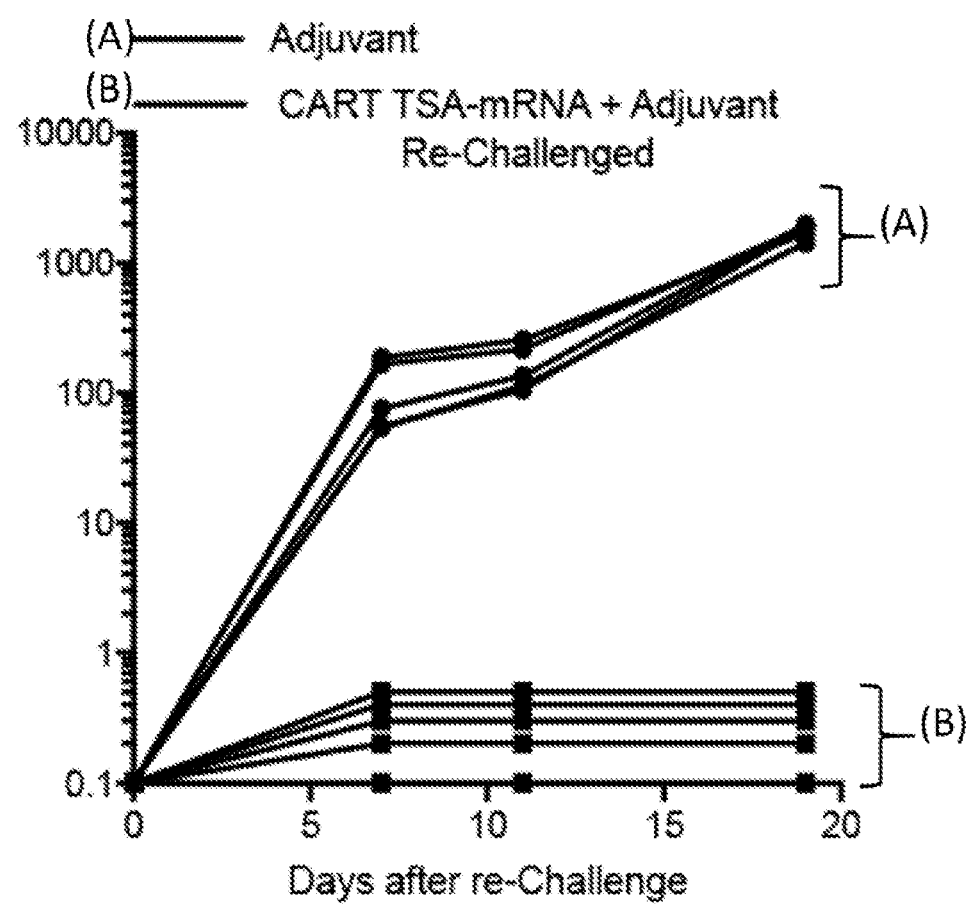
Figure 4A:
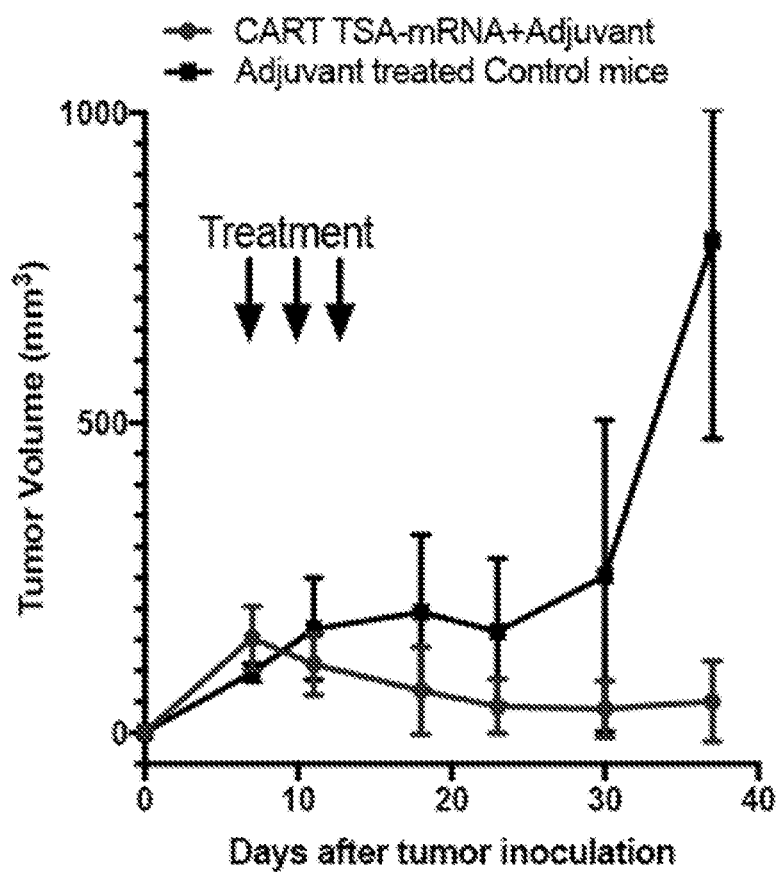
FIGS. 4A-4B. Show pre-established tumor size and survival data (initial vaccination at day 7, boosts at day 10 and 13.
Figure 4B:
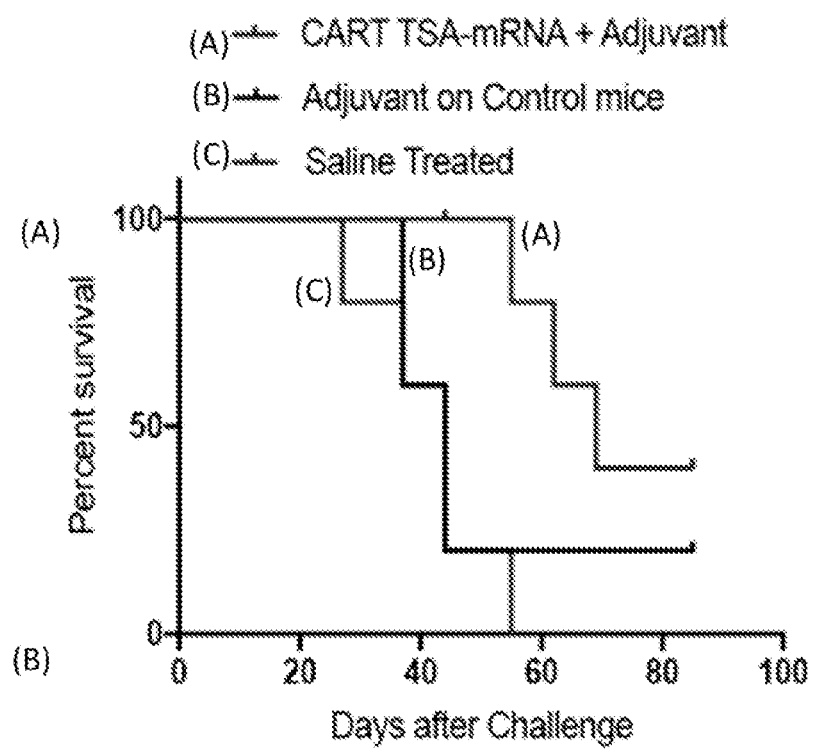

An antigen-specific prophylactic response is provided when vaccination is performed either before or at the time of tumor inoculation. These studies indicate that vaccination with CARTs containing TSA-mRNA+adjuvant, in either a co-formulation embodiment or administered separately at the time of vaccination, induce protective immunity in a mouse model with TSA-expressing tumor cells. Treatment with CARTs/TSA-mRNA provides protection, and using immune-stimulatory adjuvants provides increased efficacy. Mice treated with adjuvant alone rapidly grew large tumors and were sacrificed according to the animal protocol. A robust response is garnered from a single dose, requiring no vaccine boosts, and can be recalled upon secondary tumor challenges (FIG. 3).

Specifically in this example, mice aged 6-8 weeks were simultaneously inoculated with $10^7$ Tumor-specific antigen (TSA)-expressing A20 cells through subcutaneous injection, and treated with either CARTs+TSA-mRNA+adjuvant (formulated as described previously) or adjuvant alone by subcutaneous injections on a different anatomical site than the tumor. Tumor size was measured every other day for the first 30 days. Mice with a tumor diameter >15 mm were euthanized. In a re-call response experiment, surviving mice from the CART+TSA-mRNA+adjuvant treated group were re-challenged with $10^7$ TSA-expressing A20 cells.

Treatment of an Established Tumor

An antigen-specific therapeutic response is induced when CART/mRNA+adjuvant vaccination is administered after establishment of large tumors. Seven days after the inoculation of large tumors, administration of treatments with CART/mRNA+adjuvant provides both regression and remission of tumors (3×3 μg TSA-mRNA/CART complexes).

In this study (5 animals total), mice showed significantly slowed progression of tumor growth, while 40% of mice (2/5 mice) were completely cured of tumors, even after ~60-90 days. Vaccination using mRNA/CART+adjuvant out-performs established protein vaccination strategies that have repeatedly been shown to provide protection in animal studies.

Specifically in this example, mice aged 6-8 weeks were inoculated with 107 Tumor-specific antigen (TSA)-expressing A20 lymphoma cells subcutaneously. When tumor size reached 150 mm³, mice were treated three times with either CART complexed with 3 μg TSA-mRNA+Adjuvant, Adjuvant alone, or saline solution by subcutaneous injections on a different anatomical site than the tumor with four days between each treatment. Tumor size was measured every other day for the first 40 days. Mice with a tumor diameter >15 mm were euthanized.

Intratumoral Vaccination

Figure 5A:
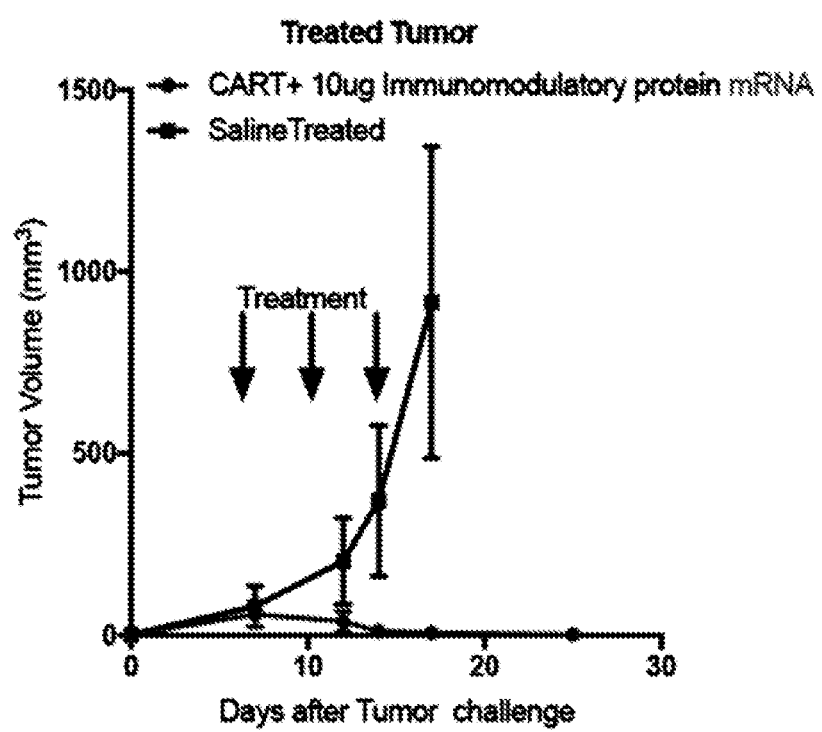
FIGS. 5A-5B. Show data illustrating in situ vaccination using CARTs and mRNA coding for immuno-stimulatory protein.
Figure 5B:
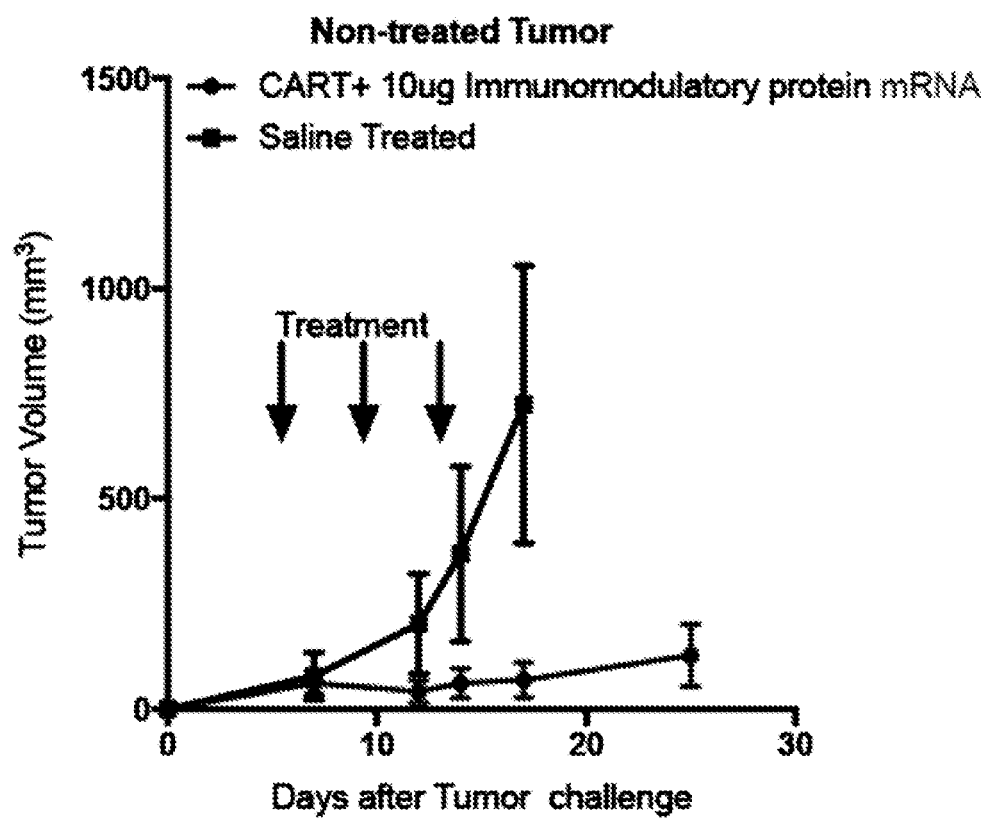

Intra-tumoral injection of CART/mRNA complexes results in regression of tumors. Established A20 lymphoma tumors treated with CART-complexed mRNA results in protein expression in a subset of four different cell populations in the tumor. A candidate protein that is believed to modulate the anti-tumor immune response by enhancing T-cell functions showed a profound effect on the treated tumor. Notably, an effect with delayed growth rate was also observed on a distal non-treated tumor in the same animal (FIG. 5). These findings suggest that in situ vaccination/augmentation strategies have therapeutic potential in metastatic disease.

Specifically in this example, mice aged 6-8 weeks were simultaneously inoculated with $10^7$ A20 cells subcutaneously on two different anatomical locations. When tumor size reached 150 mm³, one of the tumors in each mouse was treated with three intratumoral injections of either CARTs+ 10 μg immunomodulatory protein mRNA, or saline solution. The other tumor was left untreated. Both tumors were measured every other day for the first 20 days or until tumors reached a size where the mice had to be euthanized.

Example 11

Charge-Altering Releasable Transporters (CARTs) for the Delivery and Release of Messenger RNA.

Provided herewith is the step-economical synthesis and evaluation of a new, tunable and remarkably effective class of synthetic biodegradable materials, charge-altering releasable transporters (CARTs). The CARTs provided according to some embodiments herein have structurally unique and operate through an unprecedented mechanism, serving initially as α-amino ester cations that complex, protect and deliver mRNA, and then change physical properties through a degradative, charge-neutralizing intramolecular rearrangement, to release mRNA for highly efficient protein translation both in cell culture and in animals. This new mRNA delivery technology can be broadly applicable to numerous research and therapeutic applications.

Messenger RNA (mRNA) enables the in vivo synthesis of proteins for which it codes, providing the basis for a rapidly emerging class of gene therapy drugs with the potential to transform the treatment of illnesses as diverse as cancer, genetic disorders, and infectious diseases. The use of the methods and composition according to certain embodiments herein for the specific expression of mRNA-encoded proteins can be leveraged for research and imaging applications, for therapeutic use requiring protein replacement or augmentation, and for new vaccination strategies for both prophylactic and immunotherapeutic indications.

The charge-altering releasable transporters (CARTs) according to some embodiments provided herein function firstly as polycations to transiently complex and protect polyanionic mRNA, and then rapidly transform their cationic charge, and thus anion-binding ability through a controlled self-immolation mechanism.

Provided as an example of certain embodiments is development of CARTs as a new class of materials designed for the non-covalent complexation, protection, intracellular delivery and release of mRNA. These CARTs are comprised of dynamic, cationic α-amino esters that rearrange through a unique self-immolation mechanism, converting a cationic amine into a neutral amide. The materials are step-economically synthesized (two steps) through organocatalytic ring-opening polymerization (OROP) and deprotection and effectively complex mRNA into self-assembled polyelectrolyte complexes that deliver and release mRNA in multiple cell types and in animal models via intramuscular and intravenous administration. Example 10 herein further demonstrates that the efficacy of mRNA delivery by these materials is due to their the unique, charge-altering intramolecular rearrangement, which elicits robust endosomal escape and cytosolic mRNA release.

We designed a new class of oligonucleotide delivery vehicles, amphipathic oligo(carbonate-b-α-amino esters)s, with dynamic properties to address the specific challenges associated with mRNA delivery. Our previous work on siRNA demonstrated that efficient delivery can be achieved using block co-oligomers containing both a lipophilic and a cationic block designed to form nanoscale polyplexes with anionic siRNA duplexes. As single-stranded mRNA displays a shorter intracellular half-life than siRNA and pDNA, we hypothesized that rapid endosomal escape and subsequent oligonucleotide release would be crucial to efficient expression. To address both of these issues, we devised amphipathic oligomeric delivery vehicles that incorporate a rapidly self-immolating cationic block that serves to simultaneously cleave the oligomer backbone and convert cationic amines to neutral amides. Backbone degradation following cellular uptake is hypothesized to increase osmotic pressure in the endosome, thereby facilitating endosomal rupture. Additionally, this mechanism simultaneously eliminates the multi-site and electrostatic association of the polyanion and polycation components, facilitating cytosolic mRNA release and subsequent gene expression.

Figure 1:
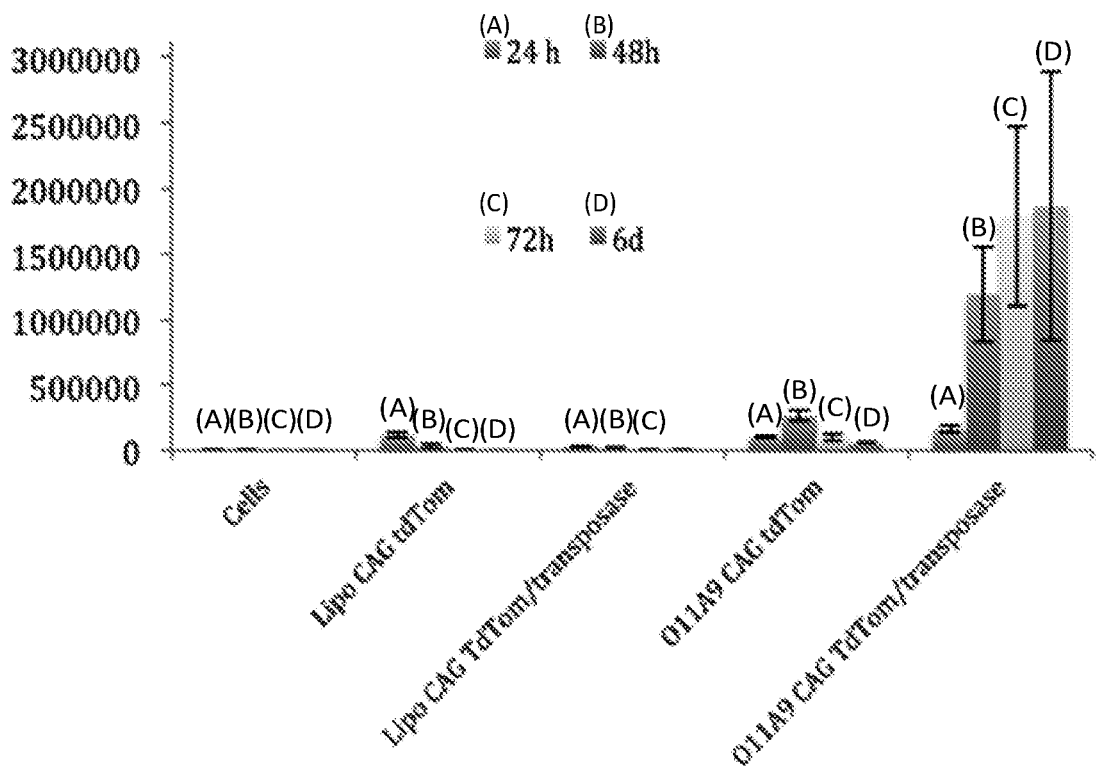
FIG. 1. Shows data illustrating average radiance (p/s/cm²/sr) of cells after stable transfection with CART system.

We have previously reported the synthesis of poly(α-amino esters) (FIG. 7A, 1) by the OROP of N-protected morpholin-2-ones, subsequently leading to the study of their use for mRNA delivery as described herein. The functionalized lactone monomers are readily generated in two high-yielding steps from commercially available starting materials. These monomers can be ring-opened with a primary alcohol initiator under organocatalytic conditions to yield poly(α-amino ester)s with precise control over chain length and dispersity.

Upon deprotection, oligomers are water-soluble (>0.5 M) and stable in unbuffered water (>2 days in D₂O). However, unlike well-known poly(β-amino ester)s, upon exposure to slightly basic conditions, they degrade in <5 minutes through a controlled self-immolative rearrangement, which is employed here to facilitate mRNA release by loss of electrostatic interactions.

Figure 7A:
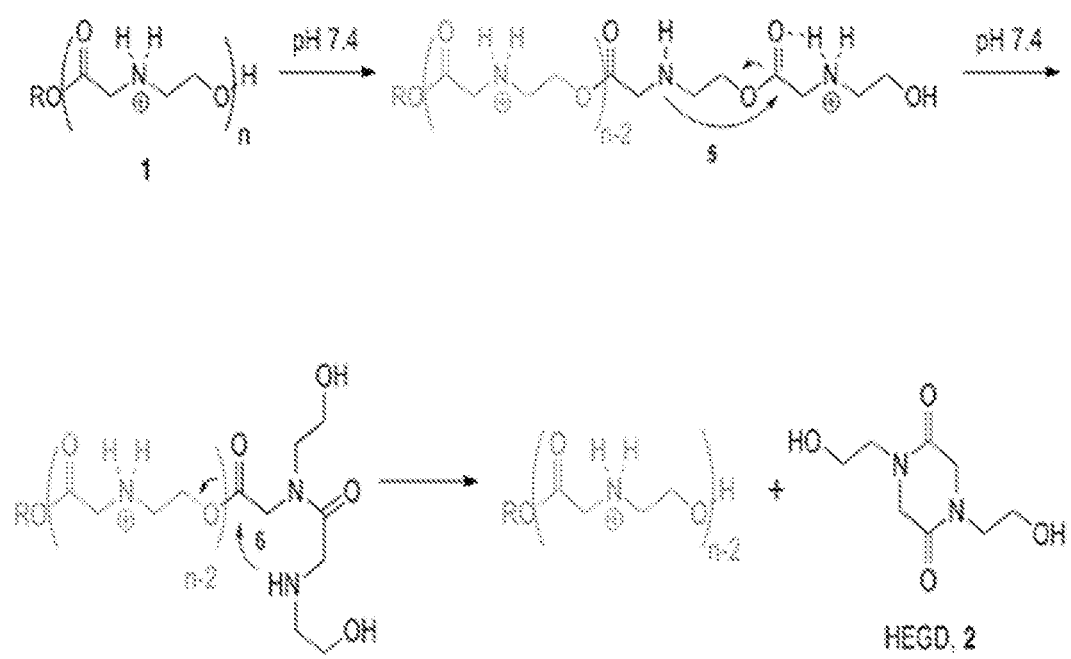
FIGS. 7A-7C. Show oligo(carbonate-b-α-amino ester) CARTs synthesized for the delivery of mRNA.

The mechanistic investigations of this degradation evince the partial deprotonation of ammonium cations, allowing for an intramolecular cyclization into the backbone ester through a 5-membered transition state (FIG. 7A). Following that initial contraction of the backbone, a nitrogen group on the adjacent monomer unit engages in a second cyclization through a 6-membered transition state to form a small molecule dimer of hydroxyethyl glycine (HEGD, 2), a known non-toxic metabolite of the Maillard reaction. This rearrangement is exceptionally fast and efficient; homo-oligomers degrade with $t_{1/2}$<2 minutes at pH 7.4. The unique reactivity of this system can be explained by complementary activation of the backbone ester carbonyl by inductive and hydrogen-bonding interactions that proceeds concurrently with carbonyl-assisted deprotonation of the required nucleophilic amine. Rigidification of the 6-membered transition state by the newly formed hydroxyethylamide facilitates the final cyclization to form HEGD 2. While further investigation of the mechanism and variations on this rearrangement will be reported separately, the unique dynamics of this system that rapidly converts a polycationic oligomer into a charge-neutral fragment represents a potentially broadly exploitable concept for polyanionic drug and probe delivery.

Figure 7B:
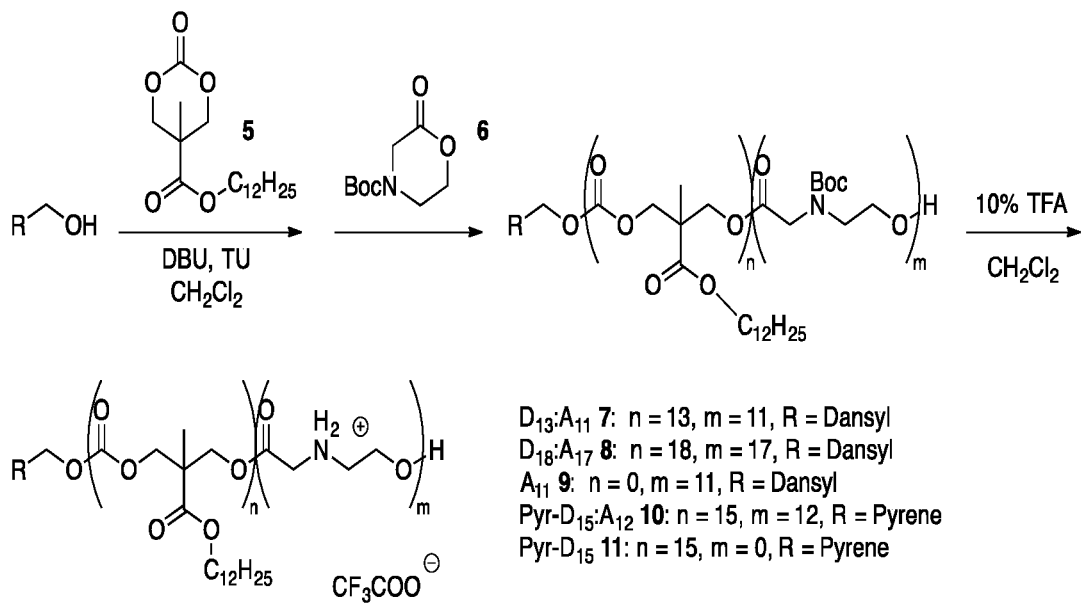
Figure 7B:
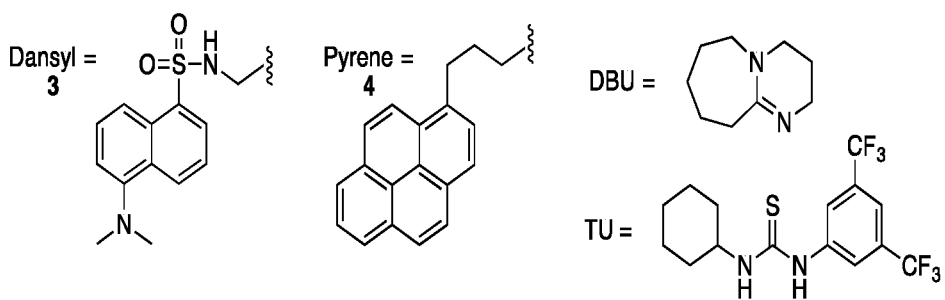
Figure 7C:
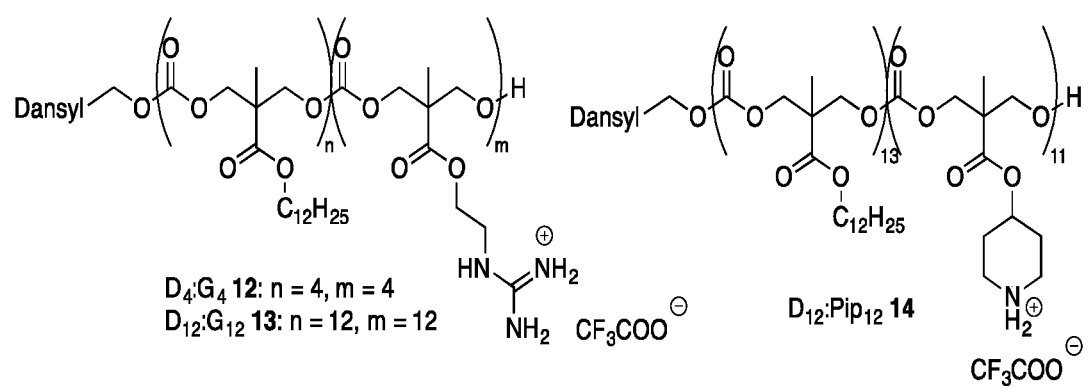

We designed materials for delivering mRNA feature a dodecanol-functionalized lipophilic carbonate block appended to a cationic block of self-immolative α-amino esters, which is easily achieved through co-polymerization of morpholin-2-one monomer with cyclic carbonates using OROP methodology (FIG. 7B).

An attractive aspect of this technology is the ability to tune performance using different lengths of lipophilic polymer domains (or lipid blocks) in the diblock co-oligomer. A small series of oligomeric delivery vehicles was synthesized using a primary alcohol to initiate ring opening of the dodecyl-carbonate block, followed by addition and oligomerization of the cationic block. Using this strategy, oligomers containing an average of 13 lipid monomer units and 11 cationic monomer units ($D_{13}:A_{11}$ 7), 18 lipid and 17 cationic units ($D_{18}:A_{17}$ 8), and a homo-oligomer of 13 cationic units ($A_{13}$ 9) were synthesized. Each new vector can be made only two steps to make, a process requiring only a few hours.

Figure 8A:
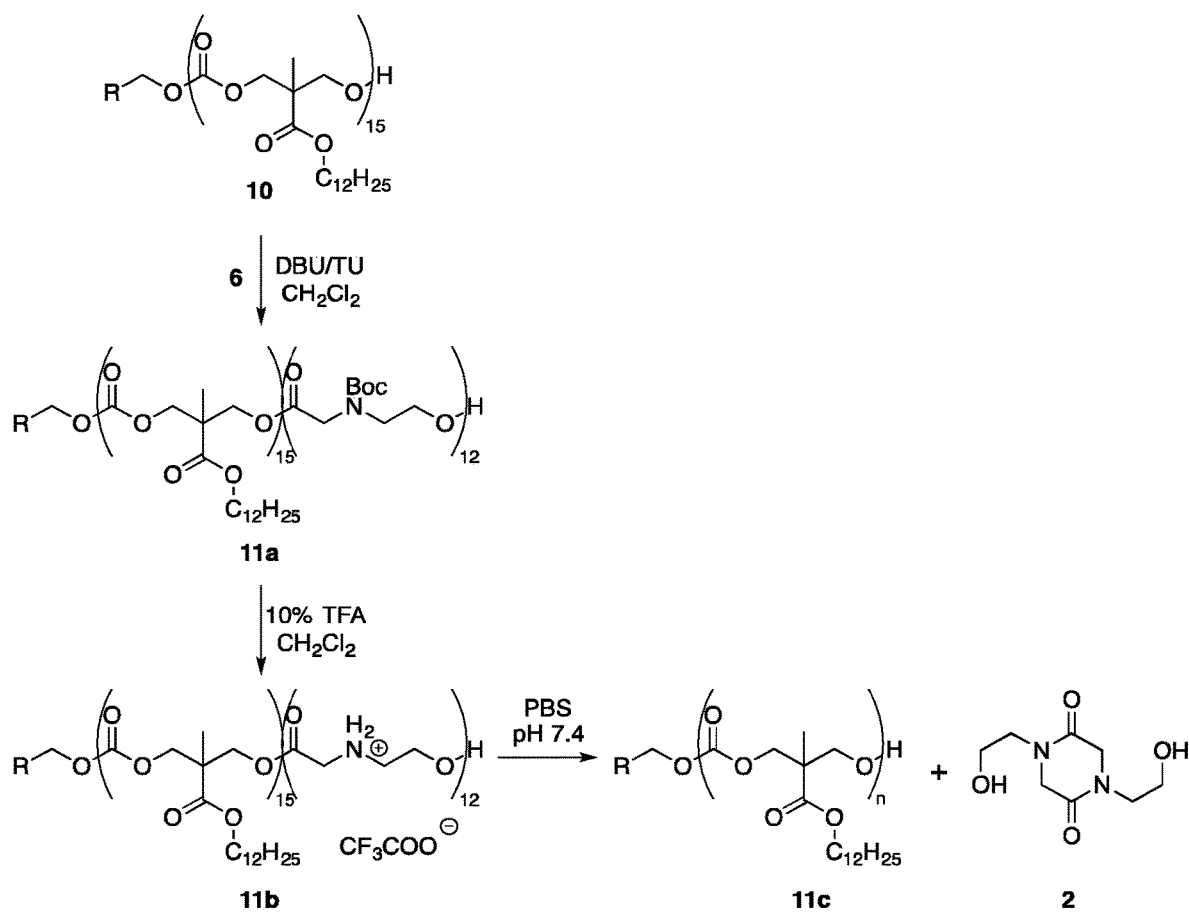
FIGS. 8A-8B. Show exploration of oligo(α-amino ester) CART rearrangement mechanism.
Figure 8B:
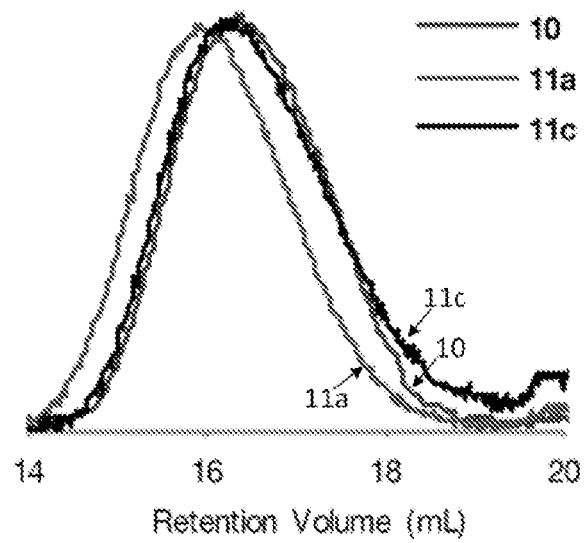

To increase our understanding of this rearrangement as it applies to the CART delivery vehicles, gel permeation chromatography (GPC), was used to analyze the dynamics of the oligo(carbonate-b-α-amino ester)s at physiological pH. In order to show that the rearrangement reaction affects only the cationic-binding portion of the amphipathic CARTs while leaving the lipophilic domain intact, a model co-oligomer, Pyr-$D_{15}:A_{12}$ 10, was dissolved in PBS buffer at pH 7.4 to effect rearrangement (FIG. 8A). After one hour, the solution was concentrated and analyzed by GPC (FIG. 8B). The GPC trace of degraded co-oligomer was compared with an independently synthesized Pyr-Dis oligomer 11, and Pyr-$D_{15}:A_{12}$ block-co-oligomer prior to rearrangement and Boc-deprotection. As expected, the GPC traces of the protected $D_{15}:A_{12}$ block-co-oligomer show higher molecular weight than the homo-oligomer Pyr-$D_{15}$ 11 (6.4 kDa and 4.6 kDa, respectively). However, after exposure to the pH 7.4 PBS buffer, the deprotected block co-oligomer showed a diminished molecular weight (4.3 kDa) that was nearly identical to the Pyr-D is lipid block (4.6 kDa), suggesting that at physiological pH, the cationic portion of the CART is degraded while the full lipophilic block remains intact. UV traces from the same GPC data indicates that the initiating alcohol (in this case pyrene butanol but other nucleophilic alcohols, amines and thiols could be used) remains attached to the lipophilic block, enabling future studies to use this alcohol for appending other functionality such as ligands to target the CARTs to various cells and organs.

In order to evaluate the efficacy of CARTs as mRNA delivery vehicles, enhanced green fluorescent protein (eGFP) mRNA was selected as a model reporter gene. Flow cytometry analysis of eGFP fluorescence following treatment allows for simultaneous quantification of the mean protein expression, as well as the fraction of cells exhibiting above-baseline levels of fluorescence (% transfection). Gene expression following treatment with CART complexes was compared to the commercial agent Lipofectamine 2000 (Lipo), as a positive control, as well as two compounds known to be especially effective for siRNA delivery ($D_4:G_4$ 12 and $D_{12}:G_{12}$ 13). When HeLa cells were treated with mRNA formulated with Lipofectamine according to the manufacturer's instructions, modest levels of gene expression were observed (FIG. 9A). However, this condition resulted in only approximately 50% cellular transfection, with half of the cell population showing no eGFP expression (FIG. 9B). In stark contrast, our designed oligo(carbonate-b-α-amino ester) CART, $D_{13}:A_{11}$ 7, afforded excellent eGFP expression with, remarkably, >99% transfection efficiency and high mean fluorescence. A second oligo(carbonate-b-amino ester) CART with longer block lengths ($D_{18}:A_{17}$ 8) also afforded high transfection efficiency (>90%) but lower mean transfection values. Complexes formed with α-amino ester homo-oligomer ($A_{13}$ 9) induced no eGFP expression. This also confirms previous observations that a significant phase separation between hydrophobic and hydrophilic domains stabilizes nanoparticle formation, and increased lipophilicity promotes membrane association and uptake. In contrast to their potency as siRNA delivery agents, guanidinium-functionalized amphipathic oligocarbonates $D_4:G_4$ 12 and $D_{12}:G_{12}$ 13 exhibited no mRNA expression. Since these materials contain no mechanism for degradation or cargo release beyond passive hydrolysis ($t_{1/2}$>8 hours), this supports our hypothesis that endosomal escape and cytosolic release must occur on a more rapid timescale for mRNA delivery as compared to siRNA.

In order to optimize the delivery parameters by CART 7, the charge ratio of cationic oligomer to anionic mRNA was varied from 1:1 to 50:1 (+/−) and the resulting eGFP fluorescence determined (FIG. 9C). Values are reported as the theoretical (+/−) charge ratio of moles of ammonium cations to moles of phosphate anions, assuming full amine protonation and phosphate deprotonation. eGFP expression showed a roughly parabolic dependence on charge ratio with maximum eGFP fluorescence resulting from complexes formed at a 10:1 (+/−) charge ratio. This value is higher than what was observed with guanidinium-rich oligocarbonate complexes used for siRNA delivery, which performed optimally at a 4.8:1 charge ratio, likely due to the slightly lower electrostatic interaction of ammonium cations with phosphate anions $\Delta G$=−0.575 kcal/mol for guanidinium ion vs. −0.417 kcal/mol for ammonium ion. All further experiments were conducted using this optimized 10:1 (+/−) charge ratio. Epifluorescence microscopy was further used to confirm flow cytometry results (FIG. 9D). HeLa cells treated with CART/mRNA complexes show significant fluorescence in nearly all viewable cells. In contrast, cells treated with Lipofectamine showed partial eGFP expression, while leaving others untransfected.

A series of experiments was conducted to further understand the immolative rearrangement mechanism that we hypothesize to be involved in the performance of oligo (carbonate-b-α-amino ester) CARTs as it applies to mRNA delivery. Under conditions similar to those used for in vitro transfection, dynamic light scattering (DLS) was used to analyze CART 7 and polyelectrolyte complexes formed between 7 and mRNA. When mRNA-containing polyplexes were added to cell media, their hydrodynamic size started at 254 nm but slowly increased to 512 nm over two hours. The observed increase in size reflects partial rearrangement of cationic α-amino ester blocks to neutral amides causing aggregation of the associated lipid segments. This was confirmed by ESI-MS which showed an increase in the relative intensity of the HEGD small molecule over the same timescale. When the mRNA/CART particles are added to unbuffered water, sizes remain consistent at 254 nm+/−10 nm over the course of the full two-hour experiment. This mirrors results for α-amino ester homooligomers which do not rearrange under these conditions. Zeta potential measurements are in line with particle size data, with surface charge starting at a highly cationic +33 mV immediately after formulation to −30 mV over two hours. This is again consistent with the cationic ammonium moieties rearranging to neutral amides and leaving the surface dominantly anionic due to the associated oligonucleotide. Particle size was not cargo-dependent. When polyplexes were formed with luciferase (Flue) mRNA which is over twice the length of eGFP (Flue=1929 nt vs. eGFP=996 nt) and added to cell media at pH 7.4, particles showed the same behavior starting at 273 nm and slowly increased to 444 nm over the course of two hours. This suggests that future delivery of a wide variety of oligonucleotides is possible with the same CART. When no mRNA cargo was added, oligo(carbonate-b-amino ester) CARTs formed micelles due to their amphipathic structure. These micelles remained stable with sizes of 68 nm in unbuffered water. However, when these micelles were added to cell media (pH 7.4), they quickly formed aggregates that could not be characterized by DLS. The combined rearrangement data for the homo-oligomer alone ($t_{1/2}$=2 min), the oligo(carbonate-b-amino ester) micelles (aggregate to >500 nm within 30 min) and the mRNA/CART complexes (aggregate to 500 nm after 2 h) indicate that polyelectrolyte complexation with mRNA increases the stability of the α-amino ester materials in aqueous environments, putatively by decreasing the rate of deprotonation and thus rearrangement. This enables these materials to degrade on therapeutically relevant timescales at pH 7.4, while remaining stable enough for storage and formulation under unbuffered conditions.

First, to determine the mechanism of cell entry, a Cy5-labeled eGFP mRNA was used to compare cellular uptake at 4° C., a condition known to inhibit endocytotic processes, to normal uptake at 37° C. When HeLa cells were treated under these conditions, a significant (85%) reduction in Cy5-mRNA uptake was observed (FIG. 10A). This is consistent with the expected endocytotic mechanism that is characteristic of 250 nm particles.

To explore the self-immolative release mechanism by oligo(carbonate-b-amino ester) CARTs, particle uptake and gene expression resulting from treatment with 7 was directly compared to cationic oligomers that are ineffective for mRNA delivery. By delivering a mixture of eGFP mRNA and Cy5 labeled eGFP mRNA, mRNA internalization and gene expression can be decoupled and simultaneously quantified; Cy5 fluorescence indicates internalized mRNA irrespective of endosomal escape or release, and eGFP fluorescence signifies cytosolic release of mRNA, enabling translation. We used this method to explore the effect of backbone structure and cation type on both uptake and expression by preparing two additional cationic block co-oligomers of equivalent length to the $D_{13}:A_{11}$ CART 7. Three oligomers were directly compared for both cellular uptake and gene expression, an immolative ammonium-containing CART ($D_{13}:A_{11}$ 7), a non-charge-altering, guanidinium-containing oligomer ($D_{13}:G_{12}$ 13), and a non-charge-altering, ammonium-containing oligomer ($D_{13}:Pip_{13}$ 14).

Oligomers 7, 13, and 14 were mixed with Cy5-eGFP mRNA at 10:1 (+/−) ratios and the resulting complexes added to HeLa cells. While all co-oligomers afforded roughly similar levels of mRNA uptake, as quantified by Cy5 fluorescence (FIG. 10B), only the charge-altering $D_{13}:A_{11}$ 7 results in detectable eGFP mRNA expression. This data indicates that all mRNA complexes are internalized by cells efficiently, but without a rapidly degrading backbone, non-CART complexes either never escape the endosome or they do not release the mRNA on a timescale necessary to enable cytosolic eGFP expression. The lack of eGFP expression by complexes formed with $D_{13}:Pip_{13}$ 14, a non-immolative ammonium-containing oligomer, further indicates that it is not simply the difference in electrostatic binding affinity of ammonium cations versus guanidinium cations that accounts for this release. Rather the specific, controlled loss of cationic charge and rearrangement to small molecules is crucial for efficacy.

The charge-altering mechanism observed with our oligo (carbonate-b-α-amino ester) materials may neutralize mRNA binding and trigger the formation of the HEGD small molecule facilitates endosomal escape and/or mRNA release. To further understand this mechanism, HeLa cells were co-treated with mRNA/CART complexes and two compounds known to influence the endosomal microenvironment. Concanamycin A (Con A) is a specific V-ATPase inhibitor which has been shown to inhibit endosomal acidification. Other cationic ammonium-containing materials used in gene delivery show sharply reduced cytosolic oligonucleotide concentrations and subsequent gene expression when co-treated with this, or similar compounds due to a decrease in endosomal buffering osmotic rupture by the proton sponge effect. While compounds such as cationic lipid nanoparticles and PEI have shown 10-200-fold decreases in gene delivery when treated with V-ATPase inhibitors, our α-amino ester CART 7 are nearly unaffected by treatment with Con A (FIG. 10C, 21% decrease, p=0.177). This indicates that endosomal acidification and buffering is not necessary to achieve endosomal escape or gene expression with this system. Chloroquine (Chl) is a lysosomotropic agent that has been used to increase gene delivery by increasing endosomal buffering and rupture. Others have shown that gene delivery materials that do not incorporate buffering functionality, such as methylated PEI, show substantial increases in gene expression (2-3 fold) while buffering vectors such as PEI are unaffected. Our CARTs showed only a slight decrease in expression (22% decrease,p=0.469), indicating that endosomal escape is not a limiting factor in mRNA delivery by oligo(carbonate-b-amino ester) CARTs, likely because efficient escape through osmotic rupture already occurs as a result of depolymerization and HEGD (2) formation.

The effect of release and endosomal escape of mRNA by oligo(ester-b-amino ester) CARTs compared to a sample ineffective delivery vehicle ($D_{12}:G_{12}$, 13) can further be confirmed by confocal microscopy with detection of transporter (using the attached Dansyl fluorophore 3), Cy5-mRNA, and tetramethylrhodamine (TRITC)-Dextran$_{4400}$, a stain for endosomal compartments. When cells are imaged 4 hours after treatment with CART (7)/Cy5-mRNA complexes, the fluorescence of both the Cy5 signal and Dansyl (3) attached to the transporter are both primarily diffuse in nature, indicating that those materials have successfully escaped the endosome and dissociated from nanoparticle complexes (FIG. 10D, i). The observed puncta in the Dansyl signal (FIG. 10D, ii) likely arises from some intracellular aggregation of the released lipid blocks. Signal from TRITC also shows relatively diffuse fluorescence which would arise when endosomes rupture and release entrapped dextran. However, when cells are treated with non-immolative D:G (13)/Cy5-mRNA complexes, both the Cy5 and Dansyl fluorescence are very punctate, and co-localized (FIG. 10D, iii). This fluorescence additionally shows strong overlap with punctate TRITC-Dextran$_{4400}$, indicative of continued endosomal entrapment. Taken together, these data strongly suggest that the charge-altering behavior of CART 7 is responsible for its excellent performance for mRNA delivery.

Oligo(carbonate-b-amino ester) $D_{13}:A_{11}$ 7 was evaluated in additional applications to explore the versatility of CARTs for mRNA delivery. eGFP mRNA expression following delivery by CART 7 was assayed in a panel of cell lines, including those typically considered difficult to transfect. In addition to the optimization experiments previously conducted in HeLa, mRNA expression was compared to that of Lipofectamine in CHO, HEK-293, human hepatocellular carcinoma (HepG2), and murine macrophage J774 cells by treating with CART complexes formed with 0.125 µg/well of eGFP mRNA (FIG. 11A). In all cell lines tested, transfection efficiency using the CART $D_{13}:A_{11}$7 was >90% while Lipofectamine induced only 22-55%. This suggests that this delivery system is general for a variety of human and non-human cell lines. Not only is CART-mediated delivery consistent in different cell lines, but also with different lengths of mRNA, as $D_{13}:A_{11}$ (7) is also highly effective, substantially out-performing Lipofectamine, in the delivery of firefly luciferase (Fluc) mRNA (FIG. 11B). Analogous to trends observed with eGFP mRNA, a 10:1 (+/−) ratio resulted in the highest level of Fluc bioluminescence, despite mRNA length differences (1929 vs 996 nt), indicating that delivery efficiency is largely independent of mRNA length.

Bioluminescence imaging (BLI) provides a powerful tool to quantify mRNA delivery, expression, and biodistribution in living animals. To assess the efficacy of CART-mRNA complexes in both systemic and local routes of administration, we evaluated intravenous and intramuscular injections of CART-complexed Fluc mRNA in anesthetized BALB/c mice using BLI. In each mouse, 7.5 µg mRNA was complexed with CART $D_{13}:A_{11}$ 7 and administered by intramuscular injection into the right thigh muscle in 75 µL PBS. As a direct control, 7.5 ug of naked mRNA was injected in the opposite flank. D-luciferin was systemically administered, and luciferase expression was evaluated over 72 h, starting one hour post-injection. When mRNA was delivered with $D_{13}:A_{11}$, high levels of luciferase activity were observed at the site of injection (FIGS. 11C, D). This expression peaked at 4 h, and was still observable after 72 hours. However, naked mRNA afforded only low levels of luciferase expression, as measured by photon flux, in all five mice.

When complexes were administered via intravenous tail vein injection at the same dose, we observed robust abdominal bioluminescence as early as one hour post-injection, peaking at 4 h and indicating that our complexes localize and deliver mRNA predominantly to the spleen, with high levels of bioluminescence also detectable in the liver (FIGS. 11E, F). High levels of expression persisted for 24 h, with detectable bioluminescence after 48 hours. This expression is primarily localized in the spleen and liver, with an average of 23% of total abdominal light output originating in the former and 70% in the latter.

No luciferase bioluminescence was observed when naked mRNA was administered in PBS. In all mice injected, no toxicity was observed immediately after injection or for several weeks following treatment.

The ability to deliver functional mRNA via multiple routes of administration in vivo is critical for a delivery technology. Local intramuscular injections can be the preferred route of administration for many therapies including vaccination due to the ease of administration and ability to access naive dendritic and antigen-presenting cells in the dermal and muscle tissue. Intravenous injections of mRNA polyplex formulations through the tail vein are broadly useful for systemic administration with specific targets laying along the reticuloendothelial system such as the liver, lymph nodes, and spleen or targeting of solid tumors. Spleen localization is particularly exciting for future studies involving immunotherapy due high levels of dendritic and other immune cells in those tissues. Liver localization can be utilized for the treatment of hepatic diseases.

Messenger RNA therapeutics have the potential to transform disease treatment, though the critical technological challenge for using mRNA remains the development of safe, versatile, and efficacious delivery methods. We have developed a unique, tunable, and step-economical strategy for mRNA delivery that operates through an unprecedented mechanism to effectively deliver mRNA to cells and animals with excellent efficiency. Our approach draws on a two-step process using OROP and global deprotection to prepare the oligo(carbonate-b-amino ester) delivery vehicles. Following intracellular delivery, these charge-altering materials undergo a remarkable intramolecular rearrangement, during which cationic amines are converted to neutral amides to release anionic mRNA from its electrostatic complex and expel the nucleic acid into the cytosol for translation. The effectiveness of mRNA delivery using these CARTs represents a new strategy for mRNA delivery that results in functional protein expression in both cells and animals.

Example 12

In Vivo Delivery of CAR Encoding mRNA or DNA to Treat Cancer

Materials. Reagents were purchased from Sigma-Aldrich and used as received unless otherwise indicated. The 1-(3, 5-bis-trifluoromethyl-phenyl)-3-cyclohexyl-thiourea (1), lipid-functionalized monomers (2,3), and Boc-morpholinone monomer (4) were all prepared according to literature procedures. Regenerated cellulose dialysis membranes (Spectra/Por 6 Standard RC; molecular weight cutoff 1,000) were purchased from Spectrum Laboratories, Inc. Lipofectamine 2000 was purchased from Life Technologies. MTT was purchased from Fluka.

mRNAs. Fluc mRNA (5meC, Ψ, L-6107), and secreted alkaline phosphatase (SEAP) (control mRNA) were purchased from Trilink BioTechnologies. All purchased mRNAs were capped and polyadenylated and contain 5-methoxyuridine modification.

CAR-19 construct: CAR-19 mRNA was produced in house by cloning the the mCDI9_28_Z.1-3 sequence into pcDNA3.1(+) plasmids. Plasmids were linearized using NotI restriction enzyme according manufacture protocol (New England biolabs) and extracted using phenol:chloroform extraction with subsequent alcohol precipitation. mRNA was then transcribed from the linearized plasmids using INCOGNITO™ T7 ARCA 5mC-& Y-RNA Transcription Kit (Cellscript).

Instrumentation. Flow cytometry analysis was performed on a BD LSRII.UV FACS Analyzer (Stanford University Shared FACS Facility). Bioluminescence was measured using a CCD camera (IVIS 100; Xenogen Corp.) and analyzed using Living Image Software (PerkinElmer).

Cell Lines. A20 cells were maintained in RPMI supplemented with 10% FBS and 1% penicillin/streptomycin. Nonadherent cells were treated with the addition of 1% poly(vinyl alcohol) (PVA) to prevent adhesion. For murine primary T cells, single-cell suspensions were prepared from spleens of 6- to 8-wk-old BALB/c mice. From these suspensions, untouched T cells were isolated using the Pan T cell Isolation kit II (Miltenyi Biotec GmbH) according to the manufacturer's protocol. All cells were grown at 37° C. in a 5% $CO_2$ atmosphere. Cells were passaged at ~80% confluence.

Preparation of mixed lipid CART: to an oven dried 1 dram vial equipped with stir bar under N2 atmosphere in a glove box was added MTColeyl (6 eq., 0.077 mmol, 31.1 mg) and TU (0.05 eq., 0.0038 mmol, 1.4 mg). To this was added benzyl alcohol as a 1M solution in toluene (1 eq., 0.0128 mmol, 12.8 µL) followed by an additional 134 µL of toluene (1M w.r.t. $M_{BOC}$ monomer). Catalytic 1,8-Diazabicyclo [5.4.0]undec-7-ene (DBU) (1 drop) was then added to the solution and the reaction was allowed to stir at rt for 1 hour in the glove box. At this time MTCnonenyl (6 eq., 0.077 mmol, 21.7 mg) was added to the reaction. After stirring for another hour, $M_{BOC}$ (12.66 eq., 0.123 mmol, 27 mg) was added to the reaction and stirred for an additional 4 hours before being quenched with benzoic acid. The reaction was dialyzed in methanol (1.0 kDa dialysis bag) overnight. Concentration yielded protected co-oligomer S9 as a clear oil. Degree of polymerization was determined by $^1$H NMR end group analysis and dispersity by GPC in THF. Subsequent deprotection in 10% TFA in DCM overnight at room temperature under $N_2$ afforded CART $O_5$-b-$N_6$:$A_9$ (9). Complete protecting group removal was confirmed by $^1$H NMR ($CD_3OD$).

In Vivo mRNA Delivery and Flow Cytometry. CART-mRNA polyplexes were prepared as described above using 5 µg mRNA per mouse in a total volume of 100 µL. Complexes were mixed for 20 s before i.v. injection into tail vain of female BALB/c mice. For Fluc expression: After 7 h, 150 mg/kg D-luciferin was injected i.p. and luminescence was measured using an IVIS Imaging System CCD camera and analyzed using living image software. For T cell isolation from spleenocyte, animals were killed and single-cell suspensions were prepared by passing the spleens through 70-µm cell strainers followed by lysis of blood cells with ACK Lysing Buffer and washing two times with PBS. T cells were isolated using pan T cell isolation kit (Miltney Biotec) according to manufacture protocol. For CAR19 expression in spleenocytes after CAR19 mRNA-CART treatment, Spleenocytes were partitioned into two staining groups and stained fluorescent antibodies for CD8 (APC), CD4 (PE), and B220 (PerCp) or CD49d(APC). CAR19 construct was detected using a mouse anti-rat kappa chain antibody conjugated to FITC. Analysis was ddone on LSR-II.UV (BD Biosciences) using the Pacific Blue channel. Experimental protocols were approved by the Stanford Administrative Panel on Laboratory Animal Care.

In vivo Bioluminescence. For bioluminescence assessment, mice were anesthetized with isoflurane gas (2% isoflurane in oxygen, 1 l/min) during injection and imaging procedures. i.p. injections of d-Luciferin (Biosynth AG) were done at a dose of 150 mg/kg, providing a saturating substrate concentration for Fluc enzyme (luciferin crosses the blood-brain barrier). Mice were imaged in a light-tight chamber using an in vivo optical imaging system (IVIS 100; Xenogen Corp.) equipped with a cooled charge-coupled device camera. During image recording, mice inhaled isofluorane delivered via a nose cone, and their body temperature was maintained at 37° C. in the dark box of the camera system. Bioluminescence images were acquired between 10 and 20 minutes after luciferin administration. Mice usually recovered from anesthesia within 2 minutes of imaging.

Mice and cells lines. Eight- to twelve-week-old female Balb/c mice were purchased from The Jackson Laboratory and housed in the Laboratory Animal Facility of the Stanford University Medical Center. All experiments were approved by the Stanford Administrative Panel on Laboratory Animal Care and conducted in accordance with Stanford University Animal Facility and NIH guidelines.

Intra-Tumoral treatment of established Tumors using CAR19 mRNA-CART. CD19 expressing tumors were implanted subcutaneous on the right side of the abdomen. Treatment began when tumors reached 7 mm to 10 mm in largest diameter. 5 ug CAR19 mRNA-CART were injected intratumorally into the tumor. Tumor size was monitored with a digital caliper (Mitutoyo) every 2 to 3 days and expressed as volume (length×width×height). Mice are sacrificed when tumor size reached 1.5 cm in the largest diameter as per guidelines.

IV treatment of established CD19 expressing and CD19 negative Tumors using CAR19 mRNA-CART. CD19 expressing and CD19 negative tumors were implanted subcutaneous on the right side of the abdomen. Treatment began when tumors reached 7 mm to 10 mm in largest diameter. 5 ug CAR19 mRNA-CART were injected intravenously. Tumor size was monitored with a digital caliper (Mitutoyo) every 2 to 3 days and expressed as volume (length×width× height). Mice are sacrificed when tumor size reached 1.5 cm in the largest diameter as per guidelines.

Statistical analysis. Prism software (GraphPad; La Jolla, CA) was used to analyze tumor growth and to determine statistical significance of differences between groups by applying an non-parametric Mann-Whitney U test. P values <0.05 were considered significant. The Kaplan-Meier method was employed for survival analysis.

Example 13

In Vivo Delivery of Chimeric Antigen Receptor (CAR) Encoding mRNA or DNA to Treat Cancer CAR-T cell therapy has revolutionized cancer therapeutics. Achievements in CAR-T cell therapy: CAR T cell succeed where most other therapies failed; Very effective, rapid and long lasting anti-tumor response; Very high response rates using anti-CD19 CAR T-cells, ~90% for B-ALL, ~80% for lymphoma. Current market: For Lymphoma, the cost of Yescarta (Axicabtagene Ciloleucel) and Kymriah (tisagenlecleucel) is $373,000, For Leukemia, Kymriah (tisagenlecleucel) is $475,000.

CAR-T cell therapy limitations and disadvantages. Technical constraints: Takes a long time to produce; ~typically 2-6 weeks depending on the CAR T cell product; Very expensive to engineer and culture the T cells. On the patient side: Requires apheresis (the process by which immune cells are collected) followed by a substantial waiting period for patients with active growing aggressive cancers; Patients must receive chemotherapy for lymphodepletion to allow the CAR T cells to be effective; this chemotherapy causes damage to the immune system, increasing risk for serious infections; After administration the rapidly expanding CAR T cells in the patient's body often cause life-threatening side effects; this rapid expansion can be difficult to control.

In situ CAR-T cell programming is a FAR better strategy. Because CARTs target the spleen, we have direct access to the T-cells we hope to program with CARs.

Summary/Claims. CARTs effectively deliver mRNA to lymphocytes, which then express the functional CAR-19 protein; IMPORTANTLY, we are not limited to T-Cells, other cells express CAR. I.V. injection of CARTs with CAR-19 mRNA, is hugely effective in decreasing tumor burden after only a single dose. No Patient-specific customization required. Multiple CAR Specificities can be mixed in to one single dose. Additional protein encoding mRNAs, such as mRNA encoding Cytokines, can easily be co-formulated with the CAR constructs to modulate effect of the treatment. Anti-inflammatory protein, such as $IL^1$ receptor antagonist, encoding mRNA can be co-formulated with the CAR constructs to dampen adverse effects such as cytokine release syndrome. Off the shelf product. Available immediately to the patient. "Mix and Shoot" strategy that does not require complexed and expensive cell culturing facilities. Not limited to one dose, but can be repeated until desired effect is reached. 100% survival after 25 days (whole control group sac. At day 15). In vivo mRNA programming of CAR-T cells is unprecedented. This could greatly accelerate an already revolutionary therapy.

Example 14

Materials and Methods

Materials. Reagents were purchased from Sigma-Aldrich and used as received unless otherwise indicated. The 1-(3,5-bis-trifluoromethyl-phenyl)-3-cyclohexyl-thiourea (1), lipid-functionalized monomers (2,3), and Boc-morpholinone monomer (4) were all prepared according to literature procedures. Regenerated cellulose dialysis membranes (Spectra/Por 6 Standard RC; molecular weight cutoff 1,000) were purchased from Spectrum Laboratories, Inc. Lipofectamine 2000 was purchased from Life Technologies. MTT was purchased from Fluka.

mRNAs. Fluc mRNA (5meC, Ψ, L-6107), and secreted alkaline phosphatase (SEAP) (control mRNA) were purchased from Trilink BioTechnologies. All purchased mRNAs were capped and polyadenylated and contain 5-methoxyuridine modification.

Car-19 Construct:

CAR-19 mRNA was produced in house by cloning the the mCD19_28_Z.1-3 sequence into pcDNA3.1(+) plasmids. Plasmids were linearized using NotI restriction enzyme according manufacture protocol (New England biolabs) and extracted using phenol:chloroform extraction with subsequent alcohol precipitation. mRNA was then transcribed from the linearized plasmids using INCOGNITO™ T7 ARCA 5mC- & Y-RNA Transcription Kit (Cellscript).

Instrumentation. Flow cytometry analysis was performed on a BD LSRII.UV FACS Analyzer (Stanford University Shared FACS Facility). Bioluminescence was measured using a CCD camera (IVIS 100; Xenogen Corp.) and analyzed using Living Image Software (PerkinElmer).

Cell Lines. A20 cells were maintained in RPMI supplemented with 10% FBS and 1% penicillin/streptomycin. Nonadherent cells were treated with the addition of 1% poly(vinyl alcohol) (PVA) to prevent adhesion. For murine primary T cells, single-cell suspensions were prepared from spleens of 6- to 8-wk-old BALB/c mice. From these suspensions, untouched T cells were isolated using the Pan T cell Isolation kit II (Miltenyi Biotec GmbH) according to the manufacturer's protocol. All cells were grown at 37° C. in a 5% CO2 atmosphere. Cells were passaged at ~80% confluence.

0.077 mmol, 31.1 mg) and TU (0.05 eq., 0.0038 mmol, 1.4 mg). To this was added benzyl alcohol as a 1M solution in toluene (1 eq., 0.0128 mmol, 12.8 µL) followed by an additional 134 µL of toluene (1M w.r.t. $M_{BOC}$ monomer). Catalytic 1,8-Diazabicyclo[5.4.0]undec-7-ene (DBU) (1 drop) was then added to the solution and the reaction was allowed to stir at rt for 1 hour in the glove box. At this time MTCnonenyl (6 eq., 0.077 mmol, 21.7 mg) was added to the reaction. After stirring for another hour, MBOC (12.66 eq., 0.123 mmol, 27 mg) was added to the reaction and stirred for an additional 4 hours before being quenched with benzoic acid. The reaction was dialyzed in methanol (1.0 kDa dialysis bag) overnight. Concentration yielded protected co-oligomer S9 as a clear oil. Degree of polymerization was determined by 1H NMR end group analysis and dispersity by GPC in THF. Subsequent deprotection in 10% TFA in DCM overnight at room temperature under N2 afforded CART O5-b-N6:A9 (9). Complete protecting group removal was confirmed by 1H NMR (CD3OD).

In Vivo mRNA Delivery and Flow Cytometry CART-mRNA polyplexes were prepared as described above using 5 µg mRNA per mouse in a total volume of 100 µL. Complexes were mixed for 20 s before i.v. injection into tail vain of female BALB/c mice. For Fluc expression: After 7 h, 150 mg/kg D-luciferin was injected i.p. and luminescence was measured using an IVIS Imaging System CCD camera and analyzed using living image software. For T cell isolation from spleenocyte, animals were killed and single-cell suspensions were prepared by passing the spleens through 70-µm cell strainers followed by lysis of blood cells with ACK Lysing Buffer and washing two times with PBS. T cells were isolated using pan T cell isolation kit (Miltney Biotec) according to manufacture protocol. For CAR19 expression in spleenocytes after CAR19 mRNA-CART treatment, Spleenocytes were partitioned into two staining groups and stained fluorescent antibodies for CD8 (APC), CD4 (PE), and B220 (PerCp) or CD49d(APC). CAR19 construct was detected using a mouse anti-rat kappa chain antibody conjugated to FITC. Analysis was ddone on LSR-II.UV (BD Biosciences) using the Pacific Blue channel. Experimental protocols were approved by the Stanford Administrative Panel on Laboratory Animal Care.

In vivo Bioluminescence i.p. injections of d-Luciferin (Biosynth AG) were done at a dose of 150 mg/kg, providing a saturating substrate concentration for Flue enzyme (luciferin crosses the blood-brain barrier). Mice were imaged in a light-tight chamber using an in vivo optical imaging system (IVIS 100; Xenogen Corp.) equipped with a cooled charge-coupled device camera. During image recording, mice inhaled isofluorane delivered via a nose cone, and their body temperature was maintained at 37° C. in the dark box of the camera system. Bioluminescence images were acquired between 10 and 20 minutes after luciferin administration. Mice usually recovered from anesthesia within 2 minutes of imaging.

Mice and Cells Lines

Eight- to twelve-week-old female Balb/c mice were purchased from The Jackson Laboratory and housed in the Laboratory Animal Facility of the Stanford University Medical Center. All experiments were approved by the Stanford Administrative Panel on Laboratory Animal Care and conducted in accordance with Stanford University Animal Facility and NIH guidelines.

Intra-Tumoral Treatment of Established Tumors Using CAR19 mRNA-CART

CD19 expressing tumors were implanted subcutaneous on the right side of the abdomen. Treatment began when tumors reached 7 mm to 10 mm in largest diameter. 5 ug CAR19 mRNA-CART were injected intratumorally into the tumor.

Tumor size was monitored with a digital caliper (Mitutoyo) every 2 to 3 days and expressed as volume (length×width×height). Mice are sacrificed when tumor size reached 1.5 cm in the largest diameter as per guidelines.

IV Treatment of Established CD19 Expressing and CD19negative Tumors Using CAR19 mRNA-CART CD19 expressing and CD19 negative tumors were implanted subcutaneous on the right side of the abdomen. Treatment began when tumors reached 7 mm to 10 mm in largest diameter. 5 ug CAR19 mRNA-CART were injected intravenously. Tumor size was monitored with a digital caliper (Mitutoyo) every 2 to 3 days and expressed as volume (length×width×height). Mice are sacrificed when tumor size reached 1.5 cm in the largest diameter as per guidelines.

Statistical Analysis

Prism software (GraphPad; La Jolla, CA) was used to analyze tumor growth and to determine statistical significance of differences between groups by applying an non-parametric Mann-Whitney U test. P values <0.05 were considered significant. The Kaplan-Meier method was employed for survival analysis.

Example 15

In Situ Generation of Chimeric Antigen Receptor (CAR) Expressing Effector Cells Using a Charge Altering Releasable Transporters (CARTs)

In vivo CAR19 mRNA therapy using CARTs.

Figure 25:
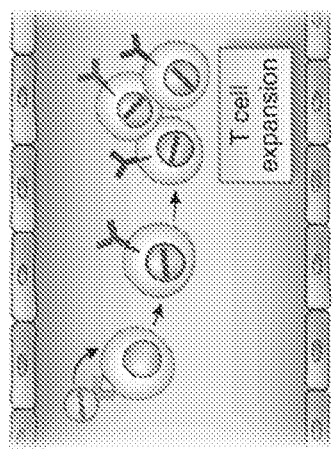

Concept. CAR-encoding genes are expressed in vivo within cells using mRNA and/or DNA, that can potentially encode multiple genes. Using this method, genetic engineering does not have to be done outside of the patients's body, there is no need to harvest cells from the patient, and there is no costly transport of patient cells. The CART delivery system described herein is easy to formulate, provides robust mRNA expression in vivo, and is non immunogenic (non-viral). Importantly, the system can deliver and express both mRNA (transiently) and DNA (stable) in vivo as shown in the schematic of FIG. 25.

Outcomes. Proof of principle studies were completed with CART-delivered mRNA encoding anti-mouse CD19 and anti-human CD19 CARs, as shown in FIG. 26. New strategies including dual target approaches, expression of new generations of CARs (Loaded/Armored CARs, TRUCKS), and co-delivery of mRNAs that encode surface or secreted molecules, which enhance effector function, reduce adverse effects and inhibits CAR suppression will be pursued within the in vivo mRNA therapy using CARTs.

Upon "systemic" administration CARTs deliver cargo to Leukocyte and Monocytes.

Applicants evaluated which cells are involved in killing the CD19 expressing target cells. Results show that the observed effect is not T cell dependent as illustrated in FIG. 30C. Prolonged overall survival is still observed in CAR19 mRNA-CART treated animals even if CD4, CD8 and CD4+CD8 T cell are depleted. CARTs transfect macrophages and B cells in vivo, and results show that leukocytes other than T cells transfected with the CAR-19 construct kill CD-19+ cells. Isolated Macrophages and naive B cells treated with CAR19 mRNA-CART kill CD19 expressing target cells as shown in FIGS. 30A-B, thus demonstrating that cell death is not an in vivo CAR-T cell maneuver. These results illustrate that CAR-T, CAR-B, CAR-Mac, and likely CAR-NK can kill target cells.

CART-mRNA humanized CAR-19 therapy in human PBMCs shows anticipated killing of native B cells observed in human clinical trials.

In human clinical trials, effective CAR T cell therapy results in the off-target effect of killing native CD19 expressing cells (B cell aplasia). When CART-mRNA CAR19 is delivered to human PBMCs, applicants observed the clinically anticipated depletion of CD19 expressing cells. Increased level of circulating cells expressing CAR19 correlates with lower levels of B-cells. The surviving B-cells typically express less CD19 than the B cells that are killed. Human CAR-19, ablates B-cells in PBMCs, while non-CD19 targeting mRNA has no effect on B-cells as shown in FIGS. 31A-31C.

Summary: CARTs for CARs

CAR-T cell therapy has already show incredible promise for revolutionizing cancer treatments, however, the current manufacturing process has numerous limitations including cost, time, supply, and scale. In situ/in vivo programing of immune cells using systemic delivery of CART-CAR-mRNA solves many of these problems. For example, CAR-mRNA delivery using CARTs allows packaging of multiple proteins, so CARs can be tuned with other immunomodulatory components as well as innovative and improved versions of CARs. Further, systemic delivery of CAR-19 encoding mRNA effectively, specifically, and therapeutically target CD19 expressing tumors. Importantly, CARs produced by mRNA are transient and can be regenerated by repeated dosing. Experiments described herein demonstrate that model system tumors were rigorously shown to be CD 19+ or CD 19−. The CARs are expressed by T-cells, B-cells, macrophages, NK cells. Because T-cells are not required to kill tumors, the CAR-19 expressing B-cells, macrophages, and NK cells are also therapeutically relevant. Finally, applicants demonstrate ex vivo CART delivery of CAR-19 mRNA to human cells kills CD19 expressing human cells, confirming their therapeutic efficacy.

REFERENCES

Dove A P, Pratt R C, Lohmeijer B G G, Waymouth R M, Hedrick J L (2005) Thiourea-based bifunctional organocatalysis: Supramolecular recognition for living polymerization. J Am Chem Soc 127:13798-13799.

McKinlay C J, et al. (2017) Charge-altering releasable transporters (CARTs) for the delivery and release of mRNA in living animals. Proc Natl Acad Sci USA 114: E448-E456.

Geihe E I, et al. (2012) Designed guanidinium-rich amphipathic oligocarbonate molecular transporters complex, deliver and release siRNA in cells. Proc Natl Acad Sci USA 109:13171-13176.

Blake T R, Waymouth R M (2014) Organocatalytic ring-opening polymerization of morpholinones: New strategies to functionalized polyesters. J Am Chem Soc 136: 9252-9255.

```
Informal Sequence Listing
CAR cDNA sequence
                                     SEQ ID NO: 1
ATGTATCGCATGCAGCTGCTGAGCTGCATTGCGCTGAGCCTGGCGCTGGT

GACCAACAGCGACATCCAGATGACCCAGTCCCCCGCTTCTCTGAGCACAT

CCCTGGGCGAGACCGTGACAATCCAGTGCCAGGCTAGCGAGGATATCTAC

TCCGGCCTGGCCTGGTACCAGCAGAAGCCTGGAAAGTCTCCCCAGCTGCT
```

-continued

GATCTACGGAGCTTCCGACCTGCAGGATGGAGTGCCTTCTAGGTTCTCTG
GAAGCGGCTCCGGAACCCAGTACTCTCTGAAGATCACCAGCATGCAGACA
GAGGACGAGGGCGTGTACTTCTGCCAGCAGGGACTGACCTACCCAAGAAC
ATTTGGCGGAGGCACAAAGCTGGAGCTGAAGGGAGGAGGAGGCTCCGGCG
GAGGAGGCTCTGGAGGAGGAGGCAGCGAGGTGCAGCTGCAGCAGAGCGGA
GCTGAGCTGGTGAGGCCTGGAACCTCCGTGAAGCTGTCTTGTAAGGTGAG
CGGCGACACCATCACATTCTACTACATGCACTTTGTGAAGCAGAGGCCTG
GCCAGGGACTGGAGTGGATCGGAAGAATCGACCCAGAGGATGAGTCCACA
AAGTACTCTGAGAAGTTCAAGAACAAGGCCACCCTGACAGCTGATACCAG
CTCCAACACAGCTTACCTGAAGCTGTCTAGCCTGACCAGCGAGGACACCG
CCACATACTTCTGCATCTACGGAGGCTACTACTTTGATTACTGGGGCCAG
GGAGTGATGGTGACAGTGTCCTCTATCGAGTTTATGTACCCCCCTCCATA
CCTGGACAACGAGAGATCCAACGGCACCATCATCCACATCAAGGAGAAGC
ACCTGTGCCACACACAGAGCTCCCCAAAGCTGTTCTGGGCTCTGGTGGTG
GTGGCTGGCGTGCTGTTTTGCTACGGACTGCTGGTGACCGTGGCCCTGTG
CGTGATCTGGACAAACAGCAGGAGAAACCGGGGAGGCCAGTCCGATTACA
TGAACATGACCCCACGGCGCCCTGGACTGACAAGGAAGCCATACCAGCCA
TACGCTCCTGCTCGCGACTTCGCTGCTTACAGGCCAAGAGCCAAGTTCAG
CAGGAGCGCCGAGACCGCTGCTAACCTGCAGGACCCCAACCAGCTGTTCA
ACGAGCTGAACCTGGGCAGGAGAGAGGAGTTTGACGTGCTGGAGAAGAAG
CGGGCTCGCGATCCCGAGATGGGAGGCAAGCAGCAGCGGCGCAGGAACCC
TCAGGAGGGCGTGTACAACGCCCTGCAGAAGGACAAGATGGCCGAGGCTT
ACTCTGAGATCGGCACCAAGGGAGAGAGACGGCGCGGCAAGGGACACGAT
GGCCTGTTCCAGGGACTGAGCACCGCCACAAAGGACACCTTTGATGCTCT
GCACATGCAGACACTGGCCCCTCGGTGA

CAR cDNA having T7 polyermase promotor site and
AflIII restriction site:
SEQ ID NO: 2
TAATACGACTCACTATAGGGAGACCCAAGCTGGCTAGCGTTTAAACTTAA
GGCCACCATGTATCGCATGCAGCTGCTGAGCTGCATTGCGCTGAGCCTGG
CGCTGGTGACCAACAGCGACATCCAGATGACCCAGTCCCCCGCTTCTCTG
AGCACATCCCTGGGCGAGACCGTGACAATCCAGTGCCAGGCTAGCGAGGA
TATCTACTCCGGCCTGGCCTGGTACCAGCAGAAGCCTGGAAAGTCTCCCC
AGCTGCTGATCTACGGAGCTTCCGACCTGCAGGATGGAGTGCCTTCTAGG
TTCTCTGGAAGCGGCTCCGGAACCCAGTACTCTCTGAAGATCACCAGCAT
GCAGACAGAGGACGAGGGCGTGTACTTCTGCCAGCAGGGACTGACCTACC
CAAGAACATTTGGCGGAGGCACAAAGCTGGAGCTGAAGGGAGGAGGAGGC
TCCGGCGGAGGAGGCTCTGGAGGAGGAGGCAGCGAGGTGCAGCTGCAGCA
GAGCGGAGCTGAGCTGGTGAGGCCTGGAACCTCCGTGAAGCTGTCTTGTA
AGGTGAGCGGCGACACCATCACATTCTACTACATGCACTTTGTGAAGCAG
AGGCCTGGCCAGGGACTGGAGTGGATCGGAAGAATCGACCCAGAGGATGA
GTCCACAAAGTACTCTGAGAAGTTCAAGAACAAGGCCACCCTGACAGCTG
ATACCAGCTCCAACACAGCTTACCTGAAGCTGTCTAGCCTGACCAGCGAG
GACACCGCCACATACTTCTGCATCTACGGAGGCTACTACTTTGATTACTG
GGGCCAGGGAGTGATGGTGACAGTGTCCTCTATCGAGTTTATGTACCCCC
CTCCATACCTGGACAACGAGAGATCCAACGGCACCATCATCCACATCAAG
GAGAAGCACCTGTGCCACACACAGAGCTCCCCAAAGCTGTTCTGGGCTCT
GGTGGTGGTGGCTGGCGTGCTGTTTTGCTACGGACTGCTGGTGACCGTGG
CCCTGTGCGTGATCTGGACAAACAGCAGGAGAAACCGGGGAGGCCAGTCC
GATTACATGAACATGACCCCACGGCGCCCTGGACTGACAAGGAAGCCATA
CCAGCCATACGCTCCTGCTCGCGACTTCGCTGCTTACAGGCCAAGAGCCA
AGTTCAGCAGGAGCGCCGAGACCGCTGCTAACCTGCAGGACCCCAACCAG
CTGTTCAACGAGCTGAACCTGGGCAGGAGAGAGGAGTTTGACGTGCTGGA
GAAGAAGCGGGCTCGCGATCCCGAGATGGGAGGCAAGCAGCAGCGGCGCA
GGAACCCTCAGGAGGGCGTGTACAACGCCCTGCAGAAGGACAAGATGGCC
GAGGCTTACTCTGAGATCGGCACCAAGGGAGAGAGACGGCGCGGCAAGGG
ACACGATGGCCTGTTCCAGGGACTGAGCACCGCCACAAAGGACACCTTTG
ATGCTCTGCACATGCAGACACTGGCCCCTCGGTGA CAR cDNA having T7 polyermase promotor site and
AflIII 5' and BamHI 3' restriction sites, 2xb-
globin 3' UTR regions, and 120 poly A tail:
SEQ ID NO: 3
TAATACGACTCACTATAGGGAGACCCAAGCTGGCTAGCGTTTAAACTTAA
GGCCACCATGTATCGCATGCAGCTGCTGAGCTGCATTGCGCTGAGCCTGG
CGCTGGTGACCAACAGCGACATCCAGATGACCCAGTCCCCCGCTTCTCTG
AGCACATCCCTGGGCGAGACCGTGACAATCCAGTGCCAGGCTAGCGAGGA
TATCTACTCCGGCCTGGCCTGGTACCAGCAGAAGCCTGGAAAGTCTCCCC
AGCTGCTGATCTACGGAGCTTCCGACCTGCAGGATGGAGTGCCTTCTAGG
TTCTCTGGAAGCGGCTCCGGAACCCAGTACTCTCTGAAGATCACCAGCAT
GCAGACAGAGGACGAGGGCGTGTACTTCTGCCAGCAGGGACTGACCTACC
CAAGAACATTTGGCGGAGGCACAAAGCTGGAGCTGAAGGGAGGAGGAGGC
TCCGGCGGAGGAGGCTCTGGAGGAGGAGGCAGCGAGGTGCAGCTGCAGCA
GAGCGGAGCTGAGCTGGTGAGGCCTGGAACCTCCGTGAAGCTGTCTTGTA
AGGTGAGCGGCGACACCATCACATTCTACTACATGCACTTTGTGAAGCAG
AGGCCTGGCCAGGGACTGGAGTGGATCGGAAGAATCGACCCAGAGGATGA
GTCCACAAAGTACTCTGAGAAGTTCAAGAACAAGGCCACCCTGACAGCTG
ATACCAGCTCCAACACAGCTTACCTGAAGCTGTCTAGCCTGACCAGCGAG
GACACCGCCACATACTTCTGCATCTACGGAGGCTACTACTTTGATTACTG
GGGCCAGGGAGTGATGGTGACAGTGTCCTCTATCGAGTTTATGTACCCCC
CTCCATACCTGGACAACGAGAGATCCAACGGCACCATCATCCACATCAAG
GAGAAGCACCTGTGCCACACACAGAGCTCCCCAAAGCTGTTCTGGGCTCT
GGTGGTGGTGGCTGGCGTGCTGTTTTGCTACGGACTGCTGGTGACCGTGG
CCCTGTGCGTGATCTGGACAAACAGCAGGAGAAACCGGGGAGGCCAGTCC
GATTACATGAACATGACCCCACGGCGCCCTGGACTGACAAGGAAGCCATA -continued

```
CCAGCCATACGCTCCTGCTCGCGACTTCGCTGCTTACAGGCCAAGAGCCA

AGTTCAGCAGGAGCGCCGAGACCGCTGCTAACCTGCAGGACCCCAACCAG

CTGTTCAACGAGCTGAACCTGGGCAGGAGAGAGGAGTTTGACGTGCTGGA

GAAGAAGCGGGCTCGCGATCCCGAGATGGGAGGCAAGCAGCAGCGGCGCA

GGAACCCTCAGGAGGGCGTGTACAACGCCCTGCAGAAGGACAAGATGGCC

GAGGCTTACTCTGAGATCGGCACCAAGGGAGAGAGACGGCGCGGCAAGGG

ACACGATGGCCTGTTCCAGGGACTGAGCACCGCCACAAAGGACACCTTTG

ATGCTCTGCACATGCAGACACTGGCCCCTCGGTGA

GGATCCgctcgctttatgctgtccaatttctattaaaggttcctttgttc cctaagtccaactactaaactgggggatattatgaagggccttgagcatc tggattctgcctaataaaaaacatttattttcattgcgctcgctttcttg ctgtccaatttctattaaaggttcctttgttccctaagtccaactactaa actgggggatattatgaagggccttgagcatctggattctgcctaataaa aaacatttattttcattgcAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAGAA
```

CERTAIN EMBODIMENTS

Embodiment 1

A cell-penetrating complex comprising a nucleic acid non-covalently bound to a cationic amphipathic polymer, said cationic amphipathic polymer comprising a pH-sensitive immolation domain.

Embodiment 2

The cell-penetrating complex of Embodiment 1, wherein said cationic amphipathic polymer comprises a pH-sensitive immolation domain and a lipophilic polymer domain.

Embodiment 3

The cell-penetrating complex of Embodiment 2, wherein said cationic amphipathic polymer has the formula:

$$R^1\text{-}[L^1\text{-}[(LP^1)_{z1}\text{-}(IM)_{z2}\text{-}(LP^2)_{z3}]_{z4}\text{-}L^2\text{-}R^2]_{z5}$$

wherein $R^1$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$ —, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1, z3 and z4 are independently integers from 0 to 100, wherein at least one of z1 or z3 is not 0; and z2 is an integer from 2 to 100.

Embodiment 4

The cell-penetrating complex of Embodiment 3, wherein said cationic amphipathic polymer has the formula:

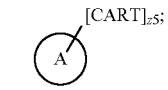

wherein

Ring A is a substituted or unsubstituted cycloalkyl, substituted or unsubstituted heterocycloalkyl, substituted or unsubstituted aryl, or substituted or unsubstituted heteroaryl;

CART has the formula: $\text{-}L^1\text{-}[(LP^1)_{z1}\text{-}(IM)_{z2}\text{-}(LP^2)_{z3}]_{z4}\text{-}L^2\text{-}R^2$ wherein, $R^2$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$C$_1$, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$ —, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1, z3 and z4 are independently integers from 0 to 100, wherein at least one of z1 or z3 is not 0; and z2 is an integer from 2 to 100.

Embodiment 5

The cell-penetrating complex of Embodiment 4, wherein Ring A is a substituted or unsubstituted aryl.

Embodiment 6

The cell-penetrating complex of Embodiment 4, wherein Ring A is a substituted or unsubstituted phenyl.

Embodiment 7

The cell-penetrating complex of Embodiment 4, wherein Ring A is a substituted or unsubstituted aryl.

Embodiment 8

The cell-penetrating complex of Embodiment 4, wherein Ring A is a substituted or unsubstituted phenyl or naphthalenyl.

Embodiment 9

The cell-penetrating complex of Embodiment 4, wherein said cationic amphipathic polymer has the formula:

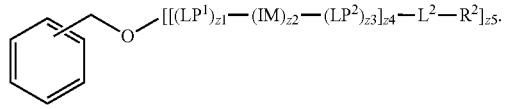

Embodiment 10

The cell-penetrating complex of Embodiment 4, wherein said cationic amphipathic polymer has the formula:

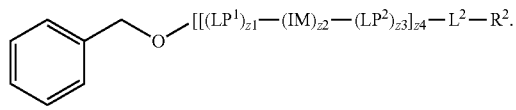

Embodiment 11

The cell-penetrating complex of Embodiment 4, wherein said cationic amphipathic polymer has the formula:

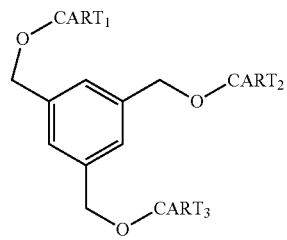

wherein $CART_1$, $CART_2$ and $CART_3$ are independently CART as defined in Embodiment 4.

Embodiment 12

The cell-penetrating complex of Embodiment 4, wherein $L^1$-$CH_2$—O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 13

The cell-penetrating complex of Embodiment 4, wherein $L^1$-$CH_2$—O—,

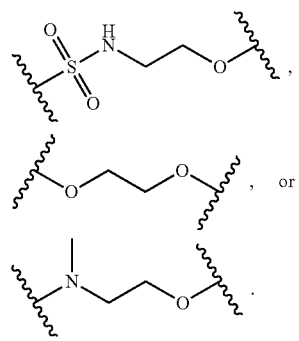

Embodiment 14

The cell-penetrating complex of Embodiment 4, wherein z5 is an integer from 1 to 3.

Embodiment 15

The cell-penetrating complex of Embodiment 4, wherein z5 is 1 or 3.

Embodiment 16

The cell-penetrating complex of Embodiment 4, wherein z5 is 1.

Embodiment 17

The cell-penetrating complex of Embodiment 4, wherein z5 is 3.

Embodiment 18

The cell-penetrating complex of Embodiment 4, wherein $R^2$ is hydrogen.

Embodiment 19

The cell-penetrating complex of Embodiment 3, wherein $L^2$ is a bond.

Embodiment 20

The cell-penetrating complex of Embodiment 1, wherein said pH-sensitive immolation domain has the formula:

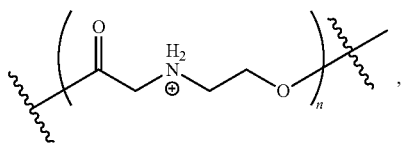

(IV)

wherein n is an integer of 2 or more.

Embodiment 21

The cell-penetrating complex of Embodiment 20, wherein n is an integer in the range of 2-50.

Embodiment 22

The cell-penetrating complex of Embodiment 1, wherein said pH-sensitive immolation domain has the formula:

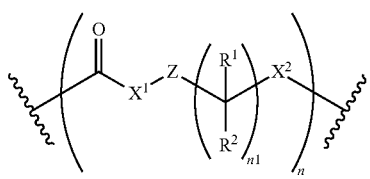

wherein
n is an integer of 2 or more;
n1 is an integer from 0 to 50;
Z is said nucleophilic moiety;
$X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—;
$X^2$ is —O— or —S—; and
$R^1$, $R^2$, $R^3$, $R^4$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 23

The cell-penetrating complex of Embodiment 1, wherein said pH-sensitive immolation domain has the formula:

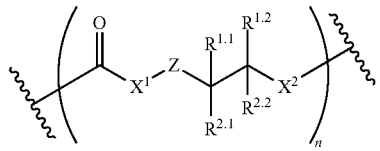

wherein
n is an integer of 2 or more;
Z is said nucleophilic moiety;
$X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—;
$X^2$ is —O— or —S—; and
$R^{1.1}$, $R^{1.2}$, $R^{2.1}$, $R^{2.2}$, $R^3$, $R^4$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 24

The cell-penetrating complex of Embodiment 1, wherein said pH-sensitive immolation domain has the formula:

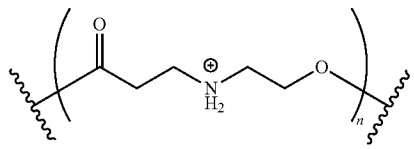

wherein n is an integer of 2 or more.

Embodiment 25

The cell-penetrating complex of Embodiment 1, wherein said pH-sensitive immolation domain has the formula:

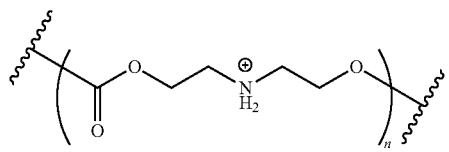

wherein n is an integer of 2 or more.

Embodiment 26

The cell-penetrating complex of Embodiment 1, wherein said pH-sensitive immolation domain has the formula:

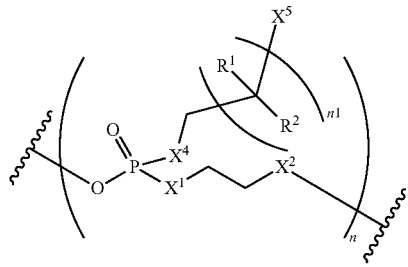

n is an integer of 2 or more;
n1 is an integer from 0 to 50;
$X^1$ is a bond, —O—, —NR$^5$—, —C(R$^5$)(R$^6$)— or —C(R$^5$)(R$^6$)—C(R$^7$)(R$^8$)—;
$X^2$ is a bond, —O—, —C(R$^9$)(R$^{10}$)— or —C(R$^9$)(R$^{10}$)—C(R$^{11}$)(R$^{12}$)—;
$X^4$ is a bond, —C(O)—, —P(O)(OR$^{16}$)$_2$—, —S(O)(OR$^{17}$)$_2$—, —C(R$^{16}$)(R$^{17}$)— or —C(R$^{16}$)(R$^{17}$)—C(R$^{18}$)(R$^{19}$)—;
$X^5$ is a nucleophilic moiety; and
$R^1$, $R^2$, $R^5$, $R^6$, $R^7$, $R^8$, $R^9$, $R^{10}$, $R^{11}$, $R^{12}$, R, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 27

The cell-penetrating complex of Embodiment 4, wherein Z is —S—, —S$^+$R$^{13}$—, —NR$^{13}$—, or —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 28

The cell-penetrating complex of Embodiment 23, wherein Z is —S—, —S$^+$R$^{13}$—, —NR$^{13}$— or —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 29

The cell-penetrating complex of Embodiment 4, wherein Z is

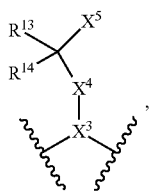

wherein
$X^3$ is C(R$^{15}$) or N;
$X^4$ is a bond, —C(O)—, —P(O)(OR$^{16}$)$_2$—, —S(O)(OR$^{17}$)$_2$—, —C(R$^{16}$)(R$^{17}$)— or —C(R$^{16}$)(R$^{17}$)—C(R$^{18}$)(R$^{19}$)—
$X^5$ is a nucleophilic moiety; and
$R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 30

The cell-penetrating complex of Embodiment 23, wherein Z is

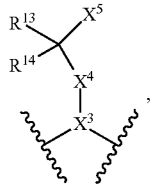

wherein
$X^3$ is C(R$^{15}$) or N;
$X^4$ is a bond, —C(O)—, —P(O)(OR$^{16}$)$_2$—, —S(O)(OR$^{17}$)$_2$—, —C(R$^{16}$)(R$^{17}$)— or —C(R$^{16}$)(R$^{17}$)—C(R$^{18}$)(R$^{19}$)—;
$X^5$ is a nucleophilic moiety; and
$R^{13}$, $R^{14}$, $R^{15}$, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 31

The cell-penetrating complex of Embodiment 29, wherein $X^5$ is —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 32

The cell-penetrating complex of Embodiment 2, wherein said lipophilic polymer domain has the formula:

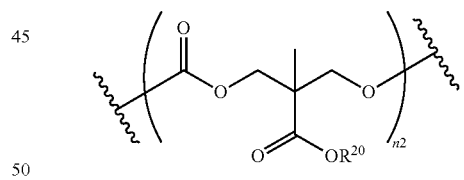

wherein
n2 is an integer from 1 to 100;
$R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 33

The cell-penetrating complex of Embodiment 1, wherein said nucleic acid is an messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA).

Embodiment 34

A nanoparticle composition comprising a plurality of cell-penetrating complexes according to Embodiment 1.

Embodiment 35

A cationic amphipathic polymer of the formula:

$$R^1-[L^1-[(LP^1)_{z1}-(IM)_{z2}-(LP^2)_{z3}]_{z4}-L^2-R^2]_{z5}$$

wherein $R^1$ is hydrogen, halogen, —CCl$_3$, —CBr$_3$, —CF$_3$, —Cl$_3$, CHCl$_2$, —CHBr$_2$, —CHF$_2$, CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1, z3 and z4 are independently integers from 0 to 100, wherein at least one of z1 or z3 is not 0; and z2 is an integer from 2 to 100.

Embodiment 36

The cationic amphipathic polymer of Embodiment 1, wherein said cationic amphipathic polymer has the formula:

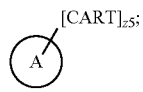

wherein

Ring A is a substituted or unsubstituted cycloalkyl, substituted or unsubstituted heterocycloalkyl, substituted or unsubstituted aryl, or substituted or unsubstituted heteroaryl;

CART has the formula: $-L^1-[(LP^1)_{z1}-(IM)_{z2}-(LP^2)_{z3}]_{z4}-L^2-R^2$ wherein, $R^2$ is hydrogen, halogen, —CCl$_3$, —CBr$_3$, —CF$_3$, —C$_{13}$, CHCl$_2$, —CHBr$_2$, —CHF$_2$, —CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, CNHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1, z3 and z4 are independently integers from 0 to 100, wherein at least one of z1 or z3 is not 0; and z2 is an integer from 2 to 100.

Embodiment 37

A method of transfecting a nucleic acid into a cell, the method comprising contacting a cell with the complex of Embodiment 1, said complex comprising a nucleic acid non-covalently bound to a cationic amphipathic polymer.

Embodiment 38

The method of Embodiment 37, further comprising allowing said cationic amphipathic polymer to degrade within said cell thereby forming a degradation product.

Embodiment 39

The method of Embodiment 38, wherein said degradation product is a substituted or unsubstituted diketopiperazine.

Embodiment 40

The method of Embodiment 37, wherein said nucleic acid comprises one or more selected from the group consisting of an messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA).

Embodiment 41

The method of Embodiment 40, further comprising allowing said mRNA to be expressed in said cell.

Embodiment 42

The method of Embodiment 37, wherein the expression of one or more gene products is increased.

Embodiment 43

The method of Embodiment 37, wherein the expression of one or more gene products is decreased.

Embodiment 44

The method of Embodiment 37, wherein said cell is an eukaryotic cell.

Embodiment 45

The method of Embodiment 37, wherein said cell is a mammalian or human cell.

Embodiment 46

The method of Embodiment 37, wherein said cell forms part of an organism.

Embodiment 47

The method of Embodiment 46, wherein said organism is a human.

Embodiment 48

The method of Embodiment 37, wherein the method causes gene-edition in the cell.

Embodiment 49

The method of Embodiment 48, wherein said nucleic acid comprises one or more vectors comprising:
a) a first nucleotide sequence encoding a CRISPR-Cas system guide RNA that hybridizes with a target sequence in the genome of the cell, and
b) a second nucleotide sequence encoding a Cas9 protein, wherein said (a) and (b) are located on the same or different vectors.

Embodiment 50

The method of Embodiment 48, wherein said nucleic acid comprises a CRISPR RNA (crRNA).

Embodiment 51

The method of Embodiment 50, wherein said crRNA is in the same vector of first nucleotide sequence.

Embodiment 52

The method of Embodiment 48, wherein said nucleic acid comprises a transactivating RNA (tracrRNA).

Embodiment 53

The method of Embodiment 52, wherein said tracrRNA is in the same vector of the second nucleotide sequence.

Embodiment 54

The method of Embodiment 48, wherein the Cas9 protein is codon optimized for expression in said cell.

Embodiment 55

The method of Embodiment 48, wherein said nucleic acid comprises:
a) a first nucleotide sequence encoding a transposase; and
b) a second nucleotide sequence comprising a nucleic acid sequence of a gene of interest flanked by a transposase recognition site,
wherein said (a) and (b) are located on the same or different vectors.

Embodiment 56

The method of Embodiment 55, wherein said transposase recognizes and excises a genomic sequence of interest.

Embodiment 57

The method of Embodiment 55, wherein the nucleic acid sequence of the gene of interest is integrated into a genome of the cell.

Embodiment 58

The method of Embodiment 48, wherein said gene-editing is selected from the group consisting of a DNA deletion, a gene disruption, a DNA insertion, a DNA inversion, a point mutation, a DNA replacement, a knock-in, and a knock-down.

Embodiment 59

The method of Embodiment 37, wherein the method causes induction of stem cells.

Embodiment 60

A method of inducing an immune response in a subject in need thereof, the method comprising:
administering an effective amount of the complex of Embodiment 1 to said subject, said complex comprising a nucleic acid non-covalently bound to a cationic amphipathic polymer.

Embodiment 61

The method of Embodiment 60, wherein the disease is an infectious disease.

Embodiment 62

The method of Embodiment 60, wherein the disease is cancer.

Embodiment 63

The method of Embodiment 60, wherein the subject is previously diagnosed with the disease.

Embodiment 64

The method of Embodiment 60, wherein the subject does not have a detectable symptom associated with the disease.

Embodiment 65

The method of Embodiment 60, wherein the subject is a human.

Embodiment 66

The method of Embodiment 60, wherein the complex of Embodiment 1 is included in a pharmaceutical composition that comprises a pharmaceutically acceptable carrier.

Embodiment 67

The method of Embodiment 66, wherein the pharmaceutical composition is a cancer vaccine.

Embodiment 68

The method of Embodiment 67, wherein the subject does not have cancer and the cancer vaccine induces an immune response in the subject that prevents the occurrence of the cancer.

Embodiment 69

The method of Embodiment 67, wherein the subject has been diagnosed with cancer and the cancer vaccine induce an immune response in the subject that treats the cancer.

Embodiment 70

The method of Embodiment 60, wherein said nucleic acid is an messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA).

Embodiment 71

The method of Embodiment 60, wherein said nucleic acid is transfected into one or more cells in the subject.

Embodiment 72

The method of Embodiment 71, wherein the transfected nucleic acid provides an anti-cancer activity in the subject.

Embodiment 73

The method of Embodiment 71, wherein the nucleic acid encodes one or more peptides that are associated with cancer.

Embodiment 74

The method of Embodiment 72, wherein said anti-cancer activity is selected from the group consisting of reduction of cancer cell number, reduction of cancer size, killing of cancer cells, reduction and/or inhibition of metastasis, and reduction of cancer cell growth and/or proliferation.

Embodiment 75

The method of Embodiment 66, wherein said pharmaceutically acceptable carrier comprises an immunological adjuvant.

Embodiment 76

The method of Embodiment 60, wherein the method further comprises:
administering one or more pharmaceutical composition in an effective amount to the subject, said additional pharmaceutical composition comprising an anti-cancer agent and a pharmaceutically acceptable carrier.

Embodiment 77

A cell-penetrating complex comprising a nucleic acid non-covalently bound to a cationic amphipathic polymer, said cationic amphipathic polymer comprising a pH-sensitive immolation domain.

Embodiment 78

The cell-penetrating complex of Embodiment 77, wherein said cationic amphipathic polymer comprises a pH-sensitive immolation domain and a lipophilic polymer domain.

Embodiment 79

The cell-penetrating complex of Embodiment 78, wherein said cationic amphipathic polymer has the formula:

$$H-L^1-[(LP^1)_{z1}-(IM)_{z2}-(LP^2)_{z3}]_{z4}-L^2-H \quad (I)$$

wherein,
$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$LP^1$ and $LP^2$ are independently a bond or a lipophilic polymer domain, wherein at least one of $LP^1$ or $LP^2$ is a lipophilic polymer domain;
IM is said pH-sensitive immolation domain;
z1, z3 and z4 are independently integers from 0 to 100, wherein at least one of z1 or z3 is not 0; and
z2 is an integer from 2 to 100.

Embodiment 80

The cell-penetrating complex of one of Embodiments 77 to 79, wherein said pH-sensitive immolation domain has the formula:

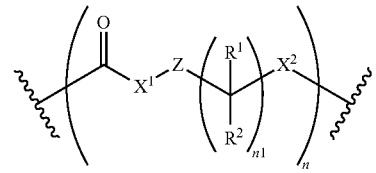

wherein n is an integer of 2 or more;

n1 is an integer from 0 to 50;

Z is said nucleophilic moiety;

$X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—;

$X^2$ is —O— or —S—; and $R^1$, $R^2$, $R^3$, $R^4$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 81

The cell-penetrating complex of one of Embodiments 77 to 80, wherein said pH-sensitive immolation domain has the formula:

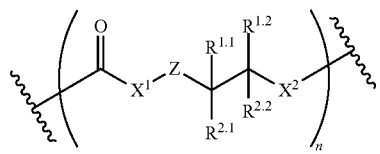

wherein n is an integer of 2 or more;

Z is said nucleophilic moiety;

$X^1$ is a bond, —C($R^5$)($R^6$)—, —C($R^5$)($R^6$)—C($R^7$)($R^8$)—, —O—C($R^5$)($R^6$)—, or —O—C($R^5$)($R^6$)—C($R^7$)($R^8$)—;

$X^2$ is —O— or —S—; and $R^{1.1}$, $R^{1.2}$, $R^{2.1}$, $R^{2.2}$, $R^3$, $R^4$, $R^5$, $R^6$, $R^7$, and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 82

The cell-penetrating complex of one of Embodiments 77 to 80, wherein said pH-sensitive immolation domain has the formula:

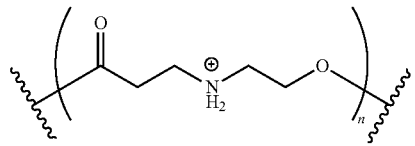

wherein n is an integer of 2 or more.

Embodiment 83

The cell-penetrating complex of one of Embodiments 77 to 82, wherein said pH-sensitive immolation domain has the formula:

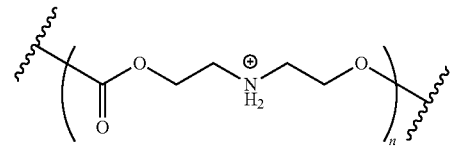

wherein n is an integer of 2 or more.

Embodiment 84

The cell-penetrating complex of one of Embodiments 77 to 82, wherein said pH-sensitive immolation domain has the formula:

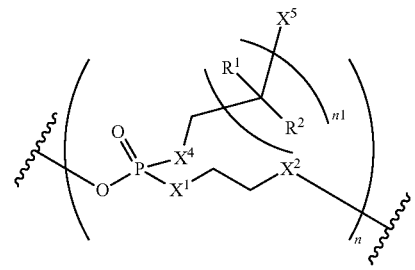

n is an integer of 2 or more;
n1 is an integer from 0 to 50;
$X^1$ is a bond, —O—, —$NR^5$—, —C($R^5$)($R^6$)— or —C($R^5$)($R^6$)—C($R^7$)($R^8$)—;
$X^2$ is a bond, —O—, —C($R^9$)($R^{10}$)— or —C($R^9$)($R^{10}$)—C($R^{11}$)($R^{12}$)—;
$X^4$ is a bond, —C(O)—, —P(O)(O$R^{16}$)$_2$—, —S(O)(O$R^{17}$)$_2$—, —C($R^{16}$)($R^{17}$)— or —C($R^{16}$)($R^{17}$)—C($R^{18}$)($R^{19}$)—
$X^5$ is a nucleophilic moiety; and
$R^1$, $R^2$, $R^5$, $R^6$, $R^7$, $R^8$, $R^9$, $R^{10}$, $R^1$, $R^{12}$, R, $R^{16}$, $R^{17}$, $R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 85

The cell-penetrating complex of one of Embodiments 77 to 80, wherein said pH-sensitive immolation domain has the formula:

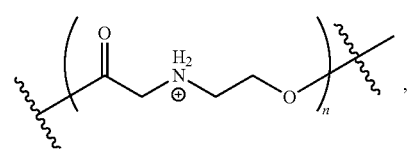
(IV)

wherein n is an integer of 2 or more.

Embodiment 86

The cell-penetrating complex of Embodiment 85, wherein n is an integer in the range of 2-50.

Embodiment 87

The cell-penetrating complex of Embodiment 78 or 79, wherein Z is —S—, —S$^+$R$^{13}$—, —NR$^{13}$— or —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 88

The cell-penetrating complex of Embodiment 78 or 79, wherein Z is

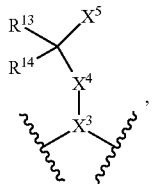

wherein
X$^3$ is C(R$^{15}$) or N;
X$^4$ is a bond, —C(O)—, —P(O)(OR$^{16}$)$_2$—, —S(O)(OR$^{17}$)$_2$—, —C(R$^{16}$)(R$^{17}$)— or —C(R$^{16}$)(R$^{17}$)—C(R$^{18}$)(R$^{19}$)—;
X$^5$ is a nucleophilic moiety; and
R$^{13}$, R$^{14}$, R$^{15}$, R$^{16}$, R$^{17}$, R$^{18}$ and R$^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 89

The cell-penetrating complex of Embodiment 88, wherein X$^5$ is —N$^+$(R$^{13}$)(H)—, wherein R$^{13}$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 90

The cell-penetrating complex of one of Embodiments 78-89, wherein said lipophilic polymer domain has the formula:

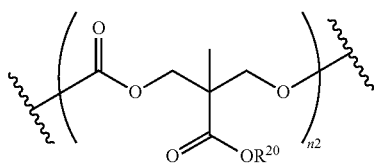

wherein
n2 is an interger from 1 to 100;
R$^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Embodiment 91

The cell-penetrating complex of one of Embodiments 77 to 87, wherein said nucleic acid is an mRNA, siRNA, pDNA, shRNA or gDNA.

Embodiment 92

A nanoparticle composition comprising a plurality of cell-penetrating complexes according to one of Embodiments 77 to 91.

Embodiment 93

A cationic amphipathic polymer of the formula:

$$H\text{-}L^1\text{-}[(LP^1)_{z1}\text{-}(IM)_{z2}\text{-}(LP^2)_{z3}]_{z4}\text{-}L^2\text{-}H \qquad (I)$$

wherein:
L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
LP$^1$ and LP$^2$ are independently a bond or a lipophilic polymer domain, wherein at least one of LP$^1$ or LP$^2$ is a lipophilic polymer domain;
IM is said pH-sensitive immolation domain;
z1, z3 and z4 are independently integers from 0 to 100, wherein at least one of z1 or z3 is not 0; and
z2 is an integer from 2 to 100.

Embodiment 94

A method of transfecting a nucleic acid into a cell, the method comprising contacting a cell with the complex of one of Embodiments 77 to 90.

Embodiment 95

The method of Embodiment 94, further comprising allowing said cationic amphipathic polymer to degrade within said cell thereby forming a degradation product.

Embodiment 96

The method of Embodiment 95, wherein said degradation product is a substituted or unsubstituted diketopiperazine.

Embodiment 97

The method of one of Embodiments 94 to 96, wherein said nucleic acid is an mRNA.

Embodiment 98

The method of Embodiment 97, further comprising allowing said mRNA to be expressed in said cell.

Embodiment 99

The method of one of Embodiments 94 to 97, wherein said cell forms part of an organism.

Embodiment 100

The method of Embodiment 99, wherein said organism is a human.

P EMBODIMENTS

P Embodiment 1. A cell-penetrating complex comprising a nucleic acid non-covalently bound to a cationic amphipathic polymer, said cationic amphipathic polymer comprising a pH-sensitive immolation domain and a lipophilic polymer domain,
wherein said cationic amphipathic polymer has the formula:

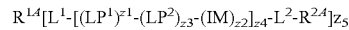

wherein
$R^{1.4}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$C$_1$, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2.4}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$LP^1$ and $LP^2$ are independently a lipophilic polymer domain;
IM is said pH-sensitive immolation domain;
z5 is an integer from 1 to 10;
z1 and z3 are independently integers from 0 to 100, wherein at least one of z1 or z3 is not 0; z4 is an integer from 1 to 100, and
z2 is an integer from 2 to 100

P Embodiment 2. The cell-penetrating complex of P Embodiment 1, wherein said cationic amphipathic polymer has the formula:

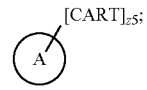

wherein
Ring A is a substituted or unsubstituted cycloalkyl, substituted or unsubstituted heterocycloalkyl, substituted or unsubstituted aryl, or substituted or unsubstituted heteroaryl;
CART has the formula: -L$^1$-[(LP$^1$)$_{z1}$-(LP$^2$)$_{z3}$-(IM)$_{z2}$]$_{z4}$-L$^2$-R$^{2.4}$
wherein,
$R^{2.4}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$C$_1$, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^1$ and $L^2$ are independently a bond, —C(O)O—, —O—, —S—, —NH—, —C(O)NH—, —NHC(O)—, —S(O)$_2$ —, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$LP^1$ and $LP^2$ are independently a lipophilic polymer domain;
IM is said pH-sensitive immolation domain;
z5 is an integer from 1 to 10;
z1 and z3 are independently integers from 0 to 100, wherein at least one of z1 or z3 is not 0; z4 is an integer from 1 to 100, and z2 is an integer from 2 to 100.

P Embodiment 3. The cell-penetrating complex of P Embodiment 2, wherein Ring A is a substituted or unsubstituted aryl.

P Embodiment 4. The cell-penetrating complex of P Embodiment 2, wherein Ring A is a substituted or unsubstituted phenyl.

P Embodiment 5. The cell-penetrating complex of P Embodiment 2, wherein Ring A is a substituted or unsubstituted aryl.

P Embodiment 6. The cell-penetrating complex of P Embodiment 2, wherein Ring A is a substituted or unsubstituted phenyl or naphthalenyl.

P Embodiment 7. The cell-penetrating complex of P Embodiment 1 or 2, wherein said cationic amphipathic polymer has the formula:

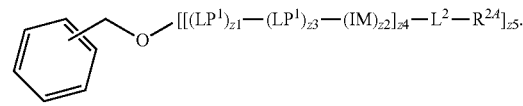

P Embodiment 8. The cell-penetrating complex of P Embodiment 1 or 2, wherein said cationic amphipathic polymer has the formula:

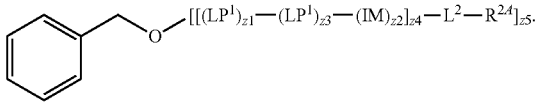

P Embodiment 9. The cell-penetrating complex of P Embodiment 1 or 2, wherein said cationic amphipathic polymer has the formula:

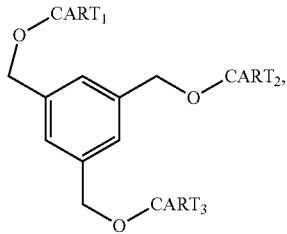

wherein $CART_1$, $CART_2$ and $CART_3$ are independently CART as defined in claim 2

P Embodiment 10. The cell-penetrating complex of P Embodiment 1 or 2, wherein z5 is an integer from 1 to 3

P Embodiment 11. The cell-penetrating complex of P Embodiment 1 or 2, wherein z5 is 1 or 3.

P Embodiment 12. The cell-penetrating complex of P Embodiment 1 or 2, wherein z5 is 1.

P Embodiment 13. The cell-penetrating complex of P Embodiment 1 or 2, wherein z5 is 3.

P Embodiment 14. The cell-penetrating complex of P Embodiment 1 or 2, wherein $R^{2.4}$ is hydrogen.

P Embodiment 15. The cell-penetrating complex of P Embodiment 1 or 2, wherein $L^2$ is a bond.

P Embodiment 16. The cell-penetrating complex of P Embodiment 1, wherein said pH-sensitive immolation domain has the formula:

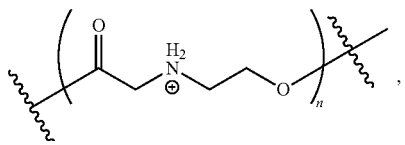

(IV)

wherein n is an integer of 2 or more

P Embodiment 17. The cell-penetrating complex of P Embodiment 16, wherein n is an integer in the range of 2-50.

P Embodiment 18. The cell-penetrating complex of P Embodiment 16, wherein n is 7.

P Embodiment 19. The cell-penetrating complex of P Embodiment 1 or 2, wherein said lipophilic polymer domain has the formula:

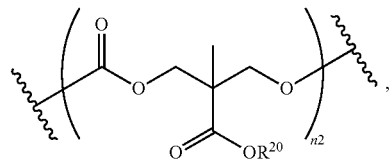

wherein
n2 is an integer from 1 to 100;
$R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl P Embodiment 20. The cell-penetrating complex of any one of P Embodiments 1-19, wherein $LP^1$ has the formula:

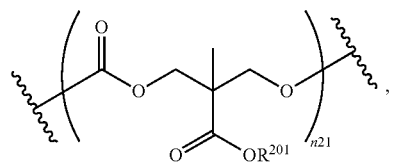

wherein
n21 is an integer from 1 to 100;
$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl P Embodiment 21. The cell-penetrating complex of claim 20, wherein n21 is 5 and $R^{201}$ is unsubstituted $C_{18}$ alkenyl P Embodiment 22. The cell-penetrating complex of P Embodiment 21, wherein said unsubstituted Cis alkenyl is oleyl.

P Embodiment 23. The cell-penetrating complex of any one of P Embodiments 1-22, wherein $LP^2$ has the formula:

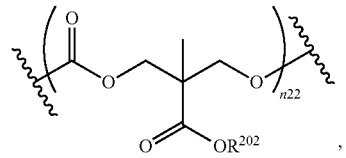

wherein
n22 is an integer from 1 to 100;
$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl P Embodiment 24. The cell-penetrating complex of P Embodiment 23, wherein n22 is 5 and $R^{202}$ is unsubstituted $C_9$ alkenyl.

P Embodiment 25. The cell-penetrating complex of P Embodiment 24, wherein said unsubstituted $C_9$ alkenyl is nonenyl.

P Embodiment 26. The cell-penetrating complex of any one of P Embodiments 1-25, wherein said cationic amphipathic polymer has the formula:

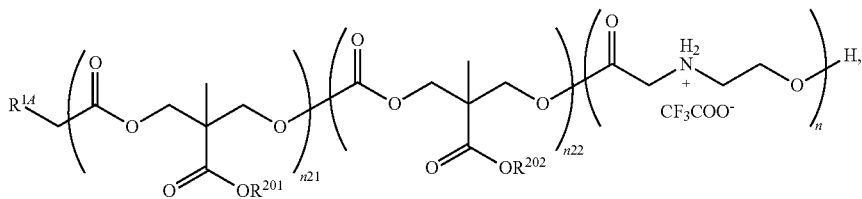

wherein n21 is 5, $R^{201}$ is oleyl, n22 is 5, $R^{202}$ is nonenyl and n is 7.

P Embodiment 27. The cell-penetrating complex of any one of P Embodiments 1-26, wherein said nucleic acid is an messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, genomic DNA (gNDA).

P Embodiment 28. The cell-penetrating complex of any one of P Embodiments 1-27, wherein said nucleic acid comprises a sequence encoding a chimeric antigen receptor (CAR).

P Embodiment 29. A nanoparticle composition comprising a plurality of cell-penetrating complexes according to any one of P Embodiments 1-28.

P Embodiment 30. A pharmaceutical composition comprising the complex of any of P Embodiments 1-28 and a pharmaceutically acceptable carrier.

P Embodiment 31. A method of transfecting a nucleic acid into a cell, the method comprising contacting a cell with the complex of any one of P Embodiments 1-28.

P Embodiment 32. The method of P Embodiment 31, further comprising allowing said cationic amphipathic polymer to degrade within said cell thereby forming a degradation product.

P Embodiment 33. The method of P Embodiment 32, wherein said degradation product is a substituted or unsubstituted diketopiperazine.

P Embodiment 34. The method of P Embodiment 31, wherein said nucleic acid comprises a CAR encoding messenger RNA (mRNA).

P Embodiment 35. The method of P Embodiment 34, further comprising allowing said mRNA to be expressed in said cell.

P Embodiment 36. The method of P Embodiment 35, wherein said cell is an eukaryotic cell.

P Embodiment 37. The method of P Embodiment 35, wherein said cell is a mammalian or human cell.

P Embodiment 38. The method of P Embodiment 35, wherein said cell forms part of an organism.

P Embodiment 39. The method of P Embodiment 38, wherein said organism is a human.

P Embodiment 40. The method of claim of any one of P Embodiments 35-39, wherein said cell is a lymphoid cell or a myeloid cell.

P Embodiment 41. The method of claim of any one of P Embodiments 35-40, wherein said cell is a T cell.

P Embodiment 42. The method of claim of any one of P Embodiments 35-40, wherein said cell is a myeloid cell.

P Embodiment 43. A method of inducing an immune response in a subject in need thereof, the method comprising administering an effective amount of the complex of any one of P Embodiments 1-28 to said subject.

P Embodiment 44. The method of P Embodiment 43, wherein said immune response is an anti-cancer immune response.

P Embodiment 45. A method of treating cancer in a subject in need thereof, the method comprising administering an effective amount of the complex of any one of P Embodiments 1-28 to said subject.

P Embodiment 46. The method of any one of claims P Embodiments 43-45, wherein said administering comprises intravenous injection or subcutaneous injection.

P Embodiment 47. A method of transfecting a nucleic acid encoding a chimeric antigen receptor (CAR) into a cell, the method comprising contacting a cell with a cell-penetrating complex comprising a nucleic acid non-covalently bound to a cationic amphipathic polymer, said cationic amphipathic polymer comprising a pH-sensitive immolation domain and a lipophilic polymer domain, and said nucleic acid comprising a sequence encoding a chimeric antigen receptor.

P Embodiment 48. The method of P Embodiment 47, wherein said cationic amphipathic polymer has the formula:

$$R^{1A}\text{-}[L^1\text{-}[(LP^1)_{z1}\text{-}(IM)_{z2}\text{-}(LP^2)_{z3}]_{z4}\text{-}L^2\text{-}R^{2A}]_{z5}$$

wherein $R^{1A}$ is hydrogen, halogen, —$CCl_3$, —$CBr_3$, —$CF_3$, —$C_{13}$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —O $CHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ is hydrogen, halogen, —$CCl_3$, —$CBr_3$, —$CF_3$, —$Cl_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —O $CHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 49. The method of P Embodiment 47 or 48, wherein said cationic amphipathic polymer has the formula:

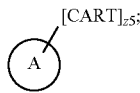

wherein

Ring A is a substituted or unsubstituted cycloalkyl, substituted or unsubstituted heterocycloalkyl, substituted or unsubstituted aryl, or substituted or unsubstituted heteroaryl;

CART has the formula: $-L^1-[(LP^1)_{z1}-(IM)_{z2}-(LP^2)_{z3}]_{z4}-L^2-R^{24}$ wherein, $R^{24}$ is hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ and $L^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$LP^1$ and $LP^2$ are independently a bond or a lipophilic polymer domain, wherein at least one of $LP^1$ or $LP^2$ is a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 50. The method of P Embodiment 49, wherein Ring A is a substituted or unsubstituted aryl.

P Embodiment 51. The method of P Embodiment 49, wherein Ring A is a substituted or unsubstituted phenyl.

P Embodiment 52. The method of P Embodiment 49, wherein Ring A is a substituted or unsubstituted aryl.

P Embodiment 53. The method of P Embodiment 49, wherein Ring A is a substituted or unsubstituted phenyl or naphthalenyl.

P Embodiment 54. The method of P Embodiment 48 or 49, wherein said cationic amphipathic polymer has the formula:

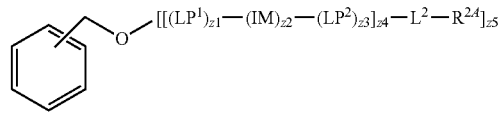

P Embodiment 55. The method of P Embodiment 48 or 49, wherein said cationic amphipathic polymer has the formula:

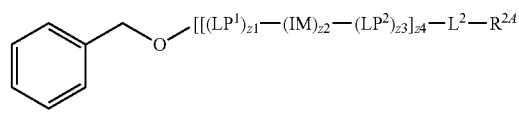

P Embodiment 56. The method of P Embodiment 48 or 49, wherein said cationic amphipathic polymer has the formula:

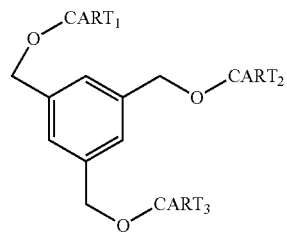

wherein CART$_1$, CART$_2$ and CART$_3$ are independently CART as defined in claim 4.

P Embodiment 57. The method of P Embodiment 48 or 49, wherein $L^1$ is —CH$_2$—O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

P Embodiment 58. The method of any one of P Embodiments 47-57, wherein said pH-sensitive immolation domain has the formula:

(IV)

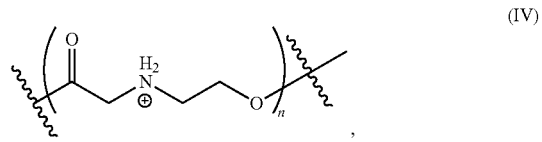

wherein n is an integer of 2 or more.

P Embodiment 59. The method of P Embodiment 47, wherein said cationic amphipathic polymer has the formula:

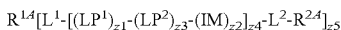

wherein $R^{14}$ is hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{24}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OC$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

LP$^1$ and LP$^2$ are independently a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 60. The method of P Embodiment 47 or 49, wherein said cationic amphipathic polymer has the formula:

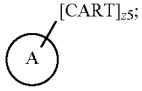

wherein

Ring A is a substituted or unsubstituted cycloalkyl, substituted or unsubstituted heterocycloalkyl, substituted or unsubstituted aryl, or substituted or unsubstituted heteroaryl;

CART has the formula: -L$^1$-[(LP$^1$)$_{z1}$-(LP$^2$)$_{z3}$-(IM)$_{z2}$]$_{z4}$-L$^2$-R$^{24}$ wherein, R$^{24}$ is hydrogen, halogen, —CCl$_3$, —CBr$_3$, —CF$_3$, —Cl$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

LP$^1$ and LP$^2$ are independently a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 61. The method of P Embodiment 60, wherein Ring A is a substituted or unsubstituted aryl.

P Embodiment 62. The method of P Embodiment 60, wherein Ring A is a substituted or unsubstituted phenyl.

P Embodiment 63. The method of P Embodiment 60, wherein Ring A is a substituted or unsubstituted aryl.

P Embodiment 64. The method of P Embodiment 60, wherein Ring A is a substituted or unsubstituted phenyl or naphthalenyl.

P Embodiment 65. The method of any one of P Embodiments 59-64, wherein said cationic amphipathic polymer has the formula:

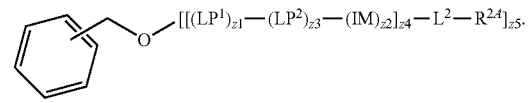

P Embodiment 66. The method of any one of P Embodiments 59-65, wherein said cationic amphipathic polymer has the formula:

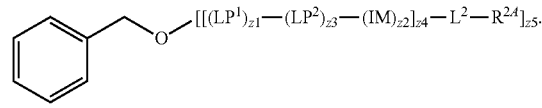

P Embodiment 67. The method of any one of P Embodiments 59-66, wherein said cationic amphipathic polymer has the formula:

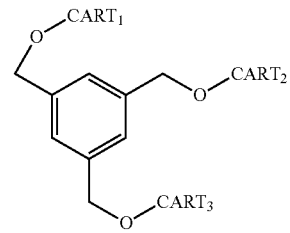

wherein CART$_1$, CART$_2$ and CART$_3$ are independently CART as defined in P Embodiment 4.

P Embodiment 68. The method of any one of P Embodiments 59-67, wherein z5 is an integer from 1 to 3.

P Embodiment 69. The method of any one of P Embodiments 59-67, wherein z5 is 1 or 3.

P Embodiment 70. The method of any one of P Embodiments 59-67, wherein z5 is 1.

P Embodiment 71. The method of any one of P Embodiments 59-67, wherein z5 is 3.

P Embodiment 72. The method of any one of P Embodiments 59-71, wherein $R^{2A}$ is hydrogen.

P Embodiment 73. The method of any one of P Embodiments 59-72, wherein $L^2$ is a bond.

P Embodiment 74. The method of any one of P Embodiments 59-73, wherein said pH-sensitive immolation domain has the formula:

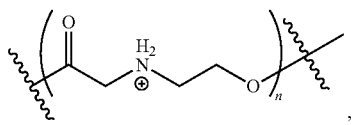

(IV)

wherein n is an integer of 2 or more.

P Embodiment 75. The method of P Embodiment 74, wherein n is an integer in the range of 2-50.

P Embodiment 76. The method of P Embodiment 74, wherein n is 7.

P Embodiment 77. The method of any one of P Embodiments 59-76, wherein said lipophilic polymer domain has the formula:

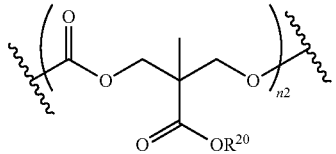

wherein
n2 is an integer from 1 to 100;
$R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 78. The method of any one of P Embodiments 59-77, wherein $LP^1$ has the formula:

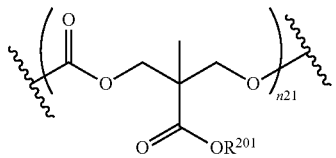

wherein
n21 is an integer from 1 to 100;
$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 79. The method of P Embodiment 78, wherein n21 is 5 and $R^{201}$ is unsubstituted Cis alkenyl.

P Embodiment 80. The method of any one of P Embodiments 59-77, wherein $LP^2$ has the formula:

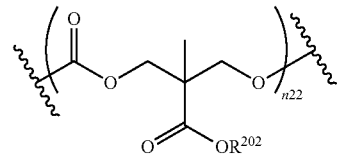

wherein
n22 is an integer from 1 to 100;
$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 81. The method of P Embodiments 80, wherein n22 is 5 and $R^{202}$ is unsubstituted $C_9$ alkenyl.

P Embodiment 82. The method of any one of P Embodiments 47-81, wherein said cell is an eukaryotic cell.

P Embodiment 83. The method of any one of P Embodiments 47-81, wherein said cell is a mammalian or human cell.

P Embodiment 84. The method of any one of P Embodiments 47-81, wherein said cell forms part of an organism.

P Embodiment 85. The method of any one of P Embodiments 47-81, wherein said organism is a human.

P Embodiment 86. The method of any one of P Embodiments 47-81, wherein said cell is a lymphoid cell or a myeloid cell.

P Embodiment 87. The method of any one of P Embodiments 47-81, wherein said cell is a T cell.

P Embodiment 88. The method of any one of P Embodiments 47-81, wherein said cell is a myeloid cell.

P Embodiment 89. A cationic amphipathic polymer of the formula:

$$R^{1A}[L^1-[(LP^1)_{z1}-(LP^2)_{z3}-(IM)_{z2}]_{z4}-L^2-R^{2A}]_{z5}$$

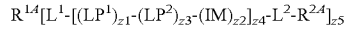

wherein
$R^{1A}$ is hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2A}$ is hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

LP$^1$ and LP$^2$ are independently a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 90. The cationic amphipathic polymer of P Embodiment 89, wherein said cationic amphipathic polymer has the formula:

wherein

Ring A is a substituted or unsubstituted cycloalkyl, substituted or unsubstituted heterocycloalkyl, substituted or unsubstituted aryl, or substituted or unsubstituted heteroaryl;

CART has the formula: -L$^1$-[(LP$^1$)$_{z1}$-(LP$^2$)$_{z3}$-(IM)$_{z2}$]$_{z4}$-L$^2$-R$^{24}$ wherein, R$^{24}$ is hydrogen, halogen, —CCl$_3$, —CBr$_3$, —CF$_3$, —C$_{13}$, CHCl$_2$, —CHBr$_2$, —CHF$_2$, —CHI$_2$, —CH$_2$C$_1$, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, E NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^1$ and L$^2$ are independently a bond, —C(O)O—, —O—, —S—, —NH—, —C(O)NH—, —NHC(O)—, —S(O)$_2$—, —S(O)NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

LP$^1$ and LP$^2$ are independently a lipophilic polymer domain;

IM is said pH-sensitive immolation domain;

z5 is an integer from 1 to 10;

z1 and z3 are independently integers from 0 to 100, wherein at least one of z1 or z3 is not 0; z4 is an integer from 1 to 100, and z2 is an integer from 2 to 100.

P Embodiment 91. The cationic amphipathic polymer of P Embodiment 90, wherein Ring A is a substituted or unsubstituted aryl.

P Embodiment 92. The cationic amphipathic polymer of P Embodiment 90, wherein Ring A is a substituted or unsubstituted phenyl.

P Embodiment 93. The cationic amphipathic polymer of P Embodiment 90, wherein Ring A is a substituted or unsubstituted aryl.

P Embodiment 94. The cationic amphipathic polymer of P Embodiment 90, wherein Ring A is a substituted or unsubstituted phenyl or naphthalenyl.

P Embodiment 95. The cationic amphipathic polymer of any one of P Embodiments 89-94, wherein said cationic amphipathic polymer has the formula:

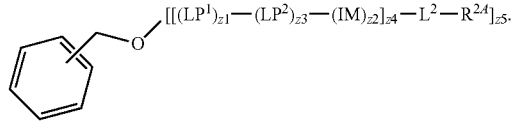

P Embodiment 96. The cationic amphipathic polymer of any one of P Embodiments 89-94, wherein said cationic amphipathic polymer has the formula:

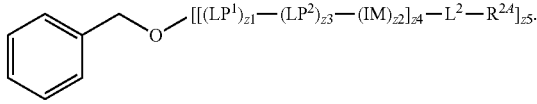

P Embodiment 97. The cationic amphipathic polymer of any one of P Embodiments 89-94, wherein said cationic amphipathic polymer has the formula:

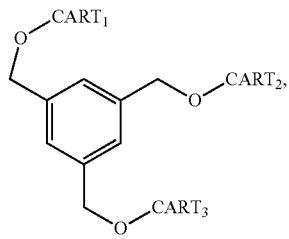

wherein CART$_1$, CART$_2$ and CART$_3$ are independently CART as defined in P Embodiment 4.

P Embodiment 98. The cationic amphipathic polymer of any one of P Embodiments 89-97, wherein z5 is an integer from 1 to 3.

P Embodiment 99. The cationic amphipathic polymer of any one of P Embodiments 89-97, wherein z5 is 1 or 3.

P Embodiment 100. The cationic amphipathic polymer of any one of P Embodiments 89-97, wherein z5 is 1.

P Embodiment 101. The cationic amphipathic polymer of any one of P Embodiments 89-97, wherein z5 is 3.

P Embodiment 102. The cationic amphipathic polymer of any one of P Embodiments 89-101, wherein $R^{24}$ is hydrogen.

P Embodiment 103. The cationic amphipathic polymer of any one of P Embodiments 89-102, wherein $L^2$ is a bond.

P Embodiment 104. The cationic amphipathic polymer of any one of P Embodiments 89-103, wherein said pH-sensitive immolation domain has the formula:

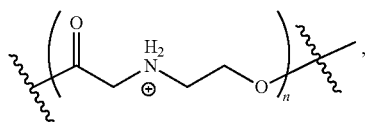

(IV)

wherein n is an integer of 2 or more.

P Embodiment 105. The cationic amphipathic polymer of P Embodiment 104, wherein n is an integer in the range of 2-50.

P Embodiment 106. The cationic amphipathic polymer of P Embodiment 105, wherein n is 7.

P Embodiment 107. The cationic amphipathic polymer of any one of P Embodiments 89-106, wherein said lipophilic polymer domain has the formula:

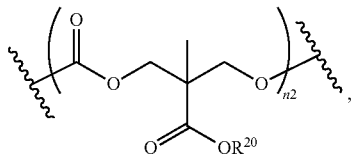

wherein
n2 is an integer from 1 to 100;
$R^{20}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 108. The cationic amphipathic polymer of any one of P Embodiments 89-107, wherein $LP^1$ has the formula:

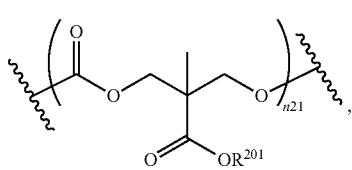

wherein
n21 is an integer from 1 to 100;
$R^{201}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 109. The cationic amphipathic polymer of P Embodiment 108, wherein n21 is 5 and $R^{201}$ is unsubstituted CIS alkenyl.

P Embodiment 110. The cationic amphipathic polymer of P Embodiment 109, wherein said unsubstituted CIS alkenyl is oleyl.

P Embodiment 111. The cationic amphipathic polymer of any one of P Embodiments 89-110, wherein $LP^2$ has the formula:

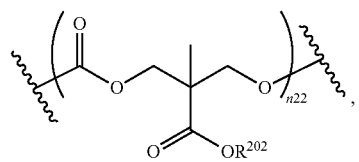

wherein
n22 is an integer from 1 to 100;
$R^{202}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

P Embodiment 112. The cationic amphipathic polymer of P Embodiment 111, wherein n22 is 5 and $R^{202}$ is unsubstituted $C_9$ alkenyl.

P Embodiment 113. The cationic amphipathic polymer of P Embodiment 112, wherein said unsubstituted $C_9$ alkenyl is nonenyl.

P Embodiment 114. The cationic amphipathic polymer of any one of P Embodiments 89-113, wherein said cationic amphipathic polymer has the formula:

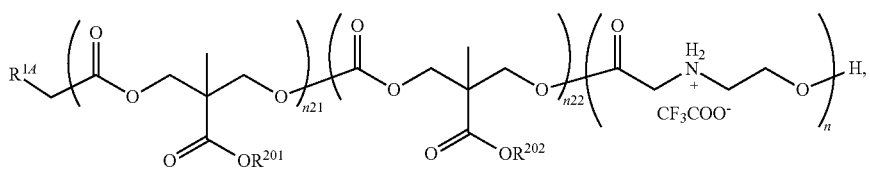

wherein n21 is 5, $R^{201}$ is oleyl, n22 is 5, $R^{202}$ is nonenyl and n is 7.

P Embodiment 115. A method of transfecting a nucleic acid encoding a receptor protein into a cell in a subject, the method comprising administering to a subject a cell-penetrating complex comprising a nucleic acid encoding a receptor protein bound to a compound, wherein said compound degrades upon delivery into said cell, thereby transfecting a nucleic acid encoding a receptor protein into a cell in a subject.

P Embodiment 116. The method of P Embodiment 115, wherein said cellular receptor is a T cell receptor (TCR).

P Embodiment 117. The method of P Embodiment 115, wherein said cellular receptor is a chimeric antigen receptor (CAR).

P Embodiment 118. A method of transfecting a nucleic acid encoding a T cell receptor (TCR) into a cell in a subject, the method comprising administering to a subject a cell-penetrating complex comprising a nucleic acid encoding a TCR bound to a compound, wherein said compound degrades upon delivery into said cell, thereby transfecting a nucleic acid encoding a TCR into a cell in a subject.

P Embodiment 119. A method of transfecting a nucleic acid encoding a chimeric antigen receptor (CAR) into a cell in a subject, the method comprising administering to a subject a cell-penetrating complex comprising a nucleic acid encoding a CAR bound to a compound, wherein said compound degrades upon delivery into said cell, thereby transfecting a nucleic acid encoding a CAR into a cell in a subject.

P Embodiment 120. The method of any one of claims P Embodiments 115, 118, or 119, wherein said compound is a cationic amphipathic polymer compound.

P Embodiment 121. The method of any one of P Embodiments 115, 118, or 119, wherein said compound is a compound of any one of P Embodiments 89-114.

P Embodiment 122. The method of any one of P Embodiments 115 or 118-121, wherein said nucleic acid is an mRNA.

P Embodiment 123. The method of any one of P Embodiments 115 or 118-121, wherein said nucleic acid is a DNA.

P Embodiment 124. The method of any one of P Embodiments 119-123, wherein said CAR is an anti-CD19 CAR.

P Embodiment 125. The method of any one of P Embodiments 115 or 118-124, wherein said nucleic acid further encodes an effector enhancing protein.

P Embodiment 126. The method of any one of P Embodiments 115 or 118-125, wherein said nucleic acid is a plurality of nucleic acids.

P Embodiment 127. The method of any one of P Embodiments 115 or 118-124, wherein said cell is a myeloid cell or a lymphoid cell.

P Embodiment 128. The method of any one of P Embodiments 115-127, wherein said cell is a T cell, a B cell, or a natural killer cell.

P Embodiment 129. The method of any one of P Embodiments 115-127, wherein said cell is a macrophage, an eosinophil or a neutrophil.

P Embodiment 130. The method of any one of P Embodiments 115-128, wherein said administering is intravenous, subcutaneous or intratumoral.

What is claimed is:

1. A cationic amphipathic polymer of the formula:

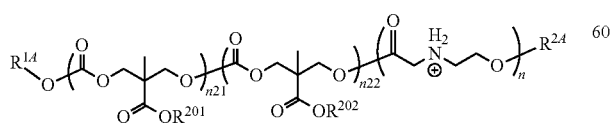

wherein
$R^{1A}$ and $R^{2A}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{201}$ is oleyl;
$R^{202}$ is nonenyl;
n21 is 1 to 100;
n22 is 1 to 100; and
n is 2 to 50.

2. The cationic amphipathic polymer of claim 1, wherein $R^{1A}$ is a substituted or unsubstituted phenyl or naphthalenyl; and
$R^{2A}$ is H.

3. The cationic amphipathic polymer of claim 2, wherein the cationic amphipathic polymer has the formula:

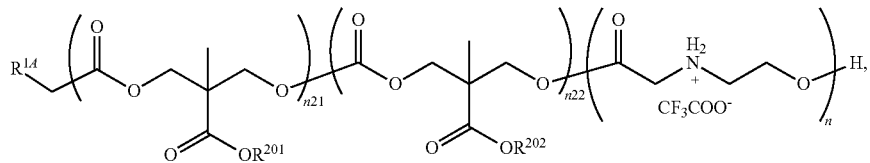

wherein n21 is 5, n22 is 5, and n is 7.

4. The cationic amphipathic polymer of claim 1, wherein the polymer is non-covalently bound to nucleic acid.

5. The cationic amphipathic polymer of claim 4, wherein the non-covalently bound nucleic acid is a messenger RNA (mRNA), small interference RNA (siRNA), short hairpin RNA (shRNA), micro RNA (miRNA), guide RNA (gRNA), CRISPR RNA (crRNA), transactivating RNA (tracrRNA), plasmid DNA (pDNA), minicircle DNA, or genomic DNA (gNDA).

6. The cationic amphipathic polymer of claim 5, wherein the non-covalently bound nucleic acid is messenger RNA (mRNA) encoding a cellular receptor protein, a T cell receptor (TCR), or a chimeric antigen receptor (CAR).

7. A nanoparticle composition comprising the cationic amphipathic polymer of claim 4.

8. A pharmaceutical composition comprising the cationic amphipathic polymer of claim 4.

9. A pharmaceutical composition comprising the nanoparticle of claim 7.

10. A method of transfecting a nucleic acid into a cell, the method comprising contacting a cell with the cationic amphipathic polymer of claim 4.

11. A method of transfecting a nucleic acid encoding a receptor protein into a cell in a subject, the method comprising administering to a subject the cationic amphipathic polymer of claim 6.

12. The method of claim 11, wherein the cell is a T lymphocyte cell, a B cell, or a macrophage cell.

13. A method of treating cancer in a subject in need thereof comprising administering to the subject the cationic amphipathic polymer of claim 6.

14. A method of inducing an immune response in a subject comprising administering to the subject the cationic amphipathic polymer of claim 4, non-covalently bound to an mRNA encoding an antigenic or immunogenic epitope.

15. The method of claim 11, wherein the subject is human.

* * * * *

SEQUENCE LISTING

```
<160> NUMBER OF SEQ ID NOS: 3

<210> SEQ ID NO 1
<211> LENGTH: 1428
<212> TYPE: DNA
<213> ORGANISM: Artificial Sequence
<220> FEATURE:
<223> OTHER INFORMATION: Synthetic construct

<400> SEQUENCE: 1
atgtatcgca tgcagctgct gagctgcatt gcgctgagcc tggcgctggt gaccaacagc      60
gacatccaga tgacccagtc ccccgcttct ctgagcacat ccctgggcga gaccgtgaca     120
atccagtgcc aggctagcga ggatatctac tccggcctgg cctggtacca gcagaagcct     180
ggaaagtctc cccagctgct gatctacgga gcttccgacc tgcaggatgg agtgccttct     240
aggttctctg gaagcggctc cggaacccag tactctctga agatcaccag catgcagaca     300
gaggacgagg gcgtgtactt ctgccagcag ggactgacct acccaagaac atttggcgga     360
ggcacaaagc tggagctgaa gggaggagga ggctccggcg gaggaggctc tggaggagga     420
ggcagcgagg tgcagctgca gcagagcgga gctgagctgg tgaggcctgg aacctccgtg     480
aagctgtctt gtaaggtgag cggcgacacc atcacattct actacatgca ctttgtgaag     540
cagaggcctg gccagggact ggagtggatc ggaagaatcg acccagagga tgagtccaca     600
aagtactctg agaagttcaa gaacaaggcc accctgacag ctgataccag ctccaacaca     660
gcttacctga gctgtctag cctgaccagc gaggacaccg ccacatactt ctgcatctac     720
ggaggctact actttgatta ctggggccag ggagtgatgg tgacagtgtc ctctatcgag     780
tttatgtacc cccctccata cctggacaac gagagatcca acggcaccat catccacatc     840
aaggagaagc acctgtgcca cacacagagc tccccaaagc tgttctgggc tctggtggtg     900
gtggctggcg tgctgttttg ctacggactg ctggtgaccg tggccctgtg cgtgatctgg     960
acaaacagca ggagaaaccg gggaggccag tccgattaca tgaacatgac cccacggcgc    1020
cctggactga caaggaagcc ataccagcca tacgctcctg ctcgcgactt cgctgcttac    1080
aggccaagag ccaagttcag caggagcgcc gagaccgctg ctaacctgca ggaccccaac    1140
cagctgttca acgagctgaa cctgggcagg agagaggagt ttgacgtgct ggagaagaag    1200
```

```
cgggctcgcg atcccgagat gggaggcaag cagcagcggc gcaggaaccc tcaggagggc    1260
gtgtacaacg ccctgcagaa ggacaagatg gccgaggctt actctgagat cggcaccaag    1320
ggagagagac ggcgcggcaa gggacacgat ggcctgttcc agggactgag caccgccaca    1380
aaggacacct tgatgctctc gcacatgcag acactggccc ctcggtga                1428

<210> SEQ ID NO 2
<211> LENGTH: 1485
<212> TYPE: DNA
<213> ORGANISM: Artificial Sequence
<220> FEATURE:
<223> OTHER INFORMATION: Synthetic construct

<400> SEQUENCE: 2
taatacgact cactataggg agacccaagc tggctagcgt ttaaacttaa ggccaccatg      60
tatcgcatgc agctgctgag ctgcattgcg ctgagcctgg cgctggtgac caacagcgac     120
atccagatga cccagtcccc cgcttctctg agcacatccc tgggcgagac cgtgacaatc     180
cagtgccagg ctagcgagga tatctactcc ggcctggcct ggtaccagca gaagcctgga     240
aagtctcccc agctgctgat ctacggagct tccgacctgc aggatggagt gccttctagg     300
ttctctggaa gcggctccgg aacccagtac tctctgaaga tcaccagcat gcagacagag     360
gacgagggcg tgtacttctg ccagcaggga ctgacctacc caagaacatt tggcggaggc     420
acaaagctgg agctgaaggg aggaggaggc tccggcggag gaggctctgg aggaggaggc     480
agcgaggtgc agctgcagca gagcggagct gagctggtga ggcctggaac ctccgtgaag     540
ctgtcttgta aggtgagcgg cgacaccatc acattctact acatgcactt tgtgaagcag     600
aggcctggcc agggactgga gtggatcgga agaatcgacc cagaggatga gtccacaaag     660
tactctgaga agttcaagaa caaggccacc ctgacagctg ataccagctc caacacagct     720
tacctgaagc tgtctagcct gaccagcgag gacaccgcca catacttctg catctacgga     780
ggctactact ttgattactg gggccaggga gtgatggtga cagtgtcctc tatcgagttt     840
atgtaccccc ctccatacct ggacaacgag agatccaacg gcaccatcat ccacatcaag     900
gagaagcacc tgtgccacac acagagctcc ccaaagctgt tctgggctct ggtggtggtg     960
gctggcgtgc tgttttgcta cggactgctg gtgaccgtgg ccctgtgcgt gatctggaca    1020
aacagcagga gaaaccgggg aggccagtcc gattacatga acatgacccc acggcgcccc    1080
ggactgacaa ggaagccata ccagccatac gctcctgctc gcgacttcgc tgcttacagg    1140
ccaagagcca agttcagcag gagcgccgag accgctgcta acctgcagga ccccaaccag    1200
ctgttcaacg agctgaacct gggcaggaga gaggagtttg acgtgctgga gaagaagcgg    1260
gctcgcgatc ccgagatggg aggcaagcag cagcggcgca ggaaccctca ggagggcgtg    1320
tacaacgccc tgcagaagga caagatggcc gaggcttact ctgagatcgg caccaaggga    1380
gagagacggc gcggcaaggg acacgatggc ctgttccagg gactgagcac cgccacaaag    1440
gacacctttg atgctctgca catgcagaca ctggccccct cggtga                   1485

<210> SEQ ID NO 3
<211> LENGTH: 1878
<212> TYPE: DNA
<213> ORGANISM: Artificial Sequence
<220> FEATURE:
<223> OTHER INFORMATION: Synthetic construct

<400> SEQUENCE: 3
```

```
taatacgact cactataggg agacccaagc tggctagcgt ttaaacttaa ggccaccatg      60
tatcgcatgc agctgctgag ctgcattgcg ctgagcctgg cgctggtgac caacagcgac     120
atccagatga cccagtcccc cgcttctctg agcacatccc tgggcgagac cgtgacaatc     180
cagtgccagg ctagcgagga tatctactcc ggcctggcct ggtaccagca gaagcctgga     240
aagtctcccc agctgctgat ctacggagct tccgacctgc aggatggagt gccttctagg     300
ttctctggaa gcggctccgg aacccagtac tctctgaaga tcaccagcat gcagacagag     360
gacgagggcg tgtacttctg ccagcaggga ctgacctacc aagaacatt tggcggaggc      420 acaaagctgg agctgaaggg aggaggaggc tccggcggag gaggctctgg aggaggaggc     480
agcgaggtgc agctgcagca gagcggagct gagctggtga ggcctggaac ctccgtgaag     540
ctgtcttgta aggtgagcgg cgacaccatc acattctact acatgcactt tgtgaagcag     600
aggcctggcc agggactgga gtggatcgga agaatcgacc cagaggatga gtccacaaag     660
tactctgaga agttcaagaa caaggccacc ctgacagctg ataccagctc caacacagct     720
tacctgaagc tgtctagcct gaccagcgag gacaccgcca catacttctg catctacgga     780
ggctactact ttgattactg gggccaggga gtgatggtga cagtgtcctc tatcgagttt     840
atgtaccccc ctccatacct ggacaacgag agatccaacg gcaccatcat ccacatcaag     900
gagaagcacc tgtgccacac acagagctcc ccaaagctgt tctgggctct ggtggtggtg     960
gctggcgtgc tgttttgcta cggactgctg gtgaccgtgg ccctgtgcgt gatctggaca    1020
aacagcagga gaaaccgggg aggccagtcc gattacatga acatgacccc acggcgccct    1080
ggactgacaa ggaagccata ccagccatac gctcctgctc gcgacttcgc tgcttacagg    1140
ccaagagcca agttcagcag gagcgccgag accgctgcta acctgcagga ccccaaccag    1200
ctgttcaacg agctgaacct gggcaggaga gaggagtttg acgtgctgga gaagaagcgg    1260
gctcgcgatc ccgagatggg aggcaagcag cagcggcgca ggaaccctca ggagggcgtg    1320
tacaacgccc tgcagaagga caagatggcc gaggcttact ctgagatcgg caccaaggga    1380
gagagacggc gcggcaaggg acacgatggc ctgttccagg gactgagcac cgccacaaag    1440
gacacctttg atgctctgca catgcagaca ctggcccctc ggtgaggatc cgctcgcttt    1500
cttgctgtcc aatttctatt aaaggttcct tgttcccta agtccaacta ctaaactggg     1560
ggatattatg aagggccttg agcatctgga ttctgcctaa taaaaaacat ttattttcat    1620
tgcgctcgct ttcttgctgt ccaatttcta ttaaaggttc ctttgttccc taagtccaac    1680
tactaaactg ggggatatta tgaagggcct tgagcatctg gattctgcct aataaaaaac    1740
atttatttct attgcaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaagaa                                                  1878
```

UNITED STATES PATENT AND TRADEMARK OFFICE
CERTIFICATE OF CORRECTION

PATENT NO. : 12,215,341 B2
APPLICATION NO. : 17/292370
DATED : February 4, 2025
INVENTOR(S) : Tim R. Blake et al.

Page 1 of 1

It is certified that error appears in the above-identified patent and that said Letters Patent is hereby corrected as shown below:

In the Claims

Column 188, Line 63, should read "n is 2 to 50".

Signed and Sealed this
Twentieth Day of May, 2025

Coke Morgan Stewart
*Acting Director of the United States Patent and Trademark Office*